US011020475B1

(12) United States Patent
Seo et al.

(10) Patent No.: US 11,020,475 B1
(45) Date of Patent: Jun. 1, 2021

(54) COLD-ADAPTED LIVE ATTENUATED SEVERE ACUTE RESPIRATORY SYNDROME CORONAVIRUS AND VACCINE CONTAINING THE SAME

(71) Applicant: The Industry & Academic Cooperation in Chungnam National University (IAC), Daejeon (KR)

(72) Inventors: Sang-Heui Seo, Daejeon (KR); Yun-Yueng Jang, Daejeon (KR)

(73) Assignee: The Industry & Academic Cooperation in Chungnam National University (IAC), Daejeon (KR)

( * ) Notice: Subject to any disclaimer, the term of this patent is extended or adjusted under 35 U.S.C. 154(b) by 0 days.

(21) Appl. No.: 17/080,224

(22) Filed: Oct. 26, 2020

(30) Foreign Application Priority Data

Aug. 14, 2020  (KR) .................. 10-2020-0102525

(51) Int. Cl.
*A61K 39/215* (2006.01)
*A61P 31/14* (2006.01)
*A61K 39/00* (2006.01)

(52) U.S. Cl.
CPC ............ *A61K 39/215* (2013.01); *A61P 31/14* (2018.01); *A61K 2039/5254* (2013.01); *A61K 2039/53* (2013.01); *A61K 2039/543* (2013.01)

(58) Field of Classification Search
None
See application file for complete search history.

(56) References Cited

U.S. PATENT DOCUMENTS 4,867,975 A * 9/1989 Gelb, Jr. .............. A61K 39/215
424/222.1

OTHER PUBLICATIONS

Wu, F., Zhao, S., Yu, B. et al. A new coronavirus associated with human respiratory disease in China. Nature 579, 265-269 (Year: 2020).*
Fett et al., Journal of Virology, vol. 87 No. 12p. 6551-6559 (Year: 2013).*

* cited by examiner

*Primary Examiner* — Shanon A. Foley
*Assistant Examiner* — Myron G Hill
(74) *Attorney, Agent, or Firm* — Sughrue Mion, PLLC

(57) ABSTRACT

Disclosed is cold-adapted live attenuated severe acute respiratory syndrome coronavirus (SARS-CoV-2) prepared by infecting cells with severe acute respiratory syndrome coronavirus and then adapting the severe acute respiratory syndrome coronavirus to a temperature from 37° C. to 22° C. in a step by step manner. Further, a vaccine containing the cold-adapted live attenuated severe acute respiratory syndrome coronavirus (SARS-CoV-2) is disclosed.

7 Claims, 46 Drawing Sheets

Specification includes a Sequence Listing.

```
——— Cold-adapted SARS-CoV-2 vaccinated (20,000 pfu) & challenged mice
······· Cold-adapted SARS-CoV-2 vaccinated (2000 pfu) & challenged mice
· · · · PBS-mock & challenged mice
— — PBS-mock & unchallenged mice
```

□ Cold-adapted SARS-CoV-2 vaccinated (20,000 pfu) & challenged mice
▨ Cold-adapted SARS-CoV-2 vaccinated (2000 pfu) & challenged mice
■ PBS-mock & challenged mice

Fig. 10B

SEQUENCE LISTING

```
<160> NUMBER OF SEQ ID NOS: 111

<210> SEQ ID NO 1
<211> LENGTH: 21291
<212> TYPE: DNA
<213> ORGANISM: Unknown
<220> FEATURE:
<223> OTHER INFORMATION: SARS-CoV-2 ORF1ab polyprotein

<400> SEQUENCE: 1
atggagagcc ttgtccctgg tttcaacgag aaaacacacg tccaactcag tttgcctgtt      60
ttacaggttc gcgacgtgct cgtacgtggc tttggagact ccgtggagga ggtcttatca     120
gaggcacgtc aacatcttaa agatggcact tgtggcttag tagaagttga aaaaggcgtt     180
ttgcctcaac ttgaacagcc ctatgtgttc atcaaacgtt cggatgctcg aactgcacct     240
catggtcatg ttatggttga gctggtagca gaactcgaag gcattcagta cggtcgtagt     300
ggtgagacac ttggtgtcct tgtccctcat gtgggcgaaa taccagtggc ttaccgcaag     360
gttcttcttc gtaagaacgg taataaagga gctggtggcc atagttacgg cgccgatcta     420
aagtcatttg acttaggcga cgagcttggc actgatcctt atgaagattt tcaagaaaac     480
tggaacacta acatagcag tggtgttacc cgtgaactca tgcgtgagct taacggaggg     540
```

```
gcatacactc gctatgtcga taacaacttc tgtggccctg atggctaccc tcttgagtgc      600
attaaagacc ttctagcacg tgctggtaaa gcttcatgca ctttgtccga caactggac       660 tttattgaca ctaagagggg tgtatactgc tgccgtggac atgagcatga aattgcttgg      720
tacacggaac gttctgaaaa gagctatgaa ttgcagacac cttttgaaat taaattggca      780
aagaaatttg acaccttcaa tggggaatgt ccaaattttg tatttccctt aaattccata      840
atcaagacta ttcaaccaag ggttgaaaag aaaaagcttg atggctttat gggtagaatt      900
cgatctgtct atccagttgc gtcaccaaat gaatgcaacc aaatgtgcct ttcaactctc      960
atgaagtgtg atcattgtgg tgaaacttca tggcagacgg gcgattttgt aaagccact      1020 tgcgaatttt gtggcactga gaatttgact aaagaaggtg ccactacttg tggttactta     1080
ccccaaaatg ctgttgttaa aatttattgt ccagcatgtc acaattcaga gtaggacct      1140 gagcatagtc ttgccgaata ccataatgaa tctggcttga aaccattct tcgtaagggt      1200 ggtcgcacta ttgcctttgg aggctgtgtg ttctcttatg ttggttgcca taacaagtgt     1260
gcctatgggt tccacgtgc tagcgctaac ataggttgta accatacagg tgttgttgga      1320
gaaggttccg aaggtcttaa tgacaacctt cttgaaatac tccaaaaaga gaaagtcaac     1380
atcaatattg ttggtgactt taaacttaat gaagagatcg ccattatttt ggcatctttt     1440
tctgcttcca caagtgcttt tgtggaaact gtgaaaggtt tggattataa agcattcaaa     1500
caaattgttg aatcctgtgg taatttttaaa gttacaaaag gaaaagctaa aaaaggtgcc    1560
tggaatattg gtgaacagaa atcaatactg agtcctcttt atgcatttgc atcagaggct     1620
gctcgtgttg tacgatcaat tttctcccgc actcttgaaa ctgctcaaaa ttctgtgcgt     1680
gttttacaga aggccgctat aacaatacta gatggaattt cacagtattc actgagactc     1740
attgatgcta tgatgttcac atctgatttg gctactaaca atctagttgt aatggcctac     1800
attacaggtg gtgttgttca gttgacttcg cagtggctaa ctaacatctt tggcactgtt     1860
tatgaaaaac tcaaacccgt ccttgattgg cttgaagaga gtttaagga aggtgtagag     1920 tttcttagag acggttggga aattgttaaa tttatctcaa cctgtgcttg tgaaattgtc     1980 ggtgacaaa ttgtcacctg tgcaaaggaa attaaggaga gtgttcagac attctttaag     2040
cttgtaaata aattttttggc tttgtgtgct gactctatca ttattggtgg agctaaactt    2100
aaagccttga atttaggtga acatttgtc acgcactcaa agggattgta cagaaagtgt     2160
gttaaatcca gagaagaaac tggcctactc atgcctctaa agcccccaaa agaaattatc    2220
ttcttagagg gagaaacact tcccacagaa gtgttaacag aggaagttgt tttgaaaact    2280
ggtgatttac aaccattaga acaacctact agtgaagctg ttgaagctcc attggttggt    2340
acaccagttt gtattaacgg gcttatgttg ctcgaaatca aagacacaga aaagtactgt    2400
gcccttgcac ctaatatgat ggtaacaaac aataccttca cactcaaagg cggtgcacca    2460
acaaaggtta cttttggtga tgacactgtg atagaagtgc aaggttacaa gagtgtgaat    2520
atcacttttg aacttgatga aaggattgat aaagtactta atgagaagtg ctctgcctat    2580
acagttgaac tcggtacaga agtaaatgag ttcgcctgtg ttgtggcaga tgctgtcata    2640
aaaactttgc aaccagtatc tgaattactt acaccactgg gcattgattt agatgagtgg    2700
agtatggcta catactactt atttgatgag tctggtgagt ttaaattggc ttcacatatg    2760
tattgttctt tctaccctcc agatgaggat gaagaagaag gtgattgtga agaagaagag    2820
tttgagccat caactcaata tgagtatggt actgaagatg attaccaagg taaacctttg    2880
gaatttggtg ccacttctgc tgctcttcaa cctgaagaag agcaagaaga agattggtta    2940
```

```
gatgatgata gtcaacaaac tgttggtcaa caagacggca gtgaggacaa tcagacaact    3000
actattcaaa caattgttga ggttcaacct caattagaga tggaacttac accagttgtt    3060
cagactattg aagtgaatag ttttagtggt tatttaaaac ttactgacaa tgtatacatt    3120
aaaaatgcag acattgtgga agaagctaaa aaggtaaaac caacagtggt tgttaatgca    3180
gccaatgttt accttaaaca tggaggaggt gttgcaggag ccttaaataa ggctactaac    3240
aatgccatgc aagttgaatc tgatgattac atagctacta atggaccgct taaagtgggt    3300
ggtagttgtg ttttaagcgg acacaatctt gctaaacact gtcttcatgt tgtcggccca    3360
aatgttaaca aggtgaaga cattcaactt cttaagagtg cttatgaaaa ttttaatcag    3420
cacgaagttc tacttgcacc attattatca gctggtattt ttggtgctga ccctatacat    3480
tctttaagag tttgtgtaga tactgttcgc acaaatgtct acttagctgt ctttgataaa    3540
aatctctata caaacttgt ttcaagcttt ttggaaatga gagtgaaaa gcaagttgaa    3600 caaaagatcg ctgagattcc taagaggaa gttaagccat ttataactga agtaaacct    3660 tcagttgaac agagaaaaca agatgataag aaaatcaaag cttgtgttga agaagttaca    3720
acaactctgg aagaaactaa gttcctcaca gaaaacttgt tactttatat tgacattaat    3780
ggcaatcttc atccagattc tgccactctt gttagtgaca ttgacatcac tttcttaaag    3840
aaagatgctc catacatagt gggtgatgtt gttcaagagg gtgtttttaac tgctgtggtt    3900 atacctacta aaaggctgg tggcactact gaaatgctag cgaaagcttt gagaaaagtg    3960
ccaacagaca attatataac cacttacccg ggtcagggtt taaatggtta cactgtagag    4020
gaggcaaaga cagtgcttaa aaagtgtaaa agtgccttt acattctacc atctattatc    4080
tctaatgaga agcaagaaat tcttggaact gtttcttgga atttgcgaga atgctcgca    4140 catgcagaag aaacacgcaa attaatgcct gtctgtgtgg aaactaaagc catagtttca    4200
actatacagc gtaaatataa gggtattaaa atacaagagg gtgtggttga ttatggtgct    4260 agatttact tttacaccag taaaacaact gtagcgtcac ttatcaacac acttaacgat    4320
ctaaatgaaa ctcttgttac aatgccactt ggctatgtaa cacatggctt aaatttggaa    4380
gaagctgctc ggtatatgag atctctcaaa gtgccagcta cagtttctgt ttcttcacct    4440
gatgctgtta cagcgtataa tggttatctt acttcttctt ctaaaacacc tgaagaacat    4500
tttattgaaa ccatctcact tgctggttcc tataaagatt ggtcctattc tggacaatct    4560
acacaactag gtatagaatt tcttaagaga ggtgataaaa gtgtatatta cactagtaat    4620
cctaccacat tccacctaga tggtgaagtt atcacctttg acaatcttaa gacacttctt    4680
tctttgagag aagtgaggac tattaaggtg tttacaacag tagacaacat taacctccac    4740
acgcaagttg tgggcatgtc aatgacatat ggacaacagt tggtccaac ttattttgat    4800 ggagctgatg ttactaaaat aaaacctcat aattcacatg aaggtaaaac attttatgtt    4860
ttacctaatg atgacactct acgtgttgag cttttgagt actaccacac aactgatcct    4920
agttttctgg gtaggtacat gtcagcatta aatcacacta aaagtggaa atacccacaa    4980 gttaatggtt taacttctat taatgggca gataacaact gttatcttgc cactgcattg    5040
ttaacactcc aacaaataga gttgaagttt aatccacctg ctctacaaga tgcttattac    5100
agagcaaggg ctggtgaagc tgctaacttt tgtgcactta tcttagccta ctgtaataag    5160
acagtaggta gttaggtga tgttagagaa acaatgagtt acttgtttca acatgccaat    5220
ttagattctt gcaaaagagt cttgaacgtg gtgtgtaaaa cttgtggaca acagcagaca    5280
```

```
accccttaagg gtgtagaagc tgttatgtac atgggcacac tttcttatga acaatttaag    5340
aaaggtgttc agatacccttg tacgtgtggt aaacaagcta caaatatctt agtacaacag    5400
gagtcacctt ttgttatgat gtcagcacca cctgctcagt atgaacttaa gcatggtaca    5460
tttacttgtg ctagtgagta cactggtaat taccagtgtg gtcactataa acatataact    5520
tctaaagaaa ctttgtattg catagacggt gctttactta caaagtcctc agaatacaaa    5580
ggtcctatta cggatgtttt ctacaaagaa aacagttaca caacaaccat aaaaccagtt    5640
acttataaat tggatggtgt tgtttgtaca gaaattgacc ctaagttgga caattattat    5700
aagaaagaca attcttattt cacagagcaa ccaattgatc ttgtaccaaa ccaaccatat    5760
ccaagcgcaa gcttcgataa ttttaagttt gtatgtgata atatcaaatt tgctgatgat    5820
ttaaaccagt taactggtta taagaaacct gcttcaagag agcttaaagt tacatttttc    5880
cctgacttaa atggtgatgt ggtggctatt gattataaac actacacacc ctcttttaag    5940
aaaggagcta aattgttaca taaacctatt gtttggcatg ttaacaatgc aactaataaa    6000
gccacgtata aaccaaatac ctggtgtata cgttgtcttt ggagcacaaa accagttgaa    6060
acatcaaatt cgtttgatgt actgaagtca gaggacgcgc agggaatgga taatcttgcc    6120
tgcgaggatc taaaaccagt ctctgaagaa gtagtggaaa atcctaccat acagaaagac    6180
gttcttgagt gtaatgtgaa aactaccgaa gttgtaggag acattatact taaaccagcg    6240
aataatagtt taaaaattac agaagaggtt ggccacacag atctaatggc tgcttatgta    6300
gacaattcta gtcttactat taagaaacct aatgaattat ctagagtatt aggtttgaaa    6360
acccttgcta ctcatggttt agctgctgtt aatagtgtcc cttgggatac atagctaat    6420 tatgctaagc tttttcttaa caaagttgtt agtacaacta ctaacatagt tacacggtgt    6480
ttaaaccgtg tttgtactaa ttatatgcct tatttcttta ctttattgct acaattgtgt    6540
acttttacta gaagtacaaa ttctagaatt aaagcatcta tgccgactac tatagcaaag    6600
aatactgtta gagtgtcgg taaattttgt ctagaggctt catttaatta tttgaagtca    6660
cctaattttt ctaaactgat aaatattata atttggtttt tactattaag tgtttgccta    6720
ggttctttaa tctactcaac cgctgcttta ggtgttttaa tgtctaattt aggcatgcct    6780
tcttactgta ctggttacag agaaggctat ttgaactcta ctaatgtcac tattgcaacc    6840
tactgtactg gttctatacc ttgtagtgtt tgtcttagtg gtttagattc tttagacacc    6900
tatccttctt tagaaactat acaaattacc atctcatctt taaatgggaa tttaactgct    6960
tttggcttag ttgcagagtg gttttttggca tatattcttt tcactaggtt tttctatgta    7020
cttggattgg ctgcaatcat gcaattgttt ttcagctatt ttgcagtaca ttttattagt    7080
aattcttggc ttatgtggtt aataattaat cttgcacaaa tggccccgat ttcagctatg    7140
gttagaatgt acatcttctt tgcatcattt tattatgtat ggaaaagtta tgtgcatgtt    7200
gtagacggtt gtaattcatc aacttgtatg atgtgttaca acgtaataag agcaacaaga    7260
gtcgaatgta caactattgt taatggtgtt agaaggtcct tttatgtcta cgctaatgga    7320
ggtaaaggct tttgcaaact acacaattgg aattgtgtta ttgtgatac attctgtgct    7380 ggtagtacat ttattagtga tgaagttcg agagacttat cactcagtt taaaagacca    7440 ataaatccta ctgaccagtc ttcttacatc gttgatagtg ttacagtgaa gaatggttcc    7500
atccatcttt actttgataa agctggtcaa aagacttatg aaagacattc tctctctcat    7560
tttgttaact tagacaacct gagagctaat aacactaaag gttcattgcc tattaatgtt    7620 atagttttg atggtaaatc aaaatgtgaa gaatcatctg caaaatcagc gtctgtttac    7680
```

```
tacagtcagc ttatgtgtca acctatactg ttactagatc aggcattagt gtctgatgtt    7740
ggtgatagtg cggaagttgc agttaaaatg tttgatgctt acgttaatac gttttcatca    7800
acttttaacg taccaatgga aaaactcaaa acactagttg caactgcaga agctgaactt    7860
gcaaagaatg tgtccttaga caatgtctta tctactttta tttcagcagc tcggcaaggg    7920
tttgttgatt cagatgtaga aactaaagat gttgttgaat gtcttaaatt gtcacatcaa    7980
tctgacatag aagttactgg cgatagttgt aataactata tgctcaccta caacaaagtt    8040
gaaaacatga caccccgtga ccttggtgct tgtattgact gtagtgcgcg tcatattaat    8100
gcgcaggtag caaaaagtca caacattgct ttgatatgga acgttaaaga tttcatgtca    8160
ttgtctgaac aaccacgaaa acaaatacgt agtgctgcta aaagaataa cttacctttt    8220 aagttgacat gtgcaactac tagacaagtt gttaatgctg taacaacaaa gatagcactt    8280
aagggtggta aaattgttaa taattggttg aagcagttaa ttaaagttac acttgtgttc    8340 cttttttgttg ctgctatttt ctatttaata acacctgttc atgtcatgtc taaacatact    8400
gacttttcaa gtgaaatcat aggatacaag gctattgatg gtggtgtcac tcgtgacata    8460
gcatctacag atacttgttt tgctaacaaa catgctgatt ttgacacatg gtttagtcag    8520
cgtggtggta gttatactaa tgacaaagct tgcccattga ttgctgcagt cataacaaga    8580
gaagtggggt tgtcgtgcc tggtttgcct agcacgatat tacgcacaac taatggtgac    8640 ttttttgcatt tcttacctag agttttttagt gcagttggta acatctgtta cacaccatca    8700
aaacttatag agtacactga ctttgcaaca tcagcttgtg ttttggctgc tgaatgtaca    8760
atttttaaag atgcttctgg taagccagta ccatattgtt atgataccaa tgtactagaa    8820
ggttctgttg cttatgaaag tttacgccct gacacacgtt atgtgctcat ggatggctct    8880
attattcaat ttcctaacac ctaccttgaa ggtcctgtta gagtggtaac aacttttgat    8940
tctgagtact gtgggcacgg cacttgtgaa agatcagaag ctggtgtttg tgtatctact    9000
agtggtagat gggtacttaa caatgattat tacagatctt taccaggagt tttctgtggt    9060
gtagatgctg taaatttact tactaatatg tttacaccac taattcaacc tattggtgct    9120
ttggacatat cagcatctat agtagctggt ggtattgtag ctatcgtagt aacatgcctt    9180
gcctactatt ttatgaggtt tagaagagct tttggtgaat acagtcatgt agttgccttt    9240
aatactttac tattccttat gtcattcact gtactctgtt taacaccagt ttactcattc    9300
ttacctggtg tttattctgt tatttacttg tacttgacat tttatcttac taatgatgtt    9360
tcttttttag cacatattca gtggatggtt atgttcacac ctttagtacc tttctggata    9420
acaattgctt atatcatttg tatttccaca aagcatttct attggttctt tagtaattac    9480
ctaaagagac gtgtagtctt taatggtgtt tcctttagta cttttgaaga agctgcgctg    9540
tgcacctttt tgttaaataa agaaatgtat ctaaagttgc gtagtgatgt gctattacct    9600
cttacgcaat ataatagata cttagctctt tataataagt acaagtattt tagtggagca    9660
atggatacaa ctagctacag agaagctgct tgttgtcatc tcgcaaaggc tctcaatgac    9720
ttcagtaact caggttctga tgttctttac caaccaccac aaacctctat cacctcagct    9780
gttttgcaga gtggttttag aaaaatggca ttcccatctg gtaaagttga gggttgtatg    9840
gtacaagtaa cttgtggtac aactacactt aacggtcttt ggcttgatga cgtagtttac    9900
tgtccaagac atgtgatctg cacctctgaa gacatgctta accctaatta tgaagattta    9960
ctcattcgta agtctaatca taatttcttg gtacaggctg gtaatgttca actcagggtt    10020
```

```
attggacatt ctatgcaaaa ttgtgtactt aagcttaagg ttgatacagc caatcctaag    10080
acacctaagt ataagtttgt tcgcattcaa ccaggacaga cttttcagt gttagcttgt      10140 tacaatggtt caccatctgg tgtttaccaa tgtgctatga ggcccaattt cactattaag    10200
ggttcattcc ttaatggttc atgtggtagt gttggtttta acatagatta tgactgtgtc    10260 tcttttgtt acatgcacca tatggaatta ccaactggag ttcatgctgg cacagactta     10320
gaaggtaact tttatggacc ttttgttgac aggcaaacag cacaagcagc tggtacggac    10380
acaactatta cagttaatgt tttagcttgg ttgtacgctg ctgttataaa tggagacagg    10440
tggtttctca atcgatttac cacaactctt aatgacttta accttgtggc tatgaagtac    10500
aattatgaac ctctaacaca agaccatgtt gacatactag gacctctttc tgctcaaact    10560
ggaattgccg ttttagatat gtgtgcttca ttaaaagaat tactgcaaaa tggtatgaat    10620
ggacgtacca tattgggtag tgctttatta gaagatgaat ttacaccttt tgatgttgtt    10680
agacaatgct caggtgttac tttccaaagt gcagtgaaaa gaacaatcaa gggtacacac    10740
cactggttgt tactcacaat tttgacttca cttttagttt tagtccagag tactcaatgg    10800
tctttgttct ttttttta tgaaaatgcc ttttaccttt tgctatggg tattattgct       10860 atgtctgctt ttgcaatgat gtttgtcaaa cataagcatg catttctctg tttgtttttg    10920
ttaccttctc ttgccactgt agcttatttt aatatggtct atatgcctgc tagttgggtg    10980
atgcgtatta tgacatggtt ggatatggta atcactagtt tgtctggttt taagctaaaa    11040
gactgtgtta tgtatgcatc agctgtagtg ttactaatcc ttatgacagc aagaactgtg    11100
tatgatgatg gtgctaggag agtgtggaca cttatgaatg tcttgacact cgtttataaa    11160
gtttattatg gtaatgctt agatcaagcc atttccatgt gggctcttat aatctctgtt    11220
acttctaact actcaggtgt agttacaact gtcatgtttt tggccagagg tattgttttt    11280
atgtgtgttg agtattgccc tattttcttc ataactggta atacacttca gtgtataatg    11340
ctagtttatt gtttcttagg ctattttgt acttgttact ttggcctctt tgtttactc      11400 aaccgctact ttagactgac tcttggtgtt tatgattact agtttctac acaggagttt     11460 agatatatga attcacaggg actactccca cccaagaata gcatagatgc cttcaaactc    11520
aacattaaat tgttgggtgt tggtggcaaa ccttgtatca agtagccac tgtacagtct     11580 aaaatgtcag atgtaaagtg cacatcagta gtcttactct cagttttgca acaactcaga   11640
gtagaatcat catctaaatt gtgggctcaa tgtgtccagt tacacaatga cattctctta    11700
gctaaagata ctactgaagc ctttgaaaaa atggtttcac tacttttctgt tttgctttcc   11760 atgcagggtg ctgtagacat aaacaagctt tgtgaagaaa tgctggacaa cagggcaacc   11820
ttacaagcta tagcctcaga gtttagttcc cttccatcat atgcagcttt tgctactgct   11880
caagaagctt atgagcaggc tgttgctaat ggtgattctg aagttgttct taaaaagttg    11940
aagaagtctt tgaatgtggc taaatctgaa tttgaccgtg atgcagccat gcaacgtaag    12000
ttggaaaaga tggctgatca agctatgacc caaatgtata acaggctag atctgaggac     12060 aagagggcaa aagttactag tgctatgcag acaatgcttt tcactatgct tagaaagttg    12120
gataatgatg cactcaacaa cattatcaac aatgcaagag atggttgtgt tcccttgaac    12180 ataataccctc ttacaacagc agccaaacta atggttgtca taccagacta taacacatat   12240
aaaaatacgt gtgatggtac aacattact tatgcatcag cattgtggga aatccaacag     12300
gttgtagatg cagatagtaa aattgttcaa cttagtgaaa ttagtatgga caattcacct    12360
aatttagcat ggcctcttat tgtaacagct ttaagggcca attctgctgt caaattacag    12420
```

```
aataatgagc ttagtcctgt tgcactacga cagatgtctt gtgctgccgg tactacacaa   12480
actgcttgca ctgatgacaa tgcgttagct tactacaaca caacaaaggg aggtaggttt   12540
gtacttgcac tgttatccga tttacaggat ttgaaatggg ctagattccc taagagtgat   12600
ggaactggta ctatctatac agaactggaa ccaccttgta ggtttgttac agacacacct   12660
aaaggtccta aagtgaagta tttatacttt attaaaggat taaacaacct aaatagaggt   12720
atggtacttg gtagtttagc tgccacagta cgtctacaag ctggtaatgc aacagaagtg   12780
cctgccaatt caactgtatt atctttctgt gcttttgctg tagatgctgc taaagcttac   12840
aaagattatc tagctagtgg gggacaacca atcactaatt gcgttaagat gttgtgtaca   12900
cacactggta ctggtcaggc aataacagtt acaccggaag ccaatatgga tcaagaatcc   12960
tttggtggtg catcgtgttg tctgtactgc cgttgccaca tagatcatcc aaatcctaaa   13020
ggattttgtg acttaaaagg taagtatgtg caaatacctaa caacttgtgc taatgaccct   13080
gtgggtttta cacttaaaaa cacagtctgt accgtctgcg gtatgtggaa aggttatggc   13140
tgtagttgtg atcaactccg cgaacccatg cttcagtcag ctgatgcaca atcgttttta   13200
aaccgggttt gcggtgtaag tgcagcccgt cttacaccgt gcggcacagg cactagtact   13260
gatgtcgtat acagggcttt tgacatctac aatgataaag tagctggttt tgctaaattc   13320
ctaaaaacta attgttgtcg cttccaagaa aaggacgaag atgacaattt aattgattct   13380
tactttgtag ttaagagaca cactttctct aactaccaac atgaagaaac aatttataat   13440
ttacttaagg attgtccagc tgttgctaaa catgacttct ttaagtttag aatagacggt   13500
gacatggtac cacatatatc acgtcaacgt cttactaaat acacaatggc agacctcgtc   13560
tatgctttaa ggcattttga tgaaggtaat tgtgacacat aaaagaaat acttgtcaca   13620 tacaattgtt gtgatgatga ttatttcaat aaaaaggact ggtatgattt tgtagaaaac   13680
ccagatatat tacgcgtata cgccaactta ggtgaacgtg tacgccaagc tttgttaaaa   13740
acagtacaat tctgtgatgc catgcgaaat gctggtattg ttggtgtact gacattagat   13800
aatcaagatc tcaatggtaa ccggtatgat ttcggtgatt tcatacaaac cacgccaggt   13860
agtggagttc ctgttgtaga ttcttattat tcattgttaa tgcctatatt aaccttgacc   13920
agggctttaa ctgcagagtc acatgttgac actgacttaa caaagcctta cattaagtgg   13980
gatttgttaa aatatgactt cacggaagag aggttaaaac tctttgaccg ttattttaaa   14040
tattgggatc agacatacca cccaaattgt gttaactgtt tggatgacag atgcattctg   14100
cattgtgcaa actttaatgt tttattctct acagtgttcc cacctacaag ttttggacca   14160
ctagtgagaa aaatatttgt tgatggtgtt ccatttgtag tttcaactgg ataccacttc   14220
agagagctag gtgttgtaca taatcaggat gtaaacttac atagctctag acttagtttt   14280
aaggaattac ttgtgtatgc tgctgaccct gctatgcacg ctgcttctgg taatctatta   14340
ctagataaac gcactacgtg ctttttcagta gctgcactta ctaacaatgt tgcttttcaa   14400
actgtcaaac ccggtagttt taacaaagac ttctatgact ttgctgtgtc taagggtttc   14460
tttaaggaag gaagttctgt tgaattaaaa cacttcttct ttgctcagga tggtaatgct   14520
gctatcagcg attatgacta ctatcgttat aatctaccaa caatgtgtga tatcagacaa   14580
ctactatttg tagttgaagt tgttgataag tactttgatt gttacgatgg tggctgtatt   14640
aatgctaacc aagtcatcgt caacaaccta gacaaatcag ctggttttcc atttaataaa   14700
tggggtaagg ctagacttta ttatgattca atgagttatg aggatcaaga tgcacttttc   14760
```

```
gcatatacaa aacgtaatgt catccctact ataactcaaa tgaatcttaa gtatgccatt    14820
agtgcaaaga atagagctcg caccgtagct ggtgtctcta tctgtagtac tatgaccaat    14880
agacagtttc atcaaaaatt attgaaatca atagccgcca ctagaggagc tactgtagta    14940
attggaacaa gcaaattcta tggtggttgg cacaacatgt taaaaactgt ttatagtgat    15000
gtagaaaacc ctcaccttat gggttgggat tatcctaaat gtgatagagc catgcctaac    15060
atgcttagaa ttatggcctc acttgttctt gctcgaaac atacaacgtg ttgtagcttg     15120
tcacaccgtt tctatagatt agctaatgag tgtgctcaag tattgagtga aatggtcatg    15180
tgtggcggtt cactatatgt taaaccaggt ggaacctcat caggagatgc cacaactgct    15240
tatgctaata gtgttttttaa catttgtcaa gctgtcacgg ccaatgttaa tgcactttta    15300
tctactgatg gtaacaaaat tgccgataag tatgtccgca atttacaaca cagactttat    15360
gagtgtctct atagaaatag agatgttgac acagactttg tgaatgagtt ttacgcatat    15420
ttgcgtaaac atttctcaat gatgatactc tctgacgatg ctgctgtgtg tttcaatagc    15480
acttatgcat ctcaaggtct agtggctagc ataaagaact ttaagtcagt tctttattat    15540
caaaacaatg ttttttatgtc tgaagcaaaa tgttggactg agactgacct tactaaagga    15600
cctcatgaat tttgctctca acatacaatg ctagttaaac agggtgatga ttatgtgtac    15660
cttccttacc cagatccatc aagaatccta ggggccggct gttttgtaga tgatatcgta    15720
aaaacagatg gtacacttat gattgaacgg ttcgtgtctt tagctataga tgcttaccca    15780
cttactaaac atcctaatca ggagtatgct gatgtctttc atttgtactt acaatacata    15840
agaaagctac atgatgagtt aacaggacac atgttagaca tgtattctgt tatgcttact    15900
aatgataaca cttcaaggta ttgggaacct gagtttatg aggctatgta cacaccgcat    15960
acagtcttac aggctgttgg ggcttgtgtt ctttgcaatt cacagacttc attaagatgt    16020
ggtgcttgca tacgtagacc attcttatgt tgtaaatgct gttacgacca tgtcatatca    16080
acatcacata aattagtctt gtctgttaat ccgtatgttt gcaatgctcc aggttgtgat    16140
gtcacagatg tgactcaact ttacttagga ggtatgagct attattgtaa atcacataaa    16200
ccacccatta gttttccatt gtgtgctaat ggacaagttt tggtttata taaaaataca    16260 tgtgttggta gcgataatgt tactgacttt aatgcaattg caacatgtga ctggacaaat    16320
gctggtgatt acatttttagc taacacctgt actgaaagac tcaagctttt tgcagcagaa    16380
acgctcaaag ctactgagga gacatttaaa ctgtcttatg gtattgctac tgtacgtgaa    16440
gtgctgtctg acagagaatt acatctttca tgggaagttg gtaaacctag accaccactt    16500
aaccgaaatt atgtctttac tggttatcgt gtaactaaaa acagtaaagt acaaatagga    16560
gagtacacct ttgaaaaagg tgactatggt gatgctgttg tttaccgagg tacaacaact    16620
tacaaattaa atgttggtga ttattttgtg ctgacatcac atacagtaat gccattaagt    16680
gcacctacac tagtgccaca agagcactat gttagaatta ctggcttata cccaacactc    16740
aatatctcag atgagttttc tagcaatgtt gcaaattatc aaaaggttgg tatgcaaaag    16800
tattctacac tccagggacc acctggtact ggtaagagtc attttgctat tggcctagct    16860
ctctactacc cttctgctcg catagtgtat acagcttgct ctcatgccgc tgttgatgca    16920
ctatgtgaga aggcattaaa atatttgcct atagataaat gtagtagaat tataccctgca   16980 cgtgctcgtg tagagtgttt tgataaattc aaagtgaatt caacattaga acagtatgtc    17040
ttttgtactg taaatgcatt gcctgagacg acagcagata tagttgtctt tgatgaaatt    17100
tcaatggcca caaattatga tttgagtgtt gtcaatgcca gattacgtgc taagcactat    17160
```

```
gtgtacattg gcgaccctgc tcaattacct gcaccacgca cattgctaac taagggcaca   17220
ctagaaccag aatatttcaa ttcagtgtgt agacttatga aaactatagg tccagacatg   17280
ttcctcggaa cttgtcggcg ttgtcctgct gaaattgttg acactgtgag tgctttggtt   17340
tatgataata agcttaaagc acataaagac aaatcagctc aatgctttaa aatgttttat   17400
aagggtgtta tcacgcatga tgtttcatct gcaattaaca ggccacaaat aggcgtggta   17460
agagaattcc ttacacgtaa ccctgcttgg agaaaagctg tctttatctc accttataat   17520
tcacagaatg ctgtagcctc aaaggttttg ggactaccaa ctcaaactgt tgattcatca   17580
cagggctcag aatatgacta tgtcatattc actcaaacca ctgaaacagc tcactcttgt   17640
aatgtaaaca gatttaatgt tgctattacc agagcaaaag taggcatact ttgcataatg   17700
tctgatagag acctttatga caagttgcaa tttacaagtc ttgaaattcc acgtaggaat   17760
gtggcaactt tacaagctga aaatgtaaca ggactcttta agattgtag taaggtaatc   17820 actgggttac atcctacaca ggcacctaca cacctcagtg ttgacactaa attcaaaact   17880
gaaggtttat gtgttgacat acctggcata cctaaggaca tgacctatag aagactcatc   17940
tctatgatgg gttttaaaat gaattatcaa gttaatggtt accctaacat gtttatcacc   18000
cgcgaagaag ctataagaca tgtacgtgca tggattggct tcgatgtcga ggggtgtcat   18060
gctactagag aagctgttgg taccaattta ccttttacagc taggttttc tacaggtgtt   18120 aacctagttg ctgtacctac aggttatgtt gatacaccta ataatacaga ttttttccaga   18180 gttagtgcta aaccaccgcc tggagatcaa tttaaacacc tcataccact tatgtacaaa   18240
ggacttcctt ggaatgtagt gcgtataaag attgtacaaa tgttaagtga cacacttaaa   18300
aatctctctg acagagtcgt atttgtctta tgggcacatg gctttgagct gacatctatg   18360
aagtattttg tgaaaatagg acctgagcgc acctgttgtc tatgtgatag acgtgccaca   18420
tgcttttcca ctgcttcaga cacttatgcc tgttggcatc attctattgg atttgattac   18480
gtctataatc cgtttatgat tgatgttcaa caatgggggtt ttacaggtaa cctacaaagc   18540
aaccatgatc tgtattgtca agtccatggt aatgcacatg tagctagttg tgatgcaatc   18600
atgactaggt gtctagctgt ccacgagtgc tttgttaagc gtgttgactg gactattgaa   18660
tatcctataa ttggtgatga actgaagatt aatgcggctt gtagaaaggt tcaacacatg   18720
gttgttaaag ctgcattatt agcagacaaa ttcccagttc ttcacgacat tggtaaccct   18780
aaagctatta gtgtgtacc tcaagctgat gtagaatgga gttctatga tgcacagcct   18840 tgtagtgaca aagcttataa aatagaagaa ttattctatt cttatgccac acattctgac   18900
aaattcacag atggtgtatg cctattttgg aattgcaatg tcgatagata tcctgctaat   18960
tccattgttt gtagatttga cactagagtg ctatctaacc ttaacttgcc tggttgtgat   19020
ggtggcagtt tgtatgtaaa taaacatgca ttccacacac cagcttttga taaaagtgct   19080
tttgttaatt taaaacaatt accattttc tattactctg acagtccatg tgagtctcat   19140
ggaaaacaag tagtgtcaga tatagattat gtaccactaa agtctgctac gtgtataaca   19200
cgttgcaatt taggtggtgc tgtctgtaga catcatgcta atgagtacag attgtatctc   19260
gatgcttata acatgatgat ctcagctggc tttagcttgt gggttacaa acaatttgat   19320 acttataacc tctggaacac ttttacaaga cttcagagtt tagaaaatgt ggcttttaat   19380
gttgtaaata agggacactt tgatggacaa caggtgaag taccagtttc tatcattaat   19440
aacactgttt acacaaaagt tgatggtgtt gatgtagaat tgtttgaaaaa taaaacaaca   19500
```

```
ttacctgtta atgtagcatt tgagctttgg gctaagcgca acattaaacc agtaccagag    19560
gtgaaaatac tcaataattt gggtgtggac attgctgcta atactgtgat ctgggactac    19620
aaaagagatg ctccagcaca tatatctact attggtgttt gttctatgac tgacatagcc    19680
aagaaaccaa ctgaaacgat tgtgcaccac ctcactgtct tttttgatgg tagagttgat    19740
ggtcaagtag acttatttag aaatgcccgt aatggtgttc ttattacaga aggtagtgtt    19800
aaaggtttac aaccatctgt aggtcccaaa caagctagtc ttaatggagt cacattaatt    19860
ggagaagccg taaaaacaca gttcaattat tataagaaag ttgatggtgt tgtccaacaa    19920
ttacctgaaa cttactttac tcagagtaga aatttacaag aatttaaacc caggagtcaa    19980
atggaaattg atttcttaga attagctatg gatgaattca ttgaacggta taaattagaa    20040
ggctatgcct tcgaacatat cgtttatgga gattttagtc atagtcagtt aggtggttta    20100
catctactga ttggactagc taaacgtttt aaggaatcac ttttgaatt agaagatttt    20160 attcctatgg acagtacagt aaaaactat ttcataacag atgcgcaaac aggttcatct    20220
aagtgtgtgt gttctgttat tgatttatta cttgatgatt ttgttgaaat aataaaatcc    20280
caagatttat ctgtagtttc taaggttgtc aaagtgacta ttgactatac agaaatttca    20340
tttatgcttt ggtgtaaaga tggccatgta gaaacatttt acccaaaatt acaatctagt    20400
caagcgtggc aaccgggtgt tgctatgcct aatctttaca aaatgcaaag aatgctatta    20460
gaaaagtgtg accttcaaaa ttatggtgat agtgcaacat tacctaaagg cataatgatg    20520
aatgtcgcaa atatactca actgtgtcaa tatttaaaca cattaacatt agctgtaccc    20580
tataatatga gagttataca ttttggtgct ggttctgata aggagttgc accaggtaca    20640 gctgttttaa gacagtggtt gcctacgggt acgctgcttg tcgattcaga tcttaatgac    20700
tttgtctctg atgcagattc aactttgatt ggtgattgtg caactgtaca tacagctaat    20760
aaatgggatc tcattattag tgatatgtac gaccctaaga ctaaaaatgt tacaaaagaa    20820
aatgactcta agagggttt tttcacttac atttgtgggt ttatacaaca aaagctagct    20880
cttggaggtt ccgtggctat aaagataaca gaacattctt ggaatgctga tcttataag    20940 ctcatgggac acttcgcatg gtggacagcc tttgttacta atgtgaatgc gtcatcatct    21000
gaagcatttt taattggatg taattatctt ggcaaaccac gcgaacaaat agatggttat    21060
gtcatgcatg caaattacat attttggagg aatacaaatc caattcagtt gtgttctat    21120 tctttatttg acatgagtaa atttccctt aaattaaggg gtactgccgt tatgcctta    21180 aaagaaggtc aaatcaatga tatgatttta tctcttctta gtaaaggtag acttataatt    21240
agagaaaaca acagagttgt tatttctagt gatgttcttg ttaacaacta a             21291
```

<210> SEQ ID NO 2
<211> LENGTH: 13218
<212> TYPE: DNA
<213> ORGANISM: Unknown
<220> FEATURE:
<223> OTHER INFORMATION: SARS-CoV-2 ORF1a polyprotein

<400> SEQUENCE: 2

```
atggagagcc ttgtccctgg tttcaacgag aaaacacacg tccaactcag tttgcctgtt     60
ttacaggttc gcgacgtgct cgtacgtggc tttggagact ccgtggagga ggtcttatca    120
gaggcacgtc aacatcttaa agatggcact tgtggcttag tagaagttga aaaaggcgtt    180
ttgcctcaac ttgaacagcc ctatgtgttc atcaaacgtt cggatgctcg aactgcacct    240
catggtcatg ttatggttga gctggtagca gaactcgaag gcattcagta cggtcgtagt    300
```

```
ggtgagacac ttggtgtcct tgtccctcat gtgggcgaaa taccagtggc ttaccgcaag    360
gttcttcttc gtaagaacgg taataaagga gctggtggcc atagttacgg cgccgatcta    420
aagtcatttg acttaggcga cgagcttggc actgatcctt atgaagattt tcaagaaaac    480
tggaacacta aacatagcag tggtgttacc cgtgaactca tgcgtgagct taacggaggg    540
gcatacactc gctatgtcga taacaacttc tgtggccctg atggctaccc tcttgagtgc    600
attaaagacc ttctagcacg tgctggtaaa gcttcatgca ctttgtccga caactggac     660 tttattgaca ctaagagggg tgtatactgc tgccgtggac atgagcatga aattgcttgg    720
tacacggaac gttctgaaaa gagctatgaa ttgcagacac ttttgaaat taaattggca     780 aagaaatttg acaccttcaa tggggaatgt ccaaattttg tatttcccttt aaattccata   840 atcaagacta ttcaaccaag ggttgaaaag aaaaagcttg atggctttat gggtagaatt    900
cgatctgtct atccagttgc gtcaccaaat gaatgcaacc aaatgtgcct ttcaactctc    960
atgaagtgtg atcattgtgg tgaaacttca tggcagacgg gcgattttgt taaagccact    1020
tgcgaatttt gtggcactga gaatttgact aaagaaggtg ccactacttg tggttactta    1080
ccccaaaatg ctgttgttaa aatttattgt ccagcatgtc acaattcaga agtaggacct    1140
gagcatagtc ttgccgaata ccataatgaa tctggcttga aaccattct tcgtaagggt     1200 ggtcgcacta ttgcctttgg aggctgtgtg ttctctttatg ttggttgcca taacaagtgt    1260
gcctattggg ttccacgtgc tagcgctaac ataggttgta accatacagg tgttgttgga    1320
gaaggttccg aaggtcttaa tgacaacctt cttgaaatac tccaaaaga gaaagtcaac     1380 atcaatattg ttggtgactt taaacttaat gaagagatcg ccattatttt ggcatctttt    1440
tctgcttcca caagtgcttt tgtggaaact gtgaaaggtt tggattataa agcattcaaa    1500
caaattgttg aatcctgtgg taattttaaa gttacaaaag aaaagctaa aaaaggtgcc     1560 tggaatattg gtgaacagaa atcaaatactg agtcctcttt atgcatttgc atcagaggct    1620
gctcgtgttg tacgatcaat tttctcccgc actcttgaaa ctgctcaaaa ttctgtgcgt    1680
gtttacagag aggccgctat aacaatacta gatggaattt cacagtattc actgagactc    1740
attgatgcta tgatgttcac atctgatttg gctactaaca atctagttgt aatggcctac    1800
attacaggtg gtgttgttca gttgacttcg cagtggctaa ctaacatctt tggcactgtt    1860
tatgaaaaac tcaaacccgt ccttgattgg cttgaagaga gtttaagga aggtgtagag    1920 tttcttagag acggttggga aattgttaaa tttatctcaa cctgtgcttg tgaaattgtc    1980
ggtggacaaa ttgtcacctg tgcaaaggaa attaaggaga gtgttcagac attctttaag    2040
cttgtaaata aattttttggc tttgtgtgct gactctatca ttattggtgg agctaaactt    2100
aaagccttga atttaggtga acatttgtc acgcactcaa agggattgta cagaaagtgt    2160
gttaaatcca gagaagaaac tggcctactc atgcctctaa agcccccaaa agaaattatc    2220
ttcttagagg gagaaacact tcccacagaa gtgttaacag aggaagttgt tttgaaaact    2280
ggtgatttac aaccattaga acaacctact agtgaagctg ttgaagctcc attggttggt    2340
acaccagttt gtattaacgg gcttatgttg ctcgaaatca aagacacaga aaagtactgt    2400
gcccttgcac ctaatatgat ggtaacaaac aataccttca cactcaaagg cggtgcacca    2460
acaaaggtta cttttggtga tgacactgtg atagaagtgc aaggttacaa gagtgtgaat    2520
atcacttttg aacttgatga aaggattgat aaagtactta atgagaagtg ctctgcctat    2580
acagttgaac tcggtacaga agtaaatgag ttcgcctgtg ttgtggcaga tgctgtcata    2640
```

```
aaaactttgc aaccagtatc tgaattactt acaccactgg gcattgattt agatgagtgg   2700
agtatggcta catactactt atttgatgag tctggtgagt ttaaattggc ttcacatatg   2760
tattgttctt tctaccctcc agatgaggat gaagaagaag gtgattgtga agaagaagag   2820
tttgagccat caactcaata tgagtatggt actgaagatg attaccaagg taaacctttg   2880
gaatttggtg ccacttctgc tgctcttcaa cctgaagaag agcaagaaga agattggtta   2940
gatgatgata gtcaacaaac tgttggtcaa caagacggca gtgaggacaa tcagacaact   3000
actattcaaa caattgttga ggttcaacct caattagaga tggaacttac accagttgtt   3060
cagactattg aagtgaatag ttttagtggt tatttaaaac ttactgacaa tgtatacatt   3120
aaaaatgcag acattgtgga agaagctaaa aaggtaaaac caacagtggt tgttaatgca   3180
gccaatgttt accttaaaca tggaggaggt gttgcaggag ccttaaataa ggctactaac   3240
aatgccatgc aagttgaatc tgatgattac atagctacta atggaccgct taaagtgggt   3300
ggtagttgtg ttttaagcgg acacaatctt gctaaacact gtcttcatgt tgtcggccca   3360
aatgttaaca aggtgaaga cattcaactt cttaagagtg cttatgaaaa ttttaatcag   3420
cacgaagttc tacttgcacc attattatca gctggtattt tggtgctga ccctatacat   3480 tctttaagag tttgtgtaga tactgttcgc acaaatgtct acttagctgt ctttgataaa   3540
aatctctata caaacttgt ttcaagcttt ttggaaatga agagtgaaaa gcaagttgaa   3600
caaaagatcg ctgagattcc taagaggaa gttaagccat ttataactga aagtaaacct   3660
tcagttgaac agagaaaaca agatgataag aaaatcaaag cttgtgttga agaagttaca   3720
acaactctgg aagaaactaa gttcctcaca gaaaacttgt tactttatat tgacattaat   3780
ggcaatcttc atccagattc tgccactctt gttagtgaca ttgacatcac tttcttaaag   3840
aaagatgctc catacatagt gggtgatgtt gttcaagagg gtgttttaac tgctgtggtt   3900
atacctacta aaaaggctgg tggcactact gaaatgctag cgaaagcttt gagaaagtg   3960 ccaacagaca attatataac cacttacccg ggtcagggtt taaatggtta cactgtagag   4020
gaggcaaaga cagtgcttaa aaagtgtaaa agtgccttt acattctacc atctattatc   4080
tctaatgaga agcaagaaat tcttggaact gtttcttgga atttgcgaga aatgctcgca   4140
catgcagaag aaacacgcaa attaatgcct gtctgtgtgg aaactaaagc catagtttca   4200
actatacagc gtaaatataa gggtattaaa atacaagagg gtgtggttga ttatggtgct   4260 agatttact tttacaccag taaaacaact gtagcgtcac ttatcaacac acttaacgat   4320
ctaaatgaaa ctcttgttac aatgccactt ggctatgtaa cacatggctt aaatttggaa   4380
gaagctgctc ggtatatgag atctctcaaa gtgccagcta cagtttctgt ttcttcacct   4440
gatgctgtta cagcgtataa tggttatctt acttcttctt ctaaaacacc tgaagaacat   4500
tttattgaaa ccatctcact tgctggttcc tataaagatt ggtcctattc tggacaatct   4560
acacaactag gtatagaatt tcttaagaga ggtgataaaa gtgtatatta cactagtaat   4620
cctaccacat tccacctaga tggtgaagtt atcacctttg acaatcttaa gacacttctt   4680
tctttgagag aagtgaggac tattaaggtg tttacaacag tagacaacat taacctccac   4740
acgcaagttc tgggcatgtc aatgacatat ggacaacagt ttggtccaac ttattttgat   4800
ggagctgatg ttactaaaat aaaacctcat aattcacatg aaggtaaaac attttatgtt   4860
ttacctaatg atgacactct acgtgttgag gcttttgagt actaccacac aactgatcct   4920
agttttctgg gtaggtacat gtcagcatta aatcacacta aaaagtggaa atacccacaa   4980
gttaatggtt taacttctat taaatgggca gataacaact gttatcttgc cactgcattg   5040
```

```
ttaacactcc aacaaataga gttgaagttt aatccacctg ctctacaaga tgcttattac   5100
agagcaaggg ctggtgaagc tgctaacttt tgtgcactta tcttagccta ctgtaataag   5160
acagtaggtg agttaggtga tgttagagaa acaatgagtt acttgtttca acatgccaat   5220
ttagattctt gcaaagagt cttgaacgtg tgtgtaaaa cttgtggaca acagcagaca    5280
accctttaagg gtgtagaagc tgttatgtac atgggcacac tttcttatga acaatttaag  5340
aaaggtgttc agataccttg tacgtgtggt aaacaagcta caaatatct agtacaacag    5400
gagtcacctt ttgttatgat gtcagcacca cctgctcagt atgaacttaa gcatggtaca   5460
tttacttgtg ctagtgagta cactggtaat taccagtgtg gtcactataa acatataact   5520
tctaaagaaa ctttgtattg catagacggt gctttactta caaagtcctc agaatacaaa   5580
ggtcctatta cggatgtttt ctacaaagaa aacagttaca caacaaccat aaaaccagtt   5640
acttataaat tggatggtgt tgtttgtaca gaaattgacc ctaagttgga caattattat    5700
aagaaagaca attcttattt cacagagcaa ccaattgatc ttgtaccaaa ccaaccatat   5760
ccaagcgcaa gcttcgataa ttttaagttt gtatgtgata atatcaaatt tgctgatgat   5820
ttaaaccagt taactggtta taagaaacct gcttcaagag agcttaaagt tacattttc    5880
cctgacttaa atggtgatgt ggtggctatt gattataaac actacacacc ctcttttaag   5940
aaaggagcta aattgttaca taaacctatt gtttggcatg ttaacaatgc aactaataaa   6000
gccacgtata aaccaaatac ctggtgtata cgttgtcttt ggagcacaaa accagttgaa   6060
acatcaaatt cgtttgatgt actgaagtca gaggacgcgc agggaatgga taatcttgcc   6120
tgcgaggatc taaaccagt ctctgaagaa gtagtggaaa atcctaccat acagaaagac    6180
gttcttgagt gtaatgtgaa aactaccgaa gttgtaggag acattatact taaaccagcg   6240
aataatagtt taaaattac agaagaggtt ggccacacag atctaatggc tgcttatgta    6300
gacaattcta gtcttactat taagaaacct aatgaattat ctagagtatt aggttttgaaa  6360
acccttgcta ctcatggttt agctgctgtt aatagtgtcc cttgggatac tatagctaat    6420
tatgctaagc tttttcttaa caaagttgtt agtacaacta ctaacatagt tacacggtgt    6480
ttaaaccgtg tttgtactaa ttatatgcct tatttcttta ctttattgct acaattgtgt    6540
acttttacta gaagtacaaa ttctagaatt aaagcatcta tgccgactac tatagcaaag   6600
aatactgtta agagtgtcgg taatttttgt ctagaggctt catttaatta tttgaagtca   6660
cctaattttt ctaaactgat aaatattata atttggttttt tactattaag tgtttgccta   6720
ggttcttaa tctactcaac cgctgcttta ggtgttttaa tgtctaattt aggcatgcct     6780
tcttactgta ctggttacag agaaggctat ttgaactcta ctaatgtcac tattgcaacc   6840
tactgtactg gttctatacc ttgtagtgtt tgtcttagtg gtttagattc tttagacacc    6900
tatccttctt tagaaactat acaaattacc atctcatctt ttaaatggga tttaactgct    6960
tttggcttag ttgcagagtg gtttttggca tatattcttt tcactaggtt tttctatgta   7020
cttggattgg ctgcaatcat gcaattgttt ttcagctatt ttgcagtaca ttttattagt    7080
aattcttggc ttatgtggtt aataattaat cttgcacaaa tggccccgat ttcagctatg   7140
gttagaatgt acatcttctt tgcatcattt tattatgtat ggaaaagtta tgtgcatgtt   7200
gtagacggtt gtaattcatc aacttgtatg atgtgttaca acgtaatag agcaacaaga    7260
gtcgaatgta caactattgt taatggtgtt agaaggtcct tttatgtcta cgctaatgga   7320
ggtaaaggct tttgcaaact acacaattgg aattgtgtta attgtgatac attctgtgct   7380
```

```
ggtagtacat ttattagtga tgaagttgcg agagacttat cactacagtt taaaagacca    7440
ataaatccta ctgaccagtc ttcttacatc gttgatagtg ttacagtgaa gaatggttcc    7500
atccatcttt actttgataa agctggtcaa aagacttatg aaagacattc tctctctcat    7560
tttgttaact tagacaacct gagagctaat aacactaaag gttcattgcc tattaatgtt    7620 atagttttg atggtaaatc aaaatgtgaa gaatcatctg caaaatcagc gtctgtttac      7680
tacagtcagc ttatgtgtca acctatactg ttactagatc aggcattagt gtctgatgtt    7740
ggtgatagtg cggaagttgc agttaaaatg tttgatgctt acgttaatac gttttcatca    7800
acttttaacg taccaatgga aaaactcaaa acactagttg caactgcaga agctgaactt    7860
gcaaagaatg tgtccttaga caatgtctta tctactttta tttcagcagc tcggcaaggg    7920
tttgttgatt cagatgtaga aactaaagat gttgttgaat gtcttaaatt gtcacatcaa    7980
tctgacatag aagttactgg cgatagttgt aataactata tgctcaccta caacaaagtt    8040
gaaaacatga cacccgtga ccttggtgct tgtattgact gtagtgcgcg tcatattaat      8100
gcgcaggtag caaaaagtca caacattgct ttgatatgga acgttaaaga tttcatgtca    8160
ttgtctgaac aaccacgaaa acaaatacgt agtgctgcta aaaagaataa cttaccttt     8220 aagttgacat gtgcaactac tagacaagtt gttaatgctg taacaacaaa gatagcactt    8280
aagggtggta aaattgttaa taattggttg aagcagttaa ttaaagttac acttgtgttc    8340 cttttgttg ctgctatttt ctatttaata cacctgttc atgtcatgtc taaacatact       8400
gacttttcaa gtgaaatcat aggatacaag gctattgatg gtggtgtcac tcgtgacata    8460
gcatctacag atacttgttt tgctaacaaa catgctgatt ttgacacatg gtttagtcag    8520
cgtggtggta gttatactaa tgacaaagct tgcccattga ttgctgcagt cataacaaga    8580 gaagtggggtt ttgtcgtgcc tggtttgcct agcacgatat tacgcacaac taatggtgac   8640 ttttgcatt tcttacctag agttttttagt gcagttggta acatctgtta cacaccatca       8700
aaacttatag agtacactga ctttgcaaca tcagcttgtg ttttggctgc tgaatgtaca    8760 attttaaag atgcttctgg taagccagta ccatattgtt atgataccaa tgtactagaa     8820
ggttctgttg cttatgaaag tttacgcct gacacacgtt atgtgctcat ggatggctct      8880
attattcaat ttcctaacac ctaccttgaa ggtcctgtta gagtggtaac aacttttgat    8940
tctgagtact gtgggcacgg cacttgtgaa agatcagaag ctggtgtttg tgtatctact    9000
agtggtagat gggtacttaa caatgattat tacagatctt taccaggagt tttctgtggt    9060
gtagatgctg taaatttact tactaatatg tttacaccac taattcaacc tattggtgct   9120
ttggacatat cagcatctat agtagctggt ggtattgtag ctatcgtagt aacatgcctt    9180
gcctactatt ttatgaggtt tagaagagct tttggtgaat acagtcatgt agttgccttt    9240
aatactttac tattccttat gtcattcact gtactctgtt taacaccagt ttactcattc    9300
ttacctggtg tttattctgt tatttacttg tacttgacat tttatcttac taatgatgtt    9360 tctttttag cacatattca gtggatggtt atgttcacac ctttagtacc tttctggata    9420
acaattgctt atatcatttg tatttccaca aagcatttct attggttctt tagtaattac    9480
ctaaagagac gtgtagtctt taatggtgtt tcctttagta cttttgaaga agctgcgctg    9540 tgcaccttt tgttaaataa agaaatgtat ctaaagttgc gtagtgatgt gctattacct     9600
cttacgcaat ataatagata cttagctctt tataataagt acaagtattt tagtggagca    9660
atggatacaa ctagctacag agaagctgct tgttgtcatc tcgcaaaggc tctcaatgac    9720
ttcagtaact caggttctga tgttcttac caaccaccac aaacctctat cacctcagct      9780
```

```
gttttgcaga gtggtttag aaaaatggca ttcccatctg gtaaagttga gggttgtatg    9840
gtacaagtaa cttgtggtac aactacactt aacggtcttt ggcttgatga cgtagtttac   9900
tgtccaagac atgtgatctg cacctctgaa gacatgctta accctaatta tgaagattta   9960
ctcattcgta agtctaatca taatttcttg gtacaggctg gtaatgttca actcagggtt  10020
attggacatt ctatgcaaaa ttgtgtactt aagcttaagg ttgatacagc caatcctaag  10080
acacctaagt ataagtttgt tcgcattcaa ccaggacaga cttttcagt gttagccttgt  10140
tacaatggtt caccatctgg tgtttaccaa tgtgctatga ggcccaattt cactattaag  10200
ggttcattcc ttaatggttc atgtggtagt gttggttta acatagatta tgactgtgtc   10260
tcttttgtt acatgcacca tatggaatta ccaactggag ttcatgctgg cacagactta   10320
gaaggtaact tttatggacc ttttgttgac aggcaaacag cacaagcagc tggtacggac  10380
acaactatta cagttaatgt tttagcttgg ttgtacgctg ctgttataaa tggagacagg  10440
tggtttctca atcgatttac cacaactctt aatgactta accttgtggc tatgaagtac  10500
aattatgaac ctctaacaca agaccatgtt gacatactag gacctctttc tgctcaaact  10560
ggaattgccg ttttagatat gtgtgcttca ttaaaagaat tactgcaaaa tggtatgaat  10620
ggacgtacca tattgggtag tgctttatta gaagatgaat ttacaccttt tgatgttgtt  10680
agacaatgct caggtgttac tttccaaagt gcagtgaaaa gaacaatcaa gggtacacac  10740
cactggttgt tactcacaat tttgacttca cttttagttt tagtccagag tactcaatgg  10800
tctttgttct tttttttta tgaaaatgcc tttttacctt ttgctatggg tattattgct  10860
atgtctgctt ttgcaatgat gtttgtcaaa cataagcatg catttctctg tttgtttttg  10920
ttaccttctc ttgccactgt agcttatttt aatatggtct atatgcctgc tagttgggtg  10980
atgcgtatta tgacatggtt ggatatggta atcactagtt tgtctggttt taagctaaaa  11040
gactgtgtta tgtatgcatc agctgtagtg ttactaatcc ttatgacagc aagaactgtg  11100
tatgatgatg gtgctaggag agtgtggaca cttatgaatg tcttgacact cgtttataaa  11160
gtttattatg gtaatgcttt agatcaagcc atttccatgt gggctcttat aatctctgtt  11220
acttctaact actcaggtgt agttacaact gtcatgtttt tggccagagg tattgttttt  11280
atgtgtgttg agtattgccc tatttcttc ataactggta atacacttca gtgtataatg  11340
ctagtttatt gtttcttagg ctattttgt acttgttact ttggcctctt tgtttactc   11400
aaccgctact ttagactgac tcttggtgtt tatgattact agtttctac acaggagttt   11460
agatatatga attcacaggg actactccca cccaagaata gcatagatgc cttcaaactc  11520
aacattaaat tgttgggtgt tggtggcaaa ccttgtatca agtagccac tgtacagtct   11580
aaaatgtcag atgtaaagtg cacatcagta gtccttactct cagttttgca acaactcaga  11640
gtagaatcat catctaaatt gtgggctcaa tgtgtccagt tacacaatga cattctctta  11700
gctaaagata ctactgaagc cttgaaaaa atggtttcac tactttctgt tttgctttcc   11760
atgcagggtg ctgtagacat aaacaagctt tgtgaagaaa tgctggacaa cagggcaacc  11820
ttacaagcta tagcctcaga gtttagttcc cttccatcat atgcagcttt tgctactgct  11880
caagaagctt atgagcaggc tgttgctaat ggtgattctg aagttgttct taaaaagttg  11940
aagaagtctt tgaatgtggc taaatctgaa tttgaccgtg atgcagccat gcaacgtaag  12000
ttggaaaaga tggctgatca agctatgacc caaatgtata acaggctag atctgaggac  12060
aagagggcaa aagttactag tgctatgcag acaatgcttt tcactatgct tagaaagttg  12120
```

```
gataatgatg cactcaacaa cattatcaac aatgcaagag atggttgtgt tcccttgaac   12180
ataatacctc ttacaacagc agccaaacta atggttgtca taccagacta taacacatat   12240
aaaaatacgt gtgatggtac aacatttact tatgcatcag cattgtggga aatccaacag   12300
gttgtagatg cagatagtaa aattgttcaa cttagtgaaa ttagtatgga caattcacct   12360
aatttagcat ggcctcttat tgtaacagct ttaagggcca attctgctgt caaattacag   12420
aataatgagc ttagtcctgt tgcactacga cagatgtctt gtgctgccgg tactacacaa   12480
actgcttgca ctgatgacaa tgcgttagct tactacaaca caacaaaggg aggtaggttt   12540
gtacttgcac tgttatccga tttacaggat ttgaaatggg ctagattccc taagagtgat   12600
ggaactggta ctatctatac agaactggaa ccaccttgta ggtttgttac agacacacct   12660
aaaggtccta agtgaagta tttatacttt attaaaggat taaacaacct aaatagaggt   12720
atggtacttg gtagtttagc tgccacagta cgtctacaag ctggtaatgc aacagaagtg   12780
cctgccaatt caactgtatt atctttctgt gcttttgctg tagatgctgc taaagcttac   12840
aaagattatc tagctagtgg gggacaacca atcactaatt gcgttaagat gttgtgtaca   12900
cacactggta ctggtcaggc aataacagtt acaccggaag ccaatatgga tcaagaatcc   12960
tttggtggtg catcgtgttg tctgtactgc cgttgccaca tagatcatcc aaatcctaaa   13020
ggattttgtg acttaaaagg taagtatgtg caaatacctal caacttgtgc taatgacccl   13080 gtgggtttta cacttaaaaa cacagtctgt accgtctgcg gtatgtggaa aggttatggc   13140
tgtagttgtg atcaactccg cgaacccatg cttcagtcag ctgatgcaca atcgttttta   13200
aacgggtttg cggtgtaa                                                 13218
```

<210> SEQ ID NO 3
<211> LENGTH: 3822
<212> TYPE: DNA
<213> ORGANISM: Unknown
<220> FEATURE:
<223> OTHER INFORMATION: SARS-CoV-2 surface glycoprotein

<400> SEQUENCE: 3

```
atgtttgttt tcttgttttt attgccacta gtctctagtc agtgtgttaa tcttacaacc     60
agaactcaat taccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatctaa tgatggtgtt tattttgctt ccattgggaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa ggttggatgg aaagtgagtt cagagtttat    480
tctagtgcga ataattgcac ttttgaatat gtctctcagc ttttctctat ggaccttgaa    540
ggaaaacagg gtaagttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga atccttcac tgtagaaaaa ggaatctatc aaacttctaa ctttagagtc    960
```

```
caaccaacag aatctattgt tagatttcct aatattacaa acttgtgccc ttttggtgaa    1020
gtttttaacg ccaccagatt tgcatctgtt tatgcttgga acaggaagag aatcagcaac    1080
tgtgttgctg attattctgt cctatataat tccgcatcat tttccacttt aagtgttat     1140 ggagtgtctc ctactaaatt aaatgatctc tgctttacta atgtctatgc agattcattt    1200
gtaattagag gtgatgaagt cagacaaatc gctccagggc aaactggaaa gattgctgat    1260
tataattata aattaccaga tgattttaca ggctgcgtta tagcttggaa ttctaacaat    1320
cttgattcta aggttggtgg taattataat tacctgtata gattgtttag gaagtctaat    1380
ctcaaacctt ttgagagaga tatttcaact gaaatctatc aggccggtag cacaccttgt    1440
aatggtgttg aaggttttaa ttgttacttt cctttacaat catatggttt ccaacccact    1500
aatggtgttg gttaccaacc atacagagta gtagtacttt cttttgaact tctacatgca    1560
ccagcaactg tttgtggacc taaaaagtct actaatttgg ttaaaaacaa atgtgtcaat    1620
ttcaacttca atggtttaac aggcacaggt gttcttactg agtctaacaa aaagtttctg    1680
cctttccaac aatttggcag agacattgct gacactactg atgctgtccg tgatccacag    1740
acacttgaga ttcttgacat taccatgt tcttttggtg gtgtcagtgt tataacacca    1800
ggaacaaata cttctaacca ggttgctgtt ctttatcagg atgttaactg cacagaagtc    1860
cctgttgcta ttcatgcaga tcaacttact cctacttggc gtgtttattc tacaggttct    1920 aatgttttc aaacacgtgc aggctgttta ataggggctg aacatgtcaa caactcatat    1980
gagtgtgaca tacccattgg tgcaggtata tgcgctagtt atcagactca gactaattct    2040
cctcggcggg cacgtagtgt agctagtcaa tccatcattg cctacactat gtcacttggt    2100
gcagaaaatt cagttgctta ctctaataac tctattgcca tacccacaaa ttttactatt    2160
agtgttacca cagaaattct accagtgtct atgaccaaga catcagtaga ttgtacaatg    2220
tacatttgtg gtgattcaac tgaatgcagc aatcttttgt tgcaatatgg cagttttgt     2280 acacaattaa accgtgcttt aactggaata gctgttgaac aagacaaaaa cacccaagaa    2340
gtttttgcac aagtcaaaca aatttacaaa acaccaccaa ttaaagattt tggtggtttt    2400
aatttttcac aaatattacc agatccatca aaaccaagca gaggtcatt tattgaagat    2460 ctacttttca caaagtgac acttgcagat gctggcttca tcaaacaata cggtgattgc    2520
cttggtgata ttgctgctag agacctcatt tgtgcacaaa agtttaacgg ccttactgtt    2580
ttgccacctt tgctcacaga tgaaatgatt gctcaataca cttctgcact gttagcgggt    2640
acaatcactt ctggttggac ctttggtgca ggtgctgcat tacaaatacc atttgctatg    2700
caaatggctt ataggtttaa tggtattgga gttacacaga tgttctcta tgagaaccaa    2760 aaattgatt ccaaccaatt taatagtgct attggcaaaa ttcaagactc actttcttcc    2820
acagcaagtg cacttggaaa acttcaagat gtggtcaacc aaaatgcaca agctttaaac    2880
acgcttgtta acaacttag ctccaatttt ggtgcaattt caagtgtttt aaatgatatc     2940
ctttcacgtc ttgacaaagt tgaggctgaa gtgcaaattg ataggttgat cacaggcaga    3000
ctccaaagtt tgcagacata tgtgactcaa caattaatta gagctgcaga aatcagagct    3060
tctgctaatc ttgctgctac taaaatgtca gagtgtgtac ttgacaatc aaaaagagtt    3120 gatttttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
```

```
cactggttttg taacacaaag gaattttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata atatttttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttt    3660
atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcaaatta cattacacat aa                      3822
```

<210> SEQ ID NO 4
<211> LENGTH: 828
<212> TYPE: DNA
<213> ORGANISM: Unknown
<220> FEATURE:
<223> OTHER INFORMATION: SARS-CoV-2 ORF3a protein

<400> SEQUENCE: 4

```
atggatttgt ttatgagaat cttcacaatt ggaactgtaa ctttgaagca aggtgaaatc     60
aaggatgcta ctccttcaga ttttgttcgc gctactgcaa cgataccgat acaagcctca    120
ctccctttcg gatggcttat tgttggcgtt gcacttcttg ctgtttttca gagcgcttcc    180
aaaatcataa ccctcaaaaa gagatggcaa ctagcactct ccaagggtgt tcactttgtt    240
tgcaacttgc tgttgttgtt tgtaacagtt tactcacacc ttttgctcgt tgctgctggc    300
cttgaagccc cttttctcta tctttatgct ttagtctact tcttgcagag tataaacttt    360
gtaagaataa taatgaggct ttggctttgc tggaaatgcc gttccaaaaa cccattactt    420
tatgatgcca actatttct ttgctggcat actaattgtt acgactattg tataccttac    480
aatagtgtaa cttcttcaat tgtcattact tcaggtgatg gcacaacaag tcctatttct    540
gaacatgact accagattgg tggttatact gaaaaatggg aatctggagt aaaagactgt    600
gttgtattac acagttactt cacttcagac tattaccagc tgtactcaac tcaattgagt    660
acagacactg gtgttgaaca tgttaccttc ttcatctaca ataaaattgt tgatgagcct    720
gaagaacatg tccaaattca cacaatcgac ggttcatccg gagttgttaa tccagtaatg    780
gaaccaattt atgatgaacc gacgacgact actagcgtgc ctttgtaa                 828
```

<210> SEQ ID NO 5
<211> LENGTH: 228
<212> TYPE: DNA
<213> ORGANISM: Unknown
<220> FEATURE:
<223> OTHER INFORMATION: SARS-CoV-2 envelope protein

<400> SEQUENCE: 5

```
atgtactcat tcgtttcgga agagacaggt acgttaatag ttaatagcgt acttctttt      60 cttgctttcg tggtattctt gctagttaca ctagccatcc ttactgcgct tcgattgtgt    120
gcgtactgct gcaatattgt taacgtgagt cttgtaaaac cttcttttta cgtttactct    180
cgtgttaaaa atctgaattc ttctagagtt cctgatcttc tggtctaa                 228
```

<210> SEQ ID NO 6
<211> LENGTH: 669
<212> TYPE: DNA
<213> ORGANISM: Unknown

```
<220> FEATURE:
<223> OTHER INFORMATION: SARS-CoV-2 membrane glycoprotein

<400> SEQUENCE: 6
atggcagatt ccaacggtac tattaccgtt gaagagctta aaaagctcct tgaacaatgg      60
aacctagtaa taggtttcct attccttaca tggatttgtc ttctacaatt tgcctatgcc     120
aacaggaata ggtttttgta tataattaag ttaattttcc tctggctgtt atggccagta     180
actttagctt gttttgtgct tgctgctgtt tacagaataa attggatcac cggtggaatt     240
gctatcgcaa tggcttgtct tgtaggcttg atgtggctca gctacttcat tgcttctttc     300
agactgtttg cgcgtacgcg ttccatgtgg tcattcaatc cagaaactaa cattcttctc     360
aacgtgccac tccatggcac tattctgacc agaccgcttc tagaaagtga actcgtaatc     420
ggagctgtga tccttcgtgg acatcttcgt attgctggac accatctagg acgctgtgac     480
atcaaggacc tgcctaaaga aatcactgtt gctacatcac gaacgctttc ttattacaaa     540
ttgggagctt cgcagcgtgt agcaggtgac tcaggttttg ctgcatacag tcgctacagg     600
attggcaact ataaattaaa cacagaccat tccagtagca gtgacaatat tgctttgctt     660
gtacagtaa                                                             669

<210> SEQ ID NO 7
<211> LENGTH: 186
<212> TYPE: DNA
<213> ORGANISM: Unknown
<220> FEATURE:
<223> OTHER INFORMATION: SARS-CoV-2 ORF6 protein

<400> SEQUENCE: 7
atgtttcatc tcgttgactt tcaggttact atagcagaga tattactaat tattatgagg      60
acttttaaag tttccatttg gaatcttgat tacatcataa acctcataat taaaaattta     120
tctaagtcac taactgagaa taaatattct caattagatg aagagcaacc aatggagatt     180
gattaa                                                                186

<210> SEQ ID NO 8
<211> LENGTH: 366
<212> TYPE: DNA
<213> ORGANISM: Unknown
<220> FEATURE:
<223> OTHER INFORMATION: SARS-CoV-2 ORF7a protein

<400> SEQUENCE: 8
atgaaaatta ttcttttctt ggcactgata acactcgcta cttgtgagct ttatcactac      60
caagagtgtg ttagaggtac aacagtactt ttaaaagaac cttgctcttc tggaacatac     120
gagggcaatt caccatttca ccctctagct gataacaaat ttgcactgac ttgctttagc     180
actcaatttg cttttgctta tcctgacggc gtaaaacacg tctatcagtt acgtgccaga     240
tcagtttcac ctaaactgtt catcagacaa gaggaagttc aagaacttta ctctccaatt     300
tttcttattg ttgcggcaat agtgtttata acactttgct tcacactcaa aagaaagaca     360
gaatga                                                                366

<210> SEQ ID NO 9
<211> LENGTH: 132
<212> TYPE: DNA
<213> ORGANISM: Unknown
<220> FEATURE:
<223> OTHER INFORMATION: SARS-CoV-2 ORF7b protein
```

```
<400> SEQUENCE: 9
atgattgaac tttcattaat tgacttctat ttgtgctttt tagcctttct gctattcctt      60
gttttaatta tgcttattat cttttggttc tcacttgaac tgcaagatca taatgaaact     120
tgtcacgcct aa                                                         132

<210> SEQ ID NO 10
<211> LENGTH: 366
<212> TYPE: DNA
<213> ORGANISM: Unknown
<220> FEATURE:
<223> OTHER INFORMATION: SARS-CoV-2 ORF8 protein

<400> SEQUENCE: 10
atgaaatttc ttgttttctt aggaatcatc acaactgtag ctgcatttca ccagaatgt       60 agcttacagt catgtactca acatcaacca tatgtagttg atgacccgtg tcctattcac    120
ttctattcta atggtatat tagagtagga gctagaaaat cagcaccttt aattgaattg     180
tgcgtggatg aggctggttc taaatcaccc attcagtaca tcgatatcgg taattataca    240
gtttcctgtt cacctttta caattaattgc caggaaccta aattgggtag tcttgtagtg    300
cgttgttcgt tctatgaaga cttttagag tatcatgacg ttcgtgttgt tttagatttc    360
atctaa                                                                366

<210> SEQ ID NO 11
<211> LENGTH: 1260
<212> TYPE: DNA
<213> ORGANISM: Unknown
<220> FEATURE:
<223> OTHER INFORMATION: SARS-CoV-2 nucleocapsid phosphoprotein

<400> SEQUENCE: 11
atgtctgata tggaccccca aaatcagcga atgcacccc gcattacgtt tggtggaccc       60
tcagattcaa ctggcagtaa ccagaatgga gaacgcagtg gggcgcgatc aaaacaacgt    120
cggccccaag gtttacccaa taatactgcg tcttggttca ccgctctcac tcaacatggc    180
aaggaagacc ttaaattccc tcaggacaa ggcgttccaa ttaacaccaa tagcagtcca     240
gacgaccaaa ttggctacta ccgaagagct accagacgaa ttcgtggtgg tgacggtaaa    300
atgaaagatc tcagtccaag atggtatttc tactacctag gaactgggcc agaagctgga    360
cttccctatg gtgctaacaa agacggcatc atatgggttg caactgaggg agccttgaat    420
acaccaaaag atcacattgg cacccgcaat cctgctaaca atgctgcaat cgtgctacaa    480
cttcctcaag gaacaacatt gccaaaaggc ttctacgcag aagggagcag aggcggcagt    540
caagcctctt ctcgttcctc atcacgtagt cgcaacagtt caagaaattc aactccaggc    600
agcagtaggg gaacttctcc tgctagaatg gctggcaatg gcggtgatgc tgctcttgct    660
ttgctgctgc ttgacagatt gaaccagctt gagagcaaaa tgtctggtaa aggccaacaa    720
caacaaggcc aaactgtcac taagaaatct gctgctgagg cttctaagaa gcctcggcaa    780
aaacgtactg ccactaaagc atacaatgta acacaagctt tcggcagacg tggtccagaa    840
caaacccaag gaaattttgg ggaccaggaa ctaatcagac aaggaactga ttacaaacat    900
tggccgcaaa ttgcacaatt tgcccccagc gcttcagcgt tcttcggaat gtcgcgcatt    960
ggcatggaag tcacaccttc gggaacgtgg ttgacctaca caggtgccat caaattggat   1020
gacaaagatc caaatttcaa agatcaagtc attttgctga ataagcatat tgacgcatac   1080
ataacattcc caccaacaga gcctaaaaag gacaaaaaga gaaggctga tgaaactcaa   1140
```

```
gccttaccgc agagacagaa gaaacagcaa actgtgactc ttcttcctgc tgcagatttg    1200
gatgatttct ccaaacaatt gcaacaatcc atgagcagtg ctgactcaac tcaggcctaa    1260

<210> SEQ ID NO 12
<211> LENGTH: 117
<212> TYPE: DNA
<213> ORGANISM: Unknown
<220> FEATURE:
<223> OTHER INFORMATION: SARS-CoV-2 ORF10 protein

<400> SEQUENCE: 12
atgggctata taaacgtttt cgcttttccg tttacgatat atagtctact cttgtgcaga     60
atgaattctc gtaactacat agcacaagta gatgtagtta actttaatct cacatag      117

<210> SEQ ID NO 13
<211> LENGTH: 21282
<212> TYPE: DNA
<213> ORGANISM: Unknown
<220> FEATURE:
<223> OTHER INFORMATION: SARS-CoV-2 ORF1ab polyprotein

<400> SEQUENCE: 13
atggagagcc ttgtccctgg tttcaacgag aaaacacacg tccaactcag tttgcctgtt     60
ttacaggttc gcgacgtgct cgtacgtggc tttggagact ccgtggagga ggtcttatca    120
gaggcacgtc aacatcttaa agatggcact tgtggcttag tagaagttga aaaaggcgtt    180
ttgcctcaac ttgaacagcc ctatgtgttc atcaaacgtt cggatgctcg aactgcacct    240
catgtggttg agctggtagc agaactcgaa ggcattcagt acggtcgtag tggtgagaca    300
cttggtgtcc ttgtccctca tgtgggcgaa ataccagtgg cttaccgcaa ggttcttctt    360
cgtaagaacg gtaataaagg agctggtggc catagttacg gcgccgatct aaagtcattt    420
gacttaggcg acgagcttgg cactgatcct tatgaagatt tcaagaaaa ctggaacact    480 aaacatagca gtggtgttac ccgtgaactc atgcgtgagc ttaacggagg ggcatacact    540
cgctatgtcg ataacaactt ctgtggcccc gatggctacc ctcttgagtg cattaaagac    600
cttctagcac gtgctggtaa agcttcatgc actttgtccg aacaactgga ctttattgac    660
actaagaggg gtgtatactg ctgccgtgaa catgagcatg aaattgcttg gtacacggaa    720
cgttctgaaa agagctatga attgcagaca ccttttgaaa ttaaattggc aaagaaattt    780
gacaccttca tgggaatg tccaaatttt gtatttcct taaattccat aatcaagact    840
attcaaccaa gggttgaaaa gaaaagctt gatggcttta tgggtagaat tcgatctgtc    900
tatccagttg cgtcaccaaa tgaatgcaac caaatgtgcc tttcaactct catgaagtgt    960
gatcattgtg gtgaaacttc atggcagacg ggcgattttg ttaaagccac ttgcgaattt   1020
tgtggcactg agaatttgac taaagaaggt gccactactt gtggttactt accccaaaat   1080
gctgttgtta aaatttattg tccagcatgt cacaattcag aagtaggacc tgagcatagt   1140
cttgccgaat accataatga atctggcttg aaaaccattc ttcgtaaggg tggtcgcact   1200
attgcctttg gaggctgtgt gttctcttat gttggttgcc ataacaagtg tgcctattgg   1260
gttccacgtg ctagcgctaa cataggttgt aaccatacag gtgttgttgg agaaggttcc   1320
gaaggtctta atgacaacct tcttgaaata ctccaaaaag agaaagtcaa catcaatatt   1380
gttggtgact ttaaacttaa tgaagagatc gccattattt ggcatcttt ttctgcttcc   1440 acaagtgctt ttgtggaaac tgtgaaaggt ttggattata agcattcaa acaaattgtt   1500
```

```
gaatcctgtg gtaattttaa agttacaaaa ggaaaagcta aaaaggtgc ctggaatatt    1560 ggtgaacaga aatcaatact gagtcctctt tatgcatttg catcagaggc tgctcgtgtt    1620
gtacgatcaa ttttctcccg cactcttgaa actgctcaaa attctgtgcg tgttttacag    1680
aaggccgcta taacaatact agatggaatt tcacagtatt cactgagact cattgatgct    1740
atgatgttca catctgattt ggctactaac aatctagttg taatggccta cattacaggt    1800
ggtgttgttc agttgacttc gcagtggcta actaacatct ttggcactgt ttatgaaaaa    1860
ctcaaacccg tccttgattg gcttgaagag aagtttaagg aaggtgtaga gtttcttaga    1920
gacggttggg aaattgttaa atttatctca acctgtgctt gtgaaattgt cggtggacaa    1980
attgtcacct gtgcaaagga aattaaggag agtgttcaga cattctttaa gcttgtaaat    2040
aaattttggg ctttgtgtgc tgactctatc attattggtg gagctaaaact taaagccttg    2100 aatttaggtg aaacatttgt cacgcactca aagggattgt acagaaagtg tgttaaatcc    2160
agagaagaaa ctggcctact catgcctcta aaagccccaa aagaaattat cttcttagag    2220
ggagaaacac ttcccacaga agtgttaaca gaggaagttg tcttgaaaac tggtgattta    2280
caaccattag aacaacctac tagtgaagct gttgaagctc cattggttgg tacaccagtt    2340
tgtattaacg gcttatgtt gctcgaaatc aaagacacag aaaagtactg tgcccttgca    2400
cctaatatga tggtaacaaa caataccttc acactcaaag gcggtgcacc aacaaaggtt    2460
acttttggtg atgacactgt gatagaagtg caaggttaca agagtgtgaa tatcactttt    2520
gaacttgatg aaaggattga taaagtactt aatgagaagt gctctgccta tacagttgaa    2580
ctcggtacag aagtaaatga gttcgcctgt gttgtggcag atgctgtcat aaaaactttg    2640
caaccagtat ctgaattact tacaccactg gcattgatt tagatgagtg gagtatggct    2700
acatactact tatttgatga gtctggtgag tttaaattgg cttcacatat gtattgttct    2760 ttctacccctc cagatgagga tgaagaagaa ggtgattgtg aagaagaaga gtttgagcca    2820
tcaactcaat atgagtatgg tactgaagat gattaccaag gtaaacctt ggaatttggt    2880 gccacttctg ctgctcttca acctgaagaa gagcaagaag aagattggtt agatgatgat    2940
agtcaacaaa ctgttggtca acaagacggc agtgaggaca tcagacaac tactattcaa    3000 acaattgttg aggttcaacc tcaattagag atggaactta caccagttgt tcagactatt    3060
gaagtgaata gttttagtgg ttatttaaaa cttactgaca atgtatacat taaaaatgca    3120
gacattgtgg aagaagctaa aaaggtaaaa ccaacagtgg ttgttaatgc agccaatgtt    3180
taccttaaac atggaggagg tgttgcagga gccttaaata aggctactaa caatgccatg    3240
caagttgaat ctgatgatta catagctact aatggaccac ttaaagtggg tggtagttgt    3300
gttttaagcg gacacaatct tgctaaacac tgtcttcatg ttgtcggccc aaatgttaac    3360
aaaggtgaag acattcaact tcttaagagt gcttatgaaa atttaatca gcacgaagtt    3420 ctacttgcac cattattatc agctggtatt tttggtgctg accctataca ttctttaaga    3480
gtttgtgtag atactgttcg cacaaatgtc tacttagctg tctttgataa aaatctctat    3540
gacaaacttg tttcaagctt tttggaaatg aagagtgaaa agcaagttga caaaagatc    3600 gctgagattc ctaaagagga agttaagcca tttataactg aaagtaaacc ttcagttgaa    3660
cagagaaaac aagatgataa gaaaatcaaa gcttgtgttg aagaagttac aacaactctg    3720
gaagaaacta gttcctcac agaaaacttg ttactttata ttgacattaa tggcaatctt    3780
catccagatt ctgccactct tgttagtgac attgacatca cttctcttaaa gaaagatgct    3840 ccatatatag tgggtgatgt tgttcaagag ggtgtttaa ctgctgtggt tataccact    3900
```

```
aaaaaggctg gtggcactac tgaaatgcta gcgaaagctt tgagaaaagt gccaacagac   3960
aattatataa ccacttaccc gggtcagggt ttaaatggtt acactgtaga ggaggcaaag   4020
acagtgctta aaaagtgtaa aagtgccttt tacattctac catctattat ctctaatgag   4080
aagcaagaaa ttcttggaac tgtttcttgg aatttgcgag aaatgctcgc acatgcagaa   4140
gaaacacgca aattaatgcc tgtctgtgtg gaaactaaag ccatagtttc aactatacag   4200
cgtaaatata agggtattaa aatacaagag ggtgtggttg attatggtgc tagattttac   4260
ttttacacca gtaaaacaac tgtagcgtca cttatcaaca cacttaacga tctaaatgaa   4320
actcttgtta caatgccact tggctatgta acacatggct taaatttgga agaagctgct   4380
cggtatatga gatctctcaa agtgccagct acagtttctg tttcttcacc tgatgctgtt   4440
acagcgtata atggttatct tacttcttct tctaaaacac ctgaagaaca ttttattgaa   4500
accatctcac ttgctggttc ctataaagat tggtcctatt ctggacaatc tacacaacta   4560
ggtatagaat tcttaagag aggtgataaa agtgtatatt acactagtaa tcctaccaca   4620
ttccacctag atggtgaagt tatcacccttt gacaatctta agacacttct ttctttgaga   4680
gaagtgagga ctattaaggt gtttacaaca gtagacaaca ttaacctcca cacgcaagtt   4740
gtggacatgt caatgacata tggacaacag tttggtccaa cttattttga tggagctgat   4800
gttactaaaa taaaacctca taattcacat gaaggtaaaa catttatgt tttacctaat   4860 gatgacactc tacgtgttga ggcttttgag tactaccaca caactgatcc tagttttctg   4920
ggtaggtaca tgtcagcatt aaatcacact aaaaagtgga atacccaca agttaatggt   4980 ttaacttcta ttaaatgggc agataacaac tgttatcttg ccactgcatt gttaacactc   5040
caacaaatag agttgaagtt taatccacct gctctacaag atgcttatta cagagcaagg   5100
gctggtgaag ctgctaactt ttgtgcactt atcttagcct actgtaataa gacagtaggt   5160
gagttaggtg atgttagaga aacaatgagt tacttgtttc aacatgccaa tttagattct   5220
tgcaaaagag tcttgaacgt ggtgtgtaaa acttgtggac aacagcagac aaccctaag   5280 ggtgtagaag ctgttatgta catgggcaca ctttcttatg aacaatttaa gaaaggtgtt   5340 cagataccctt gtacgtgtgg taaacaagct acaaatatc tagtacaaca ggagtcacct   5400
tttgttatga tgtcagcacc acctgctcag tatgaactta agcatggtac atttacttgt   5460
gctagtgagt acactggtaa ttaccagtgt ggtcactata acatataac ttctaaagaa   5520 actttgtatt gcatagacgg tgctttactt acaaagtcct cagaatacaa aggtcctatt   5580
acggatgttt tctacaaaga aaacagttac acaacaacca taaaaccagt tacttataaa   5640
ttggatggtg ttgtttgtac agaaattgac cctaagttgg acaattatta taagaaagac   5700
aattcttatt tcacagagca accaattgat cttgtaccaa ccaaccata tccaaacgca   5760 agcttcgata atttttaagtt tgtatgtgat aatatcaaat ttgctgatga tttaaaccag   5820
ttaactggtt ataagaaacc tgcttcaaga gagcttaaag ttcatttttt ccctgactta   5880
aatggtgatg tggtggctat tgattataaa cactacacac cctcttttaa gaaaggagct   5940
aaattgttac ataaacctat tgtttggcat gttaacaatg caactaataa agccacgtat   6000
aaaccaaata cctggtgtat acgttgtctt tggagcacaa aaccagttga aacatcaaat   6060
tcgtttgatg tactgaagtc agaggacgcg cagggaatgg ataatcttgc ctgcgaagat   6120
ctaaaaccag tctctgaaga agtagtggaa aatcctacca tacagaaaga cgttcttgag   6180
tgtaatgtga aaactaccga agttgtagga gacattatac ttaaaccagc aaataatagt   6240
```

```
ttaaaaatta cagaagaggt tggccacaca gatctaatgg ctgcttatgt agacaattct    6300
agtcttacta ttaagaaacc taatgaatta tctagagtat taggtttgaa aacccttgct    6360
actcatggtt tagctgctgt taatagtgtc ccttgggata ctatagctaa ttatgctaag    6420
ccttttctta acaaagttgt tagtacaact actaacatag ttacacggtg tttaaaccgt    6480
gtttgtacta attatatgcc ttatttcttt actttattgc tacaattgtg tacttttact    6540
agaagtacaa attctagaat taaagcatct atgccgacta ctatagcaaa gaatactgtt    6600
aagagtgtcg gtaaattttg tctagaggct tcatttaatt atttgaagtc acctaatttt    6660
tctaaactga taaatattat aatttggttt ttactattaa gtgtttgcct aggttcttta    6720
atctactcaa ccgctgcttt aggtgtttta atgtctaatt taggcatgcc ttcttactgt    6780
actggttaca gagaaggcta tttgaactct actaatgtca ctattgcaac ctactgtact    6840
ggttctatac cttgtagtgt ttgtcttagt ggtttagatt ctttagacac ctatccttct    6900
ttagaaacta tacaaattac catttcatct tttaaatggg atttaactgc ttttggctta    6960
gttgcagagt ggtttttggc atatattctt ttcactaggt ttttctatgt acttggattg    7020
gctgcaatca tgcaattgtt tttcagctat tttgcagtac attttattag taattcttgg    7080
cttatgtggt taataattaa tcttgtacaa atggccccga tttcagctat ggttagaatg    7140
tacatcttct ttgcatcatt ttattatgta tggaaaagtt atgtgcatgt tgtagacggt    7200
tgtaattcat caacttgtat gatgtgttac aaacgtaata gagcaacaag agtcgaatgt    7260
acaactattg ttaatggtgt tagaaggtcc ttttatgtct atgctaatgg aggtaaaggc    7320
ttttgcaaac tacacaattg gaattgtgtt aattgtgata cattctgtgc tggtagtaca    7380
tttattagtg atgaagttgc gagagacttg tcactacagt ttaaaagacc aataaatcct    7440
actgaccagt cttcttacat cgttgatagt gttacagtga agaatggttc catccatctt    7500
tactttgata agctggtca aaagacttat gaaagacatt ctctctctca ttttgttaac    7560
ttagacaacc tgagagctaa taacactaaa ggttcattgc ctattaatgt tatagttttt    7620
gatggtaaat caaaatgtga agaatcatct gcaaaatcag cgtctgttta ctacagtcag    7680
cttatgtgtc aacctatact gttactagat caggcattag tgtctgatgt tggtgatagt    7740
gcggaagttg cagttaaaat gtttgatgct tacgttaata cgttttcatc aactttaac    7800 gtaccaatgg aaaaactcaa aacactagtt gcaactgcag aagctgaact tgcaaagaat    7860
gtgtccttag acaatgtctt atctactttt atttcagcag ctcggcaagg gtttgttgat    7920
tcagatgtag aaactaaaga tgttgttgaa tgtcttaaat tgtcacatca atctgacata    7980
gaagttactg gcgatagttg taataactat atgctcacct ataacaaagt tgaaaacatg    8040
acaccccgtg accttggtgc ttgtattgac tgtagtgcgc gtcatattaa tgcgcaggta    8100
gcaaaaagtc acaacattgc tttgatatgg aacgttaaag atttcatgtc attgtctgaa    8160
caactacgaa acaaatacg tagtgctgct aaaaagaata acttacctt taagttgaca    8220 tgtgcaacta ctagacaagt tgttaatgtt gtaacaacaa agatagcact taagggtggt    8280
aaaattgtta ataattggtt gaagcagtta attaaagtta cacttgtgtt cctttttgtt    8340
gctgctattt tctatttaat aacacctgtt catgtcatgt ctaaacatac tgactttca    8400 agtgaaatca taggatacaa ggctattgat ggtggtgtca ctcgtgacat agcatctaca    8460
gatacttgtt ttgctaacaa acatgctgat tttgacacat ggtttagtca gcgtggtggt    8520
agttatacta atgacaaagc ttgcccattg attgctgcag tcataacaag agaagtgggt    8580
tttgtcgtgc ctggtttgcc tggcacgata ttacgcacaa ctaatggtga cttttttgcat    8640
```

```
ttcttaccta gagtttttag tgcagttggt aacatctgtt acacaccatc aaaacttata    8700
gagtacactg actttgcaac atcagcttgt gttttggctg ctgaatgtac aattttaaa     8760
gatgcttctg gtaagccagt accatattgt tatgatacca atgtactaga aggttctgtt    8820
gcttatgaaa gtttacgccc tgacacacgt tatgtgctca tggatggctc tattattcaa    8880
tttcctaaca cctaccttga aggttctgtt agagtggtaa caacttttga ttctgagtac    8940
tgtaggcacg gcacttgtga agatcagaa gctggtgttt gtgtatctac tagtggtaga     9000
tgggtactta acaatgatta ttacagatct ttaccaggag ttttctgtgg tgtagatgct    9060
gtaaatttac ttactaatat gtttacacca ctaattcaac ctattggtgc tttggacata    9120
tcagcatcta gtagctgg tggtattgta gctatcgtag taacatgcct tgcctactat      9180
tttatgaggt ttagaagagc ttttggtgaa tacagtcatg tagttgcctt taatactttta   9240
ctattcctta tgtcattcac tgtactctgt ttaacaccag tttactcatt cttacctggt    9300
gtttattctg ttatttactt gtacttgaca ttttatctta ctaatgatgt ttcttttta     9360
gcacatattc agtggatggt tatgttcaca cctttagtac ctttctggat aacaattgct    9420
tatatcattt gtatttccac aaagcatttc tattggttct ttagtaatta cctaaagaga    9480
cgtgtagtct ttaatggtgt ttcctttagt acttttgaag aagctgcgct gtgcacctt     9540
ttgttaaata aagaaatgta tctaaagttg cgtagtgatg tgctattacc tcttacgcaa    9600
tataatagat acttagctct ttataataag tacaagtatt ttagtggagc aatggataca    9660
actagctaca gagaagctgc ttgttgtcat ctcgcaaagg ctctcaatga cttcagtaac    9720
tcaggttctg atgttcttta ccaaccacca caaacctcta tcacctcagc tgttttgcag    9780
agtggtttta gaaaaatggc attcccatct ggtaaagttg agggttgtat ggtacaagta    9840
acttgtggta caactacact taacggtctt tggcttgatg acgtagttta ctgtccaaga    9900
catgtgatct gcacctctga agacatgctt aaccctaatt atgaagattt actcattcgt    9960
aagtctaatc ataatttctt ggtacaggct ggtaatgttc aactcagggt tattggacat    10020
tctatgcaaa attgtgtact taagcttaag gttgatacag ccaatcctaa gacacctaag    10080
tataagtttg ttcgcattca accaggacag acttttttcag tgttagcttg ttacaatggt   10140
tcaccatctg gtgtttacca atgtgctatg aggcccaatt tcactattaa gggttcattc    10200
cttaatggtt catgtggtag tgttggtttt aacatagatt atgactgtgt ctcttttgt     10260
tacatgcacc atatggaatt accaactgga gttcatgctg gcacagactt agaaggtaac    10320
ttttatggac cttttgttga caggcaaaca gcacaagcag ctggtacgga cacaactatt    10380
acagttaatg ttttagcttg gttgtacgct gctgttataa atggagacag gtggtttctc    10440
aatcgattta ccacaactct taatgacttt aaccttgtgg ctatgaagta caattatgaa    10500
cctctaacac aagaccatgt tgacatacta ggacctcttt ctgctcaaac tggaattgcc    10560
gttttagata tgtgtgcttc attaaaagaa ttactgcaaa atggtatgaa tggacgtacc    10620
atattgggta gtgctttatt agaagatgaa tttacacctt ttgatgttgt tagacaatgc    10680
tcaggtgtta ctttccaaag tgcagtgaaa agaacaatca agggtacaca ccactggttg   10740
ttactcacaa ttttgacttc acttttagtt ttagtccaga gtactcaatg gtctttgttc    10800
tttttttttgt atgaaaaagc ttttttacct tttgctatgg ggattattgc tatgtctgct    10860
tttgcaatga tgtttgtcaa acataagcat gcatttctct gtttgttttt gttaccttct    10920
cttgccactg tagcttattt taatatggtc tatatgcctg ctagttgggt gatgcgtatt    10980
```

```
atgacatggt tggatatggt aatcactagt ttgtctggtt ttaagctaaa agactgtgtt   11040
atgtatgcat cagctgtagt gttactaatc cttatgacag caagaactgt gtatgatgat   11100
ggtgctagga gagtgtggac acttatgaat gtcttgacac tcgtttataa agtttattat   11160
ggtaatgctt tagatcaagc catttccatg tgggctctta taatctctgt tacttctaac   11220
tactcaggtg tagttacaac tgtcatgttt ttggccagag gtattgtttt tatgtgtgtt   11280
gagtattgcc ctattttctt cataactggt aatacacttc agtgtataat gctagtttat   11340
tgtttcttag gctattttg tacttgttac tttggcctct tttgtttact caaccgctac   11400
tttagactga ctcttggtgt ttatgattac ttagtttcta cacaggagtt tagatatatg   11460
aattcacagg gactactccc acccaagaat agcatagatg ccttcaaact caacattaaa   11520
ttgttgggtg ttggtggcaa accttgtatc aaagtagcca ctgtacagtc taaaatgtca   11580
gatgtaaagt gcacatcagt agtcttactc tcagttttgc aacaactcag agtagaatca   11640
tcatctaaat tgtgggctca atgtgtccag ttacacaatg acattctctt agctaaagat   11700
actactgaag cctttgaaaa aatggtttca ctactttctg ttttgctttc catgcagggt   11760
gctgtagcca taaacaagct ttgtgaagaa atgctggaca acagggcaac cttacaagct   11820
atagcctcag agtttagttc ccttccatca tatgcagctt ttgctactgc tcaagaagct   11880
tatgagcagg ctgttgctaa tggtgattct gaagttgttc ttaaaaagtt gaagaagtct   11940
ttgaatgtgg ctaaatctga atttgaccgt gatgcagcca tgcaacgtaa gttggaaaag   12000
atggctgatc aagctatgac ccaaatgtat aaacaggcta gatctgagga caagagggca   12060
aaagttacta gtgctatgca gacaatgctt ttcactatgc ttagaaagtt ggataatgat   12120
gcactcaaca acattatcaa caatgcaaga gatggttgtg ttcccttgaa cataatacct   12180
cttacaacag cagccaaact aatggttgtc ataccagact ataacacata taaaaatacg   12240
tgtgatggta caacatttac ttatgcatca gcattgtggg aaatccaaca ggttgtagat   12300
gcagatagta aaattgttca acttagtgaa attagtatgg acaattcacc taatttagca   12360
tggcctctta ttgtaacagc tttaagggcc aattctgctg tcaaattaca gaataatgag   12420
cttagtcctg ttgcactacg acagatgtct tgtgctgccg gtactacaca aactgcttgc   12480
actgatgaca atgcgttagc ttactacaac acaacaaagg gaggtaggtt tgtacttgca   12540
ctgttatccg atttacagga tttgaaatgg ctagattcc ctaagagtga tggaactggt   12600
actatctata cagaactgga accaccttgt aggtttgtta cagacacacc taaaggtcct   12660
aaagtgaagt atttatactt tattaaagga ttaaacaacc taaatagagg tatggtactt   12720
ggtagtttag ctgccacagt acgtctacaa gctggtaatg caacagaagt gcctgccaat   12780
tcaactgtat tatctttctg tgcttttgct gtagatgctg ctaaagctta caaagattat   12840
ctagctagtg ggggacaacc aatcactaat tgtgttaaga tgttgtgtac acacactggt   12900
actggtcagg caataacagt tacaccggaa gccaatatgg atcaagaatc ctttggtggt   12960
gcatcgtgtt gtctgtactg ccgttgccac atagatcatc caaatcctaa aggatttgt   13020 gacttaaaag gtaagtatgt acaaatacct acaacttgtg ctaatgaccc tgtgggtttt   13080
acacttaaaa acacagtctg taccgtctgc ggtatgtgga aaggttatgg ctgtagttgt   13140
gatcaactcc gcgaacccat gcttcagtca gctgatgcac aatcgttttt aaaccgggtt   13200
tgcggtgtaa gtgcagcccg tcttacaccg tgcggcacag gcactagtac tgatgtcgta   13260
tacagggctt ttgacatcta caatgataaa gtagctggtt ttgctaaatt cctaaaaact   13320
aattgttgtc gcttccaaga aaaggacgaa gatgacaatt taattgattc ttactttgta   13380
```

```
gttaagagac acactttctc taactaccaa catgaagaaa caatttataa tttacttaag   13440
gattgtccag ctgttgctaa acatgacttc tttaagttta gaatagacgg tgacatggta   13500
ccacatatat cacgtcaacg tcttactaaa tacacaatgg cagacctcgt ctatgcttta   13560
aggcattttg atgaaggtaa ttgtgacaca ttaaaagaaa tacttgtcac atacaattgt   13620
tgtgatgatg attatttcaa taaaaaggac tggtatgatt ttgtagaaaa cccagatata   13680
ttacgcgtat acgccaactt aggtgaacgt gtacgccaag ctttgttaaa aacagtacaa   13740
ttctgtgatg ccatgcgaaa tgctggtatt gttggtgtac tgacattaga taatcaagat   13800
ctcaatggta actggtatga tttcggtgat ttcatacaaa ccacgccagg tagtggagtt   13860
cctgttgtag attcttatta ttcattgtta atgcctatat taaccttgac cagggcttta   13920
actgcagagt cacatgttga cactgactta acaaagcctt acattaagtg ggatttgtta   13980
aaatatgact tcacggaaga gaggttaaaa ctctttgacc gttattttaa atattgggat   14040
cagacatacc acccaaattg tgttaactgt ttggatgaca gatgcattct gcattgtgca   14100
aactttaatg ttttattctc tacagtgttc ccacctacaa gttttggacc actagtgaga   14160
aaaatatttg ttgatggtgt tccatttgta gtttcaactg gataccactt cagagagcta   14220
ggtgttgtac ataatcagga tgtaaactta catagctcta gacttagttt taaggaatta   14280
cttgtgtatg ctgctgaccc tgctatgcac gctgcttctg gtaatctatt actagataaa   14340
cgcactacgt gcttttcagt agctgcactt actaacaatg ttgcttttca aactgtcaaa   14400
cccggtaatt ttaacaaaga cttctatgac tttgctgtgt ctaagggttt ctttaaggaa   14460
ggaagttctg ttgaattaaa acacttcttc tttgctcagg atggtaatgc tgctatcagc   14520
gattatgact actatcgtta taatctacca acaatgtgtg atatcagaca actactattt   14580
gtagttgaag ttgttgataa gtactttgat tgttacgatg gtggctgtat taatgctaac   14640
caagtcatcg tcaacaacct agacaaatca gctggttttc catttaataa atggggtaag   14700
gctagacttt attatgattc aatgagttat gaggatcaag atgcactttt cgcatataca   14760
aaacgtaatg tcatccctac tataactcaa atgaatctta gtatgccat tagtgcaaag   14820 aatagagctc gcaccgtagc tggtgtctct atctgtagta ctatgaccaa tagacagttt   14880
catcaaaaat tattgaaatc aatagccgcc actagaggag ctactgtagt aattggaaca   14940
agcaaattct atggtggttg gcacaacatg ttaaaaactg tttatagtga tgtagaaaac   15000 cctcaccta tggggtggga ttatcctaaa tgtgatagag ccatgcctaa catgcttaga   15060
attatggcct cacttgttct tgctcgcaaa catacaacgt gttgtagctt gtcacaccgt   15120
ttctatagat tagctaatga gtgtgctcaa gtattgagtg aaatggtcat gtgtggcggt   15180
tcactatatg ttaaaccagg tggaacctca tcaggagatg ccacaactgc ttatgctaat   15240
agtgttttta acatttgtca agctgtcacg gccaatgtta atgcactttt atctactgat   15300
ggtaacaaaa ttgccgataa gtatgtccgc aatttacaac acagacttta tgagtgtctc   15360
tatagaaata gagatgttga cacagacttt gtgaatgagt tttacgcata tttgcgtaaa   15420
catttctcaa tgatgatact ctctgacgat gctgttgtgt gtttcaatag cacttatgca   15480
tctcaaggtc tagtggctag cataaagaac tttaagtcag ttctttatta tcaaaacaat   15540 gttttttatgt ctgaagcaaa atgttggact gagactgacc ttactaaagg acctcatgaa   15600
ttttgctctc aacatacaat gctagttaaa caggtgatg attatgtgta ccttccttac   15660
ccagatccat caagaatcct aggggccggc tgttttgtag atgatatcgt aaaaacagat   15720
```

```
ggtacactta tgattgaacg gttcgtgtct ttagctatag atgcttaccc acttactaaa   15780
catcctaatc aggagtatgc tgatgtcttt catttgtact tacaatacat aagaaagcta   15840
catgatgagt taacaggaca catgttagac atgtattctg ttatgcttac taatgataac   15900
acttcaaggt attgggaacc tgagttttat gaggctatgt acacaccgca tacagtctta   15960
caggctgttg gggcttgtgt tctttgcaat tcacagactt cattaagatg tggtgcttgc   16020
atacgtagac cattcttatg ttgtaaatgc tgttacgacc atgtcatatc aacatcacat   16080
aaattagtct tgtctgttaa tccgtatgtt tgcaatgctc caggttgtga tgtcacagat   16140
gtgactcaac tttacttagg aggtatgagc tattattgta aatcacataa accacccatt   16200
agttttccat tgtgtgctaa tggacaagtt tttggtttat ataaaaatac atgtgttggt   16260
agcgataatg ttactgactt taatgcaatt gcaacatgtg actggacaaa tgctggtgat   16320
tacattttag ctaacacctg tactgaaaga ctcaagcttt ttgcagcaga aacgctcaaa   16380
gctactgagg agacatttaa actgtcttat ggtattgcta ctgtacgtga agtgctgtct   16440
gacagagaat tacatctttc atgggaagtt ggtaaaccta gaccaccact taaccgaaat   16500 tatgtctttta ctggttatcg tgtaactaaa aacagtaaag tacaaatagg agagtacacc   16560
tttgaaaaag gtgactatgg tgatgctgtt gtttaccgag gtacaacaac ttacaaatta   16620
aatgttggtg attattttgt gctgacatca catacagtaa tgccattaag tgcacctaca   16680
ctagtgccac aagagcacta tgttagaatt actggcttat acccaacact caatatctca   16740
gatgagtttt ctagcaatgt tgcaaattat caaaaggttg gtatgcaaaa gtattctaca   16800
ttccagggac cacctggtac tggtaagagt cattttgcta ttggcctagc tctctactac   16860
ccttctgctc gcatagtgta tacagcttgc tctcatgccg ctgttgatgc actatgtgag   16920
aaggcattaa aatatttgcc tatagataaa tgtagtagaa ttatacctgc acgtgctcgt   16980
gtagagtgtt ttgataaatt caaagtgaat tcaacattag aacagtatgt cttttgtact   17040
gtaaatgcat tgcctgagac gacagcagat atagttgtct ttgatgaaat ttcaatggcc   17100
acaaattatg atttgagtgt tgtcaatgcc agattacgtg ctaagcacta tgtgtacatt   17160
ggcgaccctg ctcaattacc tgcaccacgc acattgctaa ctaagggcac actagaacca   17220
gaatatttca attcagtgtg tagacttatg aaaactatag gtccagacat gttcctcgga   17280
acttgtcggc gttgtcctgc tgaaattgtt gacactgtga gtgctttggt ttatgataat   17340
aagcttaaag cacataaaga caaatcagct caatgcttta aaatgttta taagggtgtt   17400 atcacgcatg atgtttcatc tgcaattaac aggccacaaa taggcgtggt aagagaattc   17460
cttacacgta accctgcttg gagaaaagct gtctttattt caccttataa ttcacagaat   17520
gctgtagcct caaagatttt gggactacca actcaaactg ttgattcatc acagggctca   17580
gaatatgact atgtcatatt cactcaaacc actgaaacag ctcactcttg taatgtaaac   17640
agatttaatg ttgctattac cagagcaaaa gtaggcatac tttgcataat gtctgataga   17700
gacctttatg acaagttgca atttacaagt cttgaaattc cacgtaggaa tgtggcaact   17760
ttacaagctg aaaatgtaac aggactcttt aaagattgta gtaaggtaat cactgggtta   17820
catcctacac aggcacctac acacctcagt gttgacacta aattcaaaac tgaaggttta   17880
tgtgttgaca tacctggcat acctaaggac atgacctata aagactcat ctctatgatg   17940 ggtttttaaaa tgaattatca agttaatggt taccctaaca tgtttatcac ccgcgaagaa   18000
gctataagac atgtacgtgc atggattggc ttcgatgtcg aggggtgtca tgctactaga   18060
gaagctgttg gtaccaattt acctttacag ctaggttttt ctacaggtgt taacctagtt   18120
```

```
gctgtaccta caggttatgt tgatacacct aataatacag attttccag agttagtgct    18180
aaaccaccgc ctggagatca atttaaacac ctcataccac ttatgtacaa aggacttcct    18240
tggaatgtag tgcgtataaa gattgtacaa atgttaagtg acacacttaa aaatctctct    18300
gacagagtcg tatttgtctt atgggcacat ggctttgagt tgacatctat gaagtatttt    18360
gtgaaaatag gacctgagcg cacctgttgt ctatgtgata gacgtgccac atgcttttcc    18420
actgcttcag acacttatgc ctgttggcat cattctattg gatttgatta cgtctataat    18480
ccgtttatga ttgatgttca acaatggggt tttacaggta acctacaaag caaccatgat    18540
ctgtattgtc aagtccatgg taatgcacat gtagctagtt gtgatgcaat catgactagg    18600
tgtctagctg tccacgagtg ctttgttaag cgtgttgact ggactattga atatcctata    18660
attggtgatg aactgaagat taatgcggct tgtagaaagg ttcaacacat ggttgttaaa    18720
gctgcattat tagcagacaa attcccagtt cttcacgaca ttggtaaccc taaagctatt    18780
aagtgtgtac ctcaagctga tgtagaatgg aagttctatg atgcacagcc ttgtagtgac    18840
aaagcttata aaatagaaga attattctat tcttatgcca cacattctga caaattcaca    18900
gatggtgtat gcctattttg gaattgcaat gtcgatagat atcctgctaa ttccattgtt    18960
tgtagatttg acactagagt gctatctaac cttaacttgc ctggttgtga tggtggcagt    19020
ttgtatgtaa ataaacatgc attccacaca ccagcttttg ataaaagtgc ttttgttaat    19080
ttaaaacaat taccattttt ctattactct gacagtccat gtgagtctca tggaaaacaa    19140
gtagtgtcag atatagatta tgtaccacta aagtctgcta cgtgtataac acgttgcaat    19200
ttaggtggtg ctgtctgtag acatcatgct aatgagtaca gattgtatct cgatgcttat    19260
aacatgatga tctcagctgg ctttagcttg tgggtttaca acaatttga tacttataac    19320
ctctggaaca cttttacaag acttcagagt ttagaaaatg tggcttttaa tgttgtaaat    19380
aagggacact tgatggaca acagggtgaa gtaccagttt ctatcattaa taacactgtt    19440
tacacaaaag ttgatggtgt tgatgtagaa ttgtttgaaa ataaacaac attaccggtt    19500
aatgtagcat ttgagctttg ggctaagcgc aacattaaac cagtaccaga ggtgaaaata    19560
ctcaataatt tgggtgtgga cattgctgct aatactgtga tctgggacta caaaagagat    19620
gctccagcac atatatctac tattggtgtt tgttctatga ctgacatagc caagaaacca    19680
actgaaacga tttgtgcacc actcactgtc ttttttgatg gtagagttga tggtcaagta    19740
gacttattta aaatgcccg taatggtgtt cttattacag aaggtagtgt taaaggttta    19800
caaccatctg taggtcccaa acaagctagt cttaatggag tcacattaat tggagaagcc    19860
gtaaaaacac agttcaatta ttataagaaa gttgatggtg ttgtccaaca attacctgaa    19920
acttacttta ctcagagtag aaatttacaa gaatttaaac ccaggagtca aatggaaatt    19980
gatttcttag aattagctat ggatgaattc attgaacggt ataaattaga aggctatgcc    20040
ttcgaacata tcgtttatgg agattttagt catagtcagt taggtggttt acatctactg    20100
attggactag ctaaacgttt taaggaatca ccttttgaat tagaagattt tattcctatg    20160
gacagtacag ttaaaaacta ttcataaca gatgcgcaaa caggttcatc taagtgtgtg    20220
tgttctgtta ttgatttatt acttgatgat tttgttgaaa aataaaatc ccaagattta    20280
tctgtagttt ctaaggttgt caaagtgact attgactata cagaaatttc atttatgctt    20340
tggtgtaaag atgccatgt agaaacattt tacccaaaat tacaatcag tcaagcgtgg    20400
caaccgggtg ttgctatgcc taatcttac aaaatgcaaa gaatgctatt agaaaagtgt    20460
```

| | | | | |
|---|---|---|---|---|
| gaccttcaaa | attatggtga | tagtgcaaca | ttacctaaag | gcataatgat gaatgtcgca 20520 |
| aaatatactc | aactgtgtca | atatttaaac | acattaacat | tagctgtacc ctataatatg 20580 |
| agagttatac | attttggtgc | tggttctgat | aaaggagttg | caccaggtac agctgtttta 20640 |
| agacagtggt | tgcctacggg | tacgctgctt | gtcgattcag | atcttaatga ctttgtctct 20700 |
| gatgcagatt | caactttgat | tggtgattgt | gcaactgtac | atacagctaa taaatgggat 20760 |
| ctcattatta | gtgatatgta | cgaccctaag | actaaaaatg | ttacaaaaga aaatgactct 20820 |
| aaagagggtt | ttttcactta | catttgtggg | tttatacaac | aaaagctagc tcttggaggt 20880 |
| tccgtggcta | taaagataac | agaacattct | tggaatgctg | atctttataa gctcatggga 20940 |
| cacttcgcat | ggtggacagc | ctttgttact | aatgtgaatg | cgtcatcatc tgaagcattt 21000 |
| ttaattggat | gtaattatct | tggcaaacca | cgcgaacaaa | tagatggtta tgtcatgcat 21060 |
| gcaaattaca | tattttggag | aatacaaat | ccaattcagt | tgtcttccta ttctttattt 21120 |
| gacatgagta | aatttcccct | taaattaagg | ggtactgctg | ttatgtcttt aaaagaaggt 21180 |
| caaatcaatg | atatgatttt | atctcttctt | agtaaaggta | gacttataat tagagaaaac 21240 |
| aacagagttg | ttatttctag | tgatgttctt | gttaacaact | aa 21282 |

<210> SEQ ID NO 14
<211> LENGTH: 13209
<212> TYPE: DNA
<213> ORGANISM: Unknown
<220> FEATURE:
<223> OTHER INFORMATION: SARS-CoV-2 ORF1a polyprotein

<400> SEQUENCE: 14

| | | | | |
|---|---|---|---|---|
| atggagagcc | ttgtccctgg | tttcaacgag | aaaacacacg | tccaactcag tttgcctgtt 60 |
| ttacaggttc | gcgacgtgct | cgtacgtggc | tttggagact | ccgtggagga ggtcttatca 120 |
| gaggcacgtc | aacatcttaa | agatggcact | tgtggcttag | tagaagttga aaaaggcgtt 180 |
| ttgcctcaac | ttgaacagcc | ctatgtgttc | atcaaacgtt | cggatgctcg aactgcacct 240 |
| catgtggttg | agctggtagc | agaactcgaa | ggcattcagt | acggtcgtag tggtgagaca 300 |
| cttggtgtcc | ttgtccctca | tgtgggcgaa | ataccagtgg | cttaccgcaa ggttcttctt 360 |
| cgtaagaacg | gtaataaagg | agctggtggc | catagttacg | gcgccgatct aaagtcattt 420 |
| gacttaggcg | acgagcttgg | cactgatcct | tatgaagatt | tcaagaaaaa ctggaacact 480 |
| aaacatagca | gtggtgttac | ccgtgaactc | atgcgtgagc | ttaacggagg ggcatacact 540 |
| cgctatgtcg | ataacaactt | ctgtggccct | gatggctacc | ctcttgagtg cattaaagac 600 |
| cttctagcac | gtgctggtaa | agcttcatgc | actttgtccg | aacaactgga ctttattgac 660 |
| actaagaggg | gtgtatactg | ctgccgtgaa | catgagcatg | aaattgcttg gtacacggaa 720 |
| cgttctgaaa | agagctatga | attgcagaca | ccttttgaaa | ttaaattggc aaagaaattt 780 |
| gacaccttca | tggggaatg | tccaaatttt | gtatttcct | aaattccat aatcaagact 840 |
| attcaaccaa | gggttgaaaa | agaaaagctt | gatggcttta | tgggtagaat tcgatctgtc 900 |
| tatccagttg | cgtcaccaaa | tgaatgcaac | caaatgtgcc | tttcaactct catgaagtgt 960 |
| gatcattgtg | gtgaaacttc | atggcagacg | ggcgattttg | ttaaagccac ttgcgaattt 1020 |
| tgtggcactg | agaatttgac | taaagaaggt | gccactactt | gtggttactt accccaaaat 1080 |
| gctgttgtta | aaatttattg | tccagcatgt | cacaattcag | aagtaggacc tgagcatagt 1140 |
| cttgccgaat | accataatga | atctggcttg | aaaaccattc | ttcgtaaggg tggtcgcact 1200 |
| attgcctttg | gaggctgtgt | gttctcttat | gttggttgcc | ataacaagtg tgcctattgg 1260 |

```
gttccacgtg ctagcgctaa cataggttgt aaccatacag gtgttgttgg agaaggttcc    1320
gaaggtctta atgacaacct tcttgaaata ctccaaaaag agaaagtcaa catcaatatt    1380
gttggtgact ttaaacttaa tgaagagatc gccattattt tggcatcttt ttctgcttcc    1440
acaagtgctt ttgtggaaac tgtgaaaggt ttggattata aagcattcaa acaaattgtt    1500
gaatcctgtg gtaattttaa agttacaaaa ggaaaagcta aaaaggtgc ctggaatatt    1560 ggtgaacaga atcaatact gagtcctctt tatgcatttg catcagaggc tgctcgtgtt    1620
gtacgatcaa ttttctcccg cactcttgaa actgctcaaa attctgtgcg tgttttacag    1680
aaggccgcta taacaatact agatggaatt tcacagtatt cactgagact cattgatgct    1740
atgatgttca catctgattt ggctactaac aatctagttg taatggccta cattacaggt    1800
ggtgttgttc agttgacttc gcagtggcta actaacatct ttggcactgt ttatgaaaaa    1860
ctcaaacccg tccttgattg gcttgaagag aagtttaagg aaggtgtaga gtttcttaga    1920
gacggttggg aaattgttaa atttatctca acctgtgctt gtgaaattgt cggtggacaa    1980
attgtcacct gtgcaaagga aattaaggag agtgttcaga cattctttaa gcttgtaaat    2040 aaattttttgg ctttgtgtgc tgactctatc attattggtg gagctaaaact taaagccttg    2100 aatttaggtg aaacatttgt cacgcactca aagggattgt acagaaagtg tgttaaatcc    2160
agagaagaaa ctggcctact catgcctcta aaagccccaa aagaaattat cttcttagag    2220
ggagaaacac ttcccacaga agtgttaaca gaggaagttg tcttgaaaac tggtgattta    2280
caaccattag aacaacctac tagtgaagct gttgaagctc cattggttgg tacaccagtt    2340
tgtattaacg ggcttatgtt gctcgaaatc aaagacacag aaaagtactg tgcccttgca    2400
cctaatatga tggtaacaaa caataccttc acactcaaag gcggtgcacc aacaaaggtt    2460 actttttggtg atgacactgt gatagaagtg caaggttaca agagtgtgaa tatcacttttt    2520 gaacttgatg aaaggattga taaagtactt aatgagaagt gctctgccta tacagttgaa    2580
ctcggtacag aagtaaatga gttcgcctgt gttgtggcag atgctgtcat aaaaactttg    2640
caaccagtat ctgaattact tacaccactg ggcattgatt tagatgagtg gagtatggct    2700
acatactact tatttgatga gtctggtgag tttaaattgg cttcacatat gtattgttct    2760
ttctaccctc cagatgagga tgaagaagaa ggtgattgtg aagaagaag gtttgagcca    2820 tcaactcaat atgagtatgg tactgaagat gattaccaag gtaaacccctt ggaatttggt    2880 gccacttctg ctgctcttca acctgaagaa gagcaagaag aagattggtt agatgatgat    2940
agtcaacaaa ctgttggtca acaagacggc agtgaggaca atcagacaac tactattcaa    3000
acaattgttg aggttcaacc tcaattagag atggaactta caccagttgt tcagactatt    3060
gaagtgaata gttttagtgg ttatttaaaa cttactgaca atgtatacat taaaaatgca    3120
gacattgtgg aagaagctaa aaaggtaaaa ccaacagtgg ttgttaatgc agccaatgtt    3180
taccttaaac atggaggagg tgttgcagga gccttaaata aggctactaa caatgccatg    3240
caagttgaat ctgatgatta catagctact aatggaccac ttaaagtggg tggtagttgt    3300
gttttaagcg gacacaatct tgctaaacac tgtcttcatg ttgtcggccc aaatgttaac    3360
aaaggtgaag acattcaact tcttaagagt gcttatgaaa attttaatca gcacgaagtt    3420
ctacttgcac cattattatc agctggtatt tttggtgctg accctataca ttctttaaga    3480
gtttgtgtag atactgttcg cacaaatgtc tacttagctg tctttgataa aaatctctat    3540
gacaaacttg tttcaagctt tttggaaatg aagagtgaaa agcaagttga acaaaagatc    3600
```

```
gctgagattc ctaaagagga agttaagcca tttataactg aaagtaaacc ttcagttgaa    3660
cagagaaaac aagatgataa gaaaatcaaa gcttgtgttg aagaagttac aacaactctg    3720
gaagaaacta agttcctcac agaaaacttg ttactttata ttgacattaa tggcaatctt    3780
catccagatt ctgccactct tgttagtgac attgacatca cttctcttaaa gaaagatgct   3840 ccatatatag tgggtgatgt tgttcaagag ggtgttttaa ctgctgtggt tatacctact    3900
aaaaaggctg gtggcactac tgaaatgcta gcgaaagctt tgagaaaagt gccaacagac    3960
aattatataa ccacttaccc gggtcagggt ttaaatggtt acactgtaga ggaggcaaag    4020
acagtgctta aaaagtgtaa aagtgccttt tacattctac catctattat ctctaatgag    4080
aagcaagaaa ttcttggaac tgtttcttgg aatttgcgag aaatgctcgc acatgcagaa    4140
gaaacacgca aattaatgcc tgtctgtgtg gaaactaaag ccatagtttc aactatacag    4200
cgtaaatata agggtattaa aatacaagag ggtgtggttg attatggtgc tagattttac    4260
ttttacacca gtaaaacaac tgtagcgtca cttatcaaca cacttaacga tctaaatgaa    4320
actcttgtta caatgccact tggctatgta acacatggct taaatttgga agaagctgct    4380
cggtatatga gatctctcaa agtgccagct acagtttctg tttcttcacc tgatgctgtt    4440
acagcgtata atggttatct tacttcttct tctaaaacac ctgaagaaca ttttattgaa    4500
accatctcac ttgctggttc ctataaagat tggtcctatt ctggacaatc tacacaacta    4560
ggtatagaat tcttaagag aggtgataaa agtgtatatt acactagtaa tcctaccaca    4620
ttccacctag atggtgaagt tatcacccttt gacaatctta agacacttct ttctttgaga    4680
gaagtgagga ctattaaggt gtttacaaca gtagacaaca ttaacctcca cacgcaagtt    4740
gtggacatgt caatgacata tggacaacag tttggtccaa cttatttga tggagctgat    4800 gttactaaaa taaaacctca taattcacat gaaggtaaaa cattttatgt tttacctaat    4860
gatgacactc tacgtgttga ggcttttgag tactaccaca caactgatcc tagttttctg    4920
ggtaggtaca tgtcagcatt aaatcacact aaaaagtgga aatacccaca agttaatggt    4980
ttaacttcta ttaaatgggc agataacaac tgttatcttg ccactgcatt gttaacactc    5040
caacaaatag agttgaagtt taatccacct gctctacaag atgcttatta cagagcaagg    5100
gctggtgaag ctgctaactt ttgtgcactt atcttagcct actgtaataa gacagtaggt    5160
gagttaggtg atgttagaga aacaatgagt tacttgtttc aacatgccaa tttagattct    5220
tgcaaaagag tcttgaacgt ggtgtgtaaa acttgtggac aacagcagac aaccccttaag    5280 ggtgtagaag ctgttatgta catgggcaca cttttcttatg aacaatttaa gaaaggtgtt    5340
cagataccct tgtacgtgtgg taaacaagct acaaaatatc tagtacaaca ggagtcacct    5400
tttgttatga tgtcagcacc acctgctcag tatgaactta agcatggtac atttacttgt    5460
gctagtgagt acactggtaa ttaccagtgt ggtcactata acatataac ttctaaagaa    5520 actttgtatt gcatagacgg tgctttactt acaaagtcct cagaatacaa aggtcctatt    5580
acggatgttt tctacaaaga aaacagttac acaacaacca taaaccagt tacttataaa    5640 ttggatggtg ttgtttgtac agaaattgac cctaagttgg acaattatta taagaaagac    5700
aattcttatt tcacagagca accaattgat cttgtaccaa ccaaccata tccaaacgca    5760 agcttcgata attttaagtt tgtatgtgat aatatcaaat ttgctgatga tttaaaccag    5820
ttaactggtt ataagaaacc tgcttcaaga gagcttaaag ttacattttt ccctgactta    5880
aatggtgatg tggtggctat tgattataaa cactacacac cctctcttaa gaaaggagct    5940
aaattgttac ataaacctat tgtttggcat gttaacaatg caactaataa agccacgtat    6000
```

```
aaaccaaata cctggtgtat acgttgtctt tggagcacaa aaccagttga aacatcaaat    6060
tcgtttgatg tactgaagtc agaggacgcg cagggaatgg ataatcttgc ctgcgaagat    6120
ctaaaaccag tctctgaaga agtagtggaa aatcctacca tacagaaaga cgttcttgag    6180
tgtaatgtga aaactaccga agttgtagga gacattatac ttaaaccagc aaataatagt    6240
ttaaaaatta cagaagaggt tggccacaca gatctaatgg ctgcttatgt agacaattct    6300
agtcttacta ttaagaaacc taatgaatta tctagagtat taggtttgaa acccttgct    6360 actcatggtt tagctgctgt taatagtgtc ccttgggata ctatagctaa ttatgctaag    6420
ccttttctta acaaagttgt tagtacaact actaacatag ttacacggtg tttaaaccgt    6480
gtttgtacta attatatgcc ttatttcttt actttattgc tacaattgtg tacttttact    6540
agaagtacaa attctagaat taaagcatct atgccgacta ctatagcaaa gaatactgtt    6600
aagagtgtcg gtaaattttg tctagaggct tcatttaatt atttgaagtc acctaatttt    6660
tctaaactga taaatattat aatttggttt ttactattaa gtgtttgcct aggttcttta    6720
atctactcaa ccgctgcttt aggtgtttta atgtctaatt taggcatgcc ttcttactgt    6780
actggttaca gagaaggcta tttgaactct actaatgtca ctattgcaac ctactgtact    6840
ggttctatac cttgtagtgt ttgtcttagt ggtttagatt cttagacac ctatccttct    6900 ttagaaacta tacaaattac catttcatct ttaaatgggg atttaactgc ttttggctta    6960
gttgcagagt ggttttggc atatattctt ttcactaggt ttttctatgt acttggattg    7020
gctgcaatca tgcaattgtt tttcagctat tttgcagtac attttattag taattcttgg    7080
cttatgtggt aataattaa tcttgtacaa atggccccga tttcagctat ggttagaatg    7140
tacatcttct ttgcatcatt ttattatgta tggaaaagtt atgtgcatgt tgtagacggt    7200
tgtaattcat caacttgtat gatgtgttac aaacgtaata gagcaacaag agtcgaatgt    7260
acaactattg ttaatggtgt tagaaggtcc ttttatgtct atgctaatgg aggtaaaggc    7320
ttttgcaaac tacacaattg gaattgtgtt aattgtgata cattctgtgc tggtagtaca    7380
tttattagtg atgaagttgc gagagacttg tcactacagt ttaaaagacc aataaatcct    7440
actgaccagt cttcttacat cgttgatagt gttacagtga agaatggttc catccatctt    7500
tactttgata agctggtca aaagacttat gaaagacatt ctctctctca ttttgttaac    7560
ttagacaacc tgagagctaa taacactaaa ggttcattgc ctattaatgt tatagttttt    7620
gatggtaaat caaaatgtga agaatcatct gcaaaatcag cgtctgttta ctacagtcag    7680
cttatgtgtc aacctatact gttactagat caggcattag tgtctgatgt tggtgatagt    7740
gcggaagttg cagttaaaat gtttgatgct tacgttaata cgttttcatc aacttttaac    7800
gtaccaatgg aaaaactcaa aacactagtt gcaactgcag aagctgaact tgcaaagaat    7860
gtgtccttag acaatgtctt atctactttt atttcagcag ctcggcaagg gtttgttgat    7920
tcagatgtag aaactaaaga tgttgttgaa tgtcttaaat tgtcacatca atctgacata    7980
gaagttactg gcgatagttg taataactat atgctcacct ataacaaagt tgaaaacatg    8040 acacccccgtg accttggtgc ttgtattgac tgtagtgcgc gtcatattaa tgcgcaggta    8100
gcaaaaagtc acaacattgc tttgatatgg aacgttaaag atttcatgtc attgtctgaa    8160
caactacgaa aacaaatacg tagtgctgct aaaaagaata acttacccttt taagttgaca    8220 tgtgcaacta ctagacaagt tgttaatgtt gtaacaacaa agatagcact taagggtggt    8280
aaaattgtta ataattggtt gaagcagtta attaaagtta cacttgtgtt cctttttgtt    8340
```

```
gctgctattt tctatttaat aacacctgtt catgtcatgt ctaaacatac tgactttcca   8400
agtgaaatca taggatacaa ggctattgat ggtggtgtca ctcgtgacat agcatctaca   8460
gatacttgtt ttgctaacaa acatgctgat tttgacacat ggtttagtca gcgtggtggt   8520
agttatacta atgacaaagc ttgcccattg attgctgcag tcataacaag agaagtgggt   8580
tttgtcgtgc ctggtttgcc tggcacgata ttacgcacaa ctaatggtga cttttttgcat  8640 ttcttaccta gagttttag tgcagttggt aacatctgtt acacaccatc aaaacttata   8700
gagtacactg actttgcaac atcagcttgt gttttggctg ctgaatgtac aattttaaa   8760 gatgcttctg gtaagccagt accatattgt tatgatacca atgtactaga aggttctgtt   8820
gcttatgaaa gtttacgccc tgacacacgt tatgtgctca tggatggctc tattattcaa   8880
tttcctaaca cctaccttga aggttctgtt agagtggtaa caactttga ttctgagtac    8940 tgtaggcacg gcacttgtga agatcagaa gctggtgttt gtgtatctac tagtggtaga   9000
tgggtactta acaatgatta ttacagatct ttaccaggag ttttctgtgg tgtagatgct   9060
gtaaatttac ttactaatat gtttacacca ctaattcaac ctattggtgc tttggacata   9120
tcagcatcta tagtagctgg tggtattgta gctatcgtag taacatgcct tgcctactat   9180
tttatgaggt ttagaagagc ttttggtgaa tacagtcatg tagttgcctt taatacttta   9240
ctattcctta tgtcattcac tgtactctgt ttaacaccag tttactcatt cttacctggt   9300
gtttattctg ttatttactt gtacttgaca ttttatctta ctaatgatgt ttcttttta   9360 gcacatattc agtggatggt tatgttcaca ccctttagtac ctttctggat aacaattgct   9420
tatatcattt gtatttccac aaagcatttc tattggttct ttagtaatta cctaaagaga   9480
cgtgtagtct ttaatggtgt ttccttagt acttttgaag aagctgcgct gtgcaccttt   9540
ttgttaaata agaaatgta tctaaagttg cgtagtgatg tgctattacc tcttacgcaa   9600
tataatagat acttagctct ttataataag tacaagtatt ttagtggagc aatggataca   9660
actagctaca gagaagctgc ttgttgtcat ctcgcaaagg ctctcaatga cttcagtaac   9720
tcaggttctg atgttctta ccaaccacca caaacctcta tcacctcagc tgttttgcag   9780 agtggttta gaaaaatggc attcccatct ggtaaagttg agggttgtat ggtacaagta   9840
acttgtggta caactacact taacggtctt tggcttgatg acgtagttta ctgtccaaga   9900
catgtgatct gcacctctga agacatgctt aaccctaatt atgaagattt actcattcgt   9960
aagtctaatc ataattctt ggtacaggct ggtaatgttc aactcagggt tattggacat  10020
tctatgcaaa attgtgtact taagcttaag gttgatacag ccaatcctaa gacacctaag  10080
tataagtttg ttcgcattca accaggacag acttttttcag tgttagcttg ttacaatggt  10140
tcaccatctg gtgtttacca atgtgctatg aggcccaatt tcactattaa gggttcattc  10200
cttaatggtt catgtggtag tgttggtttt aacatagatt atgactgtgt ctctttttgt  10260
tacatgcacc atatggaatt accaactgga gttcatgctg gcacagactt agaaggtaac  10320
ttttatggac cttttgttga caggcaaaca gcacaagcag ctggtacgga cacaactatt  10380
acagttaatg ttttagcttg gttgtacgct gctgttataa atggagacag tggttttctc  10440
aatcgattta ccacaactct taatgacttt aaccttgtgg ctatgaagta caattatgaa  10500
cctctaacac aagaccatgt tgacatacta ggacctcttt ctgctcaaac tggaattgcc  10560
gttttagata tgtgtgcttc attaaaagaa ttactgcaaa atggtatgaa tggacgtacc  10620
atattgggta gtgctttatt agaagatgaa tttacacctt ttgatgttgt tagacaatgc  10680
tcaggtgtta cttccaaag tgcagtgaaa agaacaatca agggtacaca ccactggttg  10740
```

```
ttactcacaa ttttgacttc acttttagtt ttagtccaga gtactcaatg gtctttgttc    10800 tttttttttgt atgaaaaagc cttttttacct tttgctatgg ggattattgc tatgtctgct   10860
tttgcaatga tgtttgtcaa acataagcat gcatttctct gtttgttttt gttaccttct    10920
cttgccactg tagcttattt taatatggtc tatatgcctg ctagttgggt gatgcgtatt    10980
atgacatggt tggatatggt aatcactagt ttgtctggtt ttaagctaaa agactgtgtt    11040
atgtatgcat cagctgtagt gttactaatc cttatgacag caagaactgt gtatgatgat    11100
ggtgctagga gagtgtggac acttatgaat gtcttgacac tcgtttataa agtttattat    11160
ggtaatgctt tagatcaagc catttccatg tgggctctta taatctctgt tacttctaac    11220
tactcaggtg tagttacaac tgtcatgttt ttggccagag gtattgtttt tatgtgtgtt    11280
gagtattgcc ctattttctt cataactggt aatacacttc agtgtataat gctagtttat    11340
tgtttcttag gctattttg tacttgttac tttggcctct tttgtttact caaccgctac    11400
tttagactga ctcttggtgt ttatgattac ttagtttcta cacaggagtt tagatatatg    11460
aattcacagg gactactccc acccaagaat agcatagatg ccttcaaact caacattaaa    11520
ttgttgggtg ttggtggcaa accttgtatc aaagtagcca ctgtacagtc taaaatgtca    11580
gatgtaaagt gcacatcagt agtcttactc tcagttttgc aacaactcag agtagaatca    11640
tcatctaaat tgtgggctca atgtgtccag ttacacaatg acattctctt agctaaagat    11700
actactgaag cctttgaaaa aatggtttca ctactttctg ttttgctttc catgcagggt    11760
gctgtagcca taaacaagct ttgtgaagaa atgctggaca caggcaac cttacaagct    11820 atagcctcag agtttagttc ccttccatca tatgcagctt ttgctactgc tcaagaagct    11880
tatgagcagg ctgttgctaa tggtgattct gaagttgttc ttaaaaagtt gaagaagtct    11940
ttgaatgtgg ctaaatctga atttgaccgt gatgcagcca tgcaacgtaa gttggaaaag    12000
atggctgatc aagctatgac ccaaatgtat aaacaggcta gatctgagga caagagggca    12060
aaagttacta gtgctatgca gacaatgctt ttcactatgc ttagaaagtt ggataatgat    12120
gcactcaaca acattatcaa caatgcaaga gatggttgtg ttcccttgaa cataataccg    12180
cttacaacag cagccaaact aatggttgtc ataccagact ataacacata taaaaatacg    12240
tgtgatggta caacatttac ttatgcatca gcattgtggg aaatccaaca ggttgtagat    12300
gcagatagta aaattgttca acttagtgaa attagtatgg acaattcacc taatttagca    12360
tggcctctta ttgtaacagc tttaagggcc aattctgctg tcaaattaca gaataatgag    12420
cttagtcctg ttgcactacg acagatgtct tgtgctgccg gtactacaca aactgcttgc    12480
actgatgaca atgcgttagc ttactacaac acaacaaagg gaggtaggtt tgtacttgca    12540
ctgttatccg atttacagga tttgaaatgg gctagattcc ctaagagtga tggaactggt    12600
actatctata cagaactgga accaccttgt aggtttgtta cagacacacc taaaggtcct    12660
aaagtgaagt atttatactt tattaaagga ttaaacaacc taaatagagg tatggtactt    12720
ggtagtttag ctgccacagt acgtctacaa gctggtaatg caacagaagt gcctgccaat    12780
tcaactgtat tatctttctg tgcttttgct gtagatgctg ctaaagctta caaagattat    12840
ctagctagtg ggggacaacc aatcactaat tgtgttaaga tgttgtgtac acacactggt    12900
actggtcagg caataacagt tacaccggaa gccaatatgg atcaagaatc ctttggtggt    12960
gcatcgtgtt gtctgtactg ccgttgccac atagatcatc caaatcctaa aggattttgt    13020
gacttaaaag gtaagtatgt acaaatacct acaacttgtg ctaatgaccc tgtgggtttt    13080
```

| | | |
|---|---|---|
| acacttaaaa acacagtctg taccgtctgc ggtatgtgga aaggttatgg ctgtagttgt | 13140 | |
| gatcaactcc gcgaacccat gcttcagtca gctgatgcac aatcgttttt aaacgggttt | 13200 | |
| gcggtgtaa | 13209 | |

<210> SEQ ID NO 15
<211> LENGTH: 3822
<212> TYPE: DNA
<213> ORGANISM: Unknown
<220> FEATURE:
<223> OTHER INFORMATION: SARS-CoV-2 surface glycoprotein

<400> SEQUENCE: 15

| | |
|---|---|
| atgtttgttt tcttgttttt attgccacta gtctctagtc agtgtgttaa tcttacaacc | 60 |
| agaactcaat taccccctgc atacactaat tctttcacac gtggtgttta ttaccctgac | 120 |
| aaagttttca gatcctcagt tttacattca actcaggact tgttcttacc tttcttttcc | 180 |
| aatgttactt ggttccatgc tatacatgtc tctgggacca atggtactaa gaggtttgat | 240 |
| aaccctgtcc taccatttaa tgatggtgtt tattttgctt ccattgagaa gtctaacata | 300 |
| ataagaggct ggattttggt actactttta gattcgaaga cccagtccct acttattgtt | 360 |
| aataacgcta ctaatgttgt tattaaagtc tgtgaatttc aattttgtaa tgatccattt | 420 |
| ttgggtgttt attaccacaa aaacaacaaa agttggatgg aaagtgagtt cagagtttat | 480 |
| tctagtgcga taattgcac ttttgaatat gtctctcagc cttttcttat ggaccttgaa | 540 |
| ggaaaacagg gtaagttcaa aaatcttagg gaatttgtgt ttaagaatat tgatggttat | 600 |
| tttaaaatat attctaagca cacgccatt aatttagtgc gtgatctccc tcagggtttt | 660 |
| tcggctttag aaccattggt agatttgcca ataggtatta acatcactag gtttcaaact | 720 |
| ttacttgctt tacatagaag ttatttgact cctggtgatt cttcttcagg ttggacagct | 780 |
| ggtgctgcag cttattatgt gggttatctt caacctagga cttttctatt aaaatataat | 840 |
| gaaaatggaa ccattacaga tgctgtagac tgtgcacttg accctctctc agaaacaaag | 900 |
| tgtacgttga atccttcac tgtagaaaaa ggaatctatc aaacttctaa ctttagagtc | 960 |
| caaccaacag aatctattgt tagatttcct aatattacaa acttgtgccc ttttggtgaa | 1020 |
| gtttttaacg ccaccagatt tgcatctgtt tatgcttgga acaggaagag aatcagcaac | 1080 |
| tgtgttgctg attattctgt cctatataat tccgcatcat tttccacttt taagtgttat | 1140 |
| ggagtgtctc ctactaaatt aaatgatctc tgctttacta atgtctatgc agattcattt | 1200 |
| gtaattagag gtgatgaagt cagacaaatc gctccagggc aaactggaaa gattgctgat | 1260 |
| tataattata aattaccaga tgattttaca ggctgcgtta gcttggaa ttctaacaat | 1320 |
| cttgattcta aggttggtgg taattataat acctgtata gattgtttag gaagtctaat | 1380 |
| ctcaaacctt ttgagagaga tatttcaact gaaatctatc aggccggtag cacaccttgt | 1440 |
| aatggtgttg aaggttttaa ttgttacttt cctttacaat catatggttt ccaacccact | 1500 |
| aatggtgttg gttaccaacc atacagagta gtagtacttt cttttgaact tctacatgca | 1560 |
| ccagcaactg tttgtggacc taaaaagtct actaatttgg ttaaaaacaa atgtgtcaat | 1620 |
| ttcaacttca atggtttaac aggcacaggt gttcttactg agtctaacaa aaagtttctg | 1680 |
| cctttccaac aatttggcag agacattgct gacactactg atgctgtccg tgatccacag | 1740 |
| acacttgaga ttcttgacat tacaccatgt tcttttggtg gtgtcagtgt tataacacca | 1800 |
| ggaacaaata cttctaacca ggttgctgtt ctttatcagg atgttaactg cacagaagtc | 1860 |
| cctgttgcta ttcatgcaga tcaacttact cctacttggc gtgtttattc tacaggttct | 1920 |

-continued

```
aatgttttc aaacacgtgc aggctgttta ataggggctg aacatgtcaa caactcatat      1980
gagtgtgaca tacccattgg tgcaggtata tgcgctagtt atcagactca gactaattct      2040
cctcggcggg cacgtagtgt agctagtcaa tccatcattg cctacactat gtcacttggt      2100
gcagaaaatt cagttgctta ctctaataac tctattgcca tacccacaaa ttttactatt      2160
agtgttacca cagaaattct accagtgtct atgaccaaga catcagtaga ttgtacaatg      2220
tacatttgtg gtgattcaac tgaatgcagc aatcttttgt tgcaatatgg cagttttgt      2280
acacaattaa accgtgcttt aactggaata gctgttgaac aagacaaaaa cacccaagaa      2340
gttttttgcac aagtcaaaca aatttacaaa acaccaccaa ttaaagattt tggtggtttt      2400
aattttttcac aaatattacc agatccatca aaaccaagca agaggtcatt tattgaagat      2460
ctactttttca caaagtgac acttgcagat gctggcttca tcaaacaata tggtgattgc      2520
cttggtgata ttgctgctag agacctcatt tgtgcacaaa agtttaacgg ccttactgtt      2580
ttgccaccctt tgctcacaga tgaaatgatt gctcaataca cttctgcact gttagcgggt      2640
acaatcactt ctggttggac ctttggtgca ggtgctgcat tacaaatacc atttgctatg      2700
caaatggctt ataggttaa tggtattgga gttacacaga atgttctcta tgagaaccaa      2760
aaattgattg ccaaccaatt taatagtgct attggcaaaa ttcaagactc actttcttcc      2820
acagcaagtg cacttggaaa acttcaagat gtggtcaacc aaaatgcaca agctttaaac      2880
acgcttgtta acaacttag cgccaatttt ggtgcaattt caagtgtttt aaatgatatc      2940
ctttcacgtc ttgacaaagt tgaggctgaa gtgcaaattg ataggttgat cacaggcaga      3000
cttcaaagtt tgcagacata tgtgactcaa caattaatta gagctgcaga aatcagagct      3060
tctgctaatc ttgctgctac taaaatgtca gagtgtgtac ttggacaatc aaaaagagtt      3120
gattttttgtg aaagggcta tcatcttatg tccttccctc agtcagcacc tcatggtgta      3180
gtcttcttgc atgtgactta tgtccctgca caagaaaaga acttcacaac tgctcctgcc      3240
atttgtcatg atggaaaagc acactttcct cgtgaaggtg tctttgtttc aaatggcaca      3300
cactggtttg taacacaaag gaattttttat gaaccacaaa tcattactac agacaacaca      3360
tttgtgtctg gtaactgtga tgttgtaata ggaattgtca acaacacagt ttatgatcct      3420
ttgcaacctg aattagactc attcaaggag gagttagata aatattttaa gaatcataca      3480
tcaccagatg ttgatttagg tgacatctct ggcattaatg cttcagttgt aaacattcaa      3540
aaagaaattg accgcctcaa tgaggttgcc aagaatttaa atgaatctct catcgatctc      3600
caagaacttg gaaagtatga gcagtatata aaatggccat ggtacatttg ctaggtttt      3660
atagctggct tgattgccat agtaatggtg acaattatgc tttgctgtat gaccagttgc      3720
tgtagttgtc tcaagggctg ttgttcttgt ggatcctgct gcaaatttga tgaagacgac      3780
tctgagccag tgctcaaagg agtcaaatta cattacacat aa                       3822
```

<210> SEQ ID NO 16
<211> LENGTH: 828
<212> TYPE: DNA
<213> ORGANISM: Unknown
<220> FEATURE:
<223> OTHER INFORMATION: SARS-CoV-2 ORF3a protein

<400> SEQUENCE: 16

```
atggatttgt ttatgagaat cttcacaatt ggaactgtaa ctttgaagca aggtgaaatc       60
aaggatgcta ctccttcaga ttttgttcgc gctactgcaa cgataccgat acaagcctca      120
```

```
ctcccttcg gatggcttat tgttggcgtt gcacttcttg ctgtttttca gagcgcttcc      180
aaaatcataa ccctcaaaaa gagatggcaa ctagcactct ccaagggtgt tcactttgtt      240
tgcaacttgc tgttgttgtt tgtaacagtt tactcacacc ttttgctcgt tgctgctggc      300
cttgaagccc cttttctcta tctttatgct ttagtctact tcttgcagag tataaacttt      360
gtaagaataa taatgaggct ttggctttgc tggaaatgcc gttccaaaaa cccattactt      420
tatgatgcca actattttct tgctggcat actaattgtt acgactattg tataccttac       480
aatagtgtaa cttcttcaat tgtcattact tcaggtgatg gcacaacaag tcctatttct      540
gaacatgact accagattgg tggttatact gaaaaatggg aatctggagt aaaagactgt      600
gttgtattac acagttactt cacttcagac tattaccagc tgtactcaac tcaattgagt      660
acagacactg gtgttgaaca tgttaccttc ttcatctaca ataaaattgt tgatgagcct      720
gaagaacatg tccaaattca cacaatcgac ggttcatccg gagttgttaa tccagtaatg      780
gaaccaattt atgatgaacc gacgacgact actagcgtgc ctttgtaa                   828

<210> SEQ ID NO 17
<211> LENGTH: 1260
<212> TYPE: DNA
<213> ORGANISM: Unknown
<220> FEATURE:
<223> OTHER INFORMATION: SARS-CoV-2 envelope protein

<400> SEQUENCE: 17
atgtctgata tggaccccca aaatcagcga atgcacccc gcattacgtt tggtggaccc       60
tcagattcaa ctggcagtaa ccagaatgga gaacgcagtg gggcgcgatc aaaacaacgt      120
cggccccaag gtttacccaa taatactgcg tcttggttca ccgctctcac tcaacatggc      180
aaggaagacc ttaaattccc tcgaggacaa ggcgttccaa ttaacaccaa tagcagtcca      240
gatgaccaaa ttggctacta ccgaagagct accagacgaa ttcgtggtgg tgacggtaaa      300
atgaaagatc tcagtccaag atggtatttc tactacctag gaactgggcc agaagctgga      360
cttccctatg gtgctaacaa agacggcatc atatggggttg caactgaggg agccttgaat      420
acaccaaaag atcacattgg cacccgcaat cctgctaaca atgctgcaat cgtgctacaa      480
cttcctcaag gaacaacatt gccaaaaggc ttctacgcag aagggagcag aggcggcagt      540
caagcctctt ctcgttcctc atcacgtagt cgcaacagtt caagaaattc aactccaggc      600
agcagtaggg gaacttctcc tgctagaatg gctggcaatg gcggtgatgc tgctcttgct      660
ttgctgctgc ttgacagatt gaaccagctt gagagcaaaa tgtctggtaa aggccaacaa      720
caacaaggcc aaactgtcac taagaaatct gctgctgagg cttctaagaa gcctcggcaa      780
aaacgtactg ccactaaagc atacaatgta acacaagctt tcggcagacg tggtccagaa      840
caaacccaag gaaattttgg ggaccaggaa ctaatcagac aaggaactga ttacaaacat      900
tggccgcaaa ttgcacaatt tgccccccagc gcttcagcgt tcttcggaat gtcgcgcatt      960
ggcatggaag tcacaccttc gggaacgtgg ttgacctaca caggtgccat caaattggat     1020
gacaaagatc caaatttcaa agatcaagtc attttgctga ataagcatat tgacgcatac     1080
aaaacattcc caccaacaga gcctaaaaag gacaaaaga agaaggctga tgaaactcaa    1140
gccttaccgc agagacagaa gaaacagcaa actgtgactc ttcttcctgc tgcagatttg    1200
gatgatttct ccaaacaatt gcaacaatcc atgagcagtg ctgactcaac tcaggcctaa    1260

<210> SEQ ID NO 18
<211> LENGTH: 669
```

```
<212> TYPE: DNA
<213> ORGANISM: Unknown
<220> FEATURE:
<223> OTHER INFORMATION: SARS-CoV-2 membrane glycoprotein
<400> SEQUENCE: 18
atggcagatt ccaacggtac tattaccgtt gaagagctta aaaagctcct tgaacaatgg 60
aacctagtaa taggtttcct attccttaca tggatttgtc ttctacaatt tgcctatgcc 120
aacaggaata ggtttttgta tataattaag ttaattttcc tctggctgtt atggccagta 180
actttagctt gttttgtgct tgctgctgtt tacagaataa attggatcac cggtggaatt 240
gctatcgcaa tggcttgtct tgtaggcttg atgtggctca gctacttcat tgcttctttc 300
agactgtttg cgcgtacgcg ttccatgtgg tcattcaatc cagaaactaa cattcttctc 360
aacgtgccac tccatggcac tattctgacc agaccgcttc tagaaagtga actcgtaatc 420
ggagctgtga tccttcgtgg acatcttcgt attgctggac accatctagg acgctgtgac 480
atcaaggacc tgcctaaaga aatcactgtt gctacatcac gaacgctttc ttattataaa 540
ttgggagctt cgcagcgtgt agcaggtgac tcaggttttg ctgcatacag tcgctacagg 600
attggcaact ataaattaaa cacagaccat tccagtagca gtgacaatat tgctttgctt 660
gtacagtaa 669

<210> SEQ ID NO 19
<211> LENGTH: 186
<212> TYPE: DNA
<213> ORGANISM: Unknown
<220> FEATURE:
<223> OTHER INFORMATION: SARS-CoV-2 ORF6 protein
<400> SEQUENCE: 19
atgtttcatc tcgttgactt tcaggttact atagcagaga tattactaat tattatgagg 60
acttttaaag tttccatttg gaatcttgat tacatcataa acctcataat taaaaattta 120
tctaagtcac taactgagaa taaatattct caattagatg aagagcaacc aatggagatt 180
gattaa 186

<210> SEQ ID NO 20
<211> LENGTH: 366
<212> TYPE: DNA
<213> ORGANISM: Unknown
<220> FEATURE:
<223> OTHER INFORMATION: SARS-CoV-2 ORF7a protein
<400> SEQUENCE: 20
atgaaaatta ttcttttctt ggcactgata acactcgcta cttgtgagct ttatcactac 60
caagagtgtg ttagaggtac aacagtactt ttaaaagaac cttgctcttc tggaacatac 120
gagggcaatt caccatttca tcctctagct gataacaaat ttgcactgac ttgctttagc 180
actcaatttg cttttgcttg tcctgacggc gtaaaacacg tctatcagtt acgtgccaga 240
tcagtttcac ctaaactgtt catcagacaa gaggaagttc aagaacttta ctctccaatt 300
tttcttattg ttgcggcaat agtgtttata acactttgct tcacactcaa aagaaagaca 360
gaatga 366

<210> SEQ ID NO 21
<211> LENGTH: 132
<212> TYPE: DNA
<213> ORGANISM: Unknown
<220> FEATURE:
```

<223> OTHER INFORMATION: SARS-CoV-2 ORF7b protein

<400> SEQUENCE: 21

```
atgattgaac tttcattaat tgacttctat ttgtgctttt tagcctttct gctattcctt      60
gttttaatta tgcttattat cttttggttc tcacttgaac tgcaagatca taatgaaact     120
tgtcacgcct aa                                                         132
```

```
<210> SEQ ID NO 22
<211> LENGTH: 366
<212> TYPE: DNA
<213> ORGANISM: Unknown
<220> FEATURE:
<223> OTHER INFORMATION: SARS-CoV-2 ORF8 protein
```

<400> SEQUENCE: 22

```
atgaaatttc ttgttttctt aggaatcatc acaactgtag ctgcatttca ccaagaatgt      60
agtttacagt catgtactca acatcaacca tatgtagttg atgacccgtg tcctattcac     120
ttctattcta aatggtatat tagagtagga gctagaaaat cagcaccttt aattgaattg     180
tgcgtggatg aggctggttc taaatcaccc attcagtaca tcgatatcgg taattataca     240
gtttcctgtt cacctttttac aattaattgc caggaaccta aattgggtag tcttgtagtg     300
cgttgttcgt tctatgaaga cttttttagag tatcatgacg ttcgtgttgt tttagatttc     360
atctaa                                                                366
```

```
<210> SEQ ID NO 23
<211> LENGTH: 1260
<212> TYPE: DNA
<213> ORGANISM: Unknown
<220> FEATURE:
<223> OTHER INFORMATION: SARS-CoV-2 nucleocapsid phosphoprotein
```

<400> SEQUENCE: 23

```
atgtctgata atggacccca aaatcagcga atgcacccc gcattacgtt tggtggaccc       60
tcagattcaa ctggcagtaa ccagaatgga gaacgcagtg gggcgcgatc aaaacaacgt     120
cggccccaag gtttacccaa taatactgcg tcttggttca ccgctctcac tcaacatggc     180
aaggaagacc ttaaattccc tcgaggacaa ggcgttccaa ttaacaccaa tagcagtcca     240
gatgaccaaa ttggctacta ccgaagagct accagacgaa ttcgtggtgg tgacggtaaa     300
atgaaagatc tcagtccaag atggtatttc tactacctag gaactgggcc agaagctgga     360
cttccctatg gtgctaacaa agacggcatc atatgggttg caactgaggg agccttgaat     420
acaccaaaag atcacattgg cacccgcaat cctgctaaca atgctgcaat cgtgctacaa     480
cttcctcaag gaacaacatt gccaaaaggc ttctacgcag aagggagcag aggcggcagt     540
caagcctctt ctcgttcctc atcacgtagt cgcaacagtt caagaaattc aactccaggc     600
agcagtaggg gaacttctcc tgctagaatg gctggcaatg gcggtgatgc tgctcttgct     660
ttgctgctgc ttgacagatt gaaccagctt gagagcaaaa tgtctggtaa aggccaacaa     720
caacaaggcc aaactgtcac taagaaatct gctgctgagg cttctaagaa gcctcggcaa     780
aaacgtactg ccactaaagc atacaatgta acacaagctt tcggcagacg tggtccagaa     840
caaacccaag gaaatttttgg ggaccaggaa ctaatcagac aaggaactga ttacaaacat     900
tggccgcaaa ttgcacaatt tgcccccagc gcttcagcgt tcttcggaat gtcgcgcatt     960
ggcatggaag tcacaccttc gggaacgtgg ttgacctaca caggtgccat caaattggat    1020
gacaaagatc caaatttcaa agatcaagtc attttgctga ataagcatat tgacgcatac    1080
```

-continued

```
aaaacattcc caccaacaga gcctaaaaag gacaaaaaga agaaggctga tgaaactcaa      1140
gccttaccgc agagacagaa gaaacagcaa actgtgactc ttcttcctgc tgcagatttg      1200
gatgatttct ccaaacaatt gcaacaatcc atgagcagtg ctgactcaac tcaggcctaa      1260
```

<210> SEQ ID NO 24
<211> LENGTH: 117
<212> TYPE: DNA
<213> ORGANISM: Unknown
<220> FEATURE:
<223> OTHER INFORMATION: SARS-CoV-2 ORF10 protein

<400> SEQUENCE: 24

```
atgggctata taaacgtttt cgcttttccg tttacgatat atagtctact cttgtgcaga       60
atgaattctc gtaactacat agcacaagta gatgtagtta actttaatct cacatag         117
```

<210> SEQ ID NO 25
<211> LENGTH: 7096
<212> TYPE: PRT
<213> ORGANISM: Unknown
<220> FEATURE:
<223> OTHER INFORMATION: SARS-CoV-2 ORF1ab polyprotein

<400> SEQUENCE: 25

```
Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
        115                 120                 125

Lys Gly Ala Gly Gly His Ser Tyr Gly Ala Asp Leu Lys Ser Phe Asp
    130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
        195                 200                 205

Gly Lys Ala Ser Cys Thr Leu Ser Glu Gln Leu Asp Phe Ile Asp Thr
    210                 215                 220

Lys Arg Gly Val Tyr Cys Cys Arg Gly His Glu His Glu Ile Ala Trp
225                 230                 235                 240

Tyr Thr Glu Arg Ser Glu Lys Ser Tyr Glu Leu Gln Thr Pro Phe Glu
                245                 250                 255
```

```
Ile Lys Leu Ala Lys Lys Phe Asp Thr Phe Asn Gly Glu Cys Pro Asn
            260                 265                 270

Phe Val Phe Pro Leu Asn Ser Ile Ile Lys Thr Ile Gln Pro Arg Val
        275                 280                 285

Glu Lys Lys Lys Leu Asp Gly Phe Met Gly Arg Ile Arg Ser Val Tyr
    290                 295                 300

Pro Val Ala Ser Pro Asn Glu Cys Asn Gln Met Cys Leu Ser Thr Leu
305                 310                 315                 320

Met Lys Cys Asp His Cys Gly Glu Thr Ser Trp Gln Thr Gly Asp Phe
                325                 330                 335

Val Lys Ala Thr Cys Glu Phe Cys Gly Thr Glu Asn Leu Thr Lys Glu
                340                 345                 350

Gly Ala Thr Thr Cys Gly Tyr Leu Pro Gln Asn Ala Val Val Lys Ile
                355                 360                 365

Tyr Cys Pro Ala Cys His Asn Ser Glu Val Gly Pro Glu His Ser Leu
    370                 375                 380

Ala Glu Tyr His Asn Glu Ser Gly Leu Lys Thr Ile Leu Arg Lys Gly
385                 390                 395                 400

Gly Arg Thr Ile Ala Phe Gly Gly Cys Val Phe Ser Tyr Val Gly Cys
                405                 410                 415

His Asn Lys Cys Ala Tyr Trp Val Pro Arg Ala Ser Ala Asn Ile Gly
                420                 425                 430

Cys Asn His Thr Gly Val Val Gly Glu Gly Ser Glu Gly Leu Asn Asp
                435                 440                 445

Asn Leu Leu Glu Ile Leu Gln Lys Glu Lys Val Asn Ile Asn Ile Val
450                 455                 460

Gly Asp Phe Lys Leu Asn Glu Glu Ile Ala Ile Ile Leu Ala Ser Phe
465                 470                 475                 480

Ser Ala Ser Thr Ser Ala Phe Val Glu Thr Val Lys Gly Leu Asp Tyr
                485                 490                 495

Lys Ala Phe Lys Gln Ile Val Glu Ser Cys Gly Asn Phe Lys Val Thr
                500                 505                 510

Lys Gly Lys Ala Lys Lys Gly Ala Trp Asn Ile Gly Glu Gln Lys Ser
    515                 520                 525

Ile Leu Ser Pro Leu Tyr Ala Phe Ala Ser Glu Ala Ala Arg Val Val
    530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
                580                 585                 590

Asn Asn Leu Val Val Met Ala Tyr Ile Thr Gly Gly Val Val Gln Leu
            595                 600                 605

Thr Ser Gln Trp Leu Thr Asn Ile Phe Gly Thr Val Tyr Glu Lys Leu
        610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
                660                 665                 670

Glu Ser Val Gln Thr Phe Phe Lys Leu Val Asn Lys Phe Leu Ala Leu
```

```
            675                 680                 685
Cys Ala Asp Ser Ile Ile Ile Gly Gly Ala Lys Leu Lys Ala Leu Asn
    690                 695                 700
Leu Gly Glu Thr Phe Val Thr His Ser Lys Gly Leu Tyr Arg Lys Cys
705                 710                 715                 720
Val Lys Ser Arg Glu Glu Thr Gly Leu Leu Met Pro Leu Lys Ala Pro
                725                 730                 735
Lys Glu Ile Ile Phe Leu Gly Glu Thr Leu Pro Thr Glu Val Leu
            740                 745                 750
Thr Glu Glu Val Val Leu Lys Thr Gly Asp Leu Gln Pro Leu Glu Gln
            755                 760                 765
Pro Thr Ser Glu Ala Val Glu Ala Pro Leu Val Gly Thr Pro Val Cys
    770                 775                 780
Ile Asn Gly Leu Met Leu Leu Glu Ile Lys Asp Thr Glu Lys Tyr Cys
785                 790                 795                 800
Ala Leu Ala Pro Asn Met Met Val Thr Asn Asn Thr Phe Thr Leu Lys
                805                 810                 815
Gly Gly Ala Pro Thr Lys Val Thr Phe Gly Asp Asp Thr Val Ile Glu
            820                 825                 830
Val Gln Gly Tyr Lys Ser Val Asn Ile Thr Phe Glu Leu Asp Glu Arg
            835                 840                 845
Ile Asp Lys Val Leu Asn Glu Lys Cys Ser Ala Tyr Thr Val Glu Leu
    850                 855                 860
Gly Thr Glu Val Asn Glu Phe Ala Cys Val Val Ala Asp Ala Val Ile
865                 870                 875                 880
Lys Thr Leu Gln Pro Val Ser Glu Leu Leu Thr Pro Leu Gly Ile Asp
                885                 890                 895
Leu Asp Glu Trp Ser Met Ala Thr Tyr Tyr Leu Phe Asp Glu Ser Gly
            900                 905                 910
Glu Phe Lys Leu Ala Ser His Met Tyr Cys Ser Phe Tyr Pro Pro Asp
            915                 920                 925
Glu Asp Glu Glu Glu Gly Asp Cys Glu Glu Glu Phe Glu Pro Ser
    930                 935                 940
Thr Gln Tyr Glu Tyr Gly Thr Glu Asp Asp Tyr Gln Gly Lys Pro Leu
945                 950                 955                 960
Glu Phe Gly Ala Thr Ser Ala Ala Leu Gln Pro Glu Glu Gln Glu
                965                 970                 975
Glu Asp Trp Leu Asp Asp Ser Gln Gln Thr Val Gly Gln Gln Asp
            980                 985                 990
Gly Ser Glu Asp Asn Gln Thr Thr Thr Ile Gln Thr Ile Val Glu Val
            995                 1000                1005
Gln Pro Gln Leu Glu Met Glu Leu Thr Pro Val Val Gln Thr Ile
    1010                1015                1020
Glu Val Asn Ser Phe Ser Gly Tyr Leu Lys Leu Thr Asp Asn Val
    1025                1030                1035
Tyr Ile Lys Asn Ala Asp Ile Val Glu Glu Ala Lys Lys Val Lys
    1040                1045                1050
Pro Thr Val Val Val Asn Ala Ala Asn Val Tyr Leu Lys His Gly
    1055                1060                1065
Gly Gly Val Ala Gly Ala Leu Asn Lys Ala Thr Asn Asn Ala Met
    1070                1075                1080
Gln Val Glu Ser Asp Asp Tyr Ile Ala Thr Asn Gly Pro Leu Lys
    1085                1090                1095
```

```
Val Gly Gly Ser Cys Val Leu Ser Gly His Asn Leu Ala Lys His
1100            1105                1110

Cys Leu His Val Val Gly Pro Asn Val Asn Lys Gly Glu Asp Ile
1115            1120                1125

Gln Leu Leu Lys Ser Ala Tyr Glu Asn Phe Asn Gln His Glu Val
1130            1135                1140

Leu Leu Ala Pro Leu Leu Ser Ala Gly Ile Phe Gly Ala Asp Pro
1145            1150                1155

Ile His Ser Leu Arg Val Cys Val Asp Thr Val Arg Thr Asn Val
1160            1165                1170

Tyr Leu Ala Val Phe Asp Lys Asn Leu Tyr Asn Lys Leu Val Ser
1175            1180                1185

Ser Phe Leu Glu Met Lys Ser Glu Lys Gln Val Glu Gln Lys Ile
1190            1195                1200

Ala Glu Ile Pro Lys Glu Glu Val Lys Pro Phe Ile Thr Glu Ser
1205            1210                1215

Lys Pro Ser Val Glu Gln Arg Lys Gln Asp Asp Lys Lys Ile Lys
1220            1225                1230

Ala Cys Val Glu Glu Val Thr Thr Thr Leu Glu Glu Thr Lys Phe
1235            1240                1245

Leu Thr Glu Asn Leu Leu Leu Tyr Ile Asp Ile Asn Gly Asn Leu
1250            1255                1260

His Pro Asp Ser Ala Thr Leu Val Ser Asp Ile Asp Ile Thr Phe
1265            1270                1275

Leu Lys Lys Asp Ala Pro Tyr Ile Val Gly Asp Val Val Gln Glu
1280            1285                1290

Gly Val Leu Thr Ala Val Val Ile Pro Thr Lys Lys Ala Gly Gly
1295            1300                1305

Thr Thr Glu Met Leu Ala Lys Ala Leu Arg Lys Val Pro Thr Asp
1310            1315                1320

Asn Tyr Ile Thr Thr Tyr Pro Gly Gln Gly Leu Asn Gly Tyr Thr
1325            1330                1335

Val Glu Glu Ala Lys Thr Val Leu Lys Lys Cys Lys Ser Ala Phe
1340            1345                1350

Tyr Ile Leu Pro Ser Ile Ile Ser Asn Glu Lys Gln Glu Ile Leu
1355            1360                1365

Gly Thr Val Ser Trp Asn Leu Arg Glu Met Leu Ala His Ala Glu
1370            1375                1380

Glu Thr Arg Lys Leu Met Pro Val Cys Val Glu Thr Lys Ala Ile
1385            1390                1395

Val Ser Thr Ile Gln Arg Lys Tyr Lys Gly Ile Lys Ile Gln Glu
1400            1405                1410

Gly Val Val Asp Tyr Gly Ala Arg Phe Tyr Phe Tyr Thr Ser Lys
1415            1420                1425

Thr Thr Val Ala Ser Leu Ile Asn Thr Leu Asn Asp Leu Asn Glu
1430            1435                1440

Thr Leu Val Thr Met Pro Leu Gly Tyr Val Thr His Gly Leu Asn
1445            1450                1455

Leu Glu Glu Ala Ala Arg Tyr Met Arg Ser Leu Lys Val Pro Ala
1460            1465                1470

Thr Val Ser Val Ser Ser Pro Asp Ala Val Thr Ala Tyr Asn Gly
1475            1480                1485
```

```
Tyr Leu Thr Ser Ser Ser Lys Thr Pro Glu Glu His Phe Ile Glu
    1490            1495            1500

Thr Ile Ser Leu Ala Gly Ser Tyr Lys Asp Trp Ser Tyr Ser Gly
    1505            1510            1515

Gln Ser Thr Gln Leu Gly Ile Glu Phe Leu Lys Arg Gly Asp Lys
    1520            1525            1530

Ser Val Tyr Tyr Thr Ser Asn Pro Thr Thr Phe His Leu Asp Gly
    1535            1540            1545

Glu Val Ile Thr Phe Asp Asn Leu Lys Thr Leu Leu Ser Leu Arg
    1550            1555            1560

Glu Val Arg Thr Ile Lys Val Phe Thr Thr Val Asp Asn Ile Asn
    1565            1570            1575

Leu His Thr Gln Val Val Gly Met Ser Met Thr Tyr Gly Gln Gln
    1580            1585            1590

Phe Gly Pro Thr Tyr Phe Asp Gly Ala Asp Val Thr Lys Ile Lys
    1595            1600            1605

Pro His Asn Ser His Glu Gly Lys Thr Phe Tyr Val Leu Pro Asn
    1610            1615            1620

Asp Asp Thr Leu Arg Val Glu Ala Phe Glu Tyr Tyr His Thr Thr
    1625            1630            1635

Asp Pro Ser Phe Leu Gly Arg Tyr Met Ser Ala Leu Asn His Thr
    1640            1645            1650

Lys Lys Trp Lys Tyr Pro Gln Val Asn Gly Leu Thr Ser Ile Lys
    1655            1660            1665

Trp Ala Asp Asn Asn Cys Tyr Leu Ala Thr Ala Leu Leu Thr Leu
    1670            1675            1680

Gln Gln Ile Glu Leu Lys Phe Asn Pro Pro Ala Leu Gln Asp Ala
    1685            1690            1695

Tyr Tyr Arg Ala Arg Ala Gly Glu Ala Ala Asn Phe Cys Ala Leu
    1700            1705            1710

Ile Leu Ala Tyr Cys Asn Lys Thr Val Gly Glu Leu Gly Asp Val
    1715            1720            1725

Arg Glu Thr Met Ser Tyr Leu Phe Gln His Ala Asn Leu Asp Ser
    1730            1735            1740

Cys Lys Arg Val Leu Asn Val Val Cys Lys Thr Cys Gly Gln Gln
    1745            1750            1755

Gln Thr Thr Leu Lys Gly Val Glu Ala Val Met Tyr Met Gly Thr
    1760            1765            1770

Leu Ser Tyr Glu Gln Phe Lys Lys Gly Val Gln Ile Pro Cys Thr
    1775            1780            1785

Cys Gly Lys Gln Ala Thr Lys Tyr Leu Val Gln Gln Glu Ser Pro
    1790            1795            1800

Phe Val Met Met Ser Ala Pro Pro Ala Gln Tyr Glu Leu Lys His
    1805            1810            1815

Gly Thr Phe Thr Cys Ala Ser Glu Tyr Thr Gly Asn Tyr Gln Cys
    1820            1825            1830

Gly His Tyr Lys His Ile Thr Ser Lys Glu Thr Leu Tyr Cys Ile
    1835            1840            1845

Asp Gly Ala Leu Leu Thr Lys Ser Ser Glu Tyr Lys Gly Pro Ile
    1850            1855            1860

Thr Asp Val Phe Tyr Lys Glu Asn Ser Tyr Thr Thr Thr Ile Lys
    1865            1870            1875

Pro Val Thr Tyr Lys Leu Asp Gly Val Val Cys Thr Glu Ile Asp
```

```
            1880                1885                1890

Pro Lys Leu Asp Asn Tyr Tyr Lys Lys Asp Asn Ser Tyr Phe Thr
    1895                1900                1905

Glu Gln Pro Ile Asp Leu Val Pro Asn Gln Pro Tyr Pro Ser Ala
    1910                1915                1920

Ser Phe Asp Asn Phe Lys Phe Val Cys Asp Asn Ile Lys Phe Ala
    1925                1930                1935

Asp Asp Leu Asn Gln Leu Thr Gly Tyr Lys Lys Pro Ala Ser Arg
    1940                1945                1950

Glu Leu Lys Val Thr Phe Phe Pro Asp Leu Asn Gly Asp Val Val
    1955                1960                1965

Ala Ile Asp Tyr Lys His Tyr Thr Pro Ser Phe Lys Lys Gly Ala
    1970                1975                1980

Lys Leu Leu His Lys Pro Ile Val Trp His Val Asn Asn Ala Thr
    1985                1990                1995

Asn Lys Ala Thr Tyr Lys Pro Asn Thr Trp Cys Ile Arg Cys Leu
    2000                2005                2010

Trp Ser Thr Lys Pro Val Glu Thr Ser Asn Ser Phe Asp Val Leu
    2015                2020                2025

Lys Ser Glu Asp Ala Gln Gly Met Asp Asn Leu Ala Cys Glu Asp
    2030                2035                2040

Leu Lys Pro Val Ser Glu Val Val Glu Asn Pro Thr Ile Gln
    2045                2050                2055

Lys Asp Val Leu Glu Cys Asn Val Lys Thr Thr Glu Val Val Gly
    2060                2065                2070

Asp Ile Ile Leu Lys Pro Ala Asn Asn Ser Leu Lys Ile Thr Glu
    2075                2080                2085

Glu Val Gly His Thr Asp Leu Met Ala Ala Tyr Val Asp Asn Ser
    2090                2095                2100

Ser Leu Thr Ile Lys Lys Pro Asn Glu Leu Ser Arg Val Leu Gly
    2105                2110                2115

Leu Lys Thr Leu Ala Thr His Gly Leu Ala Ala Val Asn Ser Val
    2120                2125                2130

Pro Trp Asp Thr Ile Ala Asn Tyr Ala Lys Pro Phe Leu Asn Lys
    2135                2140                2145

Val Val Ser Thr Thr Thr Asn Ile Val Thr Arg Cys Leu Asn Arg
    2150                2155                2160

Val Cys Thr Asn Tyr Met Pro Tyr Phe Phe Thr Leu Leu Leu Gln
    2165                2170                2175

Leu Cys Thr Phe Thr Arg Ser Thr Asn Ser Arg Ile Lys Ala Ser
    2180                2185                2190

Met Pro Thr Thr Ile Ala Lys Asn Thr Val Lys Ser Val Gly Lys
    2195                2200                2205

Phe Cys Leu Glu Ala Ser Phe Asn Tyr Leu Lys Ser Pro Asn Phe
    2210                2215                2220

Ser Lys Leu Ile Asn Ile Ile Trp Phe Leu Leu Leu Ser Val
    2225                2230                2235

Cys Leu Gly Ser Leu Ile Tyr Ser Thr Ala Ala Leu Gly Val Leu
    2240                2245                2250

Met Ser Asn Leu Gly Met Pro Ser Tyr Cys Thr Gly Tyr Arg Glu
    2255                2260                2265

Gly Tyr Leu Asn Ser Thr Asn Val Thr Ile Ala Thr Tyr Cys Thr
    2270                2275                2280
```

-continued

```
Gly Ser Ile Pro Cys Ser Val Cys Leu Ser Gly Leu Asp Ser Leu
    2285             2290                2295

Asp Thr Tyr Pro Ser Leu Glu Thr Ile Gln Ile Thr Ile Ser Ser
    2300             2305                2310

Phe Lys Trp Asp Leu Thr Ala Phe Gly Leu Val Ala Glu Trp Phe
    2315             2320                2325

Leu Ala Tyr Ile Leu Phe Thr Arg Phe Tyr Val Leu Gly Leu
    2330             2335                2340

Ala Ala Ile Met Gln Leu Phe Phe Ser Tyr Phe Ala Val His Phe
    2345             2350                2355

Ile Ser Asn Ser Trp Leu Met Trp Leu Ile Ile Asn Leu Ala Gln
    2360             2365                2370

Met Ala Pro Ile Ser Ala Met Val Arg Met Tyr Ile Phe Phe Ala
    2375             2380                2385

Ser Phe Tyr Tyr Val Trp Lys Ser Tyr Val His Val Val Asp Gly
    2390             2395                2400

Cys Asn Ser Ser Thr Cys Met Met Cys Tyr Lys Arg Asn Arg Ala
    2405             2410                2415

Thr Arg Val Glu Cys Thr Thr Ile Val Asn Gly Val Arg Arg Ser
    2420             2425                2430

Phe Tyr Val Tyr Ala Asn Gly Gly Lys Gly Phe Cys Lys Leu His
    2435             2440                2445

Asn Trp Asn Cys Val Asn Cys Asp Thr Phe Cys Ala Gly Ser Thr
    2450             2455                2460

Phe Ile Ser Asp Glu Val Ala Arg Asp Leu Ser Leu Gln Phe Lys
    2465             2470                2475

Arg Pro Ile Asn Pro Thr Asp Gln Ser Ser Tyr Ile Val Asp Ser
    2480             2485                2490

Val Thr Val Lys Asn Gly Ser Ile His Leu Tyr Phe Asp Lys Ala
    2495             2500                2505

Gly Gln Lys Thr Tyr Glu Arg His Ser Leu Ser His Phe Val Asn
    2510             2515                2520

Leu Asp Asn Leu Arg Ala Asn Asn Thr Lys Gly Ser Leu Pro Ile
    2525             2530                2535

Asn Val Ile Val Phe Asp Gly Lys Ser Lys Cys Glu Glu Ser Ser
    2540             2545                2550

Ala Lys Ser Ala Ser Val Tyr Tyr Ser Gln Leu Met Cys Gln Pro
    2555             2560                2565

Ile Leu Leu Leu Asp Gln Ala Leu Val Ser Asp Val Gly Asp Ser
    2570             2575                2580

Ala Glu Val Ala Val Lys Met Phe Asp Ala Tyr Val Asn Thr Phe
    2585             2590                2595

Ser Ser Thr Phe Asn Val Pro Met Glu Lys Leu Lys Thr Leu Val
    2600             2605                2610

Ala Thr Ala Glu Ala Glu Leu Ala Lys Asn Val Ser Leu Asp Asn
    2615             2620                2625

Val Leu Ser Thr Phe Ile Ser Ala Ala Arg Gln Gly Phe Val Asp
    2630             2635                2640

Ser Asp Val Glu Thr Lys Asp Val Val Glu Cys Leu Lys Leu Ser
    2645             2650                2655

His Gln Ser Asp Ile Glu Val Thr Gly Asp Ser Cys Asn Asn Tyr
    2660             2665                2670
```

```
Met Leu Thr Tyr Asn Lys Val Glu Asn Met Thr Pro Arg Asp Leu
2675                2680                2685

Gly Ala Cys Ile Asp Cys Ser Ala Arg His Ile Asn Ala Gln Val
2690                2695                2700

Ala Lys Ser His Asn Ile Ala Leu Ile Trp Asn Val Lys Asp Phe
2705                2710                2715

Met Ser Leu Ser Glu Gln Pro Arg Lys Gln Ile Arg Ser Ala Ala
2720                2725                2730

Lys Lys Asn Asn Leu Pro Phe Lys Leu Thr Cys Ala Thr Thr Arg
2735                2740                2745

Gln Val Val Asn Ala Val Thr Thr Lys Ile Ala Leu Lys Gly Gly
2750                2755                2760

Lys Ile Val Asn Asn Trp Leu Lys Gln Leu Ile Lys Val Thr Leu
2765                2770                2775

Val Phe Leu Phe Val Ala Ala Ile Phe Tyr Leu Ile Thr Pro Val
2780                2785                2790

His Val Met Ser Lys His Thr Asp Phe Ser Ser Glu Ile Ile Gly
2795                2800                2805

Tyr Lys Ala Ile Asp Gly Gly Val Thr Arg Asp Ile Ala Ser Thr
2810                2815                2820

Asp Thr Cys Phe Ala Asn Lys His Ala Asp Phe Asp Thr Trp Phe
2825                2830                2835

Ser Gln Arg Gly Gly Ser Tyr Thr Asn Asp Lys Ala Cys Pro Leu
2840                2845                2850

Ile Ala Ala Val Ile Thr Arg Glu Val Gly Phe Val Val Pro Gly
2855                2860                2865

Leu Pro Ser Thr Ile Leu Arg Thr Thr Asn Gly Asp Phe Leu His
2870                2875                2880

Phe Leu Pro Arg Val Phe Ser Ala Val Gly Asn Ile Cys Tyr Thr
2885                2890                2895

Pro Ser Lys Leu Ile Glu Tyr Thr Asp Phe Ala Thr Ser Ala Cys
2900                2905                2910

Val Leu Ala Ala Glu Cys Thr Ile Phe Lys Asp Ala Ser Gly Lys
2915                2920                2925

Pro Val Pro Tyr Cys Tyr Asp Thr Asn Val Leu Glu Gly Ser Val
2930                2935                2940

Ala Tyr Glu Ser Leu Arg Pro Asp Thr Arg Tyr Val Leu Met Asp
2945                2950                2955

Gly Ser Ile Ile Gln Phe Pro Asn Thr Tyr Leu Glu Gly Pro Val
2960                2965                2970

Arg Val Val Thr Thr Phe Asp Ser Glu Tyr Cys Gly His Gly Thr
2975                2980                2985

Cys Glu Arg Ser Glu Ala Gly Val Cys Val Ser Thr Ser Gly Arg
2990                2995                3000

Trp Val Leu Asn Asn Asp Tyr Tyr Arg Ser Leu Pro Gly Val Phe
3005                3010                3015

Cys Gly Val Asp Ala Val Asn Leu Leu Thr Asn Met Phe Thr Pro
3020                3025                3030

Leu Ile Gln Pro Ile Gly Ala Leu Asp Ile Ser Ala Ser Ile Val
3035                3040                3045

Ala Gly Gly Ile Val Ala Ile Val Val Thr Cys Leu Ala Tyr Tyr
3050                3055                3060

Phe Met Arg Phe Arg Arg Ala Phe Gly Glu Tyr Ser His Val Val
```

-continued

```
            3065                3070                3075
Ala Phe Asn Thr Leu Leu Phe Leu Met Ser Phe Thr Val Leu Cys
        3080                3085                3090
Leu Thr Pro Val Tyr Ser Phe Leu Pro Gly Val Tyr Ser Val Ile
        3095                3100                3105
Tyr Leu Tyr Leu Thr Phe Tyr Leu Thr Asn Asp Val Ser Phe Leu
        3110                3115                3120
Ala His Ile Gln Trp Met Val Met Phe Thr Pro Leu Val Pro Phe
        3125                3130                3135
Trp Ile Thr Ile Ala Tyr Ile Ile Cys Ile Ser Thr Lys His Phe
        3140                3145                3150
Tyr Trp Phe Phe Ser Asn Tyr Leu Lys Arg Arg Val Val Phe Asn
        3155                3160                3165
Gly Val Ser Phe Ser Thr Phe Glu Glu Ala Ala Leu Cys Thr Phe
        3170                3175                3180
Leu Leu Asn Lys Glu Met Tyr Leu Lys Leu Arg Ser Asp Val Leu
        3185                3190                3195
Leu Pro Leu Thr Gln Tyr Asn Arg Tyr Leu Ala Leu Tyr Asn Lys
        3200                3205                3210
Tyr Lys Tyr Phe Ser Gly Ala Met Asp Thr Thr Ser Tyr Arg Glu
        3215                3220                3225
Ala Ala Cys Cys His Leu Ala Lys Ala Leu Asn Asp Phe Ser Asn
        3230                3235                3240
Ser Gly Ser Asp Val Leu Tyr Gln Pro Pro Gln Thr Ser Ile Thr
        3245                3250                3255
Ser Ala Val Leu Gln Ser Gly Phe Arg Lys Met Ala Phe Pro Ser
        3260                3265                3270
Gly Lys Val Glu Gly Cys Met Val Gln Val Thr Cys Gly Thr Thr
        3275                3280                3285
Thr Leu Asn Gly Leu Trp Leu Asp Asp Val Val Tyr Cys Pro Arg
        3290                3295                3300
His Val Ile Cys Thr Ser Glu Asp Met Leu Asn Pro Asn Tyr Glu
        3305                3310                3315
Asp Leu Leu Ile Arg Lys Ser Asn His Asn Phe Leu Val Gln Ala
        3320                3325                3330
Gly Asn Val Gln Leu Arg Val Ile Gly His Ser Met Gln Asn Cys
        3335                3340                3345
Val Leu Lys Leu Lys Val Asp Thr Ala Asn Pro Lys Thr Pro Lys
        3350                3355                3360
Tyr Lys Phe Val Arg Ile Gln Pro Gly Gln Thr Phe Ser Val Leu
        3365                3370                3375
Ala Cys Tyr Asn Gly Ser Pro Ser Gly Val Tyr Gln Cys Ala Met
        3380                3385                3390
Arg Pro Asn Phe Thr Ile Lys Gly Ser Phe Leu Asn Gly Ser Cys
        3395                3400                3405
Gly Ser Val Gly Phe Asn Ile Asp Tyr Asp Cys Val Ser Phe Cys
        3410                3415                3420
Tyr Met His His Met Glu Leu Pro Thr Gly Val His Ala Gly Thr
        3425                3430                3435
Asp Leu Glu Gly Asn Phe Tyr Gly Pro Phe Val Asp Arg Gln Thr
        3440                3445                3450
Ala Gln Ala Ala Gly Thr Asp Thr Thr Ile Thr Val Asn Val Leu
        3455                3460                3465
```

```
Ala Trp Leu Tyr Ala Ala Val Ile Asn Gly Asp Arg Trp Phe Leu
    3470                3475                3480

Asn Arg Phe Thr Thr Thr Leu Asn Asp Phe Asn Leu Val Ala Met
    3485                3490                3495

Lys Tyr Asn Tyr Glu Pro Leu Thr Gln Asp His Val Asp Ile Leu
    3500                3505                3510

Gly Pro Leu Ser Ala Gln Thr Gly Ile Ala Val Leu Asp Met Cys
    3515                3520                3525

Ala Ser Leu Lys Glu Leu Leu Gln Asn Gly Met Asn Gly Arg Thr
    3530                3535                3540

Ile Leu Gly Ser Ala Leu Leu Glu Asp Glu Phe Thr Pro Phe Asp
    3545                3550                3555

Val Val Arg Gln Cys Ser Gly Val Thr Phe Gln Ser Ala Val Lys
    3560                3565                3570

Arg Thr Ile Lys Gly Thr His His Trp Leu Leu Leu Thr Ile Leu
    3575                3580                3585

Thr Ser Leu Leu Val Leu Val Gln Ser Thr Gln Trp Ser Leu Phe
    3590                3595                3600

Phe Phe Phe Tyr Glu Asn Ala Phe Leu Pro Phe Ala Met Gly Ile
    3605                3610                3615

Ile Ala Met Ser Ala Phe Ala Met Met Phe Val Lys His Lys His
    3620                3625                3630

Ala Phe Leu Cys Leu Phe Leu Leu Pro Ser Leu Ala Thr Val Ala
    3635                3640                3645

Tyr Phe Asn Met Val Tyr Met Pro Ala Ser Trp Val Met Arg Ile
    3650                3655                3660

Met Thr Trp Leu Asp Met Val Ile Thr Ser Leu Ser Gly Phe Lys
    3665                3670                3675

Leu Lys Asp Cys Val Met Tyr Ala Ser Ala Val Val Leu Leu Ile
    3680                3685                3690

Leu Met Thr Ala Arg Thr Val Tyr Asp Asp Gly Ala Arg Arg Val
    3695                3700                3705

Trp Thr Leu Met Asn Val Leu Thr Leu Val Tyr Lys Val Tyr Tyr
    3710                3715                3720

Gly Asn Ala Leu Asp Gln Ala Ile Ser Met Trp Ala Leu Ile Ile
    3725                3730                3735

Ser Val Thr Ser Asn Tyr Ser Gly Val Val Thr Thr Val Met Phe
    3740                3745                3750

Leu Ala Arg Gly Ile Val Phe Met Cys Val Glu Tyr Cys Pro Ile
    3755                3760                3765

Phe Phe Ile Thr Gly Asn Thr Leu Gln Cys Ile Met Leu Val Tyr
    3770                3775                3780

Cys Phe Leu Gly Tyr Phe Cys Thr Cys Tyr Phe Gly Leu Phe Cys
    3785                3790                3795

Leu Leu Asn Arg Tyr Phe Arg Leu Thr Leu Gly Val Tyr Asp Tyr
    3800                3805                3810

Leu Val Ser Thr Gln Glu Phe Arg Tyr Met Asn Ser Gln Gly Leu
    3815                3820                3825

Leu Pro Pro Lys Asn Ser Ile Asp Ala Phe Lys Leu Asn Ile Lys
    3830                3835                3840

Leu Leu Gly Val Gly Gly Lys Pro Cys Ile Lys Val Ala Thr Val
    3845                3850                3855
```

```
Gln Ser Lys Met Ser Asp Val Lys Cys Thr Ser Val Val Leu Leu
3860             3865             3870

Ser Val Leu Gln Gln Leu Arg Val Glu Ser Ser Lys Leu Trp
3875             3880             3885

Ala Gln Cys Val Gln Leu His Asn Asp Ile Leu Leu Ala Lys Asp
3890             3895             3900

Thr Thr Glu Ala Phe Glu Lys Met Val Ser Leu Leu Ser Val Leu
3905             3910             3915

Leu Ser Met Gln Gly Ala Val Asp Ile Asn Lys Leu Cys Glu Glu
3920             3925             3930

Met Leu Asp Asn Arg Ala Thr Leu Gln Ala Ile Ala Ser Glu Phe
3935             3940             3945

Ser Ser Leu Pro Ser Tyr Ala Ala Phe Ala Thr Ala Gln Glu Ala
3950             3955             3960

Tyr Glu Gln Ala Val Ala Asn Gly Asp Ser Glu Val Val Leu Lys
3965             3970             3975

Lys Leu Lys Lys Ser Leu Asn Val Ala Lys Ser Glu Phe Asp Arg
3980             3985             3990

Asp Ala Ala Met Gln Arg Lys Leu Glu Lys Met Ala Asp Gln Ala
3995             4000             4005

Met Thr Gln Met Tyr Lys Gln Ala Arg Ser Glu Asp Lys Arg Ala
4010             4015             4020

Lys Val Thr Ser Ala Met Gln Thr Met Leu Phe Thr Met Leu Arg
4025             4030             4035

Lys Leu Asp Asn Asp Ala Leu Asn Asn Ile Ile Asn Asn Ala Arg
4040             4045             4050

Asp Gly Cys Val Pro Leu Asn Ile Ile Pro Leu Thr Thr Ala Ala
4055             4060             4065

Lys Leu Met Val Val Ile Pro Asp Tyr Asn Thr Tyr Lys Asn Thr
4070             4075             4080

Cys Asp Gly Thr Thr Phe Thr Tyr Ala Ser Ala Leu Trp Glu Ile
4085             4090             4095

Gln Gln Val Val Asp Ala Asp Ser Lys Ile Val Gln Leu Ser Glu
4100             4105             4110

Ile Ser Met Asp Asn Ser Pro Asn Leu Ala Trp Pro Leu Ile Val
4115             4120             4125

Thr Ala Leu Arg Ala Asn Ser Ala Val Lys Leu Gln Asn Asn Glu
4130             4135             4140

Leu Ser Pro Val Ala Leu Arg Gln Met Ser Cys Ala Ala Gly Thr
4145             4150             4155

Thr Gln Thr Ala Cys Thr Asp Asp Asn Ala Leu Ala Tyr Tyr Asn
4160             4165             4170

Thr Thr Lys Gly Gly Arg Phe Val Leu Ala Leu Leu Ser Asp Leu
4175             4180             4185

Gln Asp Leu Lys Trp Ala Arg Phe Pro Lys Ser Asp Gly Thr Gly
4190             4195             4200

Thr Ile Tyr Thr Glu Leu Glu Pro Pro Cys Arg Phe Val Thr Asp
4205             4210             4215

Thr Pro Lys Gly Pro Lys Val Lys Tyr Leu Tyr Phe Ile Lys Gly
4220             4225             4230

Leu Asn Asn Leu Asn Arg Gly Met Val Leu Gly Ser Leu Ala Ala
4235             4240             4245

Thr Val Arg Leu Gln Ala Gly Asn Ala Thr Glu Val Pro Ala Asn
```

```
                4250                    4255                    4260
Ser  Thr  Val  Leu  Ser  Phe  Cys  Ala  Phe  Ala  Val  Asp  Ala  Ala  Lys
                4265                    4270                    4275
Ala  Tyr  Lys  Asp  Tyr  Leu  Ala  Ser  Gly  Gly  Gln  Pro  Ile  Thr  Asn
                4280                    4285                    4290
Cys  Val  Lys  Met  Leu  Cys  Thr  His  Thr  Gly  Thr  Gly  Gln  Ala  Ile
                4295                    4300                    4305
Thr  Val  Thr  Pro  Glu  Ala  Asn  Met  Asp  Gln  Glu  Ser  Phe  Gly  Gly
                4310                    4315                    4320
Ala  Ser  Cys  Cys  Leu  Tyr  Cys  Arg  Cys  His  Ile  Asp  His  Pro  Asn
                4325                    4330                    4335
Pro  Lys  Gly  Phe  Cys  Asp  Leu  Lys  Gly  Lys  Tyr  Val  Gln  Ile  Pro
                4340                    4345                    4350
Thr  Thr  Cys  Ala  Asn  Asp  Pro  Val  Gly  Phe  Thr  Leu  Lys  Asn  Thr
                4355                    4360                    4365
Val  Cys  Thr  Val  Cys  Gly  Met  Trp  Lys  Gly  Tyr  Gly  Cys  Ser  Cys
                4370                    4375                    4380
Asp  Gln  Leu  Arg  Glu  Pro  Met  Leu  Gln  Ser  Ala  Asp  Ala  Gln  Ser
                4385                    4390                    4395
Phe  Leu  Asn  Arg  Val  Cys  Gly  Val  Ser  Ala  Ala  Arg  Leu  Thr  Pro
                4400                    4405                    4410
Cys  Gly  Thr  Gly  Thr  Ser  Thr  Asp  Val  Val  Tyr  Arg  Ala  Phe  Asp
                4415                    4420                    4425
Ile  Tyr  Asn  Asp  Lys  Val  Ala  Gly  Phe  Ala  Lys  Phe  Leu  Lys  Thr
                4430                    4435                    4440
Asn  Cys  Cys  Arg  Phe  Gln  Glu  Lys  Asp  Glu  Asp  Asp  Asn  Leu  Ile
                4445                    4450                    4455
Asp  Ser  Tyr  Phe  Val  Val  Lys  Arg  His  Thr  Phe  Ser  Asn  Tyr  Gln
                4460                    4465                    4470
His  Glu  Glu  Thr  Ile  Tyr  Asn  Leu  Leu  Lys  Asp  Cys  Pro  Ala  Val
                4475                    4480                    4485
Ala  Lys  His  Asp  Phe  Phe  Lys  Phe  Arg  Ile  Asp  Gly  Asp  Met  Val
                4490                    4495                    4500
Pro  His  Ile  Ser  Arg  Gln  Arg  Leu  Thr  Lys  Tyr  Thr  Met  Ala  Asp
                4505                    4510                    4515
Leu  Val  Tyr  Ala  Leu  Arg  His  Phe  Asp  Glu  Gly  Asn  Cys  Asp  Thr
                4520                    4525                    4530
Leu  Lys  Glu  Ile  Leu  Val  Thr  Tyr  Asn  Cys  Cys  Asp  Asp  Asp  Tyr
                4535                    4540                    4545
Phe  Asn  Lys  Lys  Asp  Trp  Tyr  Asp  Phe  Val  Glu  Asn  Pro  Asp  Ile
                4550                    4555                    4560
Leu  Arg  Val  Tyr  Ala  Asn  Leu  Gly  Glu  Arg  Val  Arg  Gln  Ala  Leu
                4565                    4570                    4575
Leu  Lys  Thr  Val  Gln  Phe  Cys  Asp  Ala  Met  Arg  Asn  Ala  Gly  Ile
                4580                    4585                    4590
Val  Gly  Val  Leu  Thr  Leu  Asp  Asn  Gln  Asp  Leu  Asn  Gly  Asn  Arg
                4595                    4600                    4605
Tyr  Asp  Phe  Gly  Asp  Phe  Ile  Gln  Thr  Thr  Pro  Gly  Ser  Gly  Val
                4610                    4615                    4620
Pro  Val  Val  Asp  Ser  Tyr  Tyr  Ser  Leu  Leu  Met  Pro  Ile  Leu  Thr
                4625                    4630                    4635
Leu  Thr  Arg  Ala  Leu  Thr  Ala  Glu  Ser  His  Val  Asp  Thr  Asp  Leu
                4640                    4645                    4650
```

```
Thr Lys Pro Tyr Ile Lys Trp Asp Leu Leu Lys Tyr Asp Phe Thr
    4655            4660                4665

Glu Glu Arg Leu Lys Leu Phe Asp Arg Tyr Phe Lys Tyr Trp Asp
    4670            4675                4680

Gln Thr Tyr His Pro Asn Cys Val Asn Cys Leu Asp Asp Arg Cys
    4685            4690                4695

Ile Leu His Cys Ala Asn Phe Asn Val Leu Phe Ser Thr Val Phe
    4700            4705                4710

Pro Pro Thr Ser Phe Gly Pro Leu Val Arg Lys Ile Phe Val Asp
    4715            4720                4725

Gly Val Pro Phe Val Val Ser Thr Gly Tyr His Phe Arg Glu Leu
    4730            4735                4740

Gly Val Val His Asn Gln Asp Val Asn Leu His Ser Ser Arg Leu
    4745            4750                4755

Ser Phe Lys Glu Leu Leu Val Tyr Ala Ala Asp Pro Ala Met His
    4760            4765                4770

Ala Ala Ser Gly Asn Leu Leu Leu Asp Lys Arg Thr Thr Cys Phe
    4775            4780                4785

Ser Val Ala Ala Leu Thr Asn Asn Val Ala Phe Gln Thr Val Lys
    4790            4795                4800

Pro Gly Ser Phe Asn Lys Asp Phe Tyr Asp Phe Ala Val Ser Lys
    4805            4810                4815

Gly Phe Phe Lys Glu Gly Ser Ser Val Glu Leu Lys His Phe Phe
    4820            4825                4830

Phe Ala Gln Asp Gly Asn Ala Ala Ile Ser Asp Tyr Asp Tyr Tyr
    4835            4840                4845

Arg Tyr Asn Leu Pro Thr Met Cys Asp Ile Arg Gln Leu Leu Phe
    4850            4855                4860

Val Val Glu Val Val Asp Lys Tyr Phe Asp Cys Tyr Asp Gly Gly
    4865            4870                4875

Cys Ile Asn Ala Asn Gln Val Ile Val Asn Asn Leu Asp Lys Ser
    4880            4885                4890

Ala Gly Phe Pro Phe Asn Lys Trp Gly Lys Ala Arg Leu Tyr Tyr
    4895            4900                4905

Asp Ser Met Ser Tyr Glu Asp Gln Asp Ala Leu Phe Ala Tyr Thr
    4910            4915                4920

Lys Arg Asn Val Ile Pro Thr Ile Thr Gln Met Asn Leu Lys Tyr
    4925            4930                4935

Ala Ile Ser Ala Lys Asn Arg Ala Arg Thr Val Ala Gly Val Ser
    4940            4945                4950

Ile Cys Ser Thr Met Thr Asn Arg Gln Phe His Gln Lys Leu Leu
    4955            4960                4965

Lys Ser Ile Ala Ala Thr Arg Gly Ala Thr Val Val Ile Gly Thr
    4970            4975                4980

Ser Lys Phe Tyr Gly Gly Trp His Asn Met Leu Lys Thr Val Tyr
    4985            4990                4995

Ser Asp Val Glu Asn Pro His Leu Met Gly Trp Asp Tyr Pro Lys
    5000            5005                5010

Cys Asp Arg Ala Met Pro Asn Met Leu Arg Ile Met Ala Ser Leu
    5015            5020                5025

Val Leu Ala Arg Lys His Thr Thr Cys Cys Ser Leu Ser His Arg
    5030            5035                5040
```

```
Phe Tyr Arg Leu Ala Asn Glu Cys Ala Gln Val Leu Ser Glu Met
    5045                5050                5055

Val Met Cys Gly Gly Ser Leu Tyr Val Lys Pro Gly Gly Thr Ser
    5060                5065                5070

Ser Gly Asp Ala Thr Thr Ala Tyr Ala Asn Ser Val Phe Asn Ile
    5075                5080                5085

Cys Gln Ala Val Thr Ala Asn Val Asn Ala Leu Leu Ser Thr Asp
    5090                5095                5100

Gly Asn Lys Ile Ala Asp Lys Tyr Val Arg Asn Leu Gln His Arg
    5105                5110                5115

Leu Tyr Glu Cys Leu Tyr Arg Asn Arg Asp Val Asp Thr Asp Phe
    5120                5125                5130

Val Asn Glu Phe Tyr Ala Tyr Leu Arg Lys His Phe Ser Met Met
    5135                5140                5145

Ile Leu Ser Asp Asp Ala Ala Val Cys Phe Asn Ser Thr Tyr Ala
    5150                5155                5160

Ser Gln Gly Leu Val Ala Ser Ile Lys Asn Phe Lys Ser Val Leu
    5165                5170                5175

Tyr Tyr Gln Asn Asn Val Phe Met Ser Glu Ala Lys Cys Trp Thr
    5180                5185                5190

Glu Thr Asp Leu Thr Lys Gly Pro His Glu Phe Cys Ser Gln His
    5195                5200                5205

Thr Met Leu Val Lys Gln Gly Asp Asp Tyr Val Tyr Leu Pro Tyr
    5210                5215                5220

Pro Asp Pro Ser Arg Ile Leu Gly Ala Gly Cys Phe Val Asp Asp
    5225                5230                5235

Ile Val Lys Thr Asp Gly Thr Leu Met Ile Glu Arg Phe Val Ser
    5240                5245                5250

Leu Ala Ile Asp Ala Tyr Pro Leu Thr Lys His Pro Asn Gln Glu
    5255                5260                5265

Tyr Ala Asp Val Phe His Leu Tyr Leu Gln Tyr Ile Arg Lys Leu
    5270                5275                5280

His Asp Glu Leu Thr Gly His Met Leu Asp Met Tyr Ser Val Met
    5285                5290                5295

Leu Thr Asn Asp Asn Thr Ser Arg Tyr Trp Glu Pro Glu Phe Tyr
    5300                5305                5310

Glu Ala Met Tyr Thr Pro His Thr Val Leu Gln Ala Val Gly Ala
    5315                5320                5325

Cys Val Leu Cys Asn Ser Gln Thr Ser Leu Arg Cys Gly Ala Cys
    5330                5335                5340

Ile Arg Arg Pro Phe Leu Cys Cys Lys Cys Cys Tyr Asp His Val
    5345                5350                5355

Ile Ser Thr Ser His Lys Leu Val Leu Ser Val Asn Pro Tyr Val
    5360                5365                5370

Cys Asn Ala Pro Gly Cys Asp Val Thr Asp Val Thr Gln Leu Tyr
    5375                5380                5385

Leu Gly Gly Met Ser Tyr Tyr Cys Lys Ser His Lys Pro Pro Ile
    5390                5395                5400

Ser Phe Pro Leu Cys Ala Asn Gly Gln Val Phe Gly Leu Tyr Lys
    5405                5410                5415

Asn Thr Cys Val Gly Ser Asp Asn Val Thr Asp Phe Asn Ala Ile
    5420                5425                5430

Ala Thr Cys Asp Trp Thr Asn Ala Gly Asp Tyr Ile Leu Ala Asn
```

```
                5435                5440                5445
Thr Cys Thr Glu Arg Leu Lys Leu Phe Ala Ala Glu Thr Leu Lys
        5450                5455                5460
Ala Thr Glu Glu Thr Phe Lys Leu Ser Tyr Gly Ile Ala Thr Val
        5465                5470                5475
Arg Glu Val Leu Ser Asp Arg Glu Leu His Leu Ser Trp Glu Val
        5480                5485                5490
Gly Lys Pro Arg Pro Leu Asn Arg Asn Tyr Val Phe Thr Gly
        5495                5500                5505
Tyr Arg Val Thr Lys Asn Ser Lys Val Gln Ile Gly Glu Tyr Thr
        5510                5515                5520
Phe Glu Lys Gly Asp Tyr Gly Asp Ala Val Val Tyr Arg Gly Thr
        5525                5530                5535
Thr Thr Tyr Lys Leu Asn Val Gly Asp Tyr Phe Val Leu Thr Ser
        5540                5545                5550
His Thr Val Met Pro Leu Ser Ala Pro Thr Leu Val Pro Gln Glu
        5555                5560                5565
His Tyr Val Arg Ile Thr Gly Leu Tyr Pro Thr Leu Asn Ile Ser
        5570                5575                5580
Asp Glu Phe Ser Ser Asn Val Ala Asn Tyr Gln Lys Val Gly Met
        5585                5590                5595
Gln Lys Tyr Ser Thr Leu Gln Gly Pro Pro Gly Thr Gly Lys Ser
        5600                5605                5610
His Phe Ala Ile Gly Leu Ala Leu Tyr Tyr Pro Ser Ala Arg Ile
        5615                5620                5625
Val Tyr Thr Ala Cys Ser His Ala Ala Val Asp Ala Leu Cys Glu
        5630                5635                5640
Lys Ala Leu Lys Tyr Leu Pro Ile Asp Lys Cys Ser Arg Ile Ile
        5645                5650                5655
Pro Ala Arg Ala Arg Val Glu Cys Phe Asp Lys Phe Lys Val Asn
        5660                5665                5670
Ser Thr Leu Glu Gln Tyr Val Phe Cys Thr Val Asn Ala Leu Pro
        5675                5680                5685
Glu Thr Thr Ala Asp Ile Val Val Phe Asp Glu Ile Ser Met Ala
        5690                5695                5700
Thr Asn Tyr Asp Leu Ser Val Val Asn Ala Arg Leu Arg Ala Lys
        5705                5710                5715
His Tyr Val Tyr Ile Gly Asp Pro Ala Gln Leu Pro Ala Pro Arg
        5720                5725                5730
Thr Leu Leu Thr Lys Gly Thr Leu Glu Pro Glu Tyr Phe Asn Ser
        5735                5740                5745
Val Cys Arg Leu Met Lys Thr Ile Gly Pro Asp Met Phe Leu Gly
        5750                5755                5760
Thr Cys Arg Arg Cys Pro Ala Glu Ile Val Asp Thr Val Ser Ala
        5765                5770                5775
Leu Val Tyr Asp Asn Lys Leu Lys Ala His Lys Asp Lys Ser Ala
        5780                5785                5790
Gln Cys Phe Lys Met Phe Tyr Lys Gly Val Ile Thr His Asp Val
        5795                5800                5805
Ser Ser Ala Ile Asn Arg Pro Gln Ile Gly Val Val Arg Glu Phe
        5810                5815                5820
Leu Thr Arg Asn Pro Ala Trp Arg Lys Ala Val Phe Ile Ser Pro
        5825                5830                5835
```

-continued

```
Tyr Asn Ser Gln Asn Ala Val Ala Ser Lys Val Leu Gly Leu Pro
5840                5845                5850

Thr Gln Thr Val Asp Ser Ser Gln Gly Ser Glu Tyr Asp Tyr Val
5855                5860                5865

Ile Phe Thr Gln Thr Thr Glu Thr Ala His Ser Cys Asn Val Asn
5870                5875                5880

Arg Phe Asn Val Ala Ile Thr Arg Ala Lys Val Gly Ile Leu Cys
5885                5890                5895

Ile Met Ser Asp Arg Asp Leu Tyr Asp Lys Leu Gln Phe Thr Ser
5900                5905                5910

Leu Glu Ile Pro Arg Arg Asn Val Ala Thr Leu Gln Ala Glu Asn
5915                5920                5925

Val Thr Gly Leu Phe Lys Asp Cys Ser Lys Val Ile Thr Gly Leu
5930                5935                5940

His Pro Thr Gln Ala Pro Thr His Leu Ser Val Asp Thr Lys Phe
5945                5950                5955

Lys Thr Glu Gly Leu Cys Val Asp Ile Pro Gly Ile Pro Lys Asp
5960                5965                5970

Met Thr Tyr Arg Arg Leu Ile Ser Met Met Gly Phe Lys Met Asn
5975                5980                5985

Tyr Gln Val Asn Gly Tyr Pro Asn Met Phe Ile Thr Arg Glu Glu
5990                5995                6000

Ala Ile Arg His Val Arg Ala Trp Ile Gly Phe Asp Val Glu Gly
6005                6010                6015

Cys His Ala Thr Arg Glu Ala Val Gly Thr Asn Leu Pro Leu Gln
6020                6025                6030

Leu Gly Phe Ser Thr Gly Val Asn Leu Val Ala Val Pro Thr Gly
6035                6040                6045

Tyr Val Asp Thr Pro Asn Asn Thr Asp Phe Ser Arg Val Ser Ala
6050                6055                6060

Lys Pro Pro Pro Gly Asp Gln Phe Lys His Leu Ile Pro Leu Met
6065                6070                6075

Tyr Lys Gly Leu Pro Trp Asn Val Val Arg Ile Lys Ile Val Gln
6080                6085                6090

Met Leu Ser Asp Thr Leu Lys Asn Leu Ser Asp Arg Val Val Phe
6095                6100                6105

Val Leu Trp Ala His Gly Phe Glu Leu Thr Ser Met Lys Tyr Phe
6110                6115                6120

Val Lys Ile Gly Pro Glu Arg Thr Cys Cys Leu Cys Asp Arg Arg
6125                6130                6135

Ala Thr Cys Phe Ser Thr Ala Ser Asp Thr Tyr Ala Cys Trp His
6140                6145                6150

His Ser Ile Gly Phe Asp Tyr Val Tyr Asn Pro Phe Met Ile Asp
6155                6160                6165

Val Gln Gln Trp Gly Phe Thr Gly Asn Leu Gln Ser Asn His Asp
6170                6175                6180

Leu Tyr Cys Gln Val His Gly Asn Ala His Val Ala Ser Cys Asp
6185                6190                6195

Ala Ile Met Thr Arg Cys Leu Ala Val His Glu Cys Phe Val Lys
6200                6205                6210

Arg Val Asp Trp Thr Ile Glu Tyr Pro Ile Ile Gly Asp Glu Leu
6215                6220                6225
```

-continued

Lys Ile Asn Ala Ala Cys Arg Lys Val Gln His Met Val Val Lys
6230                    6235                6240

Ala Ala Leu Leu Ala Asp Lys Phe Pro Val Leu His Asp Ile Gly
6245                    6250                6255

Asn Pro Lys Ala Ile Lys Cys Val Pro Gln Ala Asp Val Glu Trp
6260                    6265                6270

Lys Phe Tyr Asp Ala Gln Pro Cys Ser Asp Lys Ala Tyr Lys Ile
6275                    6280                6285

Glu Glu Leu Phe Tyr Ser Tyr Ala Thr His Ser Asp Lys Phe Thr
6290                    6295                6300

Asp Gly Val Cys Leu Phe Trp Asn Cys Asn Val Asp Arg Tyr Pro
6305                    6310                6315

Ala Asn Ser Ile Val Cys Arg Phe Asp Thr Arg Val Leu Ser Asn
6320                    6325                6330

Leu Asn Leu Pro Gly Cys Asp Gly Gly Ser Leu Tyr Val Asn Lys
6335                    6340                6345

His Ala Phe His Thr Pro Ala Phe Asp Lys Ser Ala Phe Val Asn
6350                    6355                6360

Leu Lys Gln Leu Pro Phe Phe Tyr Tyr Ser Asp Ser Pro Cys Glu
6365                    6370                6375

Ser His Gly Lys Gln Val Val Ser Asp Ile Asp Tyr Val Pro Leu
6380                    6385                6390

Lys Ser Ala Thr Cys Ile Thr Arg Cys Asn Leu Gly Gly Ala Val
6395                    6400                6405

Cys Arg His His Ala Asn Glu Tyr Arg Leu Tyr Leu Asp Ala Tyr
6410                    6415                6420

Asn Met Met Ile Ser Ala Gly Phe Ser Leu Trp Val Tyr Lys Gln
6425                    6430                6435

Phe Asp Thr Tyr Asn Leu Trp Asn Thr Phe Thr Arg Leu Gln Ser
6440                    6445                6450

Leu Glu Asn Val Ala Phe Asn Val Val Asn Lys Gly His Phe Asp
6455                    6460                6465

Gly Gln Gln Gly Glu Val Pro Val Ser Ile Ile Asn Asn Thr Val
6470                    6475                6480

Tyr Thr Lys Val Asp Gly Val Asp Val Glu Leu Phe Glu Asn Lys
6485                    6490                6495

Thr Thr Leu Pro Val Asn Val Ala Phe Glu Leu Trp Ala Lys Arg
6500                    6505                6510

Asn Ile Lys Pro Val Pro Glu Val Lys Ile Leu Asn Asn Leu Gly
6515                    6520                6525

Val Asp Ile Ala Ala Asn Thr Val Ile Trp Asp Tyr Lys Arg Asp
6530                    6535                6540

Ala Pro Ala His Ile Ser Thr Ile Gly Val Cys Ser Met Thr Asp
6545                    6550                6555

Ile Ala Lys Lys Pro Thr Glu Thr Ile Cys Ala Pro Leu Thr Val
6560                    6565                6570

Phe Phe Asp Gly Arg Val Asp Gly Gln Val Asp Leu Phe Arg Asn
6575                    6580                6585

Ala Arg Asn Gly Val Leu Ile Thr Glu Gly Ser Val Lys Gly Leu
6590                    6595                6600

Gln Pro Ser Val Gly Pro Lys Gln Ala Ser Leu Asn Gly Val Thr
6605                    6610                6615

Leu Ile Gly Glu Ala Val Lys Thr Gln Phe Asn Tyr Tyr Lys Lys

```
                    6620                6625                6630

Val Asp Gly Val Val Gln Gln Leu Pro Glu Thr Tyr Phe Thr Gln
        6635                6640                6645

Ser Arg Asn Leu Gln Glu Phe Lys Pro Arg Ser Gln Met Glu Ile
        6650                6655                6660

Asp Phe Leu Glu Leu Ala Met Asp Glu Phe Ile Glu Arg Tyr Lys
        6665                6670                6675

Leu Glu Gly Tyr Ala Phe Glu His Ile Val Tyr Gly Asp Phe Ser
        6680                6685                6690

His Ser Gln Leu Gly Gly Leu His Leu Leu Ile Gly Leu Ala Lys
        6695                6700                6705

Arg Phe Lys Glu Ser Pro Phe Glu Leu Glu Asp Phe Ile Pro Met
        6710                6715                6720

Asp Ser Thr Val Lys Asn Tyr Phe Ile Thr Asp Ala Gln Thr Gly
        6725                6730                6735

Ser Ser Lys Cys Val Cys Ser Val Ile Asp Leu Leu Leu Asp Asp
        6740                6745                6750

Phe Val Glu Ile Ile Lys Ser Gln Asp Leu Ser Val Val Ser Lys
        6755                6760                6765

Val Val Lys Val Thr Ile Asp Tyr Thr Glu Ile Ser Phe Met Leu
        6770                6775                6780

Trp Cys Lys Asp Gly His Val Glu Thr Phe Tyr Pro Lys Leu Gln
        6785                6790                6795

Ser Ser Gln Ala Trp Gln Pro Gly Val Ala Met Pro Asn Leu Tyr
        6800                6805                6810

Lys Met Gln Arg Met Leu Leu Glu Lys Cys Asp Leu Gln Asn Tyr
        6815                6820                6825

Gly Asp Ser Ala Thr Leu Pro Lys Gly Ile Met Met Asn Val Ala
        6830                6835                6840

Lys Tyr Thr Gln Leu Cys Gln Tyr Leu Asn Thr Leu Thr Leu Ala
        6845                6850                6855

Val Pro Tyr Asn Met Arg Val Ile His Phe Gly Ala Gly Ser Asp
        6860                6865                6870

Lys Gly Val Ala Pro Gly Thr Ala Val Leu Arg Gln Trp Leu Pro
        6875                6880                6885

Thr Gly Thr Leu Leu Val Asp Ser Asp Leu Asn Asp Phe Val Ser
        6890                6895                6900

Asp Ala Asp Ser Thr Leu Ile Gly Asp Cys Ala Thr Val His Thr
        6905                6910                6915

Ala Asn Lys Trp Asp Leu Ile Ile Ser Asp Met Tyr Asp Pro Lys
        6920                6925                6930

Thr Lys Asn Val Thr Lys Glu Asn Asp Ser Lys Glu Gly Phe Phe
        6935                6940                6945

Thr Tyr Ile Cys Gly Phe Ile Gln Gln Lys Leu Ala Leu Gly Gly
        6950                6955                6960

Ser Val Ala Ile Lys Ile Thr Glu His Ser Trp Asn Ala Asp Leu
        6965                6970                6975

Tyr Lys Leu Met Gly His Phe Ala Trp Trp Thr Ala Phe Val Thr
        6980                6985                6990

Asn Val Asn Ala Ser Ser Ser Glu Ala Phe Leu Ile Gly Cys Asn
        6995                7000                7005

Tyr Leu Gly Lys Pro Arg Glu Gln Ile Asp Gly Tyr Val Met His
        7010                7015                7020
```

```
Ala Asn Tyr Ile Phe Trp Arg Asn Thr Asn Pro Ile Gln Leu Cys
    7025            7030            7035

Ser Tyr Ser Leu Phe Asp Met Ser Lys Phe Pro Leu Lys Leu Arg
    7040            7045            7050

Gly Thr Ala Val Met Pro Leu Lys Glu Gly Gln Ile Asn Asp Met
    7055            7060            7065

Ile Leu Ser Leu Leu Ser Lys Gly Arg Leu Ile Ile Arg Glu Asn
    7070            7075            7080

Asn Arg Val Val Ile Ser Ser Asp Val Leu Val Asn Asn
    7085            7090            7095

<210> SEQ ID NO 26
<211> LENGTH: 4405
<212> TYPE: PRT
<213> ORGANISM: Unknown
<220> FEATURE:
<223> OTHER INFORMATION: SARS-CoV-2 ORF1a polyprotein

<400> SEQUENCE: 26

Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
        115                 120                 125

Lys Gly Ala Gly Gly His Ser Tyr Gly Ala Asp Leu Lys Ser Phe Asp
    130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
        195                 200                 205

Gly Lys Ala Ser Cys Thr Leu Ser Glu Gln Leu Asp Phe Ile Asp Thr
    210                 215                 220

Lys Arg Gly Val Tyr Cys Cys Arg Gly His Glu His Glu Ile Ala Trp
225                 230                 235                 240

Tyr Thr Glu Arg Ser Glu Lys Ser Tyr Glu Leu Gln Thr Pro Phe Glu
                245                 250                 255

Ile Lys Leu Ala Lys Lys Phe Asp Thr Phe Asn Gly Glu Cys Pro Asn
            260                 265                 270

Phe Val Phe Pro Leu Asn Ser Ile Ile Lys Thr Ile Gln Pro Arg Val
        275                 280                 285
```

```
Glu Lys Lys Lys Leu Asp Gly Phe Met Gly Arg Ile Arg Ser Val Tyr
    290             295             300

Pro Val Ala Ser Pro Asn Glu Cys Asn Gln Met Cys Leu Ser Thr Leu
305             310             315             320

Met Lys Cys Asp His Cys Gly Glu Thr Ser Trp Gln Thr Gly Asp Phe
            325             330             335

Val Lys Ala Thr Cys Glu Phe Cys Gly Thr Glu Asn Leu Thr Lys Glu
            340             345             350

Gly Ala Thr Thr Cys Gly Tyr Leu Pro Gln Asn Ala Val Val Lys Ile
            355             360             365

Tyr Cys Pro Ala Cys His Asn Ser Glu Val Gly Pro Glu His Ser Leu
    370             375             380

Ala Glu Tyr His Asn Glu Ser Gly Leu Lys Thr Ile Leu Arg Lys Gly
385             390             395             400

Gly Arg Thr Ile Ala Phe Gly Gly Cys Val Phe Ser Tyr Val Gly Cys
                405             410             415

His Asn Lys Cys Ala Tyr Trp Val Pro Arg Ala Ser Ala Asn Ile Gly
            420             425             430

Cys Asn His Thr Gly Val Val Gly Glu Gly Ser Glu Gly Leu Asn Asp
            435             440             445

Asn Leu Leu Glu Ile Leu Gln Lys Glu Lys Val Asn Ile Asn Ile Val
    450             455             460

Gly Asp Phe Lys Leu Asn Glu Glu Ile Ala Ile Ile Leu Ala Ser Phe
465             470             475             480

Ser Ala Ser Thr Ser Ala Phe Val Glu Thr Val Lys Gly Leu Asp Tyr
                485             490             495

Lys Ala Phe Lys Gln Ile Val Glu Ser Cys Gly Asn Phe Lys Val Thr
            500             505             510

Lys Gly Lys Ala Lys Lys Gly Ala Trp Asn Ile Gly Glu Gln Lys Ser
            515             520             525

Ile Leu Ser Pro Leu Tyr Ala Phe Ala Ser Glu Ala Ala Arg Val Val
    530             535             540

Arg Ser Ile Phe Ser Arg Thr Leu Glu Thr Ala Gln Asn Ser Val Arg
545             550             555             560

Val Leu Gln Lys Ala Ala Ile Thr Ile Leu Asp Gly Ile Ser Gln Tyr
            565             570             575

Ser Leu Arg Leu Ile Asp Ala Met Met Phe Thr Ser Asp Leu Ala Thr
            580             585             590

Asn Asn Leu Val Val Met Ala Tyr Ile Thr Gly Gly Val Val Gln Leu
    595             600             605

Thr Ser Gln Trp Leu Thr Asn Ile Phe Gly Thr Val Tyr Glu Lys Leu
610             615             620

Lys Pro Val Leu Asp Trp Leu Glu Glu Lys Phe Lys Glu Gly Val Glu
625             630             635             640

Phe Leu Arg Asp Gly Trp Glu Ile Val Lys Phe Ile Ser Thr Cys Ala
            645             650             655

Cys Glu Ile Val Gly Gly Gln Ile Val Thr Cys Ala Lys Glu Ile Lys
            660             665             670

Glu Ser Val Gln Thr Phe Phe Lys Leu Val Asn Lys Phe Leu Ala Leu
    675             680             685

Cys Ala Asp Ser Ile Ile Ile Gly Gly Ala Lys Leu Lys Ala Leu Asn
690             695             700
```

```
Leu Gly Glu Thr Phe Thr His Ser Lys Gly Leu Tyr Arg Lys Cys
705                 710                 715                 720

Val Lys Ser Arg Glu Glu Thr Gly Leu Leu Met Pro Leu Lys Ala Pro
            725                 730                 735

Lys Glu Ile Ile Phe Leu Glu Gly Glu Thr Leu Pro Thr Glu Val Leu
                740                 745                 750

Thr Glu Glu Val Val Leu Lys Thr Gly Asp Leu Gln Pro Leu Glu Gln
                755                 760                 765

Pro Thr Ser Glu Ala Val Glu Ala Pro Leu Val Gly Thr Pro Val Cys
            770                 775                 780

Ile Asn Gly Leu Met Leu Leu Glu Ile Lys Asp Thr Glu Lys Tyr Cys
785                 790                 795                 800

Ala Leu Ala Pro Asn Met Met Val Thr Asn Asn Thr Phe Thr Leu Lys
            805                 810                 815

Gly Gly Ala Pro Thr Lys Val Thr Phe Gly Asp Asp Thr Val Ile Glu
            820                 825                 830

Val Gln Gly Tyr Lys Ser Val Asn Ile Thr Phe Glu Leu Asp Glu Arg
            835                 840                 845

Ile Asp Lys Val Leu Asn Glu Lys Cys Ser Ala Tyr Thr Val Glu Leu
850                 855                 860

Gly Thr Glu Val Asn Glu Phe Ala Cys Val Val Ala Asp Ala Val Ile
865                 870                 875                 880

Lys Thr Leu Gln Pro Val Ser Glu Leu Leu Thr Pro Leu Gly Ile Asp
            885                 890                 895

Leu Asp Glu Trp Ser Met Ala Thr Tyr Tyr Leu Phe Asp Ser Gly
            900                 905                 910

Glu Phe Lys Leu Ala Ser His Met Tyr Cys Ser Phe Tyr Pro Pro Asp
            915                 920                 925

Glu Asp Glu Glu Glu Gly Asp Cys Glu Glu Glu Glu Phe Glu Pro Ser
            930                 935                 940

Thr Gln Tyr Glu Tyr Gly Thr Glu Asp Asp Tyr Gln Gly Lys Pro Leu
945                 950                 955                 960

Glu Phe Gly Ala Thr Ser Ala Ala Leu Gln Pro Glu Glu Glu Gln Glu
                965                 970                 975

Glu Asp Trp Leu Asp Asp Asp Ser Gln Gln Thr Val Gly Gln Gln Asp
            980                 985                 990

Gly Ser Glu Asp Asn Gln Thr Thr Ile Gln Thr Ile Val Glu Val
            995                1000                1005

Gln Pro Gln Leu Glu Met Glu Leu Thr Pro Val Val Gln Thr Ile
    1010                1015                1020

Glu Val Asn Ser Phe Ser Gly Tyr Leu Lys Leu Thr Asp Asn Val
    1025                1030                1035

Tyr Ile Lys Asn Ala Asp Ile Val Glu Glu Ala Lys Lys Val Lys
    1040                1045                1050

Pro Thr Val Val Val Asn Ala Ala Asn Val Tyr Leu Lys His Gly
    1055                1060                1065

Gly Gly Val Ala Gly Ala Leu Asn Lys Ala Thr Asn Asn Ala Met
    1070                1075                1080

Gln Val Glu Ser Asp Asp Tyr Ile Ala Thr Asn Gly Pro Leu Lys
    1085                1090                1095

Val Gly Gly Ser Cys Val Leu Ser Gly His Asn Leu Ala Lys His
    1100                1105                1110

Cys Leu His Val Val Gly Pro Asn Val Asn Lys Gly Glu Asp Ile
```

-continued

```
                1115                1120                1125

Gln Leu Leu Lys Ser Ala Tyr Glu Asn Phe Asn Gln His Glu Val
        1130                1135                1140

Leu Leu Ala Pro Leu Leu Ser Ala Gly Ile Phe Gly Ala Asp Pro
        1145                1150                1155

Ile His Ser Leu Arg Val Cys Val Asp Thr Val Arg Thr Asn Val
        1160                1165                1170

Tyr Leu Ala Val Phe Asp Lys Asn Leu Tyr Asn Lys Leu Val Ser
        1175                1180                1185

Ser Phe Leu Glu Met Lys Ser Glu Lys Gln Val Glu Gln Lys Ile
        1190                1195                1200

Ala Glu Ile Pro Lys Glu Glu Val Lys Pro Phe Ile Thr Glu Ser
        1205                1210                1215

Lys Pro Ser Val Glu Gln Arg Lys Gln Asp Asp Lys Lys Ile Lys
        1220                1225                1230

Ala Cys Val Glu Glu Val Thr Thr Thr Leu Glu Glu Thr Lys Phe
        1235                1240                1245

Leu Thr Glu Asn Leu Leu Leu Tyr Ile Asp Ile Asn Gly Asn Leu
        1250                1255                1260

His Pro Asp Ser Ala Thr Leu Val Ser Asp Ile Asp Ile Thr Phe
        1265                1270                1275

Leu Lys Lys Asp Ala Pro Tyr Ile Val Gly Asp Val Val Gln Glu
        1280                1285                1290

Gly Val Leu Thr Ala Val Val Ile Pro Thr Lys Lys Ala Gly Gly
        1295                1300                1305

Thr Thr Glu Met Leu Ala Lys Ala Leu Arg Lys Val Pro Thr Asp
        1310                1315                1320

Asn Tyr Ile Thr Thr Tyr Pro Gly Gln Gly Leu Asn Gly Tyr Thr
        1325                1330                1335

Val Glu Glu Ala Lys Thr Val Leu Lys Lys Cys Lys Ser Ala Phe
        1340                1345                1350

Tyr Ile Leu Pro Ser Ile Ile Ser Asn Glu Lys Gln Glu Ile Leu
        1355                1360                1365

Gly Thr Val Ser Trp Asn Leu Arg Glu Met Leu Ala His Ala Glu
        1370                1375                1380

Glu Thr Arg Lys Leu Met Pro Val Cys Val Glu Thr Lys Ala Ile
        1385                1390                1395

Val Ser Thr Ile Gln Arg Lys Tyr Lys Gly Ile Lys Ile Gln Glu
        1400                1405                1410

Gly Val Val Asp Tyr Gly Ala Arg Phe Tyr Phe Tyr Thr Ser Lys
        1415                1420                1425

Thr Thr Val Ala Ser Leu Ile Asn Thr Leu Asn Asp Leu Asn Glu
        1430                1435                1440

Thr Leu Val Thr Met Pro Leu Gly Tyr Val Thr His Gly Leu Asn
        1445                1450                1455

Leu Glu Glu Ala Ala Arg Tyr Met Arg Ser Leu Lys Val Pro Ala
        1460                1465                1470

Thr Val Ser Val Ser Ser Pro Asp Ala Val Thr Ala Tyr Asn Gly
        1475                1480                1485

Tyr Leu Thr Ser Ser Ser Lys Thr Pro Glu Glu His Phe Ile Glu
        1490                1495                1500

Thr Ile Ser Leu Ala Gly Ser Tyr Lys Asp Trp Ser Tyr Ser Gly
        1505                1510                1515
```

```
Gln Ser Thr Gln Leu Gly Ile Glu Phe Leu Lys Arg Gly Asp Lys
    1520                1525                1530

Ser Val Tyr Tyr Thr Ser Asn Pro Thr Phe His Leu Asp Gly
    1535                1540                1545

Glu Val Ile Thr Phe Asp Asn Leu Lys Thr Leu Leu Ser Leu Arg
    1550                1555                1560

Glu Val Arg Thr Ile Lys Val Phe Thr Thr Val Asp Asn Ile Asn
    1565                1570                1575

Leu His Thr Gln Val Val Gly Met Ser Met Thr Tyr Gly Gln Gln
    1580                1585                1590

Phe Gly Pro Thr Tyr Phe Asp Gly Ala Asp Val Thr Lys Ile Lys
    1595                1600                1605

Pro His Asn Ser His Glu Gly Lys Thr Phe Tyr Val Leu Pro Asn
    1610                1615                1620

Asp Asp Thr Leu Arg Val Glu Ala Phe Glu Tyr Tyr His Thr Thr
    1625                1630                1635

Asp Pro Ser Phe Leu Gly Arg Tyr Met Ser Ala Leu Asn His Thr
    1640                1645                1650

Lys Lys Trp Lys Tyr Pro Gln Val Asn Gly Leu Thr Ser Ile Lys
    1655                1660                1665

Trp Ala Asp Asn Asn Cys Tyr Leu Ala Thr Ala Leu Leu Thr Leu
    1670                1675                1680

Gln Gln Ile Glu Leu Lys Phe Asn Pro Pro Ala Leu Gln Asp Ala
    1685                1690                1695

Tyr Tyr Arg Ala Arg Ala Gly Glu Ala Ala Asn Phe Cys Ala Leu
    1700                1705                1710

Ile Leu Ala Tyr Cys Asn Lys Thr Val Gly Glu Leu Gly Asp Val
    1715                1720                1725

Arg Glu Thr Met Ser Tyr Leu Phe Gln His Ala Asn Leu Asp Ser
    1730                1735                1740

Cys Lys Arg Val Leu Asn Val Val Cys Lys Thr Cys Gly Gln Gln
    1745                1750                1755

Gln Thr Thr Leu Lys Gly Val Glu Ala Val Met Tyr Met Gly Thr
    1760                1765                1770

Leu Ser Tyr Glu Gln Phe Lys Lys Gly Val Gln Ile Pro Cys Thr
    1775                1780                1785

Cys Gly Lys Gln Ala Thr Lys Tyr Leu Val Gln Gln Glu Ser Pro
    1790                1795                1800

Phe Val Met Met Ser Ala Pro Pro Ala Gln Tyr Glu Leu Lys His
    1805                1810                1815

Gly Thr Phe Thr Cys Ala Ser Glu Tyr Thr Gly Asn Tyr Gln Cys
    1820                1825                1830

Gly His Tyr Lys His Ile Thr Ser Lys Glu Thr Leu Tyr Cys Ile
    1835                1840                1845

Asp Gly Ala Leu Leu Thr Lys Ser Ser Glu Tyr Lys Gly Pro Ile
    1850                1855                1860

Thr Asp Val Phe Tyr Lys Glu Asn Ser Tyr Thr Thr Thr Ile Lys
    1865                1870                1875

Pro Val Thr Tyr Lys Leu Asp Gly Val Val Cys Thr Glu Ile Asp
    1880                1885                1890

Pro Lys Leu Asp Asn Tyr Tyr Lys Lys Asp Asn Ser Tyr Phe Thr
    1895                1900                1905
```

```
Glu Gln Pro Ile Asp Leu Val Pro Asn Gln Pro Tyr Pro Ser Ala
1910                1915                1920

Ser Phe Asp Asn Phe Lys Phe Val Cys Asp Asn Ile Lys Phe Ala
1925                1930                1935

Asp Asp Leu Asn Gln Leu Thr Gly Tyr Lys Lys Pro Ala Ser Arg
1940                1945                1950

Glu Leu Lys Val Thr Phe Phe Pro Asp Leu Asn Gly Asp Val Val
1955                1960                1965

Ala Ile Asp Tyr Lys His Tyr Thr Pro Ser Phe Lys Lys Gly Ala
1970                1975                1980

Lys Leu Leu His Lys Pro Ile Val Trp His Val Asn Asn Ala Thr
1985                1990                1995

Asn Lys Ala Thr Tyr Lys Pro Asn Thr Trp Cys Ile Arg Cys Leu
2000                2005                2010

Trp Ser Thr Lys Pro Val Glu Thr Ser Asn Ser Phe Asp Val Leu
2015                2020                2025

Lys Ser Glu Asp Ala Gln Gly Met Asp Asn Leu Ala Cys Glu Asp
2030                2035                2040

Leu Lys Pro Val Ser Glu Glu Val Val Glu Asn Pro Thr Ile Gln
2045                2050                2055

Lys Asp Val Leu Glu Cys Asn Val Lys Thr Thr Glu Val Val Gly
2060                2065                2070

Asp Ile Ile Leu Lys Pro Ala Asn Asn Ser Leu Lys Ile Thr Glu
2075                2080                2085

Glu Val Gly His Thr Asp Leu Met Ala Ala Tyr Val Asp Asn Ser
2090                2095                2100

Ser Leu Thr Ile Lys Lys Pro Asn Glu Leu Ser Arg Val Leu Gly
2105                2110                2115

Leu Lys Thr Leu Ala Thr His Gly Leu Ala Ala Val Asn Ser Val
2120                2125                2130

Pro Trp Asp Thr Ile Ala Asn Tyr Ala Lys Pro Phe Leu Asn Lys
2135                2140                2145

Val Val Ser Thr Thr Thr Asn Ile Val Thr Arg Cys Leu Asn Arg
2150                2155                2160

Val Cys Thr Asn Tyr Met Pro Tyr Phe Phe Thr Leu Leu Leu Gln
2165                2170                2175

Leu Cys Thr Phe Thr Arg Ser Thr Asn Ser Arg Ile Lys Ala Ser
2180                2185                2190

Met Pro Thr Thr Ile Ala Lys Asn Thr Val Lys Ser Val Gly Lys
2195                2200                2205

Phe Cys Leu Glu Ala Ser Phe Asn Tyr Leu Lys Ser Pro Asn Phe
2210                2215                2220

Ser Lys Leu Ile Asn Ile Ile Ile Trp Phe Leu Leu Leu Ser Val
2225                2230                2235

Cys Leu Gly Ser Leu Ile Tyr Ser Thr Ala Ala Leu Gly Val Leu
2240                2245                2250

Met Ser Asn Leu Gly Met Pro Ser Tyr Cys Thr Gly Tyr Arg Glu
2255                2260                2265

Gly Tyr Leu Asn Ser Thr Asn Val Thr Ile Ala Thr Tyr Cys Thr
2270                2275                2280

Gly Ser Ile Pro Cys Ser Val Cys Leu Ser Gly Leu Asp Ser Leu
2285                2290                2295

Asp Thr Tyr Pro Ser Leu Glu Thr Ile Gln Ile Thr Ile Ser Ser
```

```
                   2300                2305                2310

Phe Lys Trp Asp Leu Thr Ala Phe Gly Leu Val Ala Glu Trp Phe
    2315                2320                2325

Leu Ala Tyr Ile Leu Phe Thr Arg Phe Tyr Val Leu Gly Leu
    2330                2335                2340

Ala Ala Ile Met Gln Leu Phe Phe Ser Tyr Phe Ala Val His Phe
    2345                2350                2355

Ile Ser Asn Ser Trp Leu Met Trp Leu Ile Ile Asn Leu Ala Gln
    2360                2365                2370

Met Ala Pro Ile Ser Ala Met Val Arg Met Tyr Ile Phe Phe Ala
    2375                2380                2385

Ser Phe Tyr Tyr Val Trp Lys Ser Tyr Val His Val Val Asp Gly
    2390                2395                2400

Cys Asn Ser Ser Thr Cys Met Met Cys Tyr Lys Arg Asn Arg Ala
    2405                2410                2415

Thr Arg Val Glu Cys Thr Thr Ile Val Asn Gly Val Arg Arg Ser
    2420                2425                2430

Phe Tyr Val Tyr Ala Asn Gly Gly Lys Gly Phe Cys Lys Leu His
    2435                2440                2445

Asn Trp Asn Cys Val Asn Cys Asp Thr Phe Cys Ala Gly Ser Thr
    2450                2455                2460

Phe Ile Ser Asp Glu Val Ala Arg Asp Leu Ser Leu Gln Phe Lys
    2465                2470                2475

Arg Pro Ile Asn Pro Thr Asp Gln Ser Ser Tyr Ile Val Asp Ser
    2480                2485                2490

Val Thr Val Lys Asn Gly Ser Ile His Leu Tyr Phe Asp Lys Ala
    2495                2500                2505

Gly Gln Lys Thr Tyr Glu Arg His Ser Leu Ser His Phe Val Asn
    2510                2515                2520

Leu Asp Asn Leu Arg Ala Asn Asn Thr Lys Gly Ser Leu Pro Ile
    2525                2530                2535

Asn Val Ile Val Phe Asp Gly Lys Ser Lys Cys Glu Glu Ser Ser
    2540                2545                2550

Ala Lys Ser Ala Ser Val Tyr Tyr Ser Gln Leu Met Cys Gln Pro
    2555                2560                2565

Ile Leu Leu Leu Asp Gln Ala Leu Val Ser Asp Val Gly Asp Ser
    2570                2575                2580

Ala Glu Val Ala Val Lys Met Phe Asp Ala Tyr Val Asn Thr Phe
    2585                2590                2595

Ser Ser Thr Phe Asn Val Pro Met Glu Lys Leu Lys Thr Leu Val
    2600                2605                2610

Ala Thr Ala Glu Ala Glu Leu Ala Lys Asn Val Ser Leu Asp Asn
    2615                2620                2625

Val Leu Ser Thr Phe Ile Ser Ala Ala Arg Gln Gly Phe Val Asp
    2630                2635                2640

Ser Asp Val Glu Thr Lys Asp Val Val Glu Cys Leu Lys Leu Ser
    2645                2650                2655

His Gln Ser Asp Ile Glu Val Thr Gly Asp Ser Cys Asn Asn Tyr
    2660                2665                2670

Met Leu Thr Tyr Asn Lys Val Glu Asn Met Thr Pro Arg Asp Leu
    2675                2680                2685

Gly Ala Cys Ile Asp Cys Ser Ala Arg His Ile Asn Ala Gln Val
    2690                2695                2700
```

-continued

```
Ala Lys Ser His Asn Ile Ala Leu Ile Trp Asn Val Lys Asp Phe
2705                2710                2715

Met Ser Leu Ser Glu Gln Pro Arg Lys Gln Ile Arg Ser Ala Ala
2720                2725                2730

Lys Lys Asn Asn Leu Pro Phe Lys Leu Thr Cys Ala Thr Thr Arg
2735                2740                2745

Gln Val Val Asn Ala Val Thr Thr Lys Ile Ala Leu Lys Gly Gly
2750                2755                2760

Lys Ile Val Asn Asn Trp Leu Lys Gln Leu Ile Lys Val Thr Leu
2765                2770                2775

Val Phe Leu Phe Val Ala Ala Ile Phe Tyr Leu Ile Thr Pro Val
2780                2785                2790

His Val Met Ser Lys His Thr Asp Phe Ser Ser Glu Ile Ile Gly
2795                2800                2805

Tyr Lys Ala Ile Asp Gly Gly Val Thr Arg Asp Ile Ala Ser Thr
2810                2815                2820

Asp Thr Cys Phe Ala Asn Lys His Ala Asp Phe Asp Thr Trp Phe
2825                2830                2835

Ser Gln Arg Gly Gly Ser Tyr Thr Asn Asp Lys Ala Cys Pro Leu
2840                2845                2850

Ile Ala Ala Val Ile Thr Arg Glu Val Gly Phe Val Val Pro Gly
2855                2860                2865

Leu Pro Ser Thr Ile Leu Arg Thr Thr Asn Gly Asp Phe Leu His
2870                2875                2880

Phe Leu Pro Arg Val Phe Ser Ala Val Gly Asn Ile Cys Tyr Thr
2885                2890                2895

Pro Ser Lys Leu Ile Glu Tyr Thr Asp Phe Ala Thr Ser Ala Cys
2900                2905                2910

Val Leu Ala Ala Glu Cys Thr Ile Phe Lys Asp Ala Ser Gly Lys
2915                2920                2925

Pro Val Pro Tyr Cys Tyr Asp Thr Asn Val Leu Glu Gly Ser Val
2930                2935                2940

Ala Tyr Glu Ser Leu Arg Pro Asp Thr Arg Tyr Val Leu Met Asp
2945                2950                2955

Gly Ser Ile Ile Gln Phe Pro Asn Thr Tyr Leu Glu Gly Pro Val
2960                2965                2970

Arg Val Val Thr Thr Phe Asp Ser Glu Tyr Cys Gly His Gly Thr
2975                2980                2985

Cys Glu Arg Ser Glu Ala Gly Val Cys Val Ser Thr Ser Gly Arg
2990                2995                3000

Trp Val Leu Asn Asn Asp Tyr Tyr Arg Ser Leu Pro Gly Val Phe
3005                3010                3015

Cys Gly Val Asp Ala Val Asn Leu Leu Thr Asn Met Phe Thr Pro
3020                3025                3030

Leu Ile Gln Pro Ile Gly Ala Leu Asp Ile Ser Ala Ser Ile Val
3035                3040                3045

Ala Gly Gly Ile Val Ala Ile Val Val Thr Cys Leu Ala Tyr Tyr
3050                3055                3060

Phe Met Arg Phe Arg Arg Ala Phe Gly Glu Tyr Ser His Val Val
3065                3070                3075

Ala Phe Asn Thr Leu Leu Phe Leu Met Ser Phe Thr Val Leu Cys
3080                3085                3090
```

| | | | | | | | | | | | |
|---|---|---|---|---|---|---|---|---|---|---|---|
|Leu|Thr 3095|Pro|Val|Tyr|Ser 3100|Phe|Leu|Pro|Gly|Val 3105|Tyr|Ser|Val|Ile|
|Tyr|Leu 3110|Tyr|Leu|Thr|Phe 3115|Tyr|Leu|Thr|Asn|Asp 3120|Val|Ser|Phe|Leu|
|Ala|His 3125|Ile|Gln|Trp|Met 3130|Val|Met|Phe|Thr|Pro 3135|Leu|Val|Pro|Phe|
|Trp|Ile 3140|Thr|Ile|Ala|Tyr 3145|Ile|Ile|Cys|Ile|Ser 3150|Thr|Lys|His|Phe|
|Tyr|Trp 3155|Phe|Phe|Ser|Asn 3160|Tyr|Leu|Lys|Arg|Arg 3165|Val|Val|Phe|Asn|
|Gly|Val 3170|Ser|Phe|Ser|Thr 3175|Phe|Glu|Glu|Ala|Ala 3180|Leu|Cys|Thr|Phe|
|Leu|Leu 3185|Asn|Lys|Glu|Met 3190|Tyr|Leu|Lys|Leu|Arg 3195|Ser|Asp|Val|Leu|
|Leu|Pro 3200|Leu|Thr|Gln|Tyr 3205|Asn|Arg|Tyr|Leu|Ala 3210|Leu|Tyr|Asn|Lys|
|Tyr|Lys 3215|Tyr|Phe|Ser|Gly 3220|Ala|Met|Asp|Thr|Thr 3225|Ser|Tyr|Arg|Glu|
|Ala|Ala 3230|Cys|Cys|His|Leu 3235|Ala|Lys|Ala|Leu|Asn 3240|Asp|Phe|Ser|Asn|
|Ser|Gly 3245|Ser|Asp|Val|Leu 3250|Tyr|Gln|Pro|Pro|Gln 3255|Thr|Ser|Ile|Thr|
|Ser|Ala 3260|Val|Leu|Gln|Ser 3265|Gly|Phe|Arg|Lys|Met 3270|Ala|Phe|Pro|Ser|
|Gly|Lys 3275|Val|Glu|Gly|Cys 3280|Met|Val|Gln|Val|Thr 3285|Cys|Gly|Thr|Thr|
|Thr|Leu 3290|Asn|Gly|Leu|Trp 3295|Leu|Asp|Asp|Val|Val 3300|Tyr|Cys|Pro|Arg|
|His|Val 3305|Ile|Cys|Thr|Ser 3310|Glu|Asp|Met|Leu|Asn 3315|Pro|Asn|Tyr|Glu|
|Asp|Leu 3320|Leu|Ile|Arg|Lys 3325|Ser|Asn|His|Asn|Phe 3330|Leu|Val|Gln|Ala|
|Gly|Asn 3335|Val|Gln|Leu|Arg 3340|Val|Ile|Gly|His|Ser 3345|Met|Gln|Asn|Cys|
|Val|Leu 3350|Lys|Leu|Lys|Val 3355|Asp|Thr|Ala|Asn|Pro 3360|Lys|Thr|Pro|Lys|
|Tyr|Lys 3365|Phe|Val|Arg|Ile 3370|Gln|Pro|Gly|Gln|Thr 3375|Phe|Ser|Val|Leu|
|Ala|Cys 3380|Tyr|Asn|Gly|Ser 3385|Pro|Ser|Gly|Val|Tyr 3390|Gln|Cys|Ala|Met|
|Arg|Pro 3395|Asn|Phe|Thr|Ile 3400|Lys|Gly|Ser|Phe|Leu 3405|Asn|Gly|Ser|Cys|
|Gly|Ser 3410|Val|Gly|Phe|Asn 3415|Ile|Asp|Tyr|Asp|Cys 3420|Val|Ser|Phe|Cys|
|Tyr|Met 3425|His|His|Met|Glu 3430|Leu|Pro|Thr|Gly|Val 3435|His|Ala|Gly|Thr|
|Asp|Leu 3440|Glu|Gly|Asn|Phe 3445|Tyr|Gly|Pro|Phe|Val 3450|Asp|Arg|Gln|Thr|
|Ala|Gln 3455|Ala|Ala|Gly|Thr 3460|Asp|Thr|Thr|Ile|Thr 3465|Val|Asn|Val|Leu|
|Ala|Trp 3470|Leu|Tyr|Ala|Ala 3475|Val|Ile|Asn|Gly|Asp 3480|Arg|Trp|Phe|Leu|
|Asn|Arg|Phe|Thr|Thr|Thr|Leu|Asn|Asp|Phe|Asn|Leu|Val|Ala|Met|

-continued

```
              3485                3490                3495
Lys  Tyr  Asn  Tyr  Glu  Pro  Leu  Thr  Gln  Asp  His  Val  Asp  Ile  Leu
     3500                3505                3510
Gly  Pro  Leu  Ser  Ala  Gln  Thr  Gly  Ile  Ala  Val  Leu  Asp  Met  Cys
     3515                3520                3525
Ala  Ser  Leu  Lys  Glu  Leu  Leu  Gln  Asn  Gly  Met  Asn  Gly  Arg  Thr
     3530                3535                3540
Ile  Leu  Gly  Ser  Ala  Leu  Leu  Glu  Asp  Glu  Phe  Thr  Pro  Phe  Asp
     3545                3550                3555
Val  Val  Arg  Gln  Cys  Ser  Gly  Val  Thr  Phe  Gln  Ser  Ala  Val  Lys
     3560                3565                3570
Arg  Thr  Ile  Lys  Gly  Thr  His  His  Trp  Leu  Leu  Leu  Thr  Ile  Leu
     3575                3580                3585
Thr  Ser  Leu  Leu  Val  Leu  Val  Gln  Ser  Thr  Gln  Trp  Ser  Leu  Phe
     3590                3595                3600
Phe  Phe  Phe  Tyr  Glu  Asn  Ala  Phe  Leu  Pro  Phe  Ala  Met  Gly  Ile
     3605                3610                3615
Ile  Ala  Met  Ser  Ala  Phe  Ala  Met  Met  Phe  Val  Lys  His  Lys  His
     3620                3625                3630
Ala  Phe  Leu  Cys  Leu  Phe  Leu  Leu  Pro  Ser  Leu  Ala  Thr  Val  Ala
     3635                3640                3645
Tyr  Phe  Asn  Met  Val  Tyr  Met  Pro  Ala  Ser  Trp  Val  Met  Arg  Ile
     3650                3655                3660
Met  Thr  Trp  Leu  Asp  Met  Val  Ile  Thr  Ser  Leu  Ser  Gly  Phe  Lys
     3665                3670                3675
Leu  Lys  Asp  Cys  Val  Met  Tyr  Ala  Ser  Ala  Val  Val  Leu  Leu  Ile
     3680                3685                3690
Leu  Met  Thr  Ala  Arg  Thr  Val  Tyr  Asp  Asp  Gly  Ala  Arg  Arg  Val
     3695                3700                3705
Trp  Thr  Leu  Met  Asn  Val  Leu  Thr  Leu  Val  Tyr  Lys  Val  Tyr  Tyr
     3710                3715                3720
Gly  Asn  Ala  Leu  Asp  Gln  Ala  Ile  Ser  Met  Trp  Ala  Leu  Ile  Ile
     3725                3730                3735
Ser  Val  Thr  Ser  Asn  Tyr  Ser  Gly  Val  Val  Thr  Thr  Val  Met  Phe
     3740                3745                3750
Leu  Ala  Arg  Gly  Ile  Val  Phe  Met  Cys  Val  Glu  Tyr  Cys  Pro  Ile
     3755                3760                3765
Phe  Phe  Ile  Thr  Gly  Asn  Thr  Leu  Gln  Cys  Ile  Met  Leu  Val  Tyr
     3770                3775                3780
Cys  Phe  Leu  Gly  Tyr  Phe  Cys  Thr  Cys  Tyr  Phe  Gly  Leu  Phe  Cys
     3785                3790                3795
Leu  Leu  Asn  Arg  Tyr  Phe  Arg  Leu  Thr  Leu  Gly  Val  Tyr  Asp  Tyr
     3800                3805                3810
Leu  Val  Ser  Thr  Gln  Glu  Phe  Arg  Tyr  Met  Asn  Ser  Gln  Gly  Leu
     3815                3820                3825
Leu  Pro  Pro  Lys  Asn  Ser  Ile  Asp  Ala  Phe  Lys  Leu  Asn  Ile  Lys
     3830                3835                3840
Leu  Leu  Gly  Val  Gly  Gly  Lys  Pro  Cys  Ile  Lys  Val  Ala  Thr  Val
     3845                3850                3855
Gln  Ser  Lys  Met  Ser  Asp  Val  Lys  Cys  Thr  Ser  Val  Val  Leu  Leu
     3860                3865                3870
Ser  Val  Leu  Gln  Gln  Leu  Arg  Val  Glu  Ser  Ser  Ser  Lys  Leu  Trp
     3875                3880                3885
```

```
Ala Gln Cys Val Gln Leu His Asn Asp Ile Leu Leu Ala Lys Asp
        3890                3895                3900

Thr Thr Glu Ala Phe Glu Lys Met Val Ser Leu Leu Ser Val Leu
        3905                3910                3915

Leu Ser Met Gln Gly Ala Val Asp Ile Asn Lys Leu Cys Glu Glu
        3920                3925                3930

Met Leu Asp Asn Arg Ala Thr Leu Gln Ala Ile Ala Ser Glu Phe
        3935                3940                3945

Ser Ser Leu Pro Ser Tyr Ala Ala Phe Ala Thr Ala Gln Glu Ala
        3950                3955                3960

Tyr Glu Gln Ala Val Ala Asn Gly Asp Ser Glu Val Val Leu Lys
        3965                3970                3975

Lys Leu Lys Lys Ser Leu Asn Val Ala Lys Ser Glu Phe Asp Arg
        3980                3985                3990

Asp Ala Ala Met Gln Arg Lys Leu Glu Lys Met Ala Asp Gln Ala
        3995                4000                4005

Met Thr Gln Met Tyr Lys Gln Ala Arg Ser Glu Asp Lys Arg Ala
        4010                4015                4020

Lys Val Thr Ser Ala Met Gln Thr Met Leu Phe Thr Met Leu Arg
        4025                4030                4035

Lys Leu Asp Asn Asp Ala Leu Asn Asn Ile Ile Asn Asn Ala Arg
        4040                4045                4050

Asp Gly Cys Val Pro Leu Asn Ile Ile Pro Leu Thr Thr Ala Ala
        4055                4060                4065

Lys Leu Met Val Val Ile Pro Asp Tyr Asn Thr Tyr Lys Asn Thr
        4070                4075                4080

Cys Asp Gly Thr Thr Phe Thr Tyr Ala Ser Ala Leu Trp Glu Ile
        4085                4090                4095

Gln Gln Val Val Asp Ala Asp Ser Lys Ile Val Gln Leu Ser Glu
        4100                4105                4110

Ile Ser Met Asp Asn Ser Pro Asn Leu Ala Trp Pro Leu Ile Val
        4115                4120                4125

Thr Ala Leu Arg Ala Asn Ser Ala Val Lys Leu Gln Asn Asn Glu
        4130                4135                4140

Leu Ser Pro Val Ala Leu Arg Gln Met Ser Cys Ala Ala Gly Thr
        4145                4150                4155

Thr Gln Thr Ala Cys Thr Asp Asp Asn Ala Leu Ala Tyr Tyr Asn
        4160                4165                4170

Thr Thr Lys Gly Gly Arg Phe Val Leu Ala Leu Leu Ser Asp Leu
        4175                4180                4185

Gln Asp Leu Lys Trp Ala Arg Phe Pro Lys Ser Asp Gly Thr Gly
        4190                4195                4200

Thr Ile Tyr Thr Glu Leu Glu Pro Pro Cys Arg Phe Val Thr Asp
        4205                4210                4215

Thr Pro Lys Gly Pro Lys Val Lys Tyr Leu Tyr Phe Ile Lys Gly
        4220                4225                4230

Leu Asn Asn Leu Asn Arg Gly Met Val Leu Gly Ser Leu Ala Ala
        4235                4240                4245

Thr Val Arg Leu Gln Ala Gly Asn Ala Thr Glu Val Pro Ala Asn
        4250                4255                4260

Ser Thr Val Leu Ser Phe Cys Ala Phe Ala Val Asp Ala Ala Lys
        4265                4270                4275
```

```
Ala Tyr Lys Asp Tyr Leu Ala Ser Gly Gly Gln Pro Ile Thr Asn
    4280            4285            4290

Cys Val Lys Met Leu Cys Thr His Thr Gly Thr Gly Gln Ala Ile
4295            4300            4305

Thr Val Thr Pro Glu Ala Asn Met Asp Gln Glu Ser Phe Gly Gly
    4310            4315            4320

Ala Ser Cys Cys Leu Tyr Cys Arg Cys His Ile Asp His Pro Asn
4325            4330            4335

Pro Lys Gly Phe Cys Asp Leu Lys Gly Lys Tyr Val Gln Ile Pro
    4340            4345            4350

Thr Thr Cys Ala Asn Asp Pro Val Gly Phe Thr Leu Lys Asn Thr
4355            4360            4365

Val Cys Thr Val Cys Gly Met Trp Lys Gly Tyr Gly Cys Ser Cys
    4370            4375            4380

Asp Gln Leu Arg Glu Pro Met Leu Gln Ser Ala Asp Ala Gln Ser
4385            4390            4395

Phe Leu Asn Gly Phe Ala Val
    4400            4405

<210> SEQ ID NO 27
<211> LENGTH: 1273
<212> TYPE: PRT
<213> ORGANISM: Unknown
<220> FEATURE:
<223> OTHER INFORMATION: SARS-CoV-2 surface glycoprotein

<400> SEQUENCE: 27

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Cys Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Ser Asn Asp Gly Val Tyr Phe Ala Ser Ile Gly
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Gly Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Lys Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220
```

```
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
        260                 265                 270

Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
        340                 345                 350

Trp Asn Arg Lys Arg Ile Ser Asn Cys Val Ala Asp Tyr Ser Val Leu
    355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
        420                 425                 430

Val Ile Ala Trp Asn Ser Asn Asn Leu Asp Ser Lys Val Gly Gly Asn
    435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
        500                 505                 510

Leu Ser Phe Glu Leu Leu His Ala Pro Ala Thr Val Cys Gly Pro Lys
    515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
        580                 585                 590

Gly Gly Val Ser Val Ile Thr Pro Gly Thr Asn Thr Ser Asn Gln Val
    595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
```

```
                    645                 650                 655
Asn Asn Ser Tyr Glu Cys Asp Ile Pro Ile Gly Ala Gly Ile Cys Ala
                660                 665                 670
Ser Tyr Gln Thr Gln Thr Asn Ser Pro Arg Arg Ala Arg Ser Val Ala
                675                 680                 685
Ser Gln Ser Ile Ile Ala Tyr Thr Met Ser Leu Gly Ala Glu Asn Ser
                690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
                740                 745                 750
Leu Leu Gln Tyr Gly Ser Phe Cys Thr Gln Leu Asn Arg Ala Leu Thr
                755                 760                 765
Gly Ile Ala Val Glu Gln Asp Lys Asn Thr Gln Glu Val Phe Ala Gln
                770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
                820                 825                 830
Phe Ile Lys Gln Tyr Gly Asp Cys Leu Gly Asp Ile Ala Ala Arg Asp
                835                 840                 845
Leu Ile Cys Ala Gln Lys Phe Asn Gly Leu Thr Val Leu Pro Pro Leu
850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
                885                 890                 895
Pro Phe Ala Met Gln Met Ala Tyr Arg Phe Asn Gly Ile Gly Val Thr
                900                 905                 910
Gln Asn Val Leu Tyr Glu Asn Gln Lys Leu Ile Ala Asn Gln Phe Asn
                915                 920                 925
Ser Ala Ile Gly Lys Ile Gln Asp Ser Leu Ser Ser Thr Ala Ser Ala
                930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
                965                 970                 975
Leu Asn Asp Ile Leu Ser Arg Leu Asp Lys Val Glu Ala Glu Val Gln
                980                 985                 990
Ile Asp Arg Leu Ile Thr Gly Arg Leu Gln Ser Leu Gln Thr Tyr Val
                995                 1000                1005
Thr Gln Gln Leu Ile Arg Ala Ala Glu Ile Arg Ala Ser Ala Asn
                1010                1015                1020
Leu Ala Ala Thr Lys Met Ser Glu Cys Val Leu Gly Gln Ser Lys
                1025                1030                1035
Arg Val Asp Phe Cys Gly Lys Gly Tyr His Leu Met Ser Phe Pro
                1040                1045                1050
Gln Ser Ala Pro His Gly Val Val Phe Leu His Val Thr Tyr Val
                1055                1060                1065
```

```
Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 28
<211> LENGTH: 275
<212> TYPE: PRT
<213> ORGANISM: Unknown
<220> FEATURE:
<223> OTHER INFORMATION: SARS-CoV-2 ORF3a protein

<400> SEQUENCE: 28

Met Asp Leu Phe Met Arg Ile Phe Thr Ile Gly Thr Val Thr Leu Lys
1               5                   10                  15

Gln Gly Glu Ile Lys Asp Ala Thr Pro Ser Asp Phe Val Arg Ala Thr
            20                  25                  30

Ala Thr Ile Pro Ile Gln Ala Ser Leu Pro Phe Gly Trp Leu Ile Val
        35                  40                  45

Gly Val Ala Leu Leu Ala Val Phe Gln Ser Ala Ser Lys Ile Ile Thr
    50                  55                  60

Leu Lys Lys Arg Trp Gln Leu Ala Leu Ser Lys Gly Val His Phe Val
65                  70                  75                  80

Cys Asn Leu Leu Leu Leu Phe Val Thr Val Tyr Ser His Leu Leu Leu
                85                  90                  95

Val Ala Ala Gly Leu Glu Ala Pro Phe Leu Tyr Leu Tyr Ala Leu Val
            100                 105                 110

Tyr Phe Leu Gln Ser Ile Asn Phe Val Arg Ile Ile Met Arg Leu Trp
        115                 120                 125

Leu Cys Trp Lys Cys Arg Ser Lys Asn Pro Leu Leu Tyr Asp Ala Asn
    130                 135                 140
```

```
Tyr Phe Leu Cys Trp His Thr Asn Cys Tyr Asp Tyr Cys Ile Pro Tyr
145                 150                 155                 160

Asn Ser Val Thr Ser Ser Ile Val Ile Thr Ser Gly Asp Gly Thr Thr
                165                 170                 175

Ser Pro Ile Ser Glu His Asp Tyr Gln Ile Gly Gly Tyr Thr Glu Lys
            180                 185                 190

Trp Glu Ser Gly Val Lys Asp Cys Val Val Leu His Ser Tyr Phe Thr
        195                 200                 205

Ser Asp Tyr Tyr Gln Leu Tyr Ser Thr Gln Leu Ser Thr Asp Thr Gly
210                 215                 220

Val Glu His Val Thr Phe Phe Ile Tyr Asn Lys Ile Val Asp Glu Pro
225                 230                 235                 240

Glu Glu His Val Gln Ile His Thr Ile Asp Gly Ser Ser Gly Val Val
                245                 250                 255

Asn Pro Val Met Glu Pro Ile Tyr Asp Glu Pro Thr Thr Thr Thr Ser
                260                 265                 270

Val Pro Leu
        275

<210> SEQ ID NO 29
<211> LENGTH: 75
<212> TYPE: PRT
<213> ORGANISM: Unknown
<220> FEATURE:
<223> OTHER INFORMATION: SARS-CoV-2 envelope protein

<400> SEQUENCE: 29

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
            35                  40                  45

Val Ser Leu Val Lys Pro Ser Phe Tyr Val Tyr Ser Arg Val Lys Asn
        50                  55                  60

Leu Asn Ser Ser Arg Val Pro Asp Leu Leu Val
65                  70                  75

<210> SEQ ID NO 30
<211> LENGTH: 222
<212> TYPE: PRT
<213> ORGANISM: Unknown
<220> FEATURE:
<223> OTHER INFORMATION: SARS-CoV-2 membrane glycoprotein

<400> SEQUENCE: 30

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
                20                  25                  30

Cys Leu Leu Gln Phe Ala Tyr Ala Asn Arg Asn Arg Phe Leu Tyr Ile
            35                  40                  45

Ile Lys Leu Ile Phe Leu Trp Leu Leu Trp Pro Val Thr Leu Ala Cys
        50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
```

```
                   85                  90                  95

Ile Ala Ser Phe Arg Leu Phe Ala Arg Thr Arg Ser Met Trp Ser Phe
                100                 105                 110

Asn Pro Glu Thr Asn Ile Leu Leu Asn Val Pro Leu His Gly Thr Ile
            115                 120                 125

Leu Thr Arg Pro Leu Leu Glu Ser Glu Leu Val Ile Gly Ala Val Ile
        130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
                180                 185                 190

Phe Ala Ala Tyr Ser Arg Tyr Arg Ile Gly Asn Tyr Lys Leu Asn Thr
            195                 200                 205

Asp His Ser Ser Ser Ser Asp Asn Ile Ala Leu Leu Val Gln
        210                 215                 220

<210> SEQ ID NO 31
<211> LENGTH: 61
<212> TYPE: PRT
<213> ORGANISM: Unknown
<220> FEATURE:
<223> OTHER INFORMATION: SARS-CoV-2 ORF6 protein

<400> SEQUENCE: 31

Met Phe His Leu Val Asp Phe Gln Val Thr Ile Ala Glu Ile Leu Leu
1               5                   10                  15

Ile Ile Met Arg Thr Phe Lys Val Ser Ile Trp Asn Leu Asp Tyr Ile
                20                  25                  30

Ile Asn Leu Ile Ile Lys Asn Leu Ser Lys Ser Leu Thr Glu Asn Lys
            35                  40                  45

Tyr Ser Gln Leu Asp Glu Glu Gln Pro Met Glu Ile Asp
        50                  55                  60

<210> SEQ ID NO 32
<211> LENGTH: 121
<212> TYPE: PRT
<213> ORGANISM: Unknown
<220> FEATURE:
<223> OTHER INFORMATION: SARS-CoV-2 ORF7a protein

<400> SEQUENCE: 32

Met Lys Ile Ile Leu Phe Leu Ala Leu Ile Thr Leu Ala Thr Cys Glu
1               5                   10                  15

Leu Tyr His Tyr Gln Glu Cys Val Arg Gly Thr Thr Val Leu Leu Lys
                20                  25                  30

Glu Pro Cys Ser Ser Gly Thr Tyr Glu Gly Asn Ser Pro Phe His Pro
            35                  40                  45

Leu Ala Asp Asn Lys Phe Ala Leu Thr Cys Phe Ser Thr Gln Phe Ala
        50                  55                  60

Phe Ala Tyr Pro Asp Gly Val Lys His Val Tyr Gln Leu Arg Ala Arg
65                  70                  75                  80

Ser Val Ser Pro Lys Leu Phe Ile Arg Gln Glu Val Gln Glu Leu
                85                  90                  95

Tyr Ser Pro Ile Phe Leu Ile Val Ala Ala Ile Val Phe Ile Thr Leu
            100                 105                 110
```

```
Cys Phe Thr Leu Lys Arg Lys Thr Glu
        115                 120

<210> SEQ ID NO 33
<211> LENGTH: 43
<212> TYPE: PRT
<213> ORGANISM: Unknown
<220> FEATURE:
<223> OTHER INFORMATION: SARS-CoV-2 ORF7b proteinn

<400> SEQUENCE: 33

Met Ile Glu Leu Ser Leu Ile Asp Phe Tyr Leu Cys Phe Leu Ala Phe
1               5                   10                  15

Leu Leu Phe Leu Val Leu Ile Met Leu Ile Ile Phe Trp Phe Ser Leu
            20                  25                  30

Glu Leu Gln Asp His Asn Glu Thr Cys His Ala
        35                  40

<210> SEQ ID NO 34
<211> LENGTH: 121
<212> TYPE: PRT
<213> ORGANISM: Unknown
<220> FEATURE:
<223> OTHER INFORMATION: SARS-CoV-2 ORF8 protein

<400> SEQUENCE: 34

Met Lys Phe Leu Val Phe Leu Gly Ile Ile Thr Thr Val Ala Ala Phe
1               5                   10                  15

His Gln Glu Cys Ser Leu Gln Ser Cys Thr Gln His Gln Pro Tyr Val
            20                  25                  30

Val Asp Asp Pro Cys Pro Ile His Phe Tyr Ser Lys Trp Tyr Ile Arg
        35                  40                  45

Val Gly Ala Arg Lys Ser Ala Pro Leu Ile Glu Leu Cys Val Asp Glu
    50                  55                  60

Ala Gly Ser Lys Ser Pro Ile Gln Tyr Ile Asp Ile Gly Asn Tyr Thr
65                  70                  75                  80

Val Ser Cys Ser Pro Phe Thr Ile Asn Cys Gln Glu Pro Lys Leu Gly
                85                  90                  95

Ser Leu Val Val Arg Cys Ser Phe Tyr Glu Asp Phe Leu Glu Tyr His
            100                 105                 110

Asp Val Arg Val Val Leu Asp Phe Ile
        115                 120

<210> SEQ ID NO 35
<211> LENGTH: 419
<212> TYPE: PRT
<213> ORGANISM: Unknown
<220> FEATURE:
<223> OTHER INFORMATION: SARS-CoV-2 nucleocapsid phosphoprotein

<400> SEQUENCE: 35

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
```

```
            65                  70                  75                  80
Asp Asp Gln Ile Gly Tyr Tyr Arg Arg Ala Thr Arg Ile Arg Gly
                        85                  90                  95
Gly Asp Gly Lys Met Lys Asp Leu Ser Pro Arg Trp Tyr Phe Tyr Tyr
                    100                 105                 110
Leu Gly Thr Gly Pro Glu Ala Gly Leu Pro Tyr Gly Ala Asn Lys Asp
                115                 120                 125
Gly Ile Ile Trp Val Ala Thr Glu Gly Ala Leu Asn Thr Pro Lys Asp
            130                 135                 140
His Ile Gly Thr Arg Asn Pro Ala Asn Asn Ala Ala Ile Val Leu Gln
145                 150                 155                 160
Leu Pro Gln Gly Thr Thr Leu Pro Lys Gly Phe Tyr Ala Glu Gly Ser
                165                 170                 175
Arg Gly Gly Ser Gln Ala Ser Ser Arg Ser Ser Ser Arg Ser Arg Asn
                180                 185                 190
Ser Ser Arg Asn Ser Thr Pro Gly Ser Ser Arg Gly Thr Ser Pro Ala
            195                 200                 205
Arg Met Ala Gly Asn Gly Gly Asp Ala Ala Leu Ala Leu Leu Leu Leu
        210                 215                 220
Asp Arg Leu Asn Gln Leu Glu Ser Lys Met Ser Gly Lys Gly Gln Gln
225                 230                 235                 240
Gln Gln Gly Gln Thr Val Thr Lys Lys Ser Ala Ala Glu Ala Ser Lys
                245                 250                 255
Lys Pro Arg Gln Lys Arg Thr Ala Thr Lys Ala Tyr Asn Val Thr Gln
                260                 265                 270
Ala Phe Gly Arg Arg Gly Pro Glu Gln Thr Gln Gly Asn Phe Gly Asp
            275                 280                 285
Gln Glu Leu Ile Arg Gln Gly Thr Asp Tyr Lys His Trp Pro Gln Ile
        290                 295                 300
Ala Gln Phe Ala Pro Ser Ala Ser Ala Phe Phe Gly Met Ser Arg Ile
305                 310                 315                 320
Gly Met Glu Val Thr Pro Ser Gly Thr Trp Leu Thr Tyr Thr Gly Ala
                325                 330                 335
Ile Lys Leu Asp Asp Lys Asp Pro Asn Phe Lys Asp Gln Val Ile Leu
                340                 345                 350
Leu Asn Lys His Ile Asp Ala Tyr Ile Thr Phe Pro Pro Thr Glu Pro
            355                 360                 365
Lys Lys Asp Lys Lys Lys Ala Asp Glu Thr Gln Ala Leu Pro Gln
        370                 375                 380
Arg Gln Lys Lys Gln Gln Thr Val Thr Leu Leu Pro Ala Ala Asp Leu
385                 390                 395                 400
Asp Asp Phe Ser Lys Gln Leu Gln Gln Ser Met Ser Ser Ala Asp Ser
                405                 410                 415
Thr Gln Ala

<210> SEQ ID NO 36
<211> LENGTH: 38
<212> TYPE: PRT
<213> ORGANISM: Unknown
<220> FEATURE:
<223> OTHER INFORMATION: SARS-CoV-2 ORF10 protein

<400> SEQUENCE: 36

Met Gly Tyr Ile Asn Val Phe Ala Phe Pro Phe Thr Ile Tyr Ser Leu
1               5                   10                  15
```

-continued

```
Leu Leu Cys Arg Met Asn Ser Arg Asn Tyr Ile Ala Gln Val Asp Val
            20                  25                  30

Val Asn Phe Asn Leu Thr
            35

<210> SEQ ID NO 37
<211> LENGTH: 7093
<212> TYPE: PRT
<213> ORGANISM: Unknown
<220> FEATURE:
<223> OTHER INFORMATION: SARS-CoV-2 ORF1ab polyprotein

<400> SEQUENCE: 37

Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Val Val Glu Leu Val Ala Glu Leu Glu Gly Ile Gln Tyr Gly Arg
                85                  90                  95

Ser Gly Glu Thr Leu Gly Val Leu Val Pro His Val Gly Glu Ile Pro
            100                 105                 110

Val Ala Tyr Arg Lys Val Leu Leu Arg Lys Asn Gly Asn Lys Gly Ala
        115                 120                 125

Gly Gly His Ser Tyr Gly Ala Asp Leu Lys Ser Phe Asp Leu Gly Asp
    130                 135                 140

Glu Leu Gly Thr Asp Pro Tyr Glu Asp Phe Gln Glu Asn Trp Asn Thr
145                 150                 155                 160

Lys His Ser Ser Gly Val Thr Arg Glu Leu Met Arg Glu Leu Asn Gly
                165                 170                 175

Gly Ala Tyr Thr Arg Tyr Val Asp Asn Asn Phe Cys Gly Pro Asp Gly
            180                 185                 190

Tyr Pro Leu Glu Cys Ile Lys Asp Leu Leu Ala Arg Ala Gly Lys Ala
        195                 200                 205

Ser Cys Thr Leu Ser Glu Gln Leu Asp Phe Ile Asp Thr Lys Arg Gly
    210                 215                 220

Val Tyr Cys Cys Arg Glu His Glu His Glu Ile Ala Trp Tyr Thr Glu
225                 230                 235                 240

Arg Ser Glu Lys Ser Tyr Glu Leu Gln Thr Pro Phe Glu Ile Lys Leu
                245                 250                 255

Ala Lys Lys Phe Asp Thr Phe Asn Gly Glu Cys Pro Asn Phe Val Phe
            260                 265                 270

Pro Leu Asn Ser Ile Ile Lys Thr Ile Gln Pro Arg Val Glu Lys Lys
        275                 280                 285

Lys Leu Asp Gly Phe Met Gly Arg Ile Arg Ser Val Tyr Pro Val Ala
    290                 295                 300

Ser Pro Asn Glu Cys Asn Gln Met Cys Leu Ser Thr Leu Met Lys Cys
305                 310                 315                 320

Asp His Cys Gly Glu Thr Ser Trp Gln Thr Gly Asp Phe Val Lys Ala
                325                 330                 335
```

```
Thr Cys Glu Phe Cys Gly Thr Glu Asn Leu Thr Lys Glu Gly Ala Thr
            340                 345                 350

Thr Cys Gly Tyr Leu Pro Gln Asn Ala Val Val Lys Ile Tyr Cys Pro
            355                 360                 365

Ala Cys His Asn Ser Glu Val Gly Pro Glu His Ser Leu Ala Glu Tyr
        370                 375                 380

His Asn Glu Ser Gly Leu Lys Thr Ile Leu Arg Lys Gly Gly Arg Thr
385                 390                 395                 400

Ile Ala Phe Gly Gly Cys Val Phe Ser Tyr Val Gly Cys His Asn Lys
                405                 410                 415

Cys Ala Tyr Trp Val Pro Arg Ala Ser Ala Asn Ile Gly Cys Asn His
            420                 425                 430

Thr Gly Val Val Gly Glu Gly Ser Glu Gly Leu Asn Asp Asn Leu Leu
            435                 440                 445

Glu Ile Leu Gln Lys Glu Lys Val Asn Ile Asn Ile Val Gly Asp Phe
        450                 455                 460

Lys Leu Asn Glu Glu Ile Ala Ile Ile Leu Ala Ser Phe Ser Ala Ser
465                 470                 475                 480

Thr Ser Ala Phe Val Glu Thr Val Lys Gly Leu Asp Tyr Lys Ala Phe
                485                 490                 495

Lys Gln Ile Val Glu Ser Cys Gly Asn Phe Lys Val Thr Lys Gly Lys
            500                 505                 510

Ala Lys Lys Gly Ala Trp Asn Ile Gly Glu Gln Lys Ser Ile Leu Ser
            515                 520                 525

Pro Leu Tyr Ala Phe Ala Ser Glu Ala Ala Arg Val Val Arg Ser Ile
            530                 535                 540

Phe Ser Arg Thr Leu Glu Thr Ala Gln Asn Ser Val Arg Val Leu Gln
545                 550                 555                 560

Lys Ala Ala Ile Thr Ile Leu Asp Gly Ile Ser Gln Tyr Ser Leu Arg
                565                 570                 575

Leu Ile Asp Ala Met Met Phe Thr Ser Asp Leu Ala Thr Asn Asn Leu
            580                 585                 590

Val Val Met Ala Tyr Ile Thr Gly Gly Val Val Gln Leu Thr Ser Gln
            595                 600                 605

Trp Leu Thr Asn Ile Phe Gly Thr Val Tyr Glu Lys Leu Lys Pro Val
            610                 615                 620

Leu Asp Trp Leu Glu Glu Lys Phe Lys Glu Gly Val Glu Phe Leu Arg
625                 630                 635                 640

Asp Gly Trp Glu Ile Val Lys Phe Ile Ser Thr Cys Ala Cys Glu Ile
                645                 650                 655

Val Gly Gly Gln Ile Val Thr Cys Ala Lys Glu Ile Lys Glu Ser Val
            660                 665                 670

Gln Thr Phe Phe Lys Leu Val Asn Lys Phe Leu Ala Leu Cys Ala Asp
            675                 680                 685

Ser Ile Ile Ile Gly Gly Ala Lys Leu Lys Ala Leu Asn Leu Gly Glu
            690                 695                 700

Thr Phe Val Thr His Ser Lys Gly Leu Tyr Arg Lys Cys Val Lys Ser
705                 710                 715                 720

Arg Glu Glu Thr Gly Leu Leu Met Pro Leu Lys Ala Pro Lys Glu Ile
                725                 730                 735

Ile Phe Leu Glu Gly Glu Thr Leu Pro Thr Glu Val Leu Thr Glu Glu
            740                 745                 750
```

```
Val Val Leu Lys Thr Gly Asp Leu Gln Pro Leu Glu Gln Pro Thr Ser
            755                 760                 765

Glu Ala Val Glu Ala Pro Leu Val Gly Thr Pro Val Cys Ile Asn Gly
    770                 775                 780

Leu Met Leu Leu Glu Ile Lys Asp Thr Glu Lys Tyr Cys Ala Leu Ala
785                 790                 795                 800

Pro Asn Met Met Val Thr Asn Asn Thr Phe Thr Leu Lys Gly Gly Ala
                805                 810                 815

Pro Thr Lys Val Thr Phe Gly Asp Thr Val Ile Glu Val Gln Gly
            820                 825                 830

Tyr Lys Ser Val Asn Ile Thr Phe Glu Leu Asp Glu Arg Ile Asp Lys
            835                 840                 845

Val Leu Asn Glu Lys Cys Ser Ala Tyr Thr Val Glu Leu Gly Thr Glu
    850                 855                 860

Val Asn Glu Phe Ala Cys Val Val Ala Asp Ala Val Ile Lys Thr Leu
865                 870                 875                 880

Gln Pro Val Ser Glu Leu Leu Thr Pro Leu Gly Ile Asp Leu Asp Glu
                885                 890                 895

Trp Ser Met Ala Thr Tyr Tyr Leu Phe Asp Glu Ser Gly Glu Phe Lys
                900                 905                 910

Leu Ala Ser His Met Tyr Cys Ser Phe Tyr Pro Pro Asp Glu Asp Glu
            915                 920                 925

Glu Glu Gly Asp Cys Glu Glu Glu Phe Glu Pro Ser Thr Gln Tyr
    930                 935                 940

Glu Tyr Gly Thr Glu Asp Asp Tyr Gln Gly Lys Pro Leu Glu Phe Gly
945                 950                 955                 960

Ala Thr Ser Ala Ala Leu Gln Pro Glu Glu Gln Glu Glu Asp Trp
            965                 970                 975

Leu Asp Asp Asp Ser Gln Gln Thr Val Gly Gln Gln Asp Gly Ser Glu
            980                 985                 990

Asp Asn Gln Thr Thr Thr Ile Gln Thr Ile Val Glu Val Gln Pro Gln
            995                 1000                1005

Leu Glu Met Glu Leu Thr Pro Val Val Gln Thr Ile Glu Val Asn
    1010                1015                1020

Ser Phe Ser Gly Tyr Leu Lys Leu Thr Asp Asn Val Tyr Ile Lys
    1025                1030                1035

Asn Ala Asp Ile Val Glu Glu Ala Lys Lys Val Lys Pro Thr Val
    1040                1045                1050

Val Val Asn Ala Ala Asn Val Tyr Leu Lys His Gly Gly Gly Val
    1055                1060                1065

Ala Gly Ala Leu Asn Lys Ala Thr Asn Asn Ala Met Gln Val Glu
    1070                1075                1080

Ser Asp Asp Tyr Ile Ala Thr Asn Gly Pro Leu Lys Val Gly Gly
    1085                1090                1095

Ser Cys Val Leu Ser Gly His Asn Leu Ala Lys His Cys Leu His
    1100                1105                1110

Val Val Gly Pro Asn Val Asn Lys Gly Glu Asp Ile Gln Leu Leu
    1115                1120                1125

Lys Ser Ala Tyr Glu Asn Phe Asn Gln His Glu Val Leu Leu Ala
    1130                1135                1140

Pro Leu Leu Ser Ala Gly Ile Phe Gly Ala Asp Pro Ile His Ser
    1145                1150                1155

Leu Arg Val Cys Val Asp Thr Val Arg Thr Asn Val Tyr Leu Ala
```

-continued

```
            1160              1165              1170

Val Phe Asp Lys Asn Leu Tyr Asp Lys Leu Val Ser Ser Phe Leu
    1175              1180              1185

Glu Met Lys Ser Glu Lys Gln Val Glu Gln Lys Ile Ala Glu Ile
    1190              1195              1200

Pro Lys Glu Glu Val Lys Pro Phe Ile Thr Glu Ser Lys Pro Ser
    1205              1210              1215

Val Glu Gln Arg Lys Gln Asp Asp Lys Lys Ile Lys Ala Cys Val
    1220              1225              1230

Glu Glu Val Thr Thr Thr Leu Glu Glu Thr Lys Phe Leu Thr Glu
    1235              1240              1245

Asn Leu Leu Leu Tyr Ile Asp Ile Asn Gly Asn Leu His Pro Asp
    1250              1255              1260

Ser Ala Thr Leu Val Ser Asp Ile Asp Ile Thr Phe Leu Lys Lys
    1265              1270              1275

Asp Ala Pro Tyr Ile Val Gly Asp Val Val Gln Glu Gly Val Leu
    1280              1285              1290

Thr Ala Val Val Ile Pro Thr Lys Lys Ala Gly Gly Thr Thr Glu
    1295              1300              1305

Met Leu Ala Lys Ala Leu Arg Lys Val Pro Thr Asp Asn Tyr Ile
    1310              1315              1320

Thr Thr Tyr Pro Gly Gln Gly Leu Asn Gly Tyr Thr Val Glu Glu
    1325              1330              1335

Ala Lys Thr Val Leu Lys Lys Cys Lys Ser Ala Phe Tyr Ile Leu
    1340              1345              1350

Pro Ser Ile Ile Ser Asn Glu Lys Gln Glu Ile Leu Gly Thr Val
    1355              1360              1365

Ser Trp Asn Leu Arg Glu Met Leu Ala His Ala Glu Glu Thr Arg
    1370              1375              1380

Lys Leu Met Pro Val Cys Val Glu Thr Lys Ala Ile Val Ser Thr
    1385              1390              1395

Ile Gln Arg Lys Tyr Lys Gly Ile Lys Ile Gln Glu Gly Val Val
    1400              1405              1410

Asp Tyr Gly Ala Arg Phe Tyr Phe Tyr Thr Ser Lys Thr Thr Val
    1415              1420              1425

Ala Ser Leu Ile Asn Thr Leu Asn Asp Leu Asn Glu Thr Leu Val
    1430              1435              1440

Thr Met Pro Leu Gly Tyr Val Thr His Gly Leu Asn Leu Glu Glu
    1445              1450              1455

Ala Ala Arg Tyr Met Arg Ser Leu Lys Val Pro Ala Thr Val Ser
    1460              1465              1470

Val Ser Ser Pro Asp Ala Val Thr Ala Tyr Asn Gly Tyr Leu Thr
    1475              1480              1485

Ser Ser Ser Lys Thr Pro Glu Glu His Phe Ile Glu Thr Ile Ser
    1490              1495              1500

Leu Ala Gly Ser Tyr Lys Asp Trp Ser Tyr Ser Gly Gln Ser Thr
    1505              1510              1515

Gln Leu Gly Ile Glu Phe Leu Lys Arg Gly Asp Lys Ser Val Tyr
    1520              1525              1530

Tyr Thr Ser Asn Pro Thr Thr Phe His Leu Asp Gly Glu Val Ile
    1535              1540              1545

Thr Phe Asp Asn Leu Lys Thr Leu Leu Ser Leu Arg Glu Val Arg
    1550              1555              1560
```

-continued

```
Thr Ile Lys Val Phe Thr Thr Val Asp Asn Ile Asn Leu His Thr
1565                1570                1575

Gln Val Val Asp Met Ser Met Thr Tyr Gly Gln Gln Phe Gly Pro
1580                1585                1590

Thr Tyr Phe Asp Gly Ala Asp Val Thr Lys Ile Lys Pro His Asn
1595                1600                1605

Ser His Glu Gly Lys Thr Phe Tyr Val Leu Pro Asn Asp Asp Thr
1610                1615                1620

Leu Arg Val Glu Ala Phe Glu Tyr Tyr His Thr Thr Asp Pro Ser
1625                1630                1635

Phe Leu Gly Arg Tyr Met Ser Ala Leu Asn His Thr Lys Lys Trp
1640                1645                1650

Lys Tyr Pro Gln Val Asn Gly Leu Thr Ser Ile Lys Trp Ala Asp
1655                1660                1665

Asn Asn Cys Tyr Leu Ala Thr Ala Leu Leu Thr Leu Gln Gln Ile
1670                1675                1680

Glu Leu Lys Phe Asn Pro Pro Ala Leu Gln Asp Ala Tyr Tyr Arg
1685                1690                1695

Ala Arg Ala Gly Glu Ala Ala Asn Phe Cys Ala Leu Ile Leu Ala
1700                1705                1710

Tyr Cys Asn Lys Thr Val Gly Glu Leu Gly Asp Val Arg Glu Thr
1715                1720                1725

Met Ser Tyr Leu Phe Gln His Ala Asn Leu Asp Ser Cys Lys Arg
1730                1735                1740

Val Leu Asn Val Val Cys Lys Thr Cys Gly Gln Gln Gln Thr Thr
1745                1750                1755

Leu Lys Gly Val Glu Ala Val Met Tyr Met Gly Thr Leu Ser Tyr
1760                1765                1770

Glu Gln Phe Lys Lys Gly Val Gln Ile Pro Cys Thr Cys Gly Lys
1775                1780                1785

Gln Ala Thr Lys Tyr Leu Val Gln Gln Glu Ser Pro Phe Val Met
1790                1795                1800

Met Ser Ala Pro Pro Ala Gln Tyr Glu Leu Lys His Gly Thr Phe
1805                1810                1815

Thr Cys Ala Ser Glu Tyr Thr Gly Asn Tyr Gln Cys Gly His Tyr
1820                1825                1830

Lys His Ile Thr Ser Lys Glu Thr Leu Tyr Cys Ile Asp Gly Ala
1835                1840                1845

Leu Leu Thr Lys Ser Ser Glu Tyr Lys Gly Pro Ile Thr Asp Val
1850                1855                1860

Phe Tyr Lys Glu Asn Ser Tyr Thr Thr Thr Ile Lys Pro Val Thr
1865                1870                1875

Tyr Lys Leu Asp Gly Val Val Cys Thr Glu Ile Asp Pro Lys Leu
1880                1885                1890

Asp Asn Tyr Tyr Lys Lys Asp Asn Ser Tyr Phe Thr Glu Gln Pro
1895                1900                1905

Ile Asp Leu Val Pro Asn Gln Pro Tyr Pro Asn Ala Ser Phe Asp
1910                1915                1920

Asn Phe Lys Phe Val Cys Asp Asn Ile Lys Phe Ala Asp Asp Leu
1925                1930                1935

Asn Gln Leu Thr Gly Tyr Lys Lys Pro Ala Ser Arg Glu Leu Lys
1940                1945                1950
```

```
Val Thr Phe Phe Pro Asp Leu Asn Gly Asp Val Val Ala Ile Asp
    1955            1960            1965

Tyr Lys His Tyr Thr Pro Ser Phe Lys Lys Gly Ala Lys Leu Leu
    1970            1975            1980

His Lys Pro Ile Val Trp His Val Asn Asn Ala Thr Asn Lys Ala
    1985            1990            1995

Thr Tyr Lys Pro Asn Thr Trp Cys Ile Arg Cys Leu Trp Ser Thr
    2000            2005            2010

Lys Pro Val Glu Thr Ser Asn Ser Phe Asp Val Leu Lys Ser Glu
    2015            2020            2025

Asp Ala Gln Gly Met Asp Asn Leu Ala Cys Glu Asp Leu Lys Pro
    2030            2035            2040

Val Ser Glu Glu Val Val Glu Asn Pro Thr Ile Gln Lys Asp Val
    2045            2050            2055

Leu Glu Cys Asn Val Lys Thr Thr Glu Val Val Gly Asp Ile Ile
    2060            2065            2070

Leu Lys Pro Ala Asn Asn Ser Leu Lys Ile Thr Glu Glu Val Gly
    2075            2080            2085

His Thr Asp Leu Met Ala Ala Tyr Val Asp Asn Ser Ser Leu Thr
    2090            2095            2100

Ile Lys Lys Pro Asn Glu Leu Ser Arg Val Leu Gly Leu Lys Thr
    2105            2110            2115

Leu Ala Thr His Gly Leu Ala Ala Val Asn Ser Val Pro Trp Asp
    2120            2125            2130

Thr Ile Ala Asn Tyr Ala Lys Pro Phe Leu Asn Lys Val Val Ser
    2135            2140            2145

Thr Thr Thr Asn Ile Val Thr Arg Cys Leu Asn Arg Val Cys Thr
    2150            2155            2160

Asn Tyr Met Pro Tyr Phe Phe Thr Leu Leu Leu Gln Leu Cys Thr
    2165            2170            2175

Phe Thr Arg Ser Thr Asn Ser Arg Ile Lys Ala Ser Met Pro Thr
    2180            2185            2190

Thr Ile Ala Lys Asn Thr Val Lys Ser Val Gly Lys Phe Cys Leu
    2195            2200            2205

Glu Ala Ser Phe Asn Tyr Leu Lys Ser Pro Asn Phe Ser Lys Leu
    2210            2215            2220

Ile Asn Ile Ile Ile Trp Phe Leu Leu Leu Ser Val Cys Leu Gly
    2225            2230            2235

Ser Leu Ile Tyr Ser Thr Ala Ala Leu Gly Val Leu Met Ser Asn
    2240            2245            2250

Leu Gly Met Pro Ser Tyr Cys Thr Gly Tyr Arg Glu Gly Tyr Leu
    2255            2260            2265

Asn Ser Thr Asn Val Thr Ile Ala Thr Tyr Cys Thr Gly Ser Ile
    2270            2275            2280

Pro Cys Ser Val Cys Leu Ser Gly Leu Asp Ser Leu Asp Thr Tyr
    2285            2290            2295

Pro Ser Leu Glu Thr Ile Gln Ile Thr Ile Ser Ser Phe Lys Trp
    2300            2305            2310

Asp Leu Thr Ala Phe Gly Leu Val Ala Glu Trp Phe Leu Ala Tyr
    2315            2320            2325

Ile Leu Phe Thr Arg Phe Phe Tyr Val Leu Gly Leu Ala Ala Ile
    2330            2335            2340

Met Gln Leu Phe Phe Ser Tyr Phe Ala Val His Phe Ile Ser Asn
```

```
                    2345                2350                2355

Ser  Trp  Leu  Met  Trp  Leu  Ile  Ile  Asn  Leu  Val  Gln  Met  Ala  Pro
          2360                2365                2370

Ile  Ser  Ala  Met  Val  Arg  Met  Tyr  Ile  Phe  Phe  Ala  Ser  Phe  Tyr
          2375                2380                2385

Tyr  Val  Trp  Lys  Ser  Tyr  Val  His  Val  Val  Asp  Gly  Cys  Asn  Ser
          2390                2395                2400

Ser  Thr  Cys  Met  Met  Cys  Tyr  Lys  Arg  Asn  Arg  Ala  Thr  Arg  Val
          2405                2410                2415

Glu  Cys  Thr  Thr  Ile  Val  Asn  Gly  Val  Arg  Arg  Ser  Phe  Tyr  Val
          2420                2425                2430

Tyr  Ala  Asn  Gly  Gly  Lys  Gly  Phe  Cys  Lys  Leu  His  Asn  Trp  Asn
          2435                2440                2445

Cys  Val  Asn  Cys  Asp  Thr  Phe  Cys  Ala  Gly  Ser  Thr  Phe  Ile  Ser
          2450                2455                2460

Asp  Glu  Val  Ala  Arg  Asp  Leu  Ser  Leu  Gln  Phe  Lys  Arg  Pro  Ile
          2465                2470                2475

Asn  Pro  Thr  Asp  Gln  Ser  Ser  Tyr  Ile  Val  Asp  Ser  Val  Thr  Val
          2480                2485                2490

Lys  Asn  Gly  Ser  Ile  His  Leu  Tyr  Phe  Asp  Lys  Ala  Gly  Gln  Lys
          2495                2500                2505

Thr  Tyr  Glu  Arg  His  Ser  Leu  Ser  His  Phe  Val  Asn  Leu  Asp  Asn
          2510                2515                2520

Leu  Arg  Ala  Asn  Asn  Thr  Lys  Gly  Ser  Leu  Pro  Ile  Asn  Val  Ile
          2525                2530                2535

Val  Phe  Asp  Gly  Lys  Ser  Lys  Cys  Glu  Glu  Ser  Ser  Ala  Lys  Ser
          2540                2545                2550

Ala  Ser  Val  Tyr  Tyr  Ser  Gln  Leu  Met  Cys  Gln  Pro  Ile  Leu  Leu
          2555                2560                2565

Leu  Asp  Gln  Ala  Leu  Val  Ser  Asp  Val  Gly  Asp  Ser  Ala  Glu  Val
          2570                2575                2580

Ala  Val  Lys  Met  Phe  Asp  Ala  Tyr  Val  Asn  Thr  Phe  Ser  Ser  Thr
          2585                2590                2595

Phe  Asn  Val  Pro  Met  Glu  Lys  Leu  Lys  Thr  Leu  Val  Ala  Thr  Ala
          2600                2605                2610

Glu  Ala  Glu  Leu  Ala  Lys  Asn  Val  Ser  Leu  Asp  Asn  Val  Leu  Ser
          2615                2620                2625

Thr  Phe  Ile  Ser  Ala  Ala  Arg  Gln  Gly  Phe  Val  Asp  Ser  Asp  Val
          2630                2635                2640

Glu  Thr  Lys  Asp  Val  Val  Glu  Cys  Leu  Lys  Leu  Ser  His  Gln  Ser
          2645                2650                2655

Asp  Ile  Glu  Val  Thr  Gly  Asp  Ser  Cys  Asn  Asn  Tyr  Met  Leu  Thr
          2660                2665                2670

Tyr  Asn  Lys  Val  Glu  Asn  Met  Thr  Pro  Arg  Asp  Leu  Gly  Ala  Cys
          2675                2680                2685

Ile  Asp  Cys  Ser  Ala  Arg  His  Ile  Asn  Ala  Gln  Val  Ala  Lys  Ser
          2690                2695                2700

His  Asn  Ile  Ala  Leu  Ile  Trp  Asn  Val  Lys  Asp  Phe  Met  Ser  Leu
          2705                2710                2715

Ser  Glu  Gln  Leu  Arg  Lys  Gln  Ile  Arg  Ser  Ala  Ala  Lys  Lys  Asn
          2720                2725                2730

Asn  Leu  Pro  Phe  Lys  Leu  Thr  Cys  Ala  Thr  Thr  Arg  Gln  Val  Val
          2735                2740                2745
```

```
Asn Val Val Thr Thr Lys Ile Ala Leu Lys Gly Gly Lys Ile Val
    2750                2755                2760

Asn Asn Trp Leu Lys Gln Leu Ile Lys Val Thr Leu Val Phe Leu
    2765                2770                2775

Phe Val Ala Ala Ile Phe Tyr Leu Ile Thr Pro Val His Val Met
    2780                2785                2790

Ser Lys His Thr Asp Phe Ser Ser Glu Ile Ile Gly Tyr Lys Ala
    2795                2800                2805

Ile Asp Gly Gly Val Thr Arg Asp Ile Ala Ser Thr Asp Thr Cys
    2810                2815                2820

Phe Ala Asn Lys His Ala Asp Phe Asp Thr Trp Phe Ser Gln Arg
    2825                2830                2835

Gly Gly Ser Tyr Thr Asn Asp Lys Ala Cys Pro Leu Ile Ala Ala
    2840                2845                2850

Val Ile Thr Arg Glu Val Gly Phe Val Val Pro Gly Leu Pro Gly
    2855                2860                2865

Thr Ile Leu Arg Thr Thr Asn Gly Asp Phe Leu His Phe Leu Pro
    2870                2875                2880

Arg Val Phe Ser Ala Val Gly Asn Ile Cys Tyr Thr Pro Ser Lys
    2885                2890                2895

Leu Ile Glu Tyr Thr Asp Phe Ala Thr Ser Ala Cys Val Leu Ala
    2900                2905                2910

Ala Glu Cys Thr Ile Phe Lys Asp Ala Ser Gly Lys Pro Val Pro
    2915                2920                2925

Tyr Cys Tyr Asp Thr Asn Val Leu Glu Gly Ser Val Ala Tyr Glu
    2930                2935                2940

Ser Leu Arg Pro Asp Thr Arg Tyr Val Leu Met Asp Gly Ser Ile
    2945                2950                2955

Ile Gln Phe Pro Asn Thr Tyr Leu Glu Gly Ser Val Arg Val Val
    2960                2965                2970

Thr Thr Phe Asp Ser Glu Tyr Cys Arg His Gly Thr Cys Glu Arg
    2975                2980                2985

Ser Glu Ala Gly Val Cys Val Ser Thr Ser Gly Arg Trp Val Leu
    2990                2995                3000

Asn Asn Asp Tyr Tyr Arg Ser Leu Pro Gly Val Phe Cys Gly Val
    3005                3010                3015

Asp Ala Val Asn Leu Leu Thr Asn Met Phe Thr Pro Leu Ile Gln
    3020                3025                3030

Pro Ile Gly Ala Leu Asp Ile Ser Ala Ser Ile Val Ala Gly Gly
    3035                3040                3045

Ile Val Ala Ile Val Val Thr Cys Leu Ala Tyr Tyr Phe Met Arg
    3050                3055                3060

Phe Arg Arg Ala Phe Gly Glu Tyr Ser His Val Val Ala Phe Asn
    3065                3070                3075

Thr Leu Leu Phe Leu Met Ser Phe Thr Val Leu Cys Leu Thr Pro
    3080                3085                3090

Val Tyr Ser Phe Leu Pro Gly Val Tyr Ser Val Ile Tyr Leu Tyr
    3095                3100                3105

Leu Thr Phe Tyr Leu Thr Asn Asp Val Ser Phe Leu Ala His Ile
    3110                3115                3120

Gln Trp Met Val Met Phe Thr Pro Leu Val Pro Phe Trp Ile Thr
    3125                3130                3135
```

```
Ile Ala Tyr Ile Ile Cys Ile Ser Thr Lys His Phe Tyr Trp Phe
3140                3145                3150

Phe Ser Asn Tyr Leu Lys Arg Arg Val Val Phe Asn Gly Val Ser
3155                3160                3165

Phe Ser Thr Phe Glu Glu Ala Ala Leu Cys Thr Phe Leu Leu Asn
3170                3175                3180

Lys Glu Met Tyr Leu Lys Leu Arg Ser Asp Val Leu Leu Pro Leu
3185                3190                3195

Thr Gln Tyr Asn Arg Tyr Leu Ala Leu Tyr Asn Lys Tyr Lys Tyr
3200                3205                3210

Phe Ser Gly Ala Met Asp Thr Thr Ser Tyr Arg Glu Ala Ala Cys
3215                3220                3225

Cys His Leu Ala Lys Ala Leu Asn Asp Phe Ser Asn Ser Gly Ser
3230                3235                3240

Asp Val Leu Tyr Gln Pro Pro Gln Thr Ser Ile Thr Ser Ala Val
3245                3250                3255

Leu Gln Ser Gly Phe Arg Lys Met Ala Phe Pro Ser Gly Lys Val
3260                3265                3270

Glu Gly Cys Met Val Gln Val Thr Cys Gly Thr Thr Thr Leu Asn
3275                3280                3285

Gly Leu Trp Leu Asp Asp Val Val Tyr Cys Pro Arg His Val Ile
3290                3295                3300

Cys Thr Ser Glu Asp Met Leu Asn Pro Asn Tyr Glu Asp Leu Leu
3305                3310                3315

Ile Arg Lys Ser Asn His Asn Phe Leu Val Gln Ala Gly Asn Val
3320                3325                3330

Gln Leu Arg Val Ile Gly His Ser Met Gln Asn Cys Val Leu Lys
3335                3340                3345

Leu Lys Val Asp Thr Ala Asn Pro Lys Thr Pro Lys Tyr Lys Phe
3350                3355                3360

Val Arg Ile Gln Pro Gly Gln Thr Phe Ser Val Leu Ala Cys Tyr
3365                3370                3375

Asn Gly Ser Pro Ser Gly Val Tyr Gln Cys Ala Met Arg Pro Asn
3380                3385                3390

Phe Thr Ile Lys Gly Ser Phe Leu Asn Gly Ser Cys Gly Ser Val
3395                3400                3405

Gly Phe Asn Ile Asp Tyr Asp Cys Val Ser Phe Cys Tyr Met His
3410                3415                3420

His Met Glu Leu Pro Thr Gly Val His Ala Gly Thr Asp Leu Glu
3425                3430                3435

Gly Asn Phe Tyr Gly Pro Phe Val Asp Arg Gln Thr Ala Gln Ala
3440                3445                3450

Ala Gly Thr Asp Thr Thr Ile Thr Val Asn Val Leu Ala Trp Leu
3455                3460                3465

Tyr Ala Ala Val Ile Asn Gly Asp Arg Trp Phe Leu Asn Arg Phe
3470                3475                3480

Thr Thr Thr Leu Asn Asp Phe Asn Leu Val Ala Met Lys Tyr Asn
3485                3490                3495

Tyr Glu Pro Leu Thr Gln Asp His Val Asp Ile Leu Gly Pro Leu
3500                3505                3510

Ser Ala Gln Thr Gly Ile Ala Val Leu Asp Met Cys Ala Ser Leu
3515                3520                3525

Lys Glu Leu Leu Gln Asn Gly Met Asn Gly Arg Thr Ile Leu Gly
```

-continued

|  | | 3530 | | | | 3535 | | | | 3540 | |

Ser Ala Leu Leu Glu Asp Glu Phe Thr Pro Phe Asp Val Val Arg
3545              3550              3555

Gln Cys Ser Gly Val Thr Phe Gln Ser Ala Val Lys Arg Thr Ile
3560              3565              3570

Lys Gly Thr His His Trp Leu Leu Leu Thr Ile Leu Thr Ser Leu
3575              3580              3585

Leu Val Leu Val Gln Ser Thr Gln Trp Ser Leu Phe Phe Phe Leu
3590              3595              3600

Tyr Glu Lys Ala Phe Leu Pro Phe Ala Met Gly Ile Ile Ala Met
3605              3610              3615

Ser Ala Phe Ala Met Met Phe Val Lys His Lys His Ala Phe Leu
3620              3625              3630

Cys Leu Phe Leu Leu Pro Ser Leu Ala Thr Val Ala Tyr Phe Asn
3635              3640              3645

Met Val Tyr Met Pro Ala Ser Trp Val Met Arg Ile Met Thr Trp
3650              3655              3660

Leu Asp Met Val Ile Thr Ser Leu Ser Gly Phe Lys Leu Lys Asp
3665              3670              3675

Cys Val Met Tyr Ala Ser Ala Val Val Leu Leu Ile Leu Met Thr
3680              3685              3690

Ala Arg Thr Val Tyr Asp Asp Gly Ala Arg Arg Val Trp Thr Leu
3695              3700              3705

Met Asn Val Leu Thr Leu Val Tyr Lys Val Tyr Tyr Gly Asn Ala
3710              3715              3720

Leu Asp Gln Ala Ile Ser Met Trp Ala Leu Ile Ile Ser Val Thr
3725              3730              3735

Ser Asn Tyr Ser Gly Val Val Thr Thr Val Met Phe Leu Ala Arg
3740              3745              3750

Gly Ile Val Phe Met Cys Val Glu Tyr Cys Pro Ile Phe Phe Ile
3755              3760              3765

Thr Gly Asn Thr Leu Gln Cys Ile Met Leu Val Tyr Cys Phe Leu
3770              3775              3780

Gly Tyr Phe Cys Thr Cys Tyr Phe Gly Leu Phe Cys Leu Leu Asn
3785              3790              3795

Arg Tyr Phe Arg Leu Thr Leu Gly Val Tyr Asp Tyr Leu Val Ser
3800              3805              3810

Thr Gln Glu Phe Arg Tyr Met Asn Ser Gln Gly Leu Leu Pro Pro
3815              3820              3825

Lys Asn Ser Ile Asp Ala Phe Lys Leu Asn Ile Lys Leu Leu Gly
3830              3835              3840

Val Gly Gly Lys Pro Cys Ile Lys Val Ala Thr Val Gln Ser Lys
3845              3850              3855

Met Ser Asp Val Lys Cys Thr Ser Val Val Leu Leu Ser Val Leu
3860              3865              3870

Gln Gln Leu Arg Val Glu Ser Ser Ser Lys Leu Trp Ala Gln Cys
3875              3880              3885

Val Gln Leu His Asn Asp Ile Leu Leu Ala Lys Asp Thr Thr Glu
3890              3895              3900

Ala Phe Glu Lys Met Val Ser Leu Leu Ser Val Leu Leu Ser Met
3905              3910              3915

Gln Gly Ala Val Ala Ile Asn Lys Leu Cys Glu Glu Met Leu Asp
3920              3925              3930

```
Asn Arg Ala Thr Leu Gln Ala Ile Ala Ser Glu Phe Ser Ser Leu
    3935            3940            3945

Pro Ser Tyr Ala Ala Phe Ala Thr Ala Gln Glu Ala Tyr Glu Gln
    3950            3955            3960

Ala Val Ala Asn Gly Asp Ser Glu Val Val Leu Lys Lys Leu Lys
    3965            3970            3975

Lys Ser Leu Asn Val Ala Lys Ser Glu Phe Asp Arg Asp Ala Ala
    3980            3985            3990

Met Gln Arg Lys Leu Glu Lys Met Ala Asp Gln Ala Met Thr Gln
    3995            4000            4005

Met Tyr Lys Gln Ala Arg Ser Glu Asp Lys Arg Ala Lys Val Thr
    4010            4015            4020

Ser Ala Met Gln Thr Met Leu Phe Thr Met Leu Arg Lys Leu Asp
    4025            4030            4035

Asn Asp Ala Leu Asn Asn Ile Ile Asn Asn Ala Arg Asp Gly Cys
    4040            4045            4050

Val Pro Leu Asn Ile Ile Pro Leu Thr Thr Ala Ala Lys Leu Met
    4055            4060            4065

Val Val Ile Pro Asp Tyr Asn Thr Tyr Lys Asn Thr Cys Asp Gly
    4070            4075            4080

Thr Thr Phe Thr Tyr Ala Ser Ala Leu Trp Glu Ile Gln Gln Val
    4085            4090            4095

Val Asp Ala Asp Ser Lys Ile Val Gln Leu Ser Glu Ile Ser Met
    4100            4105            4110

Asp Asn Ser Pro Asn Leu Ala Trp Pro Leu Ile Val Thr Ala Leu
    4115            4120            4125

Arg Ala Asn Ser Ala Val Lys Leu Gln Asn Asn Glu Leu Ser Pro
    4130            4135            4140

Val Ala Leu Arg Gln Met Ser Cys Ala Ala Gly Thr Thr Gln Thr
    4145            4150            4155

Ala Cys Thr Asp Asp Asn Ala Leu Ala Tyr Tyr Asn Thr Thr Lys
    4160            4165            4170

Gly Gly Arg Phe Val Leu Ala Leu Leu Ser Asp Leu Gln Asp Leu
    4175            4180            4185

Lys Trp Ala Arg Phe Pro Lys Ser Asp Gly Thr Gly Thr Ile Tyr
    4190            4195            4200

Thr Glu Leu Glu Pro Pro Cys Arg Phe Val Thr Asp Thr Pro Lys
    4205            4210            4215

Gly Pro Lys Val Lys Tyr Leu Tyr Phe Ile Lys Gly Leu Asn Asn
    4220            4225            4230

Leu Asn Arg Gly Met Val Leu Gly Ser Leu Ala Ala Thr Val Arg
    4235            4240            4245

Leu Gln Ala Gly Asn Ala Thr Glu Val Pro Ala Asn Ser Thr Val
    4250            4255            4260

Leu Ser Phe Cys Ala Phe Ala Val Asp Ala Ala Lys Ala Tyr Lys
    4265            4270            4275

Asp Tyr Leu Ala Ser Gly Gly Gln Pro Ile Thr Asn Cys Val Lys
    4280            4285            4290

Met Leu Cys Thr His Thr Gly Thr Gly Gln Ala Ile Thr Val Thr
    4295            4300            4305

Pro Glu Ala Asn Met Asp Gln Glu Ser Phe Gly Gly Ala Ser Cys
    4310            4315            4320
```

```
Cys Leu Tyr Cys Arg Cys His Ile Asp His Pro Asn Pro Lys Gly
    4325            4330            4335

Phe Cys Asp Leu Lys Gly Lys Tyr Val Gln Ile Pro Thr Thr Cys
    4340            4345            4350

Ala Asn Asp Pro Val Gly Phe Thr Leu Lys Asn Thr Val Cys Thr
    4355            4360            4365

Val Cys Gly Met Trp Lys Gly Tyr Gly Cys Ser Cys Asp Gln Leu
    4370            4375            4380

Arg Glu Pro Met Leu Gln Ser Ala Asp Ala Gln Ser Phe Leu Asn
    4385            4390            4395

Arg Val Cys Gly Val Ser Ala Ala Arg Leu Thr Pro Cys Gly Thr
    4400            4405            4410

Gly Thr Ser Thr Asp Val Val Tyr Arg Ala Phe Asp Ile Tyr Asn
    4415            4420            4425

Asp Lys Val Ala Gly Phe Ala Lys Phe Leu Lys Thr Asn Cys Cys
    4430            4435            4440

Arg Phe Gln Glu Lys Asp Glu Asp Asp Asn Leu Ile Asp Ser Tyr
    4445            4450            4455

Phe Val Val Lys Arg His Thr Phe Ser Asn Tyr Gln His Glu Glu
    4460            4465            4470

Thr Ile Tyr Asn Leu Leu Lys Asp Cys Pro Ala Val Ala Lys His
    4475            4480            4485

Asp Phe Phe Lys Phe Arg Ile Asp Gly Asp Met Val Pro His Ile
    4490            4495            4500

Ser Arg Gln Arg Leu Thr Lys Tyr Thr Met Ala Asp Leu Val Tyr
    4505            4510            4515

Ala Leu Arg His Phe Asp Glu Gly Asn Cys Asp Thr Leu Lys Glu
    4520            4525            4530

Ile Leu Val Thr Tyr Asn Cys Cys Asp Asp Asp Tyr Phe Asn Lys
    4535            4540            4545

Lys Asp Trp Tyr Asp Phe Val Glu Asn Pro Asp Ile Leu Arg Val
    4550            4555            4560

Tyr Ala Asn Leu Gly Glu Arg Val Arg Gln Ala Leu Leu Lys Thr
    4565            4570            4575

Val Gln Phe Cys Asp Ala Met Arg Asn Ala Gly Ile Val Gly Val
    4580            4585            4590

Leu Thr Leu Asp Asn Gln Asp Leu Asn Gly Asn Trp Tyr Asp Phe
    4595            4600            4605

Gly Asp Phe Ile Gln Thr Thr Pro Gly Ser Gly Val Pro Val Val
    4610            4615            4620

Asp Ser Tyr Tyr Ser Leu Leu Met Pro Ile Leu Thr Leu Thr Arg
    4625            4630            4635

Ala Leu Thr Ala Glu Ser His Val Asp Thr Asp Leu Thr Lys Pro
    4640            4645            4650

Tyr Ile Lys Trp Asp Leu Leu Lys Tyr Asp Phe Thr Glu Glu Arg
    4655            4660            4665

Leu Lys Leu Phe Asp Arg Tyr Phe Lys Tyr Trp Asp Gln Thr Tyr
    4670            4675            4680

His Pro Asn Cys Val Asn Cys Leu Asp Asp Arg Cys Ile Leu His
    4685            4690            4695

Cys Ala Asn Phe Asn Val Leu Phe Ser Thr Val Phe Pro Pro Thr
    4700            4705            4710

Ser Phe Gly Pro Leu Val Arg Lys Ile Phe Val Asp Gly Val Pro
```

```
                4715                4720                4725
Phe Val Val Ser Thr Gly Tyr His Phe Arg Glu Leu Gly Val Val
    4730                4735                4740
His Asn Gln Asp Val Asn Leu His Ser Ser Arg Leu Ser Phe Lys
    4745                4750                4755
Glu Leu Leu Val Tyr Ala Ala Asp Pro Ala Met His Ala Ala Ser
    4760                4765                4770
Gly Asn Leu Leu Leu Asp Lys Arg Thr Thr Cys Phe Ser Val Ala
    4775                4780                4785
Ala Leu Thr Asn Asn Val Ala Phe Gln Thr Val Lys Pro Gly Asn
    4790                4795                4800
Phe Asn Lys Asp Phe Tyr Asp Phe Ala Val Ser Lys Gly Phe Phe
    4805                4810                4815
Lys Glu Gly Ser Ser Val Glu Leu Lys His Phe Phe Phe Ala Gln
    4820                4825                4830
Asp Gly Asn Ala Ala Ile Ser Asp Tyr Asp Tyr Arg Tyr Asn
    4835                4840                4845
Leu Pro Thr Met Cys Asp Ile Arg Gln Leu Leu Phe Val Val Glu
    4850                4855                4860
Val Val Asp Lys Tyr Phe Asp Cys Tyr Asp Gly Gly Cys Ile Asn
    4865                4870                4875
Ala Asn Gln Val Ile Val Asn Asn Leu Asp Lys Ser Ala Gly Phe
    4880                4885                4890
Pro Phe Asn Lys Trp Gly Lys Ala Arg Leu Tyr Tyr Asp Ser Met
    4895                4900                4905
Ser Tyr Glu Asp Gln Asp Ala Leu Phe Ala Tyr Thr Lys Arg Asn
    4910                4915                4920
Val Ile Pro Thr Ile Thr Gln Met Asn Leu Lys Tyr Ala Ile Ser
    4925                4930                4935
Ala Lys Asn Arg Ala Arg Thr Val Ala Gly Val Ser Ile Cys Ser
    4940                4945                4950
Thr Met Thr Asn Arg Gln Phe His Gln Lys Leu Leu Lys Ser Ile
    4955                4960                4965
Ala Ala Thr Arg Gly Ala Thr Val Val Ile Gly Thr Ser Lys Phe
    4970                4975                4980
Tyr Gly Gly Trp His Asn Met Leu Lys Thr Val Tyr Ser Asp Val
    4985                4990                4995
Glu Asn Pro His Leu Met Gly Trp Asp Tyr Pro Lys Cys Asp Arg
    5000                5005                5010
Ala Met Pro Asn Met Leu Arg Ile Met Ala Ser Leu Val Leu Ala
    5015                5020                5025
Arg Lys His Thr Thr Cys Cys Ser Leu Ser His Arg Phe Tyr Arg
    5030                5035                5040
Leu Ala Asn Glu Cys Ala Gln Val Leu Ser Glu Met Val Met Cys
    5045                5050                5055
Gly Gly Ser Leu Tyr Val Lys Pro Gly Gly Thr Ser Ser Gly Asp
    5060                5065                5070
Ala Thr Thr Ala Tyr Ala Asn Ser Val Phe Asn Ile Cys Gln Ala
    5075                5080                5085
Val Thr Ala Asn Val Asn Ala Leu Leu Ser Thr Asp Gly Asn Lys
    5090                5095                5100
Ile Ala Asp Lys Tyr Val Arg Asn Leu Gln His Arg Leu Tyr Glu
    5105                5110                5115
```

-continued

Cys Leu Tyr Arg Asn Arg Asp Val Asp Thr Asp Phe Val Asn Glu
5120                5125                5130

Phe Tyr Ala Tyr Leu Arg Lys His Phe Ser Met Met Ile Leu Ser
5135                5140                5145

Asp Asp Ala Val Val Cys Phe Asn Ser Thr Tyr Ala Ser Gln Gly
5150                5155                5160

Leu Val Ala Ser Ile Lys Asn Phe Lys Ser Val Leu Tyr Tyr Gln
5165                5170                5175

Asn Asn Val Phe Met Ser Glu Ala Lys Cys Trp Thr Glu Thr Asp
5180                5185                5190

Leu Thr Lys Gly Pro His Glu Phe Cys Ser Gln His Thr Met Leu
5195                5200                5205

Val Lys Gln Gly Asp Asp Tyr Val Tyr Leu Pro Tyr Pro Asp Pro
5210                5215                5220

Ser Arg Ile Leu Gly Ala Gly Cys Phe Val Asp Asp Ile Val Lys
5225                5230                5235

Thr Asp Gly Thr Leu Met Ile Glu Arg Phe Val Ser Leu Ala Ile
5240                5245                5250

Asp Ala Tyr Pro Leu Thr Lys His Pro Asn Gln Glu Tyr Ala Asp
5255                5260                5265

Val Phe His Leu Tyr Leu Gln Tyr Ile Arg Lys Leu His Asp Glu
5270                5275                5280

Leu Thr Gly His Met Leu Asp Met Tyr Ser Val Met Leu Thr Asn
5285                5290                5295

Asp Asn Thr Ser Arg Tyr Trp Glu Pro Glu Phe Tyr Glu Ala Met
5300                5305                5310

Tyr Thr Pro His Thr Val Leu Gln Ala Val Gly Ala Cys Val Leu
5315                5320                5325

Cys Asn Ser Gln Thr Ser Leu Arg Cys Gly Ala Cys Ile Arg Arg
5330                5335                5340

Pro Phe Leu Cys Cys Lys Cys Cys Tyr Asp His Val Ile Ser Thr
5345                5350                5355

Ser His Lys Leu Val Leu Ser Val Asn Pro Tyr Val Cys Asn Ala
5360                5365                5370

Pro Gly Cys Asp Val Thr Asp Val Thr Gln Leu Tyr Leu Gly Gly
5375                5380                5385

Met Ser Tyr Tyr Cys Lys Ser His Lys Pro Pro Ile Ser Phe Pro
5390                5395                5400

Leu Cys Ala Asn Gly Gln Val Phe Gly Leu Tyr Lys Asn Thr Cys
5405                5410                5415

Val Gly Ser Asp Asn Val Thr Asp Phe Asn Ala Ile Ala Thr Cys
5420                5425                5430

Asp Trp Thr Asn Ala Gly Asp Tyr Ile Leu Ala Asn Thr Cys Thr
5435                5440                5445

Glu Arg Leu Lys Leu Phe Ala Ala Glu Thr Leu Lys Ala Thr Glu
5450                5455                5460

Glu Thr Phe Lys Leu Ser Tyr Gly Ile Ala Thr Val Arg Glu Val
5465                5470                5475

Leu Ser Asp Arg Glu Leu His Leu Ser Trp Glu Val Gly Lys Pro
5480                5485                5490

Arg Pro Pro Leu Asn Arg Asn Tyr Val Phe Thr Gly Tyr Arg Val
5495                5500                5505

```
Thr Lys Asn Ser Lys Val Gln Ile Gly Glu Tyr Thr Phe Glu Lys
5510                5515                5520

Gly Asp Tyr Gly Asp Ala Val Val Tyr Arg Gly Thr Thr Thr Tyr
5525                5530                5535

Lys Leu Asn Val Gly Asp Tyr Phe Val Leu Thr Ser His Thr Val
5540                5545                5550

Met Pro Leu Ser Ala Pro Thr Leu Val Pro Gln Glu His Tyr Val
5555                5560                5565

Arg Ile Thr Gly Leu Tyr Pro Thr Leu Asn Ile Ser Asp Glu Phe
5570                5575                5580

Ser Ser Asn Val Ala Asn Tyr Gln Lys Val Gly Met Gln Lys Tyr
5585                5590                5595

Ser Thr Phe Gln Gly Pro Pro Gly Thr Gly Lys Ser His Phe Ala
5600                5605                5610

Ile Gly Leu Ala Leu Tyr Tyr Pro Ser Ala Arg Ile Val Tyr Thr
5615                5620                5625

Ala Cys Ser His Ala Ala Val Asp Ala Leu Cys Glu Lys Ala Leu
5630                5635                5640

Lys Tyr Leu Pro Ile Asp Lys Cys Ser Arg Ile Ile Pro Ala Arg
5645                5650                5655

Ala Arg Val Glu Cys Phe Asp Lys Phe Lys Val Asn Ser Thr Leu
5660                5665                5670

Glu Gln Tyr Val Phe Cys Thr Val Asn Ala Leu Pro Glu Thr Thr
5675                5680                5685

Ala Asp Ile Val Val Phe Asp Glu Ile Ser Met Ala Thr Asn Tyr
5690                5695                5700

Asp Leu Ser Val Val Asn Ala Arg Leu Arg Ala Lys His Tyr Val
5705                5710                5715

Tyr Ile Gly Asp Pro Ala Gln Leu Pro Ala Pro Arg Thr Leu Leu
5720                5725                5730

Thr Lys Gly Thr Leu Glu Pro Glu Tyr Phe Asn Ser Val Cys Arg
5735                5740                5745

Leu Met Lys Thr Ile Gly Pro Asp Met Phe Leu Gly Thr Cys Arg
5750                5755                5760

Arg Cys Pro Ala Glu Ile Val Asp Thr Val Ser Ala Leu Val Tyr
5765                5770                5775

Asp Asn Lys Leu Lys Ala His Lys Asp Lys Ser Ala Gln Cys Phe
5780                5785                5790

Lys Met Phe Tyr Lys Gly Val Ile Thr His Asp Val Ser Ser Ala
5795                5800                5805

Ile Asn Arg Pro Gln Ile Gly Val Val Arg Glu Phe Leu Thr Arg
5810                5815                5820

Asn Pro Ala Trp Arg Lys Ala Val Phe Ile Ser Pro Tyr Asn Ser
5825                5830                5835

Gln Asn Ala Val Ala Ser Lys Ile Leu Gly Leu Pro Thr Gln Thr
5840                5845                5850

Val Asp Ser Ser Gln Gly Ser Glu Tyr Asp Tyr Val Ile Phe Thr
5855                5860                5865

Gln Thr Thr Glu Thr Ala His Ser Cys Asn Val Asn Arg Phe Asn
5870                5875                5880

Val Ala Ile Thr Arg Ala Lys Val Gly Ile Leu Cys Ile Met Ser
5885                5890                5895

Asp Arg Asp Leu Tyr Asp Lys Leu Gln Phe Thr Ser Leu Glu Ile
```

```
                    5900                5905                5910

Pro  Arg  Arg  Asn  Val  Ala  Thr  Leu  Gln  Ala  Glu  Asn  Val  Thr  Gly
     5915                5920                5925

Leu  Phe  Lys  Asp  Cys  Ser  Lys  Val  Ile  Thr  Gly  Leu  His  Pro  Thr
     5930                5935                5940

Gln  Ala  Pro  Thr  His  Leu  Ser  Val  Asp  Thr  Lys  Phe  Lys  Thr  Glu
     5945                5950                5955

Gly  Leu  Cys  Val  Asp  Ile  Pro  Gly  Ile  Pro  Lys  Asp  Met  Thr  Tyr
     5960                5965                5970

Arg  Arg  Leu  Ile  Ser  Met  Met  Gly  Phe  Lys  Met  Asn  Tyr  Gln  Val
     5975                5980                5985

Asn  Gly  Tyr  Pro  Asn  Met  Phe  Ile  Thr  Arg  Glu  Glu  Ala  Ile  Arg
     5990                5995                6000

His  Val  Arg  Ala  Trp  Ile  Gly  Phe  Asp  Val  Glu  Gly  Cys  His  Ala
     6005                6010                6015

Thr  Arg  Glu  Ala  Val  Gly  Thr  Asn  Leu  Pro  Leu  Gln  Leu  Gly  Phe
     6020                6025                6030

Ser  Thr  Gly  Val  Asn  Leu  Val  Ala  Val  Pro  Thr  Gly  Tyr  Val  Asp
     6035                6040                6045

Thr  Pro  Asn  Asn  Thr  Asp  Phe  Ser  Arg  Val  Ser  Ala  Lys  Pro  Pro
     6050                6055                6060

Pro  Gly  Asp  Gln  Phe  Lys  His  Leu  Ile  Pro  Leu  Met  Tyr  Lys  Gly
     6065                6070                6075

Leu  Pro  Trp  Asn  Val  Val  Arg  Ile  Lys  Ile  Val  Gln  Met  Leu  Ser
     6080                6085                6090

Asp  Thr  Leu  Lys  Asn  Leu  Ser  Asp  Arg  Val  Val  Phe  Val  Leu  Trp
     6095                6100                6105

Ala  His  Gly  Phe  Glu  Leu  Thr  Ser  Met  Lys  Tyr  Phe  Val  Lys  Ile
     6110                6115                6120

Gly  Pro  Glu  Arg  Thr  Cys  Cys  Leu  Cys  Asp  Arg  Arg  Ala  Thr  Cys
     6125                6130                6135

Phe  Ser  Thr  Ala  Ser  Asp  Thr  Tyr  Ala  Cys  Trp  His  His  Ser  Ile
     6140                6145                6150

Gly  Phe  Asp  Tyr  Val  Tyr  Asn  Pro  Phe  Met  Ile  Asp  Val  Gln  Gln
     6155                6160                6165

Trp  Gly  Phe  Thr  Gly  Asn  Leu  Gln  Ser  Asn  His  Asp  Leu  Tyr  Cys
     6170                6175                6180

Gln  Val  His  Gly  Asn  Ala  His  Val  Ala  Ser  Cys  Asp  Ala  Ile  Met
     6185                6190                6195

Thr  Arg  Cys  Leu  Ala  Val  His  Glu  Cys  Phe  Val  Lys  Arg  Val  Asp
     6200                6205                6210

Trp  Thr  Ile  Glu  Tyr  Pro  Ile  Ile  Gly  Asp  Glu  Leu  Lys  Ile  Asn
     6215                6220                6225

Ala  Ala  Cys  Arg  Lys  Val  Gln  His  Met  Val  Val  Lys  Ala  Ala  Leu
     6230                6235                6240

Leu  Ala  Asp  Lys  Phe  Pro  Val  Leu  His  Asp  Ile  Gly  Asn  Pro  Lys
     6245                6250                6255

Ala  Ile  Lys  Cys  Val  Pro  Gln  Ala  Asp  Val  Glu  Trp  Lys  Phe  Tyr
     6260                6265                6270

Asp  Ala  Gln  Pro  Cys  Ser  Asp  Lys  Ala  Tyr  Lys  Ile  Glu  Glu  Leu
     6275                6280                6285

Phe  Tyr  Ser  Tyr  Ala  Thr  His  Ser  Asp  Lys  Phe  Thr  Asp  Gly  Val
     6290                6295                6300
```

-continued

```
Cys Leu Phe Trp Asn Cys Asn Val Asp Arg Tyr Pro Ala Asn Ser
    6305                6310                6315

Ile Val Cys Arg Phe Asp Thr Arg Val Leu Ser Asn Leu Asn Leu
    6320                6325                6330

Pro Gly Cys Asp Gly Gly Ser Leu Tyr Val Asn Lys His Ala Phe
    6335                6340                6345

His Thr Pro Ala Phe Asp Lys Ser Ala Phe Val Asn Leu Lys Gln
    6350                6355                6360

Leu Pro Phe Phe Tyr Tyr Ser Asp Ser Pro Cys Glu Ser His Gly
    6365                6370                6375

Lys Gln Val Val Ser Asp Ile Asp Tyr Val Pro Leu Lys Ser Ala
    6380                6385                6390

Thr Cys Ile Thr Arg Cys Asn Leu Gly Gly Ala Val Cys Arg His
    6395                6400                6405

His Ala Asn Glu Tyr Arg Leu Tyr Leu Asp Ala Tyr Asn Met Met
    6410                6415                6420

Ile Ser Ala Gly Phe Ser Leu Trp Val Tyr Lys Gln Phe Asp Thr
    6425                6430                6435

Tyr Asn Leu Trp Asn Thr Phe Thr Arg Leu Gln Ser Leu Glu Asn
    6440                6445                6450

Val Ala Phe Asn Val Val Asn Lys Gly His Phe Asp Gly Gln Gln
    6455                6460                6465

Gly Glu Val Pro Val Ser Ile Ile Asn Asn Thr Val Tyr Thr Lys
    6470                6475                6480

Val Asp Gly Val Asp Val Glu Leu Phe Glu Asn Lys Thr Thr Leu
    6485                6490                6495

Pro Val Asn Val Ala Phe Glu Leu Trp Ala Lys Arg Asn Ile Lys
    6500                6505                6510

Pro Val Pro Glu Val Lys Ile Leu Asn Asn Leu Gly Val Asp Ile
    6515                6520                6525

Ala Ala Asn Thr Val Ile Trp Asp Tyr Lys Arg Asp Ala Pro Ala
    6530                6535                6540

His Ile Ser Thr Ile Gly Val Cys Ser Met Thr Asp Ile Ala Lys
    6545                6550                6555

Lys Pro Thr Glu Thr Ile Cys Ala Pro Leu Thr Val Phe Phe Asp
    6560                6565                6570

Gly Arg Val Asp Gly Gln Val Asp Leu Phe Arg Asn Ala Arg Asn
    6575                6580                6585

Gly Val Leu Ile Thr Glu Gly Ser Val Lys Gly Leu Gln Pro Ser
    6590                6595                6600

Val Gly Pro Lys Gln Ala Ser Leu Asn Gly Val Thr Leu Ile Gly
    6605                6610                6615

Glu Ala Val Lys Thr Gln Phe Asn Tyr Tyr Lys Lys Val Asp Gly
    6620                6625                6630

Val Val Gln Gln Leu Pro Glu Thr Tyr Phe Thr Gln Ser Arg Asn
    6635                6640                6645

Leu Gln Glu Phe Lys Pro Arg Ser Gln Met Glu Ile Asp Phe Leu
    6650                6655                6660

Glu Leu Ala Met Asp Glu Phe Ile Glu Arg Tyr Lys Leu Glu Gly
    6665                6670                6675

Tyr Ala Phe Glu His Ile Val Tyr Gly Asp Phe Ser His Ser Gln
    6680                6685                6690
```

```
Leu Gly Gly Leu His Leu Leu Ile Gly Leu Ala Lys Arg Phe Lys
6695                6700                6705

Glu Ser Pro Phe Glu Leu Glu Asp Phe Ile Pro Met Asp Ser Thr
6710                6715                6720

Val Lys Asn Tyr Phe Ile Thr Asp Ala Gln Thr Gly Ser Ser Lys
6725                6730                6735

Cys Val Cys Ser Val Ile Asp Leu Leu Leu Asp Asp Phe Val Glu
6740                6745                6750

Ile Ile Lys Ser Gln Asp Leu Ser Val Val Ser Lys Val Val Lys
6755                6760                6765

Val Thr Ile Asp Tyr Thr Glu Ile Ser Phe Met Leu Trp Cys Lys
6770                6775                6780

Asp Gly His Val Glu Thr Phe Tyr Pro Lys Leu Gln Ser Ser Gln
6785                6790                6795

Ala Trp Gln Pro Gly Val Ala Met Pro Asn Leu Tyr Lys Met Gln
6800                6805                6810

Arg Met Leu Leu Glu Lys Cys Asp Leu Gln Asn Tyr Gly Asp Ser
6815                6820                6825

Ala Thr Leu Pro Lys Gly Ile Met Met Asn Val Ala Lys Tyr Thr
6830                6835                6840

Gln Leu Cys Gln Tyr Leu Asn Thr Leu Thr Leu Ala Val Pro Tyr
6845                6850                6855

Asn Met Arg Val Ile His Phe Gly Ala Gly Ser Asp Lys Gly Val
6860                6865                6870

Ala Pro Gly Thr Ala Val Leu Arg Gln Trp Leu Pro Thr Gly Thr
6875                6880                6885

Leu Leu Val Asp Ser Asp Leu Asn Asp Phe Val Ser Asp Ala Asp
6890                6895                6900

Ser Thr Leu Ile Gly Asp Cys Ala Thr Val His Thr Ala Asn Lys
6905                6910                6915

Trp Asp Leu Ile Ile Ser Asp Met Tyr Asp Pro Lys Thr Lys Asn
6920                6925                6930

Val Thr Lys Glu Asn Asp Ser Lys Glu Gly Phe Phe Thr Tyr Ile
6935                6940                6945

Cys Gly Phe Ile Gln Gln Lys Leu Ala Leu Gly Gly Ser Val Ala
6950                6955                6960

Ile Lys Ile Thr Glu His Ser Trp Asn Ala Asp Leu Tyr Lys Leu
6965                6970                6975

Met Gly His Phe Ala Trp Trp Thr Ala Phe Val Thr Asn Val Asn
6980                6985                6990

Ala Ser Ser Ser Glu Ala Phe Leu Ile Gly Cys Asn Tyr Leu Gly
6995                7000                7005

Lys Pro Arg Glu Gln Ile Asp Gly Tyr Val Met His Ala Asn Tyr
7010                7015                7020

Ile Phe Trp Arg Asn Thr Asn Pro Ile Gln Leu Ser Ser Tyr Ser
7025                7030                7035

Leu Phe Asp Met Ser Lys Phe Pro Leu Lys Leu Arg Gly Thr Ala
7040                7045                7050

Val Met Ser Leu Lys Glu Gly Gln Ile Asn Asp Met Ile Leu Ser
7055                7060                7065

Leu Leu Ser Lys Gly Arg Leu Ile Ile Arg Glu Asn Asn Arg Val
7070                7075                7080

Val Ile Ser Ser Asp Val Leu Val Asn Asn
```

-continued

```
        7085              7090

<210> SEQ ID NO 38
<211> LENGTH: 4402
<212> TYPE: PRT
<213> ORGANISM: Unknown
<220> FEATURE:
<223> OTHER INFORMATION: SARS-CoV-2 ORF1a polyprotein

<400> SEQUENCE: 38

Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Val Val Glu Leu Val Ala Glu Leu Glu Gly Ile Gln Tyr Gly Arg
                85                  90                  95

Ser Gly Glu Thr Leu Gly Val Leu Val Pro His Val Gly Glu Ile Pro
            100                 105                 110

Val Ala Tyr Arg Lys Val Leu Leu Arg Lys Asn Gly Asn Lys Gly Ala
        115                 120                 125

Gly Gly His Ser Tyr Gly Ala Asp Leu Lys Ser Phe Asp Leu Gly Asp
    130                 135                 140

Glu Leu Gly Thr Asp Pro Tyr Glu Asp Phe Gln Glu Asn Trp Asn Thr
145                 150                 155                 160

Lys His Ser Ser Gly Val Thr Arg Glu Leu Met Arg Glu Leu Asn Gly
                165                 170                 175

Gly Ala Tyr Thr Arg Tyr Val Asp Asn Asn Phe Cys Gly Pro Asp Gly
            180                 185                 190

Tyr Pro Leu Glu Cys Ile Lys Asp Leu Leu Ala Arg Ala Gly Lys Ala
        195                 200                 205

Ser Cys Thr Leu Ser Glu Gln Leu Asp Phe Ile Asp Thr Lys Arg Gly
    210                 215                 220

Val Tyr Cys Cys Arg Glu His Glu His Glu Ile Ala Trp Tyr Thr Glu
225                 230                 235                 240

Arg Ser Glu Lys Ser Tyr Glu Leu Gln Thr Pro Phe Glu Ile Lys Leu
                245                 250                 255

Ala Lys Lys Phe Asp Thr Phe Asn Gly Glu Cys Pro Asn Phe Val Phe
            260                 265                 270

Pro Leu Asn Ser Ile Ile Lys Thr Ile Gln Pro Arg Val Glu Lys Lys
        275                 280                 285

Lys Leu Asp Gly Phe Met Gly Arg Ile Arg Ser Val Tyr Pro Val Ala
    290                 295                 300

Ser Pro Asn Glu Cys Asn Gln Met Cys Leu Ser Thr Leu Met Lys Cys
305                 310                 315                 320

Asp His Cys Gly Glu Thr Ser Trp Gln Thr Gly Asp Phe Val Lys Ala
                325                 330                 335

Thr Cys Glu Phe Cys Gly Thr Glu Asn Leu Thr Lys Glu Gly Ala Thr
            340                 345                 350

Thr Cys Gly Tyr Leu Pro Gln Asn Ala Val Val Lys Ile Tyr Cys Pro
```

```
            355                 360                 365
Ala Cys His Asn Ser Glu Val Gly Pro Glu His Ser Leu Ala Glu Tyr
    370                 375                 380

His Asn Glu Ser Gly Leu Lys Thr Ile Leu Arg Lys Gly Gly Arg Thr
385                 390                 395                 400

Ile Ala Phe Gly Gly Cys Val Phe Ser Tyr Val Gly Cys His Asn Lys
                405                 410                 415

Cys Ala Tyr Trp Val Pro Arg Ala Ser Ala Asn Ile Gly Cys Asn His
            420                 425                 430

Thr Gly Val Val Gly Glu Gly Ser Glu Gly Leu Asn Asp Asn Leu Leu
        435                 440                 445

Glu Ile Leu Gln Lys Glu Lys Val Asn Ile Asn Ile Val Gly Asp Phe
    450                 455                 460

Lys Leu Asn Glu Glu Ile Ala Ile Ile Leu Ala Ser Phe Ser Ala Ser
465                 470                 475                 480

Thr Ser Ala Phe Val Glu Thr Val Lys Gly Leu Asp Tyr Lys Ala Phe
                485                 490                 495

Lys Gln Ile Val Glu Ser Cys Gly Asn Phe Lys Val Thr Lys Gly Lys
            500                 505                 510

Ala Lys Lys Gly Ala Trp Asn Ile Gly Glu Gln Lys Ser Ile Leu Ser
        515                 520                 525

Pro Leu Tyr Ala Phe Ala Ser Glu Ala Ala Arg Val Val Arg Ser Ile
    530                 535                 540

Phe Ser Arg Thr Leu Glu Thr Ala Gln Asn Ser Val Arg Val Leu Gln
545                 550                 555                 560

Lys Ala Ala Ile Thr Ile Leu Asp Gly Ile Ser Gln Tyr Ser Leu Arg
                565                 570                 575

Leu Ile Asp Ala Met Met Phe Thr Ser Asp Leu Ala Thr Asn Asn Leu
            580                 585                 590

Val Val Met Ala Tyr Ile Thr Gly Gly Val Val Gln Leu Thr Ser Gln
        595                 600                 605

Trp Leu Thr Asn Ile Phe Gly Thr Val Tyr Glu Lys Leu Lys Pro Val
    610                 615                 620

Leu Asp Trp Leu Glu Glu Lys Phe Lys Glu Gly Val Glu Phe Leu Arg
625                 630                 635                 640

Asp Gly Trp Glu Ile Val Lys Phe Ile Ser Thr Cys Ala Cys Glu Ile
                645                 650                 655

Val Gly Gly Gln Ile Val Thr Cys Ala Lys Glu Ile Lys Glu Ser Val
            660                 665                 670

Gln Thr Phe Phe Lys Leu Val Asn Lys Phe Leu Ala Leu Cys Ala Asp
        675                 680                 685

Ser Ile Ile Ile Gly Gly Ala Lys Leu Lys Ala Leu Asn Leu Gly Glu
    690                 695                 700

Thr Phe Val Thr His Ser Lys Gly Leu Tyr Arg Lys Cys Val Lys Ser
705                 710                 715                 720

Arg Glu Glu Thr Gly Leu Leu Met Pro Leu Lys Ala Pro Lys Glu Ile
                725                 730                 735

Ile Phe Leu Glu Gly Glu Thr Leu Pro Thr Glu Val Leu Thr Glu Glu
            740                 745                 750

Val Val Leu Lys Thr Gly Asp Leu Gln Pro Leu Glu Gln Pro Thr Ser
        755                 760                 765

Glu Ala Val Glu Ala Pro Leu Val Gly Thr Pro Val Cys Ile Asn Gly
    770                 775                 780
```

```
Leu Met Leu Leu Glu Ile Lys Asp Thr Glu Lys Tyr Cys Ala Leu Ala
785                 790                 795                 800

Pro Asn Met Met Val Thr Asn Asn Thr Phe Thr Leu Lys Gly Gly Ala
            805                 810                 815

Pro Thr Lys Val Thr Phe Gly Asp Asp Thr Val Ile Glu Val Gln Gly
                820                 825                 830

Tyr Lys Ser Val Asn Ile Thr Phe Glu Leu Asp Glu Arg Ile Asp Lys
            835                 840                 845

Val Leu Asn Glu Lys Cys Ser Ala Tyr Thr Val Glu Leu Gly Thr Glu
850                 855                 860

Val Asn Glu Phe Ala Cys Val Val Ala Asp Ala Val Ile Lys Thr Leu
865                 870                 875                 880

Gln Pro Val Ser Glu Leu Leu Thr Pro Leu Gly Ile Asp Leu Asp Glu
                885                 890                 895

Trp Ser Met Ala Thr Tyr Tyr Leu Phe Asp Glu Ser Gly Glu Phe Lys
                900                 905                 910

Leu Ala Ser His Met Tyr Cys Ser Phe Tyr Pro Pro Asp Glu Asp Glu
            915                 920                 925

Glu Glu Gly Asp Cys Glu Glu Glu Phe Glu Pro Ser Thr Gln Tyr
    930                 935                 940

Glu Tyr Gly Thr Glu Asp Asp Tyr Gln Gly Lys Pro Leu Glu Phe Gly
945                 950                 955                 960

Ala Thr Ser Ala Ala Leu Gln Pro Glu Glu Glu Gln Glu Glu Asp Trp
                965                 970                 975

Leu Asp Asp Asp Ser Gln Gln Thr Val Gly Gln Gln Asp Gly Ser Glu
                980                 985                 990

Asp Asn Gln Thr Thr Thr Ile Gln Thr Ile Val Glu Val Gln Pro Gln
            995                 1000                1005

Leu Glu Met Glu Leu Thr Pro Val Val Gln Thr Ile Glu Val Asn
    1010                1015                1020

Ser Phe Ser Gly Tyr Leu Lys Leu Thr Asp Asn Val Tyr Ile Lys
    1025                1030                1035

Asn Ala Asp Ile Val Glu Glu Ala Lys Lys Val Lys Pro Thr Val
    1040                1045                1050

Val Val Asn Ala Ala Asn Val Tyr Leu Lys His Gly Gly Gly Val
    1055                1060                1065

Ala Gly Ala Leu Asn Lys Ala Thr Asn Asn Ala Met Gln Val Glu
    1070                1075                1080

Ser Asp Asp Tyr Ile Ala Thr Asn Gly Pro Leu Lys Val Gly Gly
    1085                1090                1095

Ser Cys Val Leu Ser Gly His Asn Leu Ala Lys His Cys Leu His
    1100                1105                1110

Val Val Gly Pro Asn Val Asn Lys Gly Glu Asp Ile Gln Leu Leu
    1115                1120                1125

Lys Ser Ala Tyr Glu Asn Phe Asn Gln His Glu Val Leu Leu Ala
    1130                1135                1140

Pro Leu Leu Ser Ala Gly Ile Phe Gly Ala Asp Pro Ile His Ser
    1145                1150                1155

Leu Arg Val Cys Val Asp Thr Val Arg Thr Asn Val Tyr Leu Ala
    1160                1165                1170

Val Phe Asp Lys Asn Leu Tyr Asp Lys Leu Val Ser Ser Phe Leu
    1175                1180                1185
```

```
Glu Met Lys Ser Glu Lys Gln Val Glu Gln Lys Ile Ala Glu Ile
    1190                1195                1200

Pro Lys Glu Glu Val Lys Pro Phe Ile Thr Glu Ser Lys Pro Ser
    1205                1210                1215

Val Glu Gln Arg Lys Gln Asp Asp Lys Lys Ile Lys Ala Cys Val
    1220                1225                1230

Glu Glu Val Thr Thr Thr Leu Glu Glu Thr Lys Phe Leu Thr Glu
    1235                1240                1245

Asn Leu Leu Tyr Ile Asp Ile Asn Gly Asn Leu His Pro Asp
    1250                1255                1260

Ser Ala Thr Leu Val Ser Asp Ile Asp Ile Thr Phe Leu Lys Lys
    1265                1270                1275

Asp Ala Pro Tyr Ile Val Gly Asp Val Val Gln Glu Gly Val Leu
    1280                1285                1290

Thr Ala Val Val Ile Pro Thr Lys Lys Ala Gly Gly Thr Thr Glu
    1295                1300                1305

Met Leu Ala Lys Ala Leu Arg Lys Val Pro Thr Asp Asn Tyr Ile
    1310                1315                1320

Thr Thr Tyr Pro Gly Gln Gly Leu Asn Gly Tyr Thr Val Glu Glu
    1325                1330                1335

Ala Lys Thr Val Leu Lys Lys Cys Lys Ser Ala Phe Tyr Ile Leu
    1340                1345                1350

Pro Ser Ile Ile Ser Asn Glu Lys Gln Glu Ile Leu Gly Thr Val
    1355                1360                1365

Ser Trp Asn Leu Arg Glu Met Leu Ala His Ala Glu Glu Thr Arg
    1370                1375                1380

Lys Leu Met Pro Val Cys Val Glu Thr Lys Ala Ile Val Ser Thr
    1385                1390                1395

Ile Gln Arg Lys Tyr Lys Gly Ile Lys Ile Gln Glu Gly Val Val
    1400                1405                1410

Asp Tyr Gly Ala Arg Phe Tyr Phe Tyr Thr Ser Lys Thr Thr Val
    1415                1420                1425

Ala Ser Leu Ile Asn Thr Leu Asn Asp Leu Asn Glu Thr Leu Val
    1430                1435                1440

Thr Met Pro Leu Gly Tyr Val Thr His Gly Leu Asn Leu Glu Glu
    1445                1450                1455

Ala Ala Arg Tyr Met Arg Ser Leu Lys Val Pro Ala Thr Val Ser
    1460                1465                1470

Val Ser Ser Pro Asp Ala Val Thr Ala Tyr Asn Gly Tyr Leu Thr
    1475                1480                1485

Ser Ser Ser Lys Thr Pro Glu Glu His Phe Ile Glu Thr Ile Ser
    1490                1495                1500

Leu Ala Gly Ser Tyr Lys Asp Trp Ser Tyr Ser Gly Gln Ser Thr
    1505                1510                1515

Gln Leu Gly Ile Glu Phe Leu Lys Arg Gly Asp Lys Ser Val Tyr
    1520                1525                1530

Tyr Thr Ser Asn Pro Thr Thr Phe His Leu Asp Gly Glu Val Ile
    1535                1540                1545

Thr Phe Asp Asn Leu Lys Thr Leu Leu Ser Leu Arg Glu Val Arg
    1550                1555                1560

Thr Ile Lys Val Phe Thr Thr Val Asp Asn Ile Asn Leu His Thr
    1565                1570                1575

Gln Val Val Asp Met Ser Met Thr Tyr Gly Gln Gln Phe Gly Pro
```

```
                 1580                1585                1590
Thr Tyr Phe Asp Gly Ala Asp Val Thr Lys Ile Lys Pro His Asn
    1595                1600                1605

Ser His Glu Gly Lys Thr Phe Tyr Val Leu Pro Asn Asp Asp Thr
    1610                1615                1620

Leu Arg Val Glu Ala Phe Glu Tyr Tyr His Thr Thr Asp Pro Ser
    1625                1630                1635

Phe Leu Gly Arg Tyr Met Ser Ala Leu Asn His Thr Lys Lys Trp
    1640                1645                1650

Lys Tyr Pro Gln Val Asn Gly Leu Thr Ser Ile Lys Trp Ala Asp
    1655                1660                1665

Asn Asn Cys Tyr Leu Ala Thr Ala Leu Leu Thr Leu Gln Gln Ile
    1670                1675                1680

Glu Leu Lys Phe Asn Pro Pro Ala Leu Gln Asp Ala Tyr Tyr Arg
    1685                1690                1695

Ala Arg Ala Gly Glu Ala Ala Asn Phe Cys Ala Leu Ile Leu Ala
    1700                1705                1710

Tyr Cys Asn Lys Thr Val Gly Glu Leu Gly Asp Val Arg Glu Thr
    1715                1720                1725

Met Ser Tyr Leu Phe Gln His Ala Asn Leu Asp Ser Cys Lys Arg
    1730                1735                1740

Val Leu Asn Val Val Cys Lys Thr Cys Gly Gln Gln Gln Thr Thr
    1745                1750                1755

Leu Lys Gly Val Glu Ala Val Met Tyr Met Gly Thr Leu Ser Tyr
    1760                1765                1770

Glu Gln Phe Lys Lys Gly Val Gln Ile Pro Cys Thr Cys Gly Lys
    1775                1780                1785

Gln Ala Thr Lys Tyr Leu Val Gln Gln Glu Ser Pro Phe Val Met
    1790                1795                1800

Met Ser Ala Pro Pro Ala Gln Tyr Glu Leu Lys His Gly Thr Phe
    1805                1810                1815

Thr Cys Ala Ser Glu Tyr Thr Gly Asn Tyr Gln Cys Gly His Tyr
    1820                1825                1830

Lys His Ile Thr Ser Lys Glu Thr Leu Tyr Cys Ile Asp Gly Ala
    1835                1840                1845

Leu Leu Thr Lys Ser Ser Glu Tyr Lys Gly Pro Ile Thr Asp Val
    1850                1855                1860

Phe Tyr Lys Glu Asn Ser Tyr Thr Thr Thr Ile Lys Pro Val Thr
    1865                1870                1875

Tyr Lys Leu Asp Gly Val Val Cys Thr Glu Ile Asp Pro Lys Leu
    1880                1885                1890

Asp Asn Tyr Tyr Lys Lys Asp Asn Ser Tyr Phe Thr Glu Gln Pro
    1895                1900                1905

Ile Asp Leu Val Pro Asn Gln Pro Tyr Pro Asn Ala Ser Phe Asp
    1910                1915                1920

Asn Phe Lys Phe Val Cys Asp Asn Ile Lys Phe Ala Asp Asp Leu
    1925                1930                1935

Asn Gln Leu Thr Gly Tyr Lys Lys Pro Ala Ser Arg Glu Leu Lys
    1940                1945                1950

Val Thr Phe Phe Pro Asp Leu Asn Gly Asp Val Val Ala Ile Asp
    1955                1960                1965

Tyr Lys His Tyr Thr Pro Ser Phe Lys Lys Gly Ala Lys Leu Leu
    1970                1975                1980
```

```
His Lys Pro Ile Val Trp His Val Asn Asn Ala Thr Asn Lys Ala
    1985            1990            1995
Thr Tyr Lys Pro Asn Thr Trp Cys Ile Arg Cys Leu Trp Ser Thr
    2000            2005            2010
Lys Pro Val Glu Thr Ser Asn Ser Phe Asp Val Leu Lys Ser Glu
    2015            2020            2025
Asp Ala Gln Gly Met Asp Asn Leu Ala Cys Glu Asp Leu Lys Pro
    2030            2035            2040
Val Ser Glu Glu Val Val Glu Asn Pro Thr Ile Gln Lys Asp Val
    2045            2050            2055
Leu Glu Cys Asn Val Lys Thr Thr Glu Val Val Gly Asp Ile Ile
    2060            2065            2070
Leu Lys Pro Ala Asn Asn Ser Leu Lys Ile Thr Glu Glu Val Gly
    2075            2080            2085
His Thr Asp Leu Met Ala Ala Tyr Val Asp Asn Ser Ser Leu Thr
    2090            2095            2100
Ile Lys Lys Pro Asn Glu Leu Ser Arg Val Leu Gly Leu Lys Thr
    2105            2110            2115
Leu Ala Thr His Gly Leu Ala Ala Val Asn Ser Val Pro Trp Asp
    2120            2125            2130
Thr Ile Ala Asn Tyr Ala Lys Pro Phe Leu Asn Lys Val Val Ser
    2135            2140            2145
Thr Thr Thr Asn Ile Val Thr Arg Cys Leu Asn Arg Val Cys Thr
    2150            2155            2160
Asn Tyr Met Pro Tyr Phe Phe Thr Leu Leu Leu Gln Leu Cys Thr
    2165            2170            2175
Phe Thr Arg Ser Thr Asn Ser Arg Ile Lys Ala Ser Met Pro Thr
    2180            2185            2190
Thr Ile Ala Lys Asn Thr Val Lys Ser Val Gly Lys Phe Cys Leu
    2195            2200            2205
Glu Ala Ser Phe Asn Tyr Leu Lys Ser Pro Asn Phe Ser Lys Leu
    2210            2215            2220
Ile Asn Ile Ile Ile Trp Phe Leu Leu Leu Ser Val Cys Leu Gly
    2225            2230            2235
Ser Leu Ile Tyr Ser Thr Ala Ala Leu Gly Val Leu Met Ser Asn
    2240            2245            2250
Leu Gly Met Pro Ser Tyr Cys Thr Gly Tyr Arg Glu Gly Tyr Leu
    2255            2260            2265
Asn Ser Thr Asn Val Thr Ile Ala Thr Tyr Cys Thr Gly Ser Ile
    2270            2275            2280
Pro Cys Ser Val Cys Leu Ser Gly Leu Asp Ser Leu Asp Thr Tyr
    2285            2290            2295
Pro Ser Leu Glu Thr Ile Gln Ile Thr Ile Ser Ser Phe Lys Trp
    2300            2305            2310
Asp Leu Thr Ala Phe Gly Leu Val Ala Glu Trp Phe Leu Ala Tyr
    2315            2320            2325
Ile Leu Phe Thr Arg Phe Phe Tyr Val Leu Gly Leu Ala Ala Ile
    2330            2335            2340
Met Gln Leu Phe Phe Ser Tyr Phe Ala Val His Phe Ile Ser Asn
    2345            2350            2355
Ser Trp Leu Met Trp Leu Ile Ile Asn Leu Val Gln Met Ala Pro
    2360            2365            2370
```

```
Ile Ser Ala Met Val Arg Met Tyr Ile Phe Phe Ala Ser Phe Tyr
2375                 2380                 2385

Tyr Val Trp Lys Ser Tyr Val His Val Val Asp Gly Cys Asn Ser
2390                 2395                 2400

Ser Thr Cys Met Met Cys Tyr Lys Arg Asn Arg Ala Thr Arg Val
2405                 2410                 2415

Glu Cys Thr Thr Ile Val Asn Gly Val Arg Arg Ser Phe Tyr Val
2420                 2425                 2430

Tyr Ala Asn Gly Gly Lys Gly Phe Cys Lys Leu His Asn Trp Asn
2435                 2440                 2445

Cys Val Asn Cys Asp Thr Phe Cys Ala Gly Ser Thr Phe Ile Ser
2450                 2455                 2460

Asp Glu Val Ala Arg Asp Leu Ser Leu Gln Phe Lys Arg Pro Ile
2465                 2470                 2475

Asn Pro Thr Asp Gln Ser Ser Tyr Ile Val Asp Ser Val Thr Val
2480                 2485                 2490

Lys Asn Gly Ser Ile His Leu Tyr Phe Asp Lys Ala Gly Gln Lys
2495                 2500                 2505

Thr Tyr Glu Arg His Ser Leu Ser His Phe Val Asn Leu Asp Asn
2510                 2515                 2520

Leu Arg Ala Asn Asn Thr Lys Gly Ser Leu Pro Ile Asn Val Ile
2525                 2530                 2535

Val Phe Asp Gly Lys Ser Lys Cys Glu Glu Ser Ser Ala Lys Ser
2540                 2545                 2550

Ala Ser Val Tyr Tyr Ser Gln Leu Met Cys Gln Pro Ile Leu Leu
2555                 2560                 2565

Leu Asp Gln Ala Leu Val Ser Asp Val Gly Asp Ser Ala Glu Val
2570                 2575                 2580

Ala Val Lys Met Phe Asp Ala Tyr Val Asn Thr Phe Ser Ser Thr
2585                 2590                 2595

Phe Asn Val Pro Met Glu Lys Leu Lys Thr Leu Val Ala Thr Ala
2600                 2605                 2610

Glu Ala Glu Leu Ala Lys Asn Val Ser Leu Asp Asn Val Leu Ser
2615                 2620                 2625

Thr Phe Ile Ser Ala Ala Arg Gln Gly Phe Val Asp Ser Asp Val
2630                 2635                 2640

Glu Thr Lys Asp Val Val Glu Cys Leu Lys Leu Ser His Gln Ser
2645                 2650                 2655

Asp Ile Glu Val Thr Gly Asp Ser Cys Asn Asn Tyr Met Leu Thr
2660                 2665                 2670

Tyr Asn Lys Val Glu Asn Met Thr Pro Arg Asp Leu Gly Ala Cys
2675                 2680                 2685

Ile Asp Cys Ser Ala Arg His Ile Asn Ala Gln Val Ala Lys Ser
2690                 2695                 2700

His Asn Ile Ala Leu Ile Trp Asn Val Lys Asp Phe Met Ser Leu
2705                 2710                 2715

Ser Glu Gln Leu Arg Lys Gln Ile Arg Ser Ala Ala Lys Lys Asn
2720                 2725                 2730

Asn Leu Pro Phe Lys Leu Thr Cys Ala Thr Thr Arg Gln Val Val
2735                 2740                 2745

Asn Val Val Thr Thr Lys Ile Ala Leu Lys Gly Gly Lys Ile Val
2750                 2755                 2760

Asn Asn Trp Leu Lys Gln Leu Ile Lys Val Thr Leu Val Phe Leu
```

```
                    2765                2770                2775
Phe Val Ala Ala Ile Phe Tyr Leu Ile Thr Pro Val His Val Met
                2780                2785                2790
Ser Lys His Thr Asp Phe Ser Ser Glu Ile Ile Gly Tyr Lys Ala
                2795                2800                2805
Ile Asp Gly Gly Val Thr Arg Asp Ile Ala Ser Thr Asp Thr Cys
                2810                2815                2820
Phe Ala Asn Lys His Ala Asp Phe Asp Thr Trp Phe Ser Gln Arg
                2825                2830                2835
Gly Gly Ser Tyr Thr Asn Asp Lys Ala Cys Pro Leu Ile Ala Ala
                2840                2845                2850
Val Ile Thr Arg Glu Val Gly Phe Val Val Pro Gly Leu Pro Gly
                2855                2860                2865
Thr Ile Leu Arg Thr Thr Asn Gly Asp Phe Leu His Phe Leu Pro
                2870                2875                2880
Arg Val Phe Ser Ala Val Gly Asn Ile Cys Tyr Thr Pro Ser Lys
                2885                2890                2895
Leu Ile Glu Tyr Thr Asp Phe Ala Thr Ser Ala Cys Val Leu Ala
                2900                2905                2910
Ala Glu Cys Thr Ile Phe Lys Asp Ala Ser Gly Lys Pro Val Pro
                2915                2920                2925
Tyr Cys Tyr Asp Thr Asn Val Leu Glu Gly Ser Val Ala Tyr Glu
                2930                2935                2940
Ser Leu Arg Pro Asp Thr Arg Tyr Val Leu Met Asp Gly Ser Ile
                2945                2950                2955
Ile Gln Phe Pro Asn Thr Tyr Leu Glu Gly Ser Val Arg Val Val
                2960                2965                2970
Thr Thr Phe Asp Ser Glu Tyr Cys Arg His Gly Thr Cys Glu Arg
                2975                2980                2985
Ser Glu Ala Gly Val Cys Val Ser Thr Ser Gly Arg Trp Val Leu
                2990                2995                3000
Asn Asn Asp Tyr Tyr Arg Ser Leu Pro Gly Val Phe Cys Gly Val
                3005                3010                3015
Asp Ala Val Asn Leu Leu Thr Asn Met Phe Thr Pro Leu Ile Gln
                3020                3025                3030
Pro Ile Gly Ala Leu Asp Ile Ser Ala Ser Ile Val Ala Gly Gly
                3035                3040                3045
Ile Val Ala Ile Val Val Thr Cys Leu Ala Tyr Tyr Phe Met Arg
                3050                3055                3060
Phe Arg Arg Ala Phe Gly Glu Tyr Ser His Val Val Ala Phe Asn
                3065                3070                3075
Thr Leu Leu Phe Leu Met Ser Phe Thr Val Leu Cys Leu Thr Pro
                3080                3085                3090
Val Tyr Ser Phe Leu Pro Gly Val Tyr Ser Val Ile Tyr Leu Tyr
                3095                3100                3105
Leu Thr Phe Tyr Leu Thr Asn Asp Val Ser Phe Leu Ala His Ile
                3110                3115                3120
Gln Trp Met Val Met Phe Thr Pro Leu Val Pro Phe Trp Ile Thr
                3125                3130                3135
Ile Ala Tyr Ile Ile Cys Ile Ser Thr Lys His Phe Tyr Trp Phe
                3140                3145                3150
Phe Ser Asn Tyr Leu Lys Arg Arg Val Val Phe Asn Gly Val Ser
                3155                3160                3165
```

```
Phe Ser Thr Phe Glu Glu Ala Ala Leu Cys Thr Phe Leu Leu Asn
    3170            3175            3180

Lys Glu Met Tyr Leu Lys Leu Arg Ser Asp Val Leu Leu Pro Leu
    3185            3190            3195

Thr Gln Tyr Asn Arg Tyr Leu Ala Leu Tyr Asn Lys Tyr Lys Tyr
    3200            3205            3210

Phe Ser Gly Ala Met Asp Thr Thr Ser Tyr Arg Glu Ala Ala Cys
    3215            3220            3225

Cys His Leu Ala Lys Ala Leu Asn Asp Phe Ser Asn Ser Gly Ser
    3230            3235            3240

Asp Val Leu Tyr Gln Pro Pro Gln Thr Ser Ile Thr Ser Ala Val
    3245            3250            3255

Leu Gln Ser Gly Phe Arg Lys Met Ala Phe Pro Ser Gly Lys Val
    3260            3265            3270

Glu Gly Cys Met Val Gln Val Thr Cys Gly Thr Thr Thr Leu Asn
    3275            3280            3285

Gly Leu Trp Leu Asp Asp Val Val Tyr Cys Pro Arg His Val Ile
    3290            3295            3300

Cys Thr Ser Glu Asp Met Leu Asn Pro Asn Tyr Glu Asp Leu Leu
    3305            3310            3315

Ile Arg Lys Ser Asn His Asn Phe Leu Val Gln Ala Gly Asn Val
    3320            3325            3330

Gln Leu Arg Val Ile Gly His Ser Met Gln Asn Cys Val Leu Lys
    3335            3340            3345

Leu Lys Val Asp Thr Ala Asn Pro Lys Thr Pro Lys Tyr Lys Phe
    3350            3355            3360

Val Arg Ile Gln Pro Gly Gln Thr Phe Ser Val Leu Ala Cys Tyr
    3365            3370            3375

Asn Gly Ser Pro Ser Gly Val Tyr Gln Cys Ala Met Arg Pro Asn
    3380            3385            3390

Phe Thr Ile Lys Gly Ser Phe Leu Asn Gly Ser Cys Gly Ser Val
    3395            3400            3405

Gly Phe Asn Ile Asp Tyr Asp Cys Val Ser Phe Cys Tyr Met His
    3410            3415            3420

His Met Glu Leu Pro Thr Gly Val His Ala Gly Thr Asp Leu Glu
    3425            3430            3435

Gly Asn Phe Tyr Gly Pro Phe Val Asp Arg Gln Thr Ala Gln Ala
    3440            3445            3450

Ala Gly Thr Asp Thr Thr Ile Thr Val Asn Val Leu Ala Trp Leu
    3455            3460            3465

Tyr Ala Ala Val Ile Asn Gly Asp Arg Trp Phe Leu Asn Arg Phe
    3470            3475            3480

Thr Thr Thr Leu Asn Asp Phe Asn Leu Val Ala Met Lys Tyr Asn
    3485            3490            3495

Tyr Glu Pro Leu Thr Gln Asp His Val Asp Ile Leu Gly Pro Leu
    3500            3505            3510

Ser Ala Gln Thr Gly Ile Ala Val Leu Asp Met Cys Ala Ser Leu
    3515            3520            3525

Lys Glu Leu Leu Gln Asn Gly Met Asn Gly Arg Thr Ile Leu Gly
    3530            3535            3540

Ser Ala Leu Leu Glu Asp Glu Phe Thr Pro Phe Asp Val Val Arg
    3545            3550            3555
```

| | | | | | | | | | | | |
|---|---|---|---|---|---|---|---|---|---|---|---|
|Gln|Cys|Ser|Gly|Val|Thr|Phe|Gln|Ser|Ala|Val|Lys|Arg|Thr|Ile|
|3560| | | | |3565| | | |3570| | | | | |
|Lys|Gly|Thr|His|His|Trp|Leu|Leu|Leu|Thr|Ile|Leu|Thr|Ser|Leu|
|3575| | | | |3580| | | |3585| | | | | |
|Leu|Val|Leu|Val|Gln|Ser|Thr|Gln|Trp|Ser|Leu|Phe|Phe|Phe|Leu|
|3590| | | | |3595| | | |3600| | | | | |
|Tyr|Glu|Lys|Ala|Phe|Leu|Pro|Phe|Ala|Met|Gly|Ile|Ile|Ala|Met|
|3605| | | | |3610| | | |3615| | | | | |
|Ser|Ala|Phe|Ala|Met|Met|Phe|Val|Lys|His|Lys|His|Ala|Phe|Leu|
|3620| | | | |3625| | | |3630| | | | | |
|Cys|Leu|Phe|Leu|Leu|Pro|Ser|Leu|Ala|Thr|Val|Ala|Tyr|Phe|Asn|
|3635| | | | |3640| | | |3645| | | | | |
|Met|Val|Tyr|Met|Pro|Ala|Ser|Trp|Val|Met|Arg|Ile|Met|Thr|Trp|
|3650| | | | |3655| | | |3660| | | | | |
|Leu|Asp|Met|Val|Ile|Thr|Ser|Leu|Ser|Gly|Phe|Lys|Leu|Lys|Asp|
|3665| | | | |3670| | | |3675| | | | | |
|Cys|Val|Met|Tyr|Ala|Ser|Ala|Val|Val|Leu|Leu|Ile|Leu|Met|Thr|
|3680| | | | |3685| | | |3690| | | | | |
|Ala|Arg|Thr|Val|Tyr|Asp|Asp|Gly|Ala|Arg|Arg|Val|Trp|Thr|Leu|
|3695| | | | |3700| | | |3705| | | | | |
|Met|Asn|Val|Leu|Thr|Leu|Val|Tyr|Lys|Val|Tyr|Tyr|Gly|Asn|Ala|
|3710| | | | |3715| | | |3720| | | | | |
|Leu|Asp|Gln|Ala|Ile|Ser|Met|Trp|Ala|Leu|Ile|Ile|Ser|Val|Thr|
|3725| | | | |3730| | | |3735| | | | | |
|Ser|Asn|Tyr|Ser|Gly|Val|Val|Thr|Thr|Val|Met|Phe|Leu|Ala|Arg|
|3740| | | | |3745| | | |3750| | | | | |
|Gly|Ile|Val|Phe|Met|Cys|Val|Glu|Tyr|Cys|Pro|Ile|Phe|Phe|Ile|
|3755| | | | |3760| | | |3765| | | | | |
|Thr|Gly|Asn|Thr|Leu|Gln|Cys|Ile|Met|Leu|Val|Tyr|Cys|Phe|Leu|
|3770| | | | |3775| | | |3780| | | | | |
|Gly|Tyr|Phe|Cys|Thr|Cys|Tyr|Phe|Gly|Leu|Phe|Cys|Leu|Leu|Asn|
|3785| | | | |3790| | | |3795| | | | | |
|Arg|Tyr|Phe|Arg|Leu|Thr|Leu|Gly|Val|Tyr|Asp|Tyr|Leu|Val|Ser|
|3800| | | | |3805| | | |3810| | | | | |
|Thr|Gln|Glu|Phe|Arg|Tyr|Met|Asn|Ser|Gln|Gly|Leu|Leu|Pro|Pro|
|3815| | | | |3820| | | |3825| | | | | |
|Lys|Asn|Ser|Ile|Asp|Ala|Phe|Lys|Leu|Asn|Ile|Lys|Leu|Leu|Gly|
|3830| | | | |3835| | | |3840| | | | | |
|Val|Gly|Gly|Lys|Pro|Cys|Ile|Lys|Val|Ala|Thr|Val|Gln|Ser|Lys|
|3845| | | | |3850| | | |3855| | | | | |
|Met|Ser|Asp|Val|Lys|Cys|Thr|Ser|Val|Val|Leu|Leu|Ser|Val|Leu|
|3860| | | | |3865| | | |3870| | | | | |
|Gln|Gln|Leu|Arg|Val|Glu|Ser|Ser|Ser|Lys|Leu|Trp|Ala|Gln|Cys|
|3875| | | | |3880| | | |3885| | | | | |
|Val|Gln|Leu|His|Asn|Asp|Ile|Leu|Leu|Ala|Lys|Asp|Thr|Thr|Glu|
|3890| | | | |3895| | | |3900| | | | | |
|Ala|Phe|Glu|Lys|Met|Val|Ser|Leu|Leu|Ser|Val|Leu|Leu|Ser|Met|
|3905| | | | |3910| | | |3915| | | | | |
|Gln|Gly|Ala|Val|Ala|Ile|Asn|Lys|Leu|Cys|Glu|Glu|Met|Leu|Asp|
|3920| | | | |3925| | | |3930| | | | | |
|Asn|Arg|Ala|Thr|Leu|Gln|Ala|Ile|Ala|Ser|Glu|Phe|Ser|Ser|Leu|
|3935| | | | |3940| | | |3945| | | | | |
|Pro|Ser|Tyr|Ala|Ala|Phe|Ala|Thr|Ala|Gln|Glu|Ala|Tyr|Glu|Gln|

-continued

```
            3950                3955                3960
Ala Val Ala Asn Gly Asp Ser Glu Val Val Leu Lys Lys Leu Lys
            3965                3970                3975
Lys Ser Leu Asn Val Ala Lys Ser Glu Phe Asp Arg Asp Ala Ala
            3980                3985                3990
Met Gln Arg Lys Leu Glu Lys Met Ala Asp Gln Ala Met Thr Gln
            3995                4000                4005
Met Tyr Lys Gln Ala Arg Ser Glu Asp Lys Arg Ala Lys Val Thr
            4010                4015                4020
Ser Ala Met Gln Thr Met Leu Phe Thr Met Leu Arg Lys Leu Asp
            4025                4030                4035
Asn Asp Ala Leu Asn Asn Ile Ile Asn Asn Ala Arg Asp Gly Cys
            4040                4045                4050
Val Pro Leu Asn Ile Ile Pro Leu Thr Thr Ala Ala Lys Leu Met
            4055                4060                4065
Val Val Ile Pro Asp Tyr Asn Thr Tyr Lys Asn Thr Cys Asp Gly
            4070                4075                4080
Thr Thr Phe Thr Tyr Ala Ser Ala Leu Trp Glu Ile Gln Gln Val
            4085                4090                4095
Val Asp Ala Asp Ser Lys Ile Val Gln Leu Ser Glu Ile Ser Met
            4100                4105                4110
Asp Asn Ser Pro Asn Leu Ala Trp Pro Leu Ile Val Thr Ala Leu
            4115                4120                4125
Arg Ala Asn Ser Ala Val Lys Leu Gln Asn Asn Glu Leu Ser Pro
            4130                4135                4140
Val Ala Leu Arg Gln Met Ser Cys Ala Ala Gly Thr Thr Gln Thr
            4145                4150                4155
Ala Cys Thr Asp Asp Asn Ala Leu Ala Tyr Tyr Asn Thr Thr Lys
            4160                4165                4170
Gly Gly Arg Phe Val Leu Ala Leu Leu Ser Asp Leu Gln Asp Leu
            4175                4180                4185
Lys Trp Ala Arg Phe Pro Lys Ser Asp Gly Thr Gly Thr Ile Tyr
            4190                4195                4200
Thr Glu Leu Glu Pro Pro Cys Arg Phe Val Thr Asp Thr Pro Lys
            4205                4210                4215
Gly Pro Lys Val Lys Tyr Leu Tyr Phe Ile Lys Gly Leu Asn Asn
            4220                4225                4230
Leu Asn Arg Gly Met Val Leu Gly Ser Leu Ala Ala Thr Val Arg
            4235                4240                4245
Leu Gln Ala Gly Asn Ala Thr Glu Val Pro Ala Asn Ser Thr Val
            4250                4255                4260
Leu Ser Phe Cys Ala Phe Ala Val Asp Ala Ala Lys Ala Tyr Lys
            4265                4270                4275
Asp Tyr Leu Ala Ser Gly Gly Gln Pro Ile Thr Asn Cys Val Lys
            4280                4285                4290
Met Leu Cys Thr His Thr Gly Thr Gly Gln Ala Ile Thr Val Thr
            4295                4300                4305
Pro Glu Ala Asn Met Asp Gln Glu Ser Phe Gly Gly Ala Ser Cys
            4310                4315                4320
Cys Leu Tyr Cys Arg Cys His Ile Asp His Pro Asn Pro Lys Gly
            4325                4330                4335
Phe Cys Asp Leu Lys Gly Lys Tyr Val Gln Ile Pro Thr Thr Cys
            4340                4345                4350
```

```
Ala Asn Asp Pro Val Gly Phe Thr Leu Lys Asn Thr Val Cys Thr
4355 4360 4365

Val Cys Gly Met Trp Lys Gly Tyr Gly Cys Ser Cys Asp Gln Leu
4370 4375 4380

Arg Glu Pro Met Leu Gln Ser Ala Asp Ala Gln Ser Phe Leu Asn
4385 4390 4395

Gly Phe Ala Val
4400

<210> SEQ ID NO 39
<211> LENGTH: 1273
<212> TYPE: PRT
<213> ORGANISM: Unknown
<220> FEATURE:
<223> OTHER INFORMATION: SARS-CoV-2 surface glycoprotein

<400> SEQUENCE: 39

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Ile Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Lys Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300
```

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720
```

-continued

```
Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
                850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ala Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala  Ser Ala Asn
    1010                1015                1020

Leu Ala Ala Thr Lys Met Ser Glu Cys Val Leu Gly  Gln Ser Lys
    1025                1030                1035

Arg Val Asp Phe Cys Gly Lys Gly Tyr His Leu Met  Ser Phe Pro
    1040                1045                1050

Gln Ser Ala Pro His Gly Val Val Phe Leu His Val  Thr Tyr Val
    1055                1060                1065

Pro Ala Gln Glu Lys Asn Phe Thr Thr Ala Pro Ala  Ile Cys His
    1070                1075                1080

Asp Gly Lys Ala His Phe Pro Arg Glu Gly Val Phe  Val Ser Asn
    1085                1090                1095

Gly Thr His Trp Phe Val Thr Gln Arg Asn Phe Tyr  Glu Pro Gln
    1100                1105                1110

Ile Ile Thr Thr Asp Asn Thr Phe Val Ser Gly Asn  Cys Asp Val
    1115                1120                1125

Val Ile Gly Ile Val Asn Asn Thr Val Tyr Asp Pro  Leu Gln Pro
```

```
            1130              1135              1140

Glu Leu Asp Ser Phe Lys Glu Glu Leu Asp Lys Tyr Phe Lys Asn
    1145              1150              1155

His Thr Ser Pro Asp Val Asp Leu Gly Asp Ile Ser Gly Ile Asn
    1160              1165              1170

Ala Ser Val Val Asn Ile Gln Lys Glu Ile Asp Arg Leu Asn Glu
    1175              1180              1185

Val Ala Lys Asn Leu Asn Glu Ser Leu Ile Asp Leu Gln Glu Leu
    1190              1195              1200

Gly Lys Tyr Glu Gln Tyr Ile Lys Trp Pro Trp Tyr Ile Trp Leu
    1205              1210              1215

Gly Phe Ile Ala Gly Leu Ile Ala Ile Val Met Val Thr Ile Met
    1220              1225              1230

Leu Cys Cys Met Thr Ser Cys Cys Ser Cys Leu Lys Gly Cys Cys
    1235              1240              1245

Ser Cys Gly Ser Cys Cys Lys Phe Asp Glu Asp Asp Ser Glu Pro
    1250              1255              1260

Val Leu Lys Gly Val Lys Leu His Tyr Thr
    1265              1270

<210> SEQ ID NO 40
<211> LENGTH: 275
<212> TYPE: PRT
<213> ORGANISM: Unknown
<220> FEATURE:
<223> OTHER INFORMATION: SARS-CoV-2 ORF3a protein

<400> SEQUENCE: 40

Met Asp Leu Phe Met Arg Ile Phe Thr Ile Gly Thr Val Thr Leu Lys
1               5                   10                  15

Gln Gly Glu Ile Lys Asp Ala Thr Pro Ser Asp Phe Val Arg Ala Thr
            20                  25                  30

Ala Thr Ile Pro Ile Gln Ala Ser Leu Pro Phe Gly Trp Leu Ile Val
        35                  40                  45

Gly Val Ala Leu Leu Ala Val Phe Gln Ser Ala Ser Lys Ile Ile Thr
    50                  55                  60

Leu Lys Lys Arg Trp Gln Leu Ala Leu Ser Lys Gly Val His Phe Val
65                  70                  75                  80

Cys Asn Leu Leu Leu Leu Phe Val Thr Val Tyr Ser His Leu Leu Leu
                85                  90                  95

Val Ala Ala Gly Leu Glu Ala Pro Phe Leu Tyr Leu Tyr Ala Leu Val
            100                 105                 110

Tyr Phe Leu Gln Ser Ile Asn Phe Val Arg Ile Ile Met Arg Leu Trp
        115                 120                 125

Leu Cys Trp Lys Cys Arg Ser Lys Asn Pro Leu Leu Tyr Asp Ala Asn
    130                 135                 140

Tyr Phe Leu Cys Trp His Thr Asn Cys Tyr Asp Tyr Cys Ile Pro Tyr
145                 150                 155                 160

Asn Ser Val Thr Ser Ser Ile Val Ile Thr Ser Gly Asp Gly Thr Thr
                165                 170                 175

Ser Pro Ile Ser Glu His Asp Tyr Gln Ile Gly Gly Tyr Thr Glu Lys
            180                 185                 190

Trp Glu Ser Gly Val Lys Asp Cys Val Val Leu His Ser Tyr Phe Thr
        195                 200                 205

Ser Asp Tyr Tyr Gln Leu Tyr Ser Thr Gln Leu Ser Thr Asp Thr Gly
```

```
              210                 215                 220

Val Glu His Val Thr Phe Phe Ile Tyr Asn Lys Ile Val Asp Glu Pro
225                 230                 235                 240

Glu Glu His Val Gln Ile His Thr Ile Asp Gly Ser Ser Gly Val Val
                245                 250                 255

Asn Pro Val Met Glu Pro Ile Tyr Asp Glu Pro Thr Thr Thr Thr Ser
            260                 265                 270

Val Pro Leu
        275

<210> SEQ ID NO 41
<211> LENGTH: 75
<212> TYPE: PRT
<213> ORGANISM: Unknown
<220> FEATURE:
<223> OTHER INFORMATION: SARS-CoV-2 envelope protein

<400> SEQUENCE: 41

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
            35                  40                  45

Val Ser Leu Val Lys Pro Ser Phe Tyr Val Tyr Ser Arg Val Lys Asn
        50                  55                  60

Leu Asn Ser Ser Arg Val Pro Asp Leu Leu Val
65                  70                  75

<210> SEQ ID NO 42
<211> LENGTH: 222
<212> TYPE: PRT
<213> ORGANISM: Unknown
<220> FEATURE:
<223> OTHER INFORMATION: SARS-CoV-2 membrane glycoprotein

<400> SEQUENCE: 42

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
                20                  25                  30

Cys Leu Leu Gln Phe Ala Tyr Ala Asn Arg Asn Arg Phe Leu Tyr Ile
            35                  40                  45

Ile Lys Leu Ile Phe Leu Trp Leu Leu Trp Pro Val Thr Leu Ala Cys
        50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160
```

```
Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
            195                 200                 205

Asp His Ser Ser Ser Asp Asn Ile Ala Leu Leu Val Gln
            210                 215                 220
```

<210> SEQ ID NO 43
<211> LENGTH: 61
<212> TYPE: PRT
<213> ORGANISM: Unknown
<220> FEATURE:
<223> OTHER INFORMATION: SARS-CoV-2 ORF6 protein

<400> SEQUENCE: 43

```
Met Phe His Leu Val Asp Phe Gln Val Thr Ile Ala Glu Ile Leu Leu
1               5                   10                  15

Ile Ile Met Arg Thr Phe Lys Val Ser Ile Trp Asn Leu Asp Tyr Ile
            20                  25                  30

Ile Asn Leu Ile Ile Lys Asn Leu Ser Lys Ser Leu Thr Glu Asn Lys
        35                  40                  45

Tyr Ser Gln Leu Asp Glu Glu Gln Pro Met Glu Ile Asp
    50                  55                  60
```

<210> SEQ ID NO 44
<211> LENGTH: 121
<212> TYPE: PRT
<213> ORGANISM: Unknown
<220> FEATURE:
<223> OTHER INFORMATION: SARS-CoV-2 ORF7a protein

<400> SEQUENCE: 44

```
Met Lys Ile Ile Leu Phe Leu Ala Leu Ile Thr Leu Ala Thr Cys Glu
1               5                   10                  15

Leu Tyr His Tyr Gln Glu Cys Val Arg Gly Thr Thr Val Leu Leu Lys
            20                  25                  30

Glu Pro Cys Ser Ser Gly Thr Tyr Glu Gly Asn Ser Pro Phe His Pro
        35                  40                  45

Leu Ala Asp Asn Lys Phe Ala Leu Thr Cys Phe Ser Thr Gln Phe Ala
    50                  55                  60

Phe Ala Cys Pro Asp Gly Val Lys His Val Tyr Gln Leu Arg Ala Arg
65                  70                  75                  80

Ser Val Ser Pro Lys Leu Phe Ile Arg Gln Glu Glu Val Gln Glu Leu
                85                  90                  95

Tyr Ser Pro Ile Phe Leu Ile Val Ala Ala Ile Val Phe Ile Thr Leu
            100                 105                 110

Cys Phe Thr Leu Lys Arg Lys Thr Glu
        115                 120
```

<210> SEQ ID NO 45
<211> LENGTH: 43
<212> TYPE: PRT
<213> ORGANISM: Unknown
<220> FEATURE:
<223> OTHER INFORMATION: SARS-CoV-2 ORF7b protein

<400> SEQUENCE: 45

```
Met Ile Glu Leu Ser Leu Ile Asp Phe Tyr Leu Cys Phe Leu Ala Phe
```

```
                1               5                   10                  15
Leu Leu Phe Leu Val Leu Ile Met Leu Ile Ile Phe Trp Phe Ser Leu
                20                  25                  30

Glu Leu Gln Asp His Asn Glu Thr Cys His Ala
                35                  40

<210> SEQ ID NO 46
<211> LENGTH: 121
<212> TYPE: PRT
<213> ORGANISM: Unknown
<220> FEATURE:
<223> OTHER INFORMATION: SARS-CoV-2 ORF8 protein

<400> SEQUENCE: 46

Met Lys Phe Leu Val Phe Leu Gly Ile Ile Thr Thr Val Ala Ala Phe
1               5                   10                  15

His Gln Glu Cys Ser Leu Gln Ser Cys Thr Gln His Gln Pro Tyr Val
                20                  25                  30

Val Asp Asp Pro Cys Pro Ile His Phe Tyr Ser Lys Trp Tyr Ile Arg
                35                  40                  45

Val Gly Ala Arg Lys Ser Ala Pro Leu Ile Glu Leu Cys Val Asp Glu
                50                  55                  60

Ala Gly Ser Lys Ser Pro Ile Gln Tyr Ile Asp Ile Gly Asn Tyr Thr
65                  70                  75                  80

Val Ser Cys Ser Pro Phe Thr Ile Asn Cys Gln Glu Pro Lys Leu Gly
                85                  90                  95

Ser Leu Val Val Arg Cys Ser Phe Tyr Glu Asp Phe Leu Glu Tyr His
                100                 105                 110

Asp Val Arg Val Val Leu Asp Phe Ile
                115                 120

<210> SEQ ID NO 47
<211> LENGTH: 419
<212> TYPE: PRT
<213> ORGANISM: Unknown
<220> FEATURE:
<223> OTHER INFORMATION: SARS-CoV-2 nucleocapsid phosphoprotein

<400> SEQUENCE: 47

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
                20                  25                  30

Ser Gly Ala Arg Ser Lys Gln Arg Arg Pro Gln Gly Leu Pro Asn Asn
                35                  40                  45

Thr Ala Ser Trp Phe Thr Ala Leu Thr Gln His Gly Lys Glu Asp Leu
                50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
                100                 105                 110

Leu Gly Thr Gly Pro Glu Ala Gly Leu Pro Tyr Gly Ala Asn Lys Asp
                115                 120                 125

Gly Ile Ile Trp Val Ala Thr Glu Gly Ala Leu Asn Thr Pro Lys Asp
                130                 135                 140
```

```
His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Ala Asp Glu Thr Gln Ala Leu Pro Gln
370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala

<210> SEQ ID NO 48
<211> LENGTH: 38
<212> TYPE: PRT
<213> ORGANISM: Unknown
<220> FEATURE:
<223> OTHER INFORMATION: SARS-CoV-2 ORF10 protein

<400> SEQUENCE: 48

Met Gly Tyr Ile Asn Val Phe Ala Phe Pro Phe Thr Ile Tyr Ser Leu
1               5                   10                  15

Leu Leu Cys Arg Met Asn Ser Arg Asn Tyr Ile Ala Gln Val Asp Val
            20                  25                  30

Val Asn Phe Asn Leu Thr
        35

<210> SEQ ID NO 49
<211> LENGTH: 18
<212> TYPE: DNA
<213> ORGANISM: Artificial Sequence
<220> FEATURE:
<223> OTHER INFORMATION: N_Sarbeco_F
```

-continued

```
<400> SEQUENCE: 49
cacattggca cccgcaat                                                   18

<210> SEQ ID NO 50
<211> LENGTH: 20
<212> TYPE: DNA
<213> ORGANISM: Artificial Sequence
<220> FEATURE:
<223> OTHER INFORMATION: N_Sarbeco-R

<400> SEQUENCE: 50
gaggaacgag aagaggcttg                                                 20

<210> SEQ ID NO 51
<211> LENGTH: 25
<212> TYPE: DNA
<213> ORGANISM: Artificial Sequence
<220> FEATURE:
<223> OTHER INFORMATION: N_Sarbeco_P

<400> SEQUENCE: 51
acttcctcaa ggaacaacat tgcca                                           25

<210> SEQ ID NO 52
<211> LENGTH: 28
<212> TYPE: DNA
<213> ORGANISM: Artificial Sequence
<220> FEATURE:
<223> OTHER INFORMATION: F primer

<400> SEQUENCE: 52
attaaaggtt tataccttcc caggtaac                                        28

<210> SEQ ID NO 53
<211> LENGTH: 22
<212> TYPE: DNA
<213> ORGANISM: Artificial Sequence
<220> FEATURE:
<223> OTHER INFORMATION: F primer

<400> SEQUENCE: 53
gcaaccaaat gtgcctttca ac                                              22

<210> SEQ ID NO 54
<211> LENGTH: 28
<212> TYPE: DNA
<213> ORGANISM: Artificial Sequence
<220> FEATURE:
<223> OTHER INFORMATION: F primer

<400> SEQUENCE: 54
actcaaaggg attgtacaga aagtgtgt                                        28

<210> SEQ ID NO 55
<211> LENGTH: 27
<212> TYPE: DNA
<213> ORGANISM: Artificial Sequence
<220> FEATURE:
<223> OTHER INFORMATION: F primer

<400> SEQUENCE: 55
gacattcaac ttcttaagag tgcttat                                         27

<210> SEQ ID NO 56
```

```
<211> LENGTH: 28
<212> TYPE: DNA
<213> ORGANISM: Artificial Sequence
<220> FEATURE:
<223> OTHER INFORMATION: F primer

<400> SEQUENCE: 56
ctagatggtg aagttatcac ctttgaca                                          28

<210> SEQ ID NO 57
<211> LENGTH: 23
<212> TYPE: DNA
<213> ORGANISM: Artificial Sequence
<220> FEATURE:
<223> OTHER INFORMATION: F primer

<400> SEQUENCE: 57
gacttaaatg gtgatgtggt ggc                                               23

<210> SEQ ID NO 58
<211> LENGTH: 28
<212> TYPE: DNA
<213> ORGANISM: Artificial Sequence
<220> FEATURE:
<223> OTHER INFORMATION: F primer

<400> SEQUENCE: 58
gctatggtta gaatgtacat cttctttg                                          28

<210> SEQ ID NO 59
<211> LENGTH: 31
<212> TYPE: DNA
<213> ORGANISM: Artificial Sequence
<220> FEATURE:
<223> OTHER INFORMATION: F primer

<400> SEQUENCE: 59
cctgttcatg tcatgtctaa acatactgac t                                      31

<210> SEQ ID NO 60
<211> LENGTH: 28
<212> TYPE: DNA
<213> ORGANISM: Artificial Sequence
<220> FEATURE:
<223> OTHER INFORMATION: F primer

<400> SEQUENCE: 60
ataagtacaa gtattttagt ggagcaat                                          28

<210> SEQ ID NO 61
<211> LENGTH: 27
<212> TYPE: DNA
<213> ORGANISM: Artificial Sequence
<220> FEATURE:
<223> OTHER INFORMATION: F primer

<400> SEQUENCE: 61
gtcaaacata agcatgcatt tctctgt                                           27

<210> SEQ ID NO 62
<211> LENGTH: 28
<212> TYPE: DNA
<213> ORGANISM: Artificial Sequence
<220> FEATURE:
<223> OTHER INFORMATION: F primer

<400> SEQUENCE: 62
```
caacaacatt atcaacaatg caagagat                                28

<210> SEQ ID NO 63
<211> LENGTH: 27
<212> TYPE: DNA
<213> ORGANISM: Artificial Sequence
<220> FEATURE:
<223> OTHER INFORMATION: F primer

<400> SEQUENCE: 63
tgtagttaag agacacactt tctctaa                                 27

<210> SEQ ID NO 64
<211> LENGTH: 28
<212> TYPE: DNA
<213> ORGANISM: Artificial Sequence
<220> FEATURE:
<223> OTHER INFORMATION: F primer

<400> SEQUENCE: 64
gtattaatgc taaccaagtc atcgtcaa                                28

<210> SEQ ID NO 65
<211> LENGTH: 29
<212> TYPE: DNA
<213> ORGANISM: Artificial Sequence
<220> FEATURE:
<223> OTHER INFORMATION: F primer

<400> SEQUENCE: 65
acacatgtta gacatgtatt ctgttatgc                               29

<210> SEQ ID NO 66
<211> LENGTH: 28
<212> TYPE: DNA
<213> ORGANISM: Artificial Sequence
<220> FEATURE:
<223> OTHER INFORMATION: F primer

<400> SEQUENCE: 66
tgccagatta cgtgctaagc actatgtg                                28

<210> SEQ ID NO 67
<211> LENGTH: 23
<212> TYPE: DNA
<213> ORGANISM: Artificial Sequence
<220> FEATURE:
<223> OTHER INFORMATION: F primer

<400> SEQUENCE: 67
cctgagcgca cctgttgtct atg                                     23

<210> SEQ ID NO 68
<211> LENGTH: 28
<212> TYPE: DNA
<213> ORGANISM: Artificial Sequence
<220> FEATURE:
<223> OTHER INFORMATION: F primer

<400> SEQUENCE: 68
gcacatatat ctactattgg tgtttgtt                                28

<210> SEQ ID NO 69
<211> LENGTH: 23
<212> TYPE: DNA

```
<213> ORGANISM: Artificial Sequence
<220> FEATURE:
<223> OTHER INFORMATION: F primer

<400> SEQUENCE: 69
ggaggttccg tggctataaa gat                                          23

<210> SEQ ID NO 70
<211> LENGTH: 28
<212> TYPE: DNA
<213> ORGANISM: Artificial Sequence
<220> FEATURE:
<223> OTHER INFORMATION: F primer

<400> SEQUENCE: 70
atgaaaatgg aaccattaca gatgctgt                                     28

<210> SEQ ID NO 71
<211> LENGTH: 24
<212> TYPE: DNA
<213> ORGANISM: Artificial Sequence
<220> FEATURE:
<223> OTHER INFORMATION: F primer

<400> SEQUENCE: 71
ctacactatg tcacttggtg caga                                         24

<210> SEQ ID NO 72
<211> LENGTH: 28
<212> TYPE: DNA
<213> ORGANISM: Artificial Sequence
<220> FEATURE:
<223> OTHER INFORMATION: F primer

<400> SEQUENCE: 72
aaatcattac tacagacaac acatttgt                                     28

<210> SEQ ID NO 73
<211> LENGTH: 22
<212> TYPE: DNA
<213> ORGANISM: Artificial Sequence
<220> FEATURE:
<223> OTHER INFORMATION: F primer

<400> SEQUENCE: 73
cgacggttca tccggagttg tt                                           22

<210> SEQ ID NO 74
<211> LENGTH: 28
<212> TYPE: DNA
<213> ORGANISM: Artificial Sequence
<220> FEATURE:
<223> OTHER INFORMATION: F primer

<400> SEQUENCE: 74
attattcttt tcttggcact gataacac                                     28

<210> SEQ ID NO 75
<211> LENGTH: 22
<212> TYPE: DNA
<213> ORGANISM: Artificial Sequence
<220> FEATURE:
<223> OTHER INFORMATION: F primer

<400> SEQUENCE: 75
ttctactacc taggaactgg gc                                           22
```

```
<210> SEQ ID NO 76
<211> LENGTH: 26
<212> TYPE: DNA
<213> ORGANISM: Artificial Sequence
<220> FEATURE:
<223> OTHER INFORMATION: R primer

<400> SEQUENCE: 76
caccttcttt agtcaaattc tcagtg                                          26

<210> SEQ ID NO 77
<211> LENGTH: 28
<212> TYPE: DNA
<213> ORGANISM: Artificial Sequence
<220> FEATURE:
<223> OTHER INFORMATION: R primer

<400> SEQUENCE: 77
ttctccctct aagaagataa tttcttttt                                       28

<210> SEQ ID NO 78
<211> LENGTH: 28
<212> TYPE: DNA
<213> ORGANISM: Artificial Sequence
<220> FEATURE:
<223> OTHER INFORMATION: R primer

<400> SEQUENCE: 78
gtgcgaacag tatctacaca aactctta                                        28

<210> SEQ ID NO 79
<211> LENGTH: 28
<212> TYPE: DNA
<213> ORGANISM: Artificial Sequence
<220> FEATURE:
<223> OTHER INFORMATION: R primer

<400> SEQUENCE: 79
ggttaatgtt gtctactgtt gtaaacac                                        28

<210> SEQ ID NO 80
<211> LENGTH: 28
<212> TYPE: DNA
<213> ORGANISM: Artificial Sequence
<220> FEATURE:
<223> OTHER INFORMATION: R primer

<400> SEQUENCE: 80
gctttattag ttgcattgtt aacatgcc                                        28

<210> SEQ ID NO 81
<211> LENGTH: 28
<212> TYPE: DNA
<213> ORGANISM: Artificial Sequence
<220> FEATURE:
<223> OTHER INFORMATION: R primer

<400> SEQUENCE: 81
cacatcatac aagttgatga attacaac                                        28

<210> SEQ ID NO 82
<211> LENGTH: 27
<212> TYPE: DNA
<213> ORGANISM: Artificial Sequence
<220> FEATURE:
```

<223> OTHER INFORMATION: R primer

<400> SEQUENCE: 82
gttagcaaaa caagtatctg tagatgc                                27

<210> SEQ ID NO 83
<211> LENGTH: 28
<212> TYPE: DNA
<213> ORGANISM: Artificial Sequence
<220> FEATURE:
<223> OTHER INFORMATION: R primer

<400> SEQUENCE: 83
acctgagtta ctgaagtcat tgagagcc                               28

<210> SEQ ID NO 84
<211> LENGTH: 25
<212> TYPE: DNA
<213> ORGANISM: Artificial Sequence
<220> FEATURE:
<223> OTHER INFORMATION: R primer

<400> SEQUENCE: 84
accatatcca accatgtcat aatac                                  25

<210> SEQ ID NO 85
<211> LENGTH: 28
<212> TYPE: DNA
<213> ORGANISM: Artificial Sequence
<220> FEATURE:
<223> OTHER INFORMATION: R primer

<400> SEQUENCE: 85
tgttatagtc tggtaagaca accattag                               28

<210> SEQ ID NO 86
<211> LENGTH: 25
<212> TYPE: DNA
<213> ORGANISM: Artificial Sequence
<220> FEATURE:
<223> OTHER INFORMATION: R primer

<400> SEQUENCE: 86
taccatgtca ccgtctattc taaac                                  25

<210> SEQ ID NO 87
<211> LENGTH: 28
<212> TYPE: DNA
<213> ORGANISM: Artificial Sequence
<220> FEATURE:
<223> OTHER INFORMATION: R primer

<400> SEQUENCE: 87
actcattgaa tcataataaa gtctagcc                               28

<210> SEQ ID NO 88
<211> LENGTH: 25
<212> TYPE: DNA
<213> ORGANISM: Artificial Sequence
<220> FEATURE:
<223> OTHER INFORMATION: R primer

<400> SEQUENCE: 88
ctgtgaattg caaagaacac aagcc                                  25

<210> SEQ ID NO 89
<211> LENGTH: 28
<212> TYPE: DNA
<213> ORGANISM: Artificial Sequence
<220> FEATURE:
<223> OTHER INFORMATION: R primer

<400> SEQUENCE: 89
aatattctgg ttctagtgtg cccttagt                                   28

<210> SEQ ID NO 90
<211> LENGTH: 29
<212> TYPE: DNA
<213> ORGANISM: Artificial Sequence
<220> FEATURE:
<223> OTHER INFORMATION: R primer

<400> SEQUENCE: 90
ccccattgtt gaacatcaat cataaacgg                                  29

<210> SEQ ID NO 91
<211> LENGTH: 28
<212> TYPE: DNA
<213> ORGANISM: Artificial Sequence
<220> FEATURE:
<223> OTHER INFORMATION: R primer

<400> SEQUENCE: 91
actctaccat caaaaaagac agtgagtg                                   28

<210> SEQ ID NO 92
<211> LENGTH: 23
<212> TYPE: DNA
<213> ORGANISM: Artificial Sequence
<220> FEATURE:
<223> OTHER INFORMATION: R primer

<400> SEQUENCE: 92
gcttcagatg atgacgcatt cac                                        23

<210> SEQ ID NO 93
<211> LENGTH: 28
<212> TYPE: DNA
<213> ORGANISM: Artificial Sequence
<220> FEATURE:
<223> OTHER INFORMATION: R primer

<400> SEQUENCE: 93
tagattcctt tttctacagt gaaggatt                                   28

<210> SEQ ID NO 94
<211> LENGTH: 24
<212> TYPE: DNA
<213> ORGANISM: Artificial Sequence
<220> FEATURE:
<223> OTHER INFORMATION: R primer

<400> SEQUENCE: 94
ctgatgtctt ggtcatagac actg                                       24

<210> SEQ ID NO 95
<211> LENGTH: 28
<212> TYPE: DNA
<213> ORGANISM: Artificial Sequence
<220> FEATURE:
<223> OTHER INFORMATION: R primer

```
<400> SEQUENCE: 95
gtctaattca ggttgcaaag gatcataa                                          28

<210> SEQ ID NO 96
<211> LENGTH: 22
<212> TYPE: DNA
<213> ORGANISM: Artificial Sequence
<220> FEATURE:
<223> OTHER INFORMATION: R primer

<400> SEQUENCE: 96
ctcttccgaa acgaatgagt ac                                                22

<210> SEQ ID NO 97
<211> LENGTH: 28
<212> TYPE: DNA
<213> ORGANISM: Artificial Sequence
<220> FEATURE:
<223> OTHER INFORMATION: R primer

<400> SEQUENCE: 97
gagcaaggtt cttttaaaag tactgttg                                          28

<210> SEQ ID NO 98
<211> LENGTH: 22
<212> TYPE: DNA
<213> ORGANISM: Artificial Sequence
<220> FEATURE:
<223> OTHER INFORMATION: R primer

<400> SEQUENCE: 98
cgggtgccaa tgtgatcttt tg                                                22

<210> SEQ ID NO 99
<211> LENGTH: 28
<212> TYPE: DNA
<213> ORGANISM: Artificial Sequence
<220> FEATURE:
<223> OTHER INFORMATION: R primer

<400> SEQUENCE: 99
gtcattctcc taagaagcta ttaaaatc                                          28

<210> SEQ ID NO 100
<211> LENGTH: 28
<212> TYPE: DNA
<213> ORGANISM: Artificial Sequence
<220> FEATURE:
<223> OTHER INFORMATION: primer

<400> SEQUENCE: 100
ttctccctct aagaagataa tttctttt                                          28

<210> SEQ ID NO 101
<211> LENGTH: 28
<212> TYPE: DNA
<213> ORGANISM: Artificial Sequence
<220> FEATURE:
<223> OTHER INFORMATION: primer

<400> SEQUENCE: 101
ggttaatgtt gtctactgtt gtaaacac                                          28

<210> SEQ ID NO 102
<211> LENGTH: 28
```

<212> TYPE: DNA
<213> ORGANISM: Artificial Sequence
<220> FEATURE:
<223> OTHER INFORMATION: primer

<400> SEQUENCE: 102
cacatcatac aagttgatga attacaac                                    28

<210> SEQ ID NO 103
<211> LENGTH: 28
<212> TYPE: DNA
<213> ORGANISM: Artificial Sequence
<220> FEATURE:
<223> OTHER INFORMATION: primer

<400> SEQUENCE: 103
acctgagtta ctgaagtcat tgagagcc                                    28

<210> SEQ ID NO 104
<211> LENGTH: 28
<212> TYPE: DNA
<213> ORGANISM: Artificial Sequence
<220> FEATURE:
<223> OTHER INFORMATION: primer

<400> SEQUENCE: 104
tgttatagtc tggtaagaca accattag                                    28

<210> SEQ ID NO 105
<211> LENGTH: 28
<212> TYPE: DNA
<213> ORGANISM: Artificial Sequence
<220> FEATURE:
<223> OTHER INFORMATION: primer

<400> SEQUENCE: 105
actcattgaa tcataataaa gtctagcc                                    28

<210> SEQ ID NO 106
<211> LENGTH: 28
<212> TYPE: DNA
<213> ORGANISM: Artificial Sequence
<220> FEATURE:
<223> OTHER INFORMATION: primer

<400> SEQUENCE: 106
aatattctgg ttctagtgtg cccttagt                                    28

<210> SEQ ID NO 107
<211> LENGTH: 28
<212> TYPE: DNA
<213> ORGANISM: Artificial Sequence
<220> FEATURE:
<223> OTHER INFORMATION: primer

<400> SEQUENCE: 107
actctaccat caaaaaagac agtgagtg                                    28

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108

```
tagattcctt tttctacagt gaaggatt                                               28

<210> SEQ ID NO 109
<211> LENGTH: 28
<212> TYPE: DNA
<213> ORGANISM: Artificial Sequence
<220> FEATURE:
<223> OTHER INFORMATION: primer

<400> SEQUENCE: 109
gtctaattca ggttgcaaag gatcataa                                               28

<210> SEQ ID NO 110
<211> LENGTH: 28
<212> TYPE: DNA
<213> ORGANISM: Artificial Sequence
<220> FEATURE:
<223> OTHER INFORMATION: primer

<400> SEQUENCE: 110
gagcaaggtt cttttaaaag tactgttg                                               28

<210> SEQ ID NO 111
<211> LENGTH: 28
<212> TYPE: DNA
<213> ORGANISM: Artificial Sequence
<220> FEATURE:
<223> OTHER INFORMATION: primer

<400> SEQUENCE: 111
gtcattctcc taagaagcta ttaaaatc                                               28
```

COLD-ADAPTED LIVE ATTENUATED SEVERE ACUTE RESPIRATORY SYNDROME CORONAVIRUS AND VACCINE CONTAINING THE SAME

CROSS-REFERENCE TO RELATED APPLICATIONS

This application is based on and claims priority from Korean Patent Application No. 10-2020-0102525, filed on Aug. 14, 2020 with the Korean Intellectual Property Office, the disclosure of which is incorporated herein in its entirety by reference.

TECHNICAL FIELD

The present disclosure relates to cold-adapted live attenuated severe acute respiratory syndrome coronavirus (SARS-CoV-2), a vaccine containing the same as an active ingredient, a method for preventing or treating severe acute respiratory syndrome coronavirus (SARS-CoV-2) infectious disease by administering the vaccine to a subject, and a method for preparing the cold-adapted live attenuated severe acute respiratory syndrome coronavirus (SARS-CoV-2).

BACKGROUND

In December 2019, it was reported that humans had severely unknown pneumonia in Wuhan, eastern China. Initial symptoms thereof were similar to those of patients infected with severe acute respiratory syndrome (SARS) virus. However, as a result of sequencing a causative factor thereof, a genome thereof was similar to that of SARS which is called severe acute respiratory syndrome coronavirus-2 (SARS-CoV-2). The World Health Organization (WHO) declared a pandemic of COVID-19 (coronavirus disease 2019) as a disease caused by SARS-CoV-2 on Mar. 11, 2020.

SARS-CoV-2 is of a coronavirus family and is a positive-sense single-stranded RNA virus having an envelope. A genome size of SARS-CoV-2 is about 30 kb, and is composed of four structural proteins of nucleocapsid (N), membrane (M), envelope (E), and spike (S) proteins that form a structural backbone of the virus; 16 non-structural proteins (nsp1-nsp16); and several accessory proteins. The S protein is located on a surface of SARS-CoV-2 and binds to a human angiotensin converting enzyme 2 (hACE2) receptor to initiate infection.

Patients infected with SARS-CoV-2 commonly show fever, cough, myalgia, and fatigue, and some patients might also develop acute respiratory distress syndrome (ARDS). Among the 99 patients infected with SARS-CoV-2 in Wuhan, China, 74 showed bilateral pneumonia, 14 showed multiple mottling and ground-grass opacity in the lungs, and one patient had pneumothorax; 17 patients had ARSD, and 11 of these patients died of multiple organ failure. In Washington, USA, ARDS was observed in 15 of 21 patients, and mechanical ventilation was required for these patients. In addition to pneumonia and ARDS, SARS-CoV-2 is responsible for clinical signs related to the affliction of the central nervous system (CNS); these include loss of taste and smell, headaches, twitching, seizures, vision impairment, nerve pain, dizziness, impaired consciousness, nausea, vomiting, hemiplegia, ataxia, stroke, and cerebral haemorrhage.

As of date, there is no effective licenced vaccine for SARS-CoV-2. Therefore, there is an urgent need to develop a safe and effective SARS-CoV-2 vaccine to protect humans from the COVID-19 pandemic. Various types of SARS-CoV-2 vaccines are under development; these include DNA- and mRNA-based vaccines, encoding the S protein of SARS-CoV-2, adenovirus-, measles virus-, and vesicular stomatitis virus-based vectors expressing the S gene, and purified inactivated vaccine [T. R. F. Smith et al., Immunogenicity of a DNA vaccine candidate for COVID-19. Nat Commun. 11, 2601 (2020); M. J. Mulligan et al., Phase 1/2 Study to Describe the Safety and Immunogenicity of a COVID-19 RNA Vaccine Candidate (BNT162b1) in Adults 18 to 55 Years of Age: Interim Report *medRxiv* (2020); L. A. Jackson et al., An mRNA Vaccine against SARS-CoV-2-Preliminary Report. *N Engl J Med.* NEJMoa2022483 (2020)]. Most of the licenced human viral vaccines, such as those against measles, mumps, rubella, rotavirus, smallpox, chickenpox, yellow fever, and influenza virus (nasal inoculation), are live attenuated forms of the respective virus. Cold-adapted live influenza vaccines for seasonal influenza viruses are produced in primary chick kidney cells or embryonated eggs at 25° C. and are administered intranasally to humans. Live attenuated vaccines are similar to natural infectious agents; they elicit strong and long-lasting immune response, and thereby, have good protective effects in humans.

SUMMARY

The present inventors adapted growth of SARS-CoV-2 in Vero cells to a range from 37° C. to 22° C. in a step by step manner, thereby to prepare a cold-adapted live attenuated vaccine strain (SARS-CoV-2/human/Korea/CNUHV03-CA22° C./2020). Thus, the present disclosure has been completed.

Thus, a purpose of the present disclosure is to provide cold-adapted live attenuated severe acute respiratory syndrome coronavirus (SARS-CoV-2), a vaccine containing the same as an active ingredient, a method for preventing or treating severe acute respiratory syndrome coronavirus (SARS-CoV-2) infectious disease by administering the vaccine to a subject, and a method for preparing the cold-adapted live attenuated severe acute respiratory syndrome coronavirus (SARS-CoV-2).

An exemplary embodiment of the present disclosure provides cold-adapted live attenuated severe acute respiratory syndrome coronavirus (SARS-CoV-2) prepared by infecting cells with severe acute respiratory syndrome coronavirus (SARS-CoV-2) and then adapting the severe acute respiratory syndrome coronavirus (SARS-CoV-2) to a temperature from 37° C. to 22° C. in a step by step manner.

Further, another exemplary embodiment of the present disclosure provides a severe acute respiratory syndrome coronavirus (SARS-CoV-2) vaccine containing the cold-adapted live attenuated severe acute respiratory syndrome coronavirus (SARS-CoV-2) as an active ingredient.

Further, still another exemplary embodiment of the present disclosure provides a method for preventing or treating severe acute respiratory syndrome coronavirus (SARS-CoV-2) infectious disease by administering the vaccine to a subject.

Furthermore, still yet another exemplary embodiment of the present disclosure provides a preparation method of cold-adapted live attenuated severe acute respiratory syndrome coronavirus (SARS-CoV-2), the method including infecting cells with severe acute respiratory syndrome coronavirus (SARS-CoV-2) and then adapting the severe acute respiratory syndrome coronavirus (SARS-CoV-2) to a temperature from 37° C. to 22° C. in a step by step manner; and subculturing the adapted severe acute respiratory syndrome coronavirus (SARS-CoV-2) at 22° C. and collecting the subcultured adapted severe acute respiratory syndrome coronavirus.

According to the exemplary embodiments of the present disclosure, the cold-adapted live attenuated SARS-CoV-2 vaccine according to the present disclosure may be prepared using a simple preparation method and may effectively prevent infection of SARS-CoV-2 only with a one-dose vaccination thereof, thereby to accelerate the development of vaccines and therapeutics that may prevent and treat SARS-CoV-2 infectious diseases, especially COVID-19.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 2A shows a mice mortality (%) to identifying attenuation of the cold-adapted SARS-CoV-2 vaccine strain in hACE2 transgenic mice. Virus titers are mean of three tissues±standard deviation. Virus detection limit is 1 $TCID_{50}/0.1$ g. $*p<0.05$, $**p<0.001$.

FIG. 2B shows a change in mice body weight (%) compared to those before infection to identifying attenuation of the cold-adapted SARS-CoV-2 vaccine strain in hACE2 transgenic mice. Virus titers are mean of three tissues±standard deviation. Virus detection limit is 1 $TCID_{50}/0.1$ g. $*p<0.05$, $**p<0.001$.

FIG. 2C shows a virus titers in nasal turbinate, brain, lung, kidney and spleen of mice based on $log_{10}$ $TCID_{50}/0.1$ g to identifying attenuation of the cold-adapted SARS-CoV-2 vaccine strain in hACE2 transgenic mice. Virus titers are mean of three tissues±standard deviation. Virus detection limit is 1 $TCID_{50}/0.1$ g. $*p<0.05$, $**p<0.001$.

FIG. 3A is a graph showing the virus titer of nasal turbinate, brain, lung, kidney and spleen of hACE2 transgenic mice infected with cold-adapted SARS-CoV-2. Virus titer is mean of three tissues±standard deviation. $*p<0.05$, $**p<0.001$.

FIG. 3B is a graph showing the virus titer of brain of hACE2 transgenic mice infected with cold-adapted SARS-CoV-2. Virus titer is mean of three tissues±standard deviation. $*p<0.05$, $**p<0.001$.

FIG. 8A shows results of identifying IgG antibody titer in immunized hACE2 transgenic mice.

FIG. 8B shows results of identifying the number of T lymphocytes expressing INF-g in immunized hACE2 transgenic mice.

FIG. 9C shows mice mortality (%) in immunized hACE2 transgenic mice.

FIG. 9D shows change in mice body weight (%) compared to those before infection.

FIG. 9E shows virus titer in each of nasal turbinate, brain, lung, kidney and spleen of mice by $log_{10}$ $TCID_{50}/0.1$ g. Virus titer is mean of three tissues±standard deviation. Virus detection limit is 1 $TCID_{50}/0.1$ g. $*p<0.05$, $**p<0.001$.

FIG. 10A is a graph showing virus titer in nasal turbinate, lung, kidney and spleen of immunized and challenged hACE2 transgenic mice. Virus titer is mean of three tissues±standard deviation. $*p<0.05$, $**p<0.001$.

FIG. 10B is a graph showing virus titer in brain of immunized and challenged hACE2 transgenic mice. Virus titer is mean of three tissues±standard deviation. $*p<0.05$, $**p<0.001$

Figure 1A:
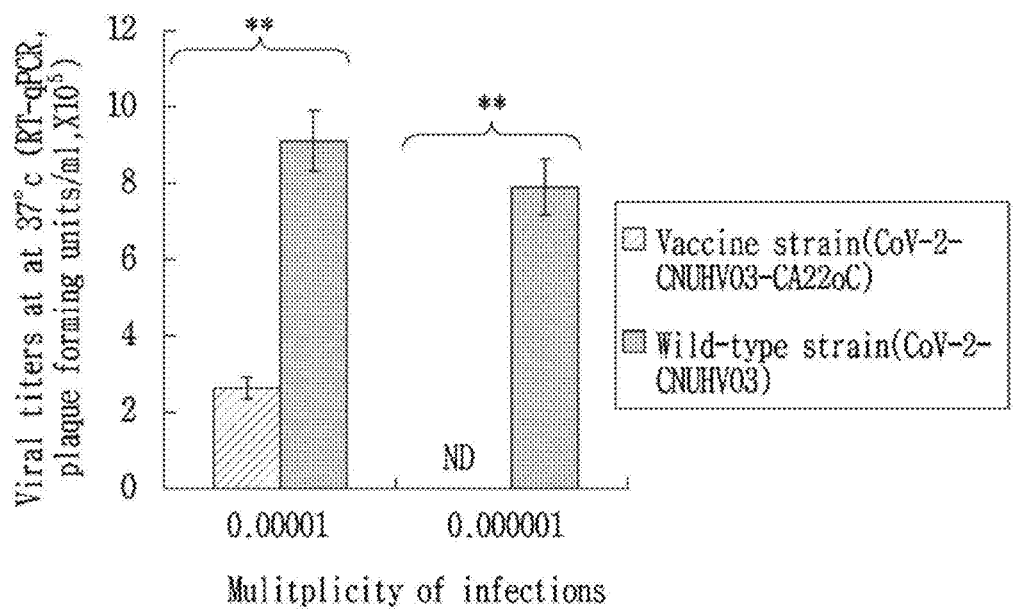
FIG. 1A is a graph showing viral titers at 37° C. to identifying a temperature sensitivity of a cold-adapted SARS-CoV-2 vaccine strain. $*p<0.05$, $**p<0.001$.

($2\times10^4$ pfu); (D) brain tissue of PBS-mock vaccinated mice challenged with CoV-2-KCDC03 ($2\times10^4$ pfu); (E) kidney tissue of PBS-mock mice; (F) kidney tissue of mice vaccinated with CoV-2-CNUHV03-CA22° C. ($2\times10^3$ pfu) and challenged with CoV-2-KCDC03 ($2\times10^4$ pfu); (G) kidney tissue of mice vaccinated with CoV-2-CNUHV03-CA22° C. ($2\times10^4$ pfu) and challenged with CoV-2-KCDC03 ($2\times10^4$ pfu); and (H) kidney tissue of PBS-mock vaccinated mice challenged with CoV-2-KCDC03 ($2\times10^4$ pfu). Arrow refers to positive antigen staining.

DETAILED DESCRIPTION

In the following detailed description, reference is made to the accompanying drawing, which forms a part hereof. The illustrative embodiments described in the detailed description, drawings, and claims are not meant to be limiting. Other embodiments may be utilized, and other changes may be made, without departing from the spirit or scope of the subject matter presented herein.

In addition, in the drawings, in order to clearly describe the present disclosure, parts irrelevant to the description are omitted, and similar reference numerals are attached to similar parts throughout the specification.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terms "about", "substantially", etc. in the present disclosure are used to indicate inherent preparation and substance related tolerance. This is intended to prevent an unscrupulous infringer to design around accurate or absolute values set forth to aid understanding of the present disclosure. The term "step of ~" used throughout the present disclosure does not mean "step for ~".

Throughout the present disclosure, the term "combination thereof" included in expression of a Makushi form means a mixture or combination of at least two selected from a group consisting of elements as recited in the expression of the Makushi form.

The present disclosure relates to cold-adapted live attenuated severe acute respiratory syndrome coronavirus (SARS-CoV-2). The cold-adapted live attenuated severe acute respiratory syndrome coronavirus (SARS-CoV-2) may be prepared by infecting cells with severe acute respiratory syndrome coronavirus (SARS-CoV-2) and then adapting the severe acute respiratory syndrome coronavirus (SARS-CoV-2) to a temperature from 37° C. to 22° C. in a step by step manner.

Specifically, the cold-adapted live attenuated severe acute respiratory syndrome coronavirus (SARS-CoV-2) may be prepared by a following preparation method including:

infecting cells with severe acute respiratory syndrome coronavirus (SARS-CoV-2) and then adapting the severe acute respiratory syndrome coronavirus (SARS-CoV-2) to a temperature from 37° C. to 22° C. in a step by step manner; and subculturing the adapted severe acute respiratory syndrome coronavirus (SARS-CoV-2) at 22° C. and collecting the subcultured adapted severe acute respiratory syndrome coronavirus.

The step of the adaptation thereof to the temperature from 37° C. to 22° C. in the stepwise manner may include, when the infected cells exhibit a cytopathic effect (CPE) at a specific temperature, adapting the virus to a subsequent temperature lower than the specific temperature. However, the present disclosure is not limited thereto.

The cells may be used without limitation as long as the virus may grow therein. For example, the cells may include Vero cells, Calu-3, A549, HUH7.0, HEK-293T cells, and the like. However, the present disclosure is not limited thereto.

The cold-adapted live attenuated severe acute respiratory syndrome coronavirus (SARS-CoV-2) may include a mutation thereof when compared to wild-type severe acute respiratory syndrome coronavirus (SARS-CoV-2). For example, the cold-adapted live attenuated severe acute respiratory syndrome coronavirus (SARS-CoV-2) may contain one or more of polynucleotides represented by nucleotide sequences represented by SEQ ID NOs: 13 to 24. However, the present disclosure is not limited thereto. For example, the cold-adapted live attenuated severe acute respiratory syndrome coronavirus (SARS-CoV-2) may contain one or more of amino acid sequences represented by SEQ ID NOs: 37 to 48. However, the present disclosure is not limited thereto.

Further, the present disclosure provides a vaccine that induces an immune response against severe acute respiratory syndrome coronavirus (SARS-CoV-2) which may invade susceptible host animals and cause disease therein, or treat diseases caused by infection thereof. Preferably, the vaccine according to the present disclosure may contain the cold-adapted live attenuated severe acute respiratory syndrome coronavirus (SARS-CoV-2) as an active ingredient.

Host animals in which the vaccine according to the present disclosure may induce the immune response against severe acute respiratory syndrome coronavirus (SARS-CoV-2) may include mammals or birds, for example, humans, dogs, cats, pigs, horses, chickens, ducks, turkeys, ferrets, and the like.

The vaccine according to the present disclosure may be a live attenuated vaccine. The term "live attenuated vaccine" as used in the present disclosure refers to a vaccine containing a live viral active ingredient. In addition, the term "attenuated" means that toxicity of a living pathogen is artificially weakened. The attenuation means that genes involved in essential metabolism of pathogens are mutated to stimulate only the immune system without causing the disease in the body to induce immunity. Virus attenuation may be achieved by ultraviolet (UV) irradiation, chemical treatment, or by higher order continuous subculture in vitro. Attenuation may also be achieved by causing clear genetic changes, for example, by specific deletions of viral sequences known to provide toxicity or insertion and mutation of sequences into the viral genome.

The vaccine according to the present disclosure may additionally contain at least one selected from the group consisting of solvent, adjuvant and excipient. The solvent may include physiological saline or distilled water. The adjuvant may include Freund's incomplete or complete adjuvants, aluminum hydroxide gels, and vegetable and mineral oils. Excipients may include aluminum phosphate, aluminum hydroxide, or aluminum potassium sulfate. However, the present disclosure is not limited thereto. The vaccine may further contain a substance used in vaccine preparation well known to those skilled in the art.

When the vaccine according to the present disclosure is administered, the cold-adapted live attenuated severe acute respiratory syndrome coronavirus (SARS-CoV-2) may be contained in an appropriate amount depending on a body weight, age, severity of symptoms, and the like of the subject. For example, the vaccine may contain the cold-adapted live attenuated severe acute respiratory syndrome coronavirus (SARS-CoV-2) at a $2 \times 10^3$ to $2 \times 10^4$ pfu level, but is not limited thereto.

The vaccine according to the present disclosure may be prepared in oral or parenteral formulations. For example, the vaccine may be administered via intradermal, intramuscular, intraperitoneal, intranasally or eidural route. Preferably, the vaccine may be administered intranasally, but is not limited thereto.

The present disclosure relates to a method of preventing or treating severe acute respiratory syndrome coronavirus (SARS-CoV-2) infectious disease by administering the vaccine to a subject.

In the present disclosure, the term "severe acute respiratory syndrome coronavirus (SARS-CoV-2) infectious disease" refers to a disease caused by infection with severe acute respiratory syndrome coronavirus, and may be, for example, coronavirus disease-19 (COVID-19). However, the present disclosure is not limited thereto.

In the present disclosure, the term "subject" refers to any animal including a human that has already been infected or may be infected with severe acute respiratory syndrome coronavirus (SARS-CoV-2). For example, the vaccine according to the present disclosure may treat humans infected with various severe acute respiratory syndrome coronavirus (SARS-CoV-2) subtypes, or mutated severe acute respiratory syndrome coronavirus (SARS-CoV-2). Further, the vaccine according to the present disclosure may treat animals infected with various severe acute respiratory syndrome coronavirus (SARS-CoV-2) subtypes or mutated severe acute respiratory syndrome coronavirus (SARS-CoV-2). The composition according to the present disclosure may be administered in combination with a conventional severe acute respiratory syndrome coronavirus (SARS-CoV-2) infectious disease treatment agent.

In the present disclosure, the term "prevention" refers to any action that inhibits infection of severe acute respiratory syndrome coronavirus (SARS-CoV-2) or delays development of disease therefrom via administration of the composition. In the present disclosure, the term "treatment" refers to any action in which symptoms caused by severe acute respiratory syndrome coronavirus (SARS-CoV-2) infection are reduced or beneficially altered via administration of the composition.

The composition according to the present disclosure is administered in a pharmaceutically effective amount. The term "pharmaceutically effective amount" means an amount sufficient to treat the disease with a reasonable benefit/risk ratio applicable to medical treatment. The effective dose level may be determined based on factors including the type and severity of the subject, age, sex thereof, the type of infected virus, drug activity, sensitivity to drug, administration time, route of administration, release rate, duration of treatment, concurrently used drugs, and other factors well known in the medical field. The composition according to the present disclosure may be administered as an individual therapeutic agent or administered in combination with other therapeutic agents, and may be administered sequentially or simultaneously with a conventional therapeutic agent. The vaccine may be administered in a single or multiple manner. It is important to administer a target amount of the vaccine capable of obtaining the maximum effect in a minimum amount without side effects in consideration of all the above factors. The target amount may be easily determined by a person skilled in the art.

Advantages and features according to the present disclosure, and a method of achieving them will become apparent with reference to Examples described below in detail. Hereinafter, the present disclosure will be described in detail based on Examples. However, these Examples are intended for specifically explaining the present disclosure, and the scope of the present disclosure is not limited to these Examples.

Preparation Example 1

Virus and Cell

The SARS-CoV-2 strain (SARS-CoV-2/human/Korea/CNUHV03/2020) (referred to as CoV-2-CNUHV03 in this paper) (GenBank accession number: MT678839), isolated in our laboratory from a human clinical sample collected at the Chungnam National University 6 Hospital (Daejeon, South Korea), and BetaCoV/South Korea/KCDC03/2020 (referred to as 7 CoV-2-KCDC03 in this paper), which was provided by the Korean Centers for Disease Control and Prevention (KCDC), were propagated in Vero-E6 cells obtained from American Type Culture Collection (Manassas, Va., USA). Minimal essential medium (MEM), supplemented with 10% foetal bovine serum (FBS) and 1×antibiotic-antimycotic solution (Sigma, St. Louis, USA), was used for the culture of cells. All experimental procedures involving potential contact with SARS-CoV-2 were conducted in a biosafety level 3 laboratory certified by the Korean government.

Animal

Female (5-6-week-old) human angiotensin converting enzyme 2 (ACE-2) transgenic mice (B6.Cg-Tg(K18-ACE2)2Prlmn/J) (referred to as K18-hACE2 in this paper) were kindly provided by The Jackson Laboratory (Bar Harbor, Me., USA). The mice were fed a standard chow diet and water.

Development of Cold-Adapted Live Attenuated SARS-CoV-2 Vaccine Strain

The SARS-CoV-2 strain (SARS-CoV-2/human/Korea/CNUHV03/2020) was gradually adapted from 37° C. to 22° C. in Vero cells in MEM with 200 mM L-glutamine (Hyclone, South Logan, Utah, USA), supplemented with 1.5% bovine serum albumin (BSA; Rocky Mountain Biologicals, Missoula, Mont., USA) and 1×antibiotic-antimycotic solution (Sigma). Vero cells were cultured in MEM with 10% FBS in a humidified 5% $CO_2$ incubator (37° C.) and washed twice with warm PBS (pH 7.4). The washed Vero cells were inoculated with SARS-CoV-2 virus (SARS-CoV-2/human/Korea/CNUHV03/2020) and incubated in a humidified 5% $CO_2$ incubator (from 37° C. to 22° C.). When the infected Vero cells showed cytopathic effects (CPE), the next lower temperature was used to adapt the virus. When SARS-CoV-2 virus was successfully passaged at 22° C. more than five times (>passage=5), it was used for the vaccine study, and for sequencing of the whole genome. The cold-adapted live attenuated vaccine strain was designated as SARS-CoV-2/human/Korea/CNUHV03-CA22° C./2020 (referred to as CoV-2-CNUHV03-CA22° C. in this paper). At passage 5, at 22° C., the SARS-CoV-2 cold-adapted vaccine virus was cloned by limited-dilution infection in Vero cells in 96-well plates three times. Virus titres for the cold passaged SARS-CoV-2 were determined by RT-qPCR using SARS-CoV-2 N primers and Taqman probe and by plaque assay at 22° C. in terms of pfu.

Example 1

Confirmation of Temperature Sensitivity of the Cold-Adapted Live Attenuated SARS-CoV-2 Vaccine Strain Vero cells grown to confluence in 6-well plates were infected with 0.00001 or 0.000001 multiplicity of infections (m.o.i) of CoV-2-CNUHV03-CA22° C. and wild-type SARS-CoV-2 (CoV-2-CNUHV03). The infected cells were incubated in a humidified 5% $CO_2$ incubator at 37° C. or 41° C., and virus titres in the supernatants were quantified 3 days later by RT-qPCR using the SARS-CoV-2 N primers and probe.

Measurement of Plaque Forming Units by Plaque Assay

Stocks of SARS-CoV-2 (CoV-2-CNUHV03 or CoV-2-CNUHV03-CA22° C.) were serially 10-fold diluted in MEM with 1.5% BSA. Confluent Vero cells growing in 24-well plates were infected with the diluted virus suspensions for 4 h in a humidified 5% $CO_2$ incubator (37° C. for CoV-2-CNUHV03 and 22° C. for CoV-2-CNUHV03-CA22° C.). After removing the inoculum, Vero cells were overlaid with 1% electrophoretic agar (LPS Solution, Korea) in MEM and incubated for 4 or 7 days in a humidified 5% $CO_2$ incubator (37° C. for CoV-2-CNUHV03 and 22° C. for CoV-2-CNUHV03-CA22° C.). The cells were then stained with 0.1% crystal violet (Sigma-Aldrich, St. Louis, Mo., USA) prepared in 37% formaldehyde solution, or with SARS-CoV-2 NP antibody and fluorescent-labelled secondary antibody. After removal of agar, the cells were fixed and permeabilised with 80% cold acetone (Samchun Pure Chemical Co., Gyeonggi-do, Korea). The cells were treated with SARS-CoV-2 nucleocapsid rabbit polyclonal antibody (Thermo Fisher Scientific, Waltham, Mass., USA) and subsequently with fluorescent-labelled goat anti-rabbit antibody (Thermo Fisher Scientific). The number of plaques was counted under a fluorescence microscope (Olympus, Tokyo, Japan).

Measurement of Virus Titers Using Real-Time Quantitative PCR

RNA was isolated from the virus sample using the RNeasy Mini Kit (QIAGEN, Hilden, Germany). Briefly, 100 µL of the supernatant containing the virus was disrupted into 350 µL buffer RLT and then 550 µL of 70% ethanol was added thereto. The sample (700 µL) was transferred to a RNeasy Mini spin column and centrifuged at 13,500 rpm for 15 seconds. After discarding the flow-through, 700 µL of RW1 buffer was added to a spin column and centrifugation was carried out at 13,500 rpm for 15 seconds. After discarding the flow-through, 500 µL of RPE buffer was added to the spin column, followed by centrifugation at 13,500 rpm for 15 seconds. The spin column was then placed in a new 1.5 mL collection tube and viral RNA was eluted with 40 µL of RNAse-free water.

To detect the virus, TaqMan real-time fluorescent PCR was used together with TOPreal™ One-stepRTqPCRKit (Enzynomics, Daejeon, Korea) and SARS-CoV-2 N primer and probe. In a total volume of 20 µL, the following ingredients were mixed with each other: 1 µL of 10 pmol primer containing 5 µL of TOPreal™ One-stepRTqPCRKit (TaqMan probe), N_Sarbeco_F (5'-CACATTGGCACCCGCAAT-3; SEQ ID NO: 49), N_Sarbeco_R (5'-GAGGAACGAGAAGAGGCTTG-3; SEQ ID NO: 50), and N_Sarbeco_P (5'FAM-ACTTCCTCAAGGAACAA-CATTGCCA-3'BHQ1; SEQ ID NO: 51), 10 µL of viral RNA, and 2 µL of nuclease-free water. Real-time amplification was carried out in a Rotor-Gene 6000 system (QIAGEN, Hilden, Germany) according to the following temperature profile: initial incubation at 50° C. for 30 minutes and 95° C. for 10 minutes, and then 45 cycles at 95° C. for 5 seconds and 60° C. for 30 seconds. A standard curve was generated using known data for stock viruses with known pfu titres determined by plaque assay.

Confirmation of Attenuation of the Cold-Adapted Live Attenuated SARS-CoV-2 Vaccine Strain in hACE-2 Transgenic Mice K18-hACE2 mice was slightly anesthetized with isoflurane USP (Gujarat, India) and then intranasally (i.n.) immunized with 50 mL ($2 \times 10^4$ pfu) of cold-adapted vaccine strain (n=14) or wild-type virus (n=6). PBS (mock)-infected mice (n=4) were used as control. The body weight change and mortality of the infected mice were monitored. On the 6th day post-infection (p.i.), 3 mice per virus (vaccine strain or wild-type virus)-infected group and 1 PBS (mock)-infected mice were euthanized and virus titer and histopathology in various tissues (nasal turbinate, brain, lung, and kidney) were determined. Tissue (0.1 g per sample) was homogenized in 1 mL of PBS (pH 7.4) using a BeadBlaster homogenizer (Benchmark Scientific, Edison, N.J., USA) to measuring virus titer by RT-qPCR and by determining $\log_{10}$ $TCID_{50}/0.1$ g values. A remaining part of the tissue was used for histopathology and antibody staining.

Staining of Tissue with Hematoxylin and Eosin

Mice tissue was fixed in 10% neutralization buffer formalin (10%) and then embedded in paraffin. Lung tissue was cut into 5 µm sections which in turn were stained with hematoxylin (H) solution for 4 minutes. The stained tissue sections were washed with tap water for 10 minutes and then stained with eosin (E) solution. The stained sections were visualized and photographed under an Olympus DP70 microscope (Olympus Corporation, Tokyo, Japan).

Tissue Staining with SARS-CoV-2 NP Antibody

Tissue sections were stained with SARS-CoV-2 nucleocapsid rabbit polyclonal antibody (Thermo Fisher Scientific). The sections were treated with antigen retrieval solution in a microwave oven and blocked with normal rabbit serum in PBS (pH 7.4). Then, the sections were incubated with rabbit antibody against SARS-CoV-2 NP (1:100 dilution), and were treated with biotin-labeled goat anti-rabbit immunoglobulin (Vector Laboratories, Burlingame, Calif., USA), and Vectastain ABC-AP (Vector Laboratories) and Vector Red alkaline phosphatase substrate (Vector Laboratories). The labelled lung section was counter-stained with hematoxylin QS (Vector Laboratories) and observed under an Olympus DP70 microscope (Olympus Corporation).

Virus Titer Measurement in Terms of $\log_{10} TCID_{50}/mL$

Vero cells grown in tissue culture flasks detached by treatment with trypsin-EDTA and were seeded in 96-well tissue culture plates with MEM containing 10% FBS and 1×antibiotic-antimycotic solution. When confluent, the cells were washed with warm PBS (pH 7.4) and infected with a virus sample diluted 10-fold with MEM having 1.5% BSA. The cells in 4 wells were infected with virus sample diluted for 4 days in a humidified incubator at 37° C. (wild-type SARS-CoV-2 strain) or 22° C. (cold-adapted SARS-CoV-2 vaccine strain). Then, the cells were fixed and permeabilised with 80% cold acetone (Samchun Pure Chemical Co.). Subsequently, the cells were incubated with SARS-CoV-2 nucleocapsid rabbit polyclonal antibody (Thermo Fisher Scientific) and fluorescent-labelled goat anti-rabbit antibody (Thermo Fisher Scientific). Titers were counted via the method described in the prior literature (L. J. Reed, H. Muench, A simple method of estimating fifty percent endpoints. *The American Journal of Hygiene*. 27, 493-497 (1938)).

Evaluation of Vaccine Efficacy in hACE-2 Transgenic Mice

On the 21st day after vaccination, the hACE-2 mice (n=8 per group) immunized with $2\times10^4$ or $2\times10^3$ pfu of CoV-2-CNUHV03-CA22° C. were challenged intranasally (i.n.) with 50 μL ($2\times10^4$ pfu) of CoV-2-KCDC03. PBS (mock)-immunized hACE-2 mice (n=6) were also challenged intranasally with 50 μL ($2\times10^4$ pfu) of CoV-2-KCDC03. PBS (mock)-vaccinated and non-infected hACE-2 mice (n=3) were used as control. Body weight change and mortality of the infected mice were monitored. On the 6th day after the challenge, 3 mice per virus (vaccine strain or wild-type virus)-infected group and 1 PBS (mock)-infected mouse were euthanized for determining virus titer in various tissues (nasal turbinate, brain, lung and kidney) and for histopathology. The virus titer was quantified by RT-qPCR and by determining $log_{10}$ $TCID_{50}$/0.1 g values.

Measurement of Neutralizing Antibody Titer

Sera (n=8 per group) collected from hACE-2 mice intranasally immunized with 50 mL ($2\times10^4$ or $2\times10^3$ pfu) of CoV-2-CNUHV03-CA22° C. on the 19th day after vaccination was diluted 10 fold in MEM having 1.5% BSA and serially diluted 2 fold and then was incubated together with 100$TCID_{50}$/mL (100 mL: 100 mL) of the wild-type SARS-CoV-2 virus, CoV-2-CNUHV03 or CoV-2-KCDC03 for 1 hour in a 5% $CO_2$ humidified incubator (37° C.). Vero cells grown in 96-well cell culture plates were washed with warm PBS (pH 7.4) and inoculated with a mixture of the serum and virus. The cells were incubated for 4 days and CPE was identified. The titer of the neutralizing antibody was determined as the reciprocal of the highest dilution of serum at which the infectivity was neutralised in 100% of the cell in wells. The assay was carried out in 4 replicates. 16 sera samples collected from hACE-2 mice before the vaccination were used as control.

Enzyme-Linked Immunosorbent Spot (ELISpot) Assay for Mice IFN-g

On the 19th day after vaccination, the immunized hACE-2 transgenic mice (n=3) inoculated intranasally with 50 mL ($2\times10^4$ pfu) of CoV-2-CNUHV03-CA22° C. were euthanized to collect spleen therefrom. The spleen samples were homogenized in PBS (pH 7.4) and the cells were collected. Nasal turbinates, lungs, and kidneys were homogenized in 10% PBS (pH 7.4) and the homogenate was used to detect IgA specific for SARS-CoV-2 using enzyme-linked immunosorbent spot (ELISpot) assay. The collected cells were overlaid on HISTOPAQUE-1077 (Sigma), followed by centrifugation for 30 minutes at 1500 rpm at 4° C. A lymphocyte layer was collected in the IFN-g ELISpot assay conducted using mouse IFN-g ELISpot$^{Plus}$kit (MABTECH, Nacka Strand, Sweden). The plate was removed from the sealed package, followed by washing 4 times with sterile PBS (200 mL/well). The plate was conditioned with RPMI 1640 medium (200 mL/well) containing 10% FBS for 30 minutes at room temperature. The purified lymphocytes (250,000/well) mixed with 0.01 m.o.i of CoV-2-CNUHV03-CA22° C. were added to the well and the plate was incubated in a 5% $CO_2$ humidified incubator at 37° C. for 24 hours. Then, the solution was poured out of the plate and the cells were washed 5 times with PBS (pH 7.4) (200 mL PBS/well for each wash). A detection antibody (R4-6A2-biotin) diluted to 1 g/mL was added to PBS (pH 7.4) containing 0.5% FBS (200 mL/well) and the plate was incubated at room temperature for 2 hours. The plate was washed 5 times with PBS (pH 7.4) (200 mL PBS/well for each wash) and streptavidin-ALP (1:1000) in PBS-0.5% FBS (100 mL/well) was added to the well. The cells were incubated for 1 hour at room temperature. The plate was washed 5 times with PBS as described above and a substrate solution (BCIP/NBT-plus) was added thereto (100 mL/well). The plate was developed until distinct spots appeared. The color development was stopped via extensive washing with tap water. Spots were examined and counted under a microscope (Olympus). Three PBS (mock)-immunized hACE-2 mice were used as control.

Detection of IgA Specific Antibody SARS-CoV-2 in Tissue of Immunized Mice Using Enzyme-Linked Immunosorbent Assay (ELISA)

The purified and inactivated SARS-CoV-2 antigen (SARS-CoV-2/human/Korea/CNUHV03/2020) was diluted with a coating buffer (carbonate-bicarbonate buffer, pH 9.6) to a final concentration of 100 μg/mL. The diluted antigen (100 μL) was incubated overnight at 4° C. to coating on wells of Nunc-Immuno™ MicroWell™ 96 well solid plate (Sigma-Aldrich). After removing the coating buffer therefrom, the plate was washed twice by filling the wells with 400 μL of washing buffer (0.05% Tween 20 PBS (pH 7.4) containing 4% horse serum). To block the remaining protein-binding sites, 400 μL of blocking buffer (PBS containing 4% skimmed milk) was added to the plate which in turn was kept at 4° C. overnight. The buffer was removed therefrom and the supernatant (100 μL) of homogenized tissue (nasal turbinate, lung, and kidney) obtained from vaccinated and non-vaccinated mice on day 19 after vaccination and diluted 10-fold with a blocking buffer was added to the plate, and was incubated at room temperature for 1 hour. The plate was washed 4 times with washing buffer. Goat anti-mouse IgA cross-adsorbed secondary antibody HRP (Invitrogen, MA, USA) (100 μL) diluted with the blocking buffer to 1:5000 was added to each well and incubated at room temperature for 1 hour. After washing the plate 4 times with the washing buffer, 100 μL TMB ELISA substrate (MABTECH) was dispensed in each well, and the plate was incubated at 4° C. for 30 minutes. Then, ABTS R Peroxidase Stop Solution (KPL, MD, USA) (100 μL) was added to each well. The absorbance of the solution in each well was measured at 450 nm using an iMARK™ Microplate Absorbance Reader (Bio-Rad, CA, USA).

Sequencing of Full Genome of Cold-Adapted Live Attenuated SARS-CoV-2 Vaccine Strain The genome of CoV-2-CNUHV03-CA22° C. was fully sequenced using an overlapping primer (Table 1). Viral RNA was extracted using the RNeasy Mini Kit (QIAGEN, Venlo, Netherlands). Tissue culture supernatant (200 μL) containing the virus was disrupted with 350 μL buffer RLT, and then 500 μL of 70% ethanol was added to the mixture. The disrupted sample (700 μL) was transferred to an RNeasy Mini spin column, and the column was centrifuged at 13,500 rpm for 15 seconds. After discarding the flow-through, 700 μL of RW1 buffer was added to the spin column, followed by centrifugation at 13,500 rpm for 15 seconds. The flow-through was discarding therefrom again and then 500 μL of RPE buffer was added to the spin column, followed by centrifugation at 13,500 rpm for 2 minutes. The spin column was placed in a new 1.5 mL collection tube and viral RNA was eluted with 50 μL of RNAse-free water. The extracted RNA was reverse transcribed into cDNA using GoScript™ ReverseTranscription System (Promega, Madison, USA) and 12 reverse primers (covid2500R, covid5000R, covid7500R, covid10000R, covid12500R, covid15000R, covid17500R, covid20000R, covid22500R, covid25000R, covid27500R, covid29843R) (Table 2). Twelve viral genes were amplified by PCR using GoTaq Hot Start Green Master Mix (Promega) and a segment-specific primer set. Amplicons were separated using gel electrophoresis and purified using QIAquick Gel Extraction Kit (QIAGEN). The purified gene was cloned into pGEM-T Easy vector (Promega), and the vector construct was used for transformation of the chemically competent *Escherichia coli* DH5α cells (Enzynomics, Daejeon, Korea). The plasmids were extracted using the HiGene Plasmid Mini Prep Kit (BIOFACT, Daejeon, Korea), and the sequence thereof was determined by Macrogen (Seoul, Korea). Three clones per segment were sequenced. The sequenced genes were arranged using DNASTAR Lasergene (Madison, Wis., USA). The sequence of CoV-2-CNUHV03-CA22° C. (SEQ ID NOs: 13 to 24) was deposited on GenBank and received an accession number MT810119.

TABLE 1

Primers used for PCR amplification of the gene segments in cold-adapted live attenuated SARS-CoV-2 vaccine strain (SARS-CoV-2/human/Korea/CNUHV03-CA22°C/2020)

| segment | F Primer | F sequence | R primer | R sequence |
|---|---|---|---|---|
| 1 | 1F | ATTAAAGGTTTATACCTTCCCAGGTAAC (SEQ ID NO. 52) | 1300R | CACCTTCTTTAGTCAAATTCTCAGTG (SEQ ID NO. 76) |
| 2 | 1200F | GCAACCAAATGTGCCTTTCAAC (SEQ ID NO. 53) | 2500R | TTCTCCCTCTAAGAAGATAATTTCTTTT (SEQ ID NO. 77) |
| 3 | 2400F | ACTCAAAGGGATTGTACAGAAAGTGTGT (SEQ ID NO. 54) | 3750R | GTGCGAACAGTATCTACACAAACTCTTA (SEQ ID NO. 78) |
| 4 | 3650F | GACATTCAACTTCTTAAGAGTGCTTAT (SEQ ID NO. 55) | 5000R | GGTTAATGTTGTCTACTGTTGTAAACAC (SEQ ID NO. 79) |
| 5 | 4901F | CTAGATGGTGAAGTTATCACCTTTGACA (SEQ ID NO. 56) | 6250R | GCTTTATTAGTTGCATTGTTAACATGCC (SEQ ID NO. 80) |
| 6 | 6150F | GACTTAAATGGTGATGTGGTGGC (SEQ ID NO. 57) | 7500R | CACATCATACAAGTTGATGAATTACAAC (SEQ ID NO. 81) |
| 7 | 7400F | GCTATGGTTAGAATGTACATCTTCTTTG (SEQ ID NO. 58) | 8750R | GTTAGCAAAACAAGTATCTGTAGATGC (SEQ ID NO. 82) |
| 8 | 8650F | CCTGTTCATGTCATGTCTAAACATACTGACT (SEQ ID NO. 59) | 10,000R | ACCTGAGTTACTGAAGTCATTGAGAGCC (SEQ ID NO. 83) |
| 9 | 9900F | ATAAGTACAAGTATTTTAGTGGAGCAAT (SEQ ID NO. 60) | 11250R | ACCATATCCAACCATGTCATAATAC (SEQ ID NO. 84) |
| 10 | 11150F | GTCAAACATAAGCATGCATTTCTCTGT (SEQ ID NO. 61) | 12,500R | TGTTATAGTCTGGTAAGACAACCATTAG (SEQ ID NO. 85) |
| 11 | 12,400F | CAACAACATTATCAACAATGCAAGAGAT (SEQ ID NO. 62) | 13750R | TACCATGTCACCGTCTATTCTAAAC (SEQ ID NO. 86) |
| 12 | 13650F | TGTAGTTAAGAGACACACTTTCTCTAA (SEQ ID NO. 63) | 15,000R | ACTCATTGAATCATAATAAAGTCTAGCC (SEQ ID NO. 87) |
| 13 | 14,900F | GTATTAATGCTAACCAAGTCATCGTCAA (SEQ ID NO. 64) | 16250R | CTGTGAATTGCAAAGAACACAAGCC (SEQ ID NO. 88) |
| 14 | 16150F | ACACATGTTAGACATGTATTCTGTTATGC (SEQ ID NO. 65) | 75,500R | AATATTCTGGTTCTAGTGTGCCCTTAGT (SEQ ID NO. 89) |
| 15 | 17,400F | TGCCAGATTACGTGCTAAGCACTATGTG (SEQ ID NO. 66) | 18750R | CCCCATTGTTGAACATCAATCAT AAACGG (SEQ ID NO. 90) |
| 16 | 18650F | CCTGAGCGCACCTGTTGTCTATG (SEQ ID NO. 67) | 20,000R | ACTCTACCATCAAAAAAGACAGTGAGTG (SEQ ID NO. 91) |
| 17 | 19,900F | GCACATATATCTACTATTGGTGTTTGTT (SEQ ID NO. 68) | 21250R | GCTTCAGATGATGACGCATTCAC (SEQ ID NO. 92) |
| 18 | 21150F | GGAGGTTCCGTGGCTATAAAGAT (SEQ ID NO. 69) | 22,500R | TAGATTCCTTTTTCTACAGTGAAGGATT (SEQ ID NO. 93) |
| 19 | 22,401F | ATGAAAATGGAACCATTACAGATGCTGT (SEQ ID NO. 70) | 23750R | CTGATGTCTTGGTCATAGACACTG (SEQ ID NO. 94) |
| 20 | 23650F | CTACACTATGTCACTTGGTGCAGA (SEQ ID NO. 71) | 25,000R | GTCTAATTCAGGTTGCAAAGGATCATAA (SEQ ID NO. 95) |
| 21 | 24,900F | AAATCATTACTACAGACAACACATTGT (SEQ ID NO. 72) | 26250R | CTCTTCCGAAACGAATGAGTAC (SEQ ID NO. 96) |

TABLE 1-continued

Primers used for PCR amplification of the gene
segments in cold-adapted live attenuated SARS-CoV-2 vaccine
strain (SARS-CoV-2/human/Korea/CNUHV03-CA22°C/2020)

| segment | F primer | F sequence | R primer | R sequence |
|---|---|---|---|---|
| 22 | 26150F | CGACGGTTCATCCGGAGTTGTT (SEQ ID NO. 73) | 27,500R | GAGCAAGGTTCTTTTAAAAGTACTGTTG (SEQ ID NO. 97) |
| 23 | 27,400F | ATTATTCTTTTCTTGGCACTGATAACAC (SEQ ID NO. 74) | 28700R | CGGGTGCCAATGTGATCTTTTGT (SEQ ID NO. 98) |
| 24 | 28600F | TTCTACTACCTAGGAACTGGGC (SEQ ID NO. 75) | 29,843R | GTCATTCTCCTAAGAAGCTATTAAAATC (SEQ ID NO. 99) |

TABLE 2

Primers for the synthesis of cDNA for
cold-adapted live attenuated
SARS-CoV-2 vaccine strain
(SARS-CoV-2/human/Korea/CNUHV03-CA22°C/2020

| Primer | Sequence |
|---|---|
| 2500R | TTCTCCCTCTAAGAAGATAATTTCTTTT (SEQ ID NO. 100) |
| 5000R | GGTTAATGTTGTCTACTGTTGTAAACAC (SEQ ID NO. 101) |
| 7500R | CACATCATACAAGTTGATGAATTACAAC (SEQ ID NO. 102) |
| 10,000R | ACCTGAGTTACTGAAGTCATTGAGAGCC (SEQ ID NO. 103) |
| 12,500R | TGTTATAGTCTGGTAAGACAACCATTAG (SEQ ID NO. 104) |
| 15,000R | ACTCATTGAATCATAATAAAGTCTAGCC (SEQ ID NO. 105) |
| 17,500R | AATATTCTGGTTCTAGTGTGCCCTTAGT (SEQ ID NO. 106) |
| 20,000R | ACTCTACCATCAAAAAAGACAGTGAGTG (SEQ ID NO. 107) |
| 22,500R | TAGATTCCTTTTTCTACAGTGAAGGATT (SEQ ID NO. 108) |
| 25,000R | GTCTAATTCAGGTTGCAAAGGATCATAA (SEQ ID NO. 109) |
| 27,500R | GAGCAAGGTTCTTTTAAAAGTACTGTTG (SEQ ID NO. 110) |
| 29,843R | GTCATTCTCCTAAGAAGCTATTAAAATC (SEQ ID NO. 111) |

Results

Figure 1B:
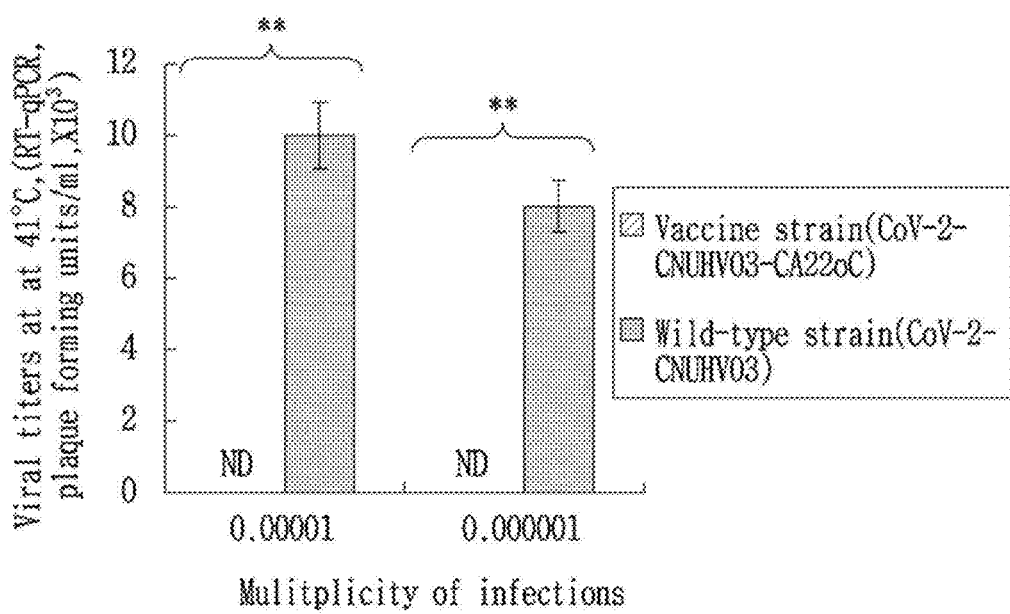
FIG. 1B is a graph showing viral titers at 41° C. to identifying a temperature sensitivity of a cold-adapted SARS-CoV-2 vaccine strain. $*p<0.05$, $**p<0.001$.

Vero cells grown in 6-well plates were infected with wild-type SARS-CoV-2 (CoV-2-CNUHV03) or cold-adapted vaccine SARS-CoV-2 (CoV-2-CNUHV03-CA22° C.) in a 5% $CO_2$ humidified incubator at 37° C. and 41° C., to determine the temperature sensitivity of the vaccine strain (FIGS. 1A and 1B). At 37° C. and 0.00001 multiplicity of infections (m.o.i) (FIG. 1A), the viral titers of CoV-2-CNUHV03-CA22° C. and CoV-2-CNUHV03 were $2.6 \times 10^5$ plaque forming units (pfu)/ml and $7.9 \times 10^5$ pfu/ml, respectively. At 37° C. and 0.000001 m.o.i (FIG. 1A), the virus titers of CoV-2-CNUHV03-CA22° C. and CoV-2-CNUHV03 were 0 pfu/ml and $7.9 \times 10^4$ pfu/ml, respectively. At 41° C. and 0.00001 m.o.i (FIG. 1B), the virus titers of CoV-2-CNUHV03-CA22° C. and CoV-2-CNUHV03 were 0 pfu/ml and $10 \times 10^3$ pfu/ml, respectively. At 41° C. and 0.000001 m.o.i (FIG. 1B), the virus titers of CoV-2-CNUHV03-CA22° C. and CoV-2-CNUHV03 were 0 pfu/ml and $8 \times 10^3$ pfu/ml, respectively.

Figure 2A:
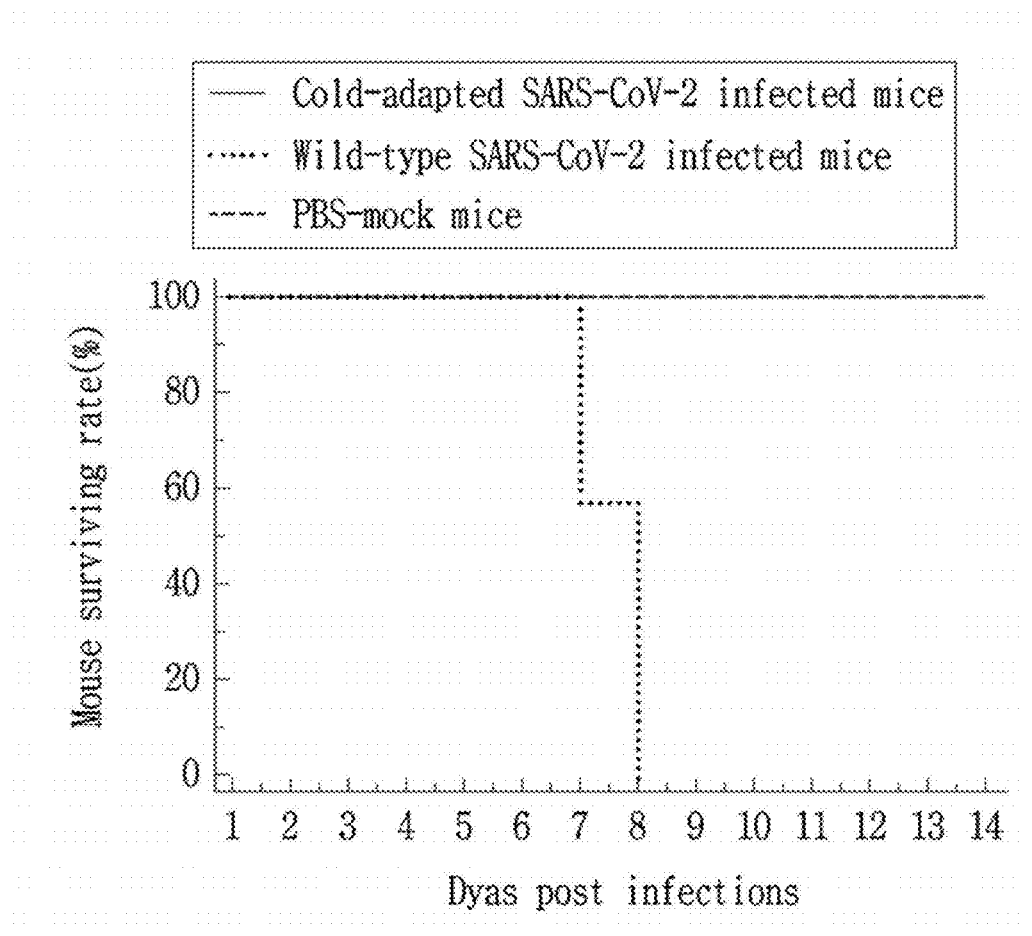
Figure 2B:
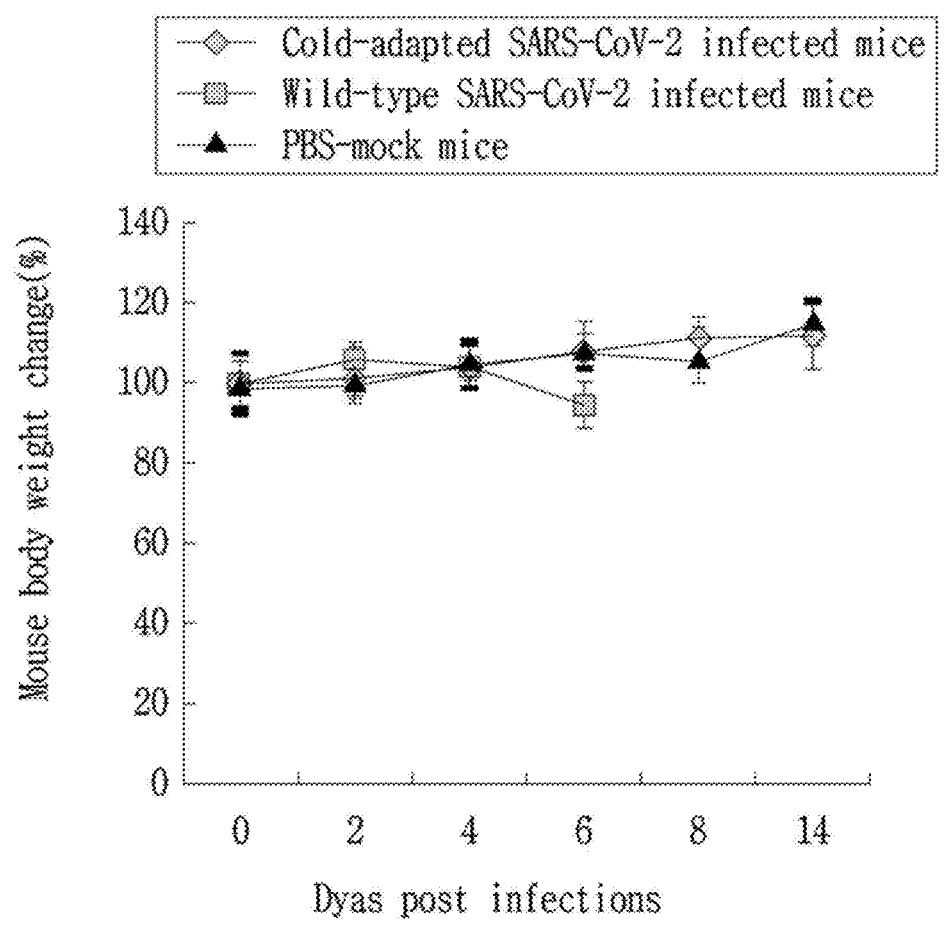

To identify the attenuation of CoV-2-CNUHV03-CA22° C. in animals, hACE-2 transgenic mice (K18-hACE2), which are very susceptible to SARS-CoV-2, were intranasally (i.n.) infected with CoV-2-CNUHV03-CA22° C. ($2 \times 10^4$ pfu) (FIG. 2). The mortality rate (FIG. 2A) and body weight change (FIG. 2B) of the infected mice were monitored for 14 days. All mice survived and exhibited no body weight loss. However, K18-hACE2 mice infected with CoV-2-CNUHV03 exhibited body weight loss until 8 days after infection (p.i.) (5.8%) and eventually died.

Figure 2C:
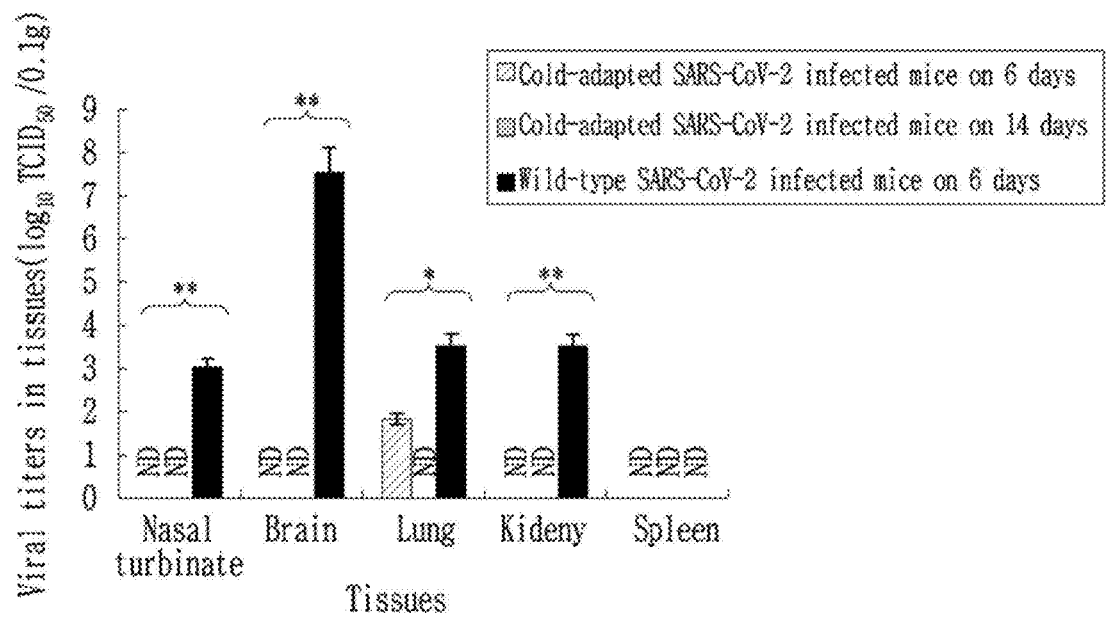
Figure 3A:
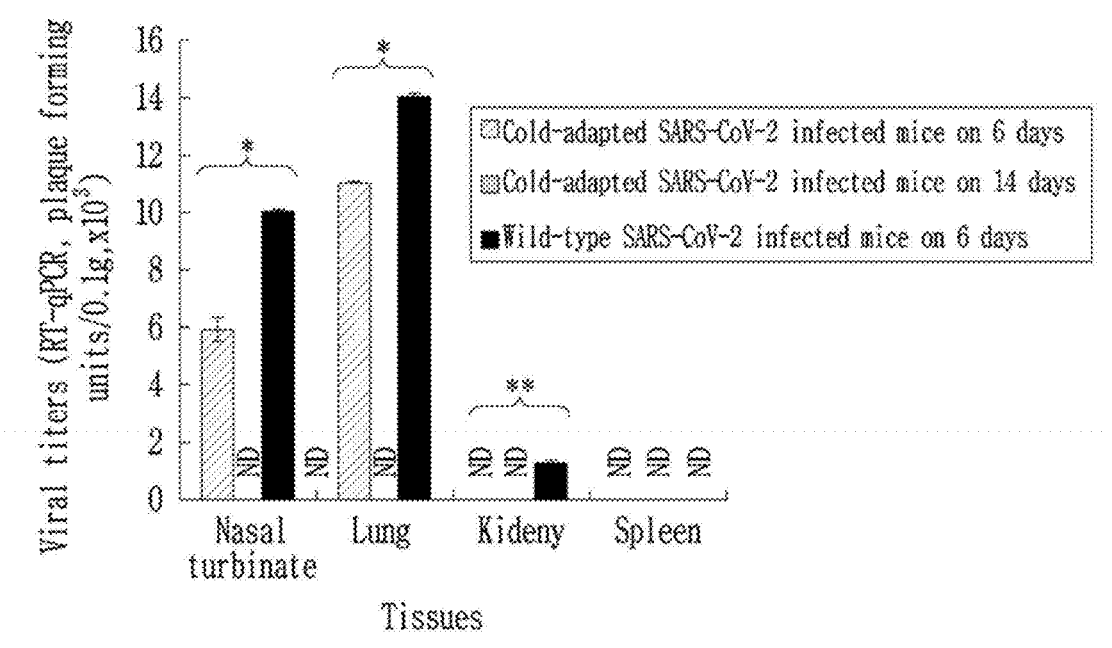
Figure 3B:
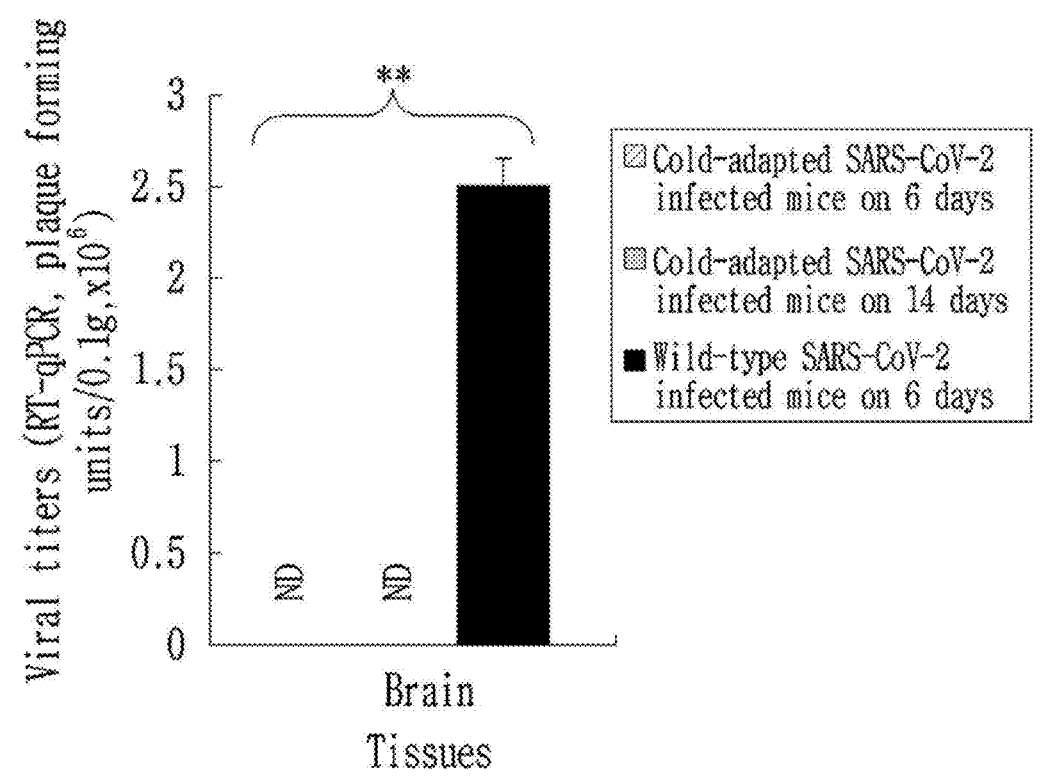

On the 6th day after infection, the virus titer in various tissues (nasal turbinate, brain, lung, kidney, spleen) of the infected mice was identified by determining $\log_{10}$ tissue culture infectious dose 50 ($\log_{10}$ $TCID_{50}$) level in Vero cells and performing a real-time quantitative polymerase chain reaction (RT-qPCR) with the SARS-CoV-2 N primer and probe. The virus titer was lower in the tissues of K18-hACE2 mice infected with CoV-2-CNUHV03-CA22° C. than that in the tissues of K18-hACE2 mice infected with CoV-2-CNUHV03 (FIG. 2C, and FIGS. 3A and 3B). When the virus titer was measured in terms of $\log_{10}$ $TCID_{50}$ level, the viruses were detected only in the lung of K18-hACE2 mice infected with virus CoV-2-CNUHV03-CA22° C. with a virus titer of 1.83 $TCID_{50}$/0.1 g; however, the virus was detected at nasal turbinate (3.0 $TCID_{50}$/0.1 g), brain (7.5 $TCID_{50}$/0.1 g), lung (3.5 $TCID_{50}$/0.1 g), and kidney (3.5 $TCID_{50}$/0.1 g) of CoV-2-CNUHV03-infected K18-hACE2 mice (FIG. 2C). Using RT-qPCR, the virus was detected in nasal turbinate ($5.9 \times 10^3$ pfu/0.1 g), and lung ($11 \times 10^3$ pfu/0.1 g) of K18-hACE2 mice infected with CoV-2-CNUHV03-CA22° C. The virus was detected at nasal turbinate ($10 \times 10^3$ pfu/0.1 g), brain ($2.5 \times 10^6$ pfu/0.1 g), lung ($14 \times 10^3$ pfu/0.1 g), and kidney ($1.3 \times 10^3$ pfu/0.1 g) of CoV-2-CNUHV03-infected K18-hACE2 mice (FIG. 3A & 3B). On the 14th day after infection, no virus was detected in the tissue of K18-hACE2 mice infected with CoV-2-CNUHV03-CA22° C. (FIG. 2C & FIG. 3A & 3B).

Figure 4A:
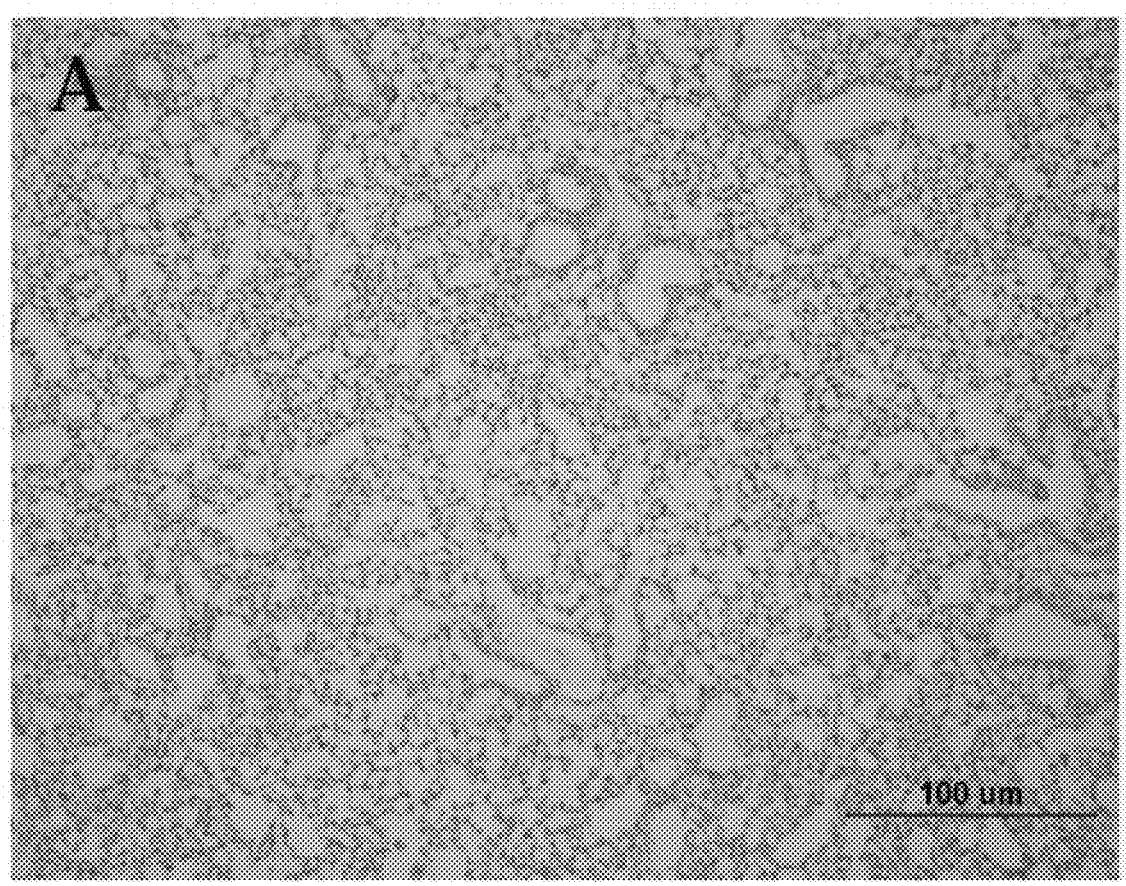
FIGS. 4A-4F show lung histopathology and antigen staining results of the cold-adapted SARS-CoV-2 vaccine strain in hACE2 transgenic mice: (A) and (D) lung tissue of PBS-mock mice, (B) and (E) lung tissue of mice intranasally infected with cold-adapted SARS-CoV-2 (CoV-2-CNUHV03-CA22° C.) ($2\times10^4$ pfu), (C) and (F) lung tissue of mice infected with wild-type SARS-CoV-2 (CoV-2-CNUHV03) ($2\times10^4$ pfu). Arrow refers to positive antigen staining.
Figure 4B:
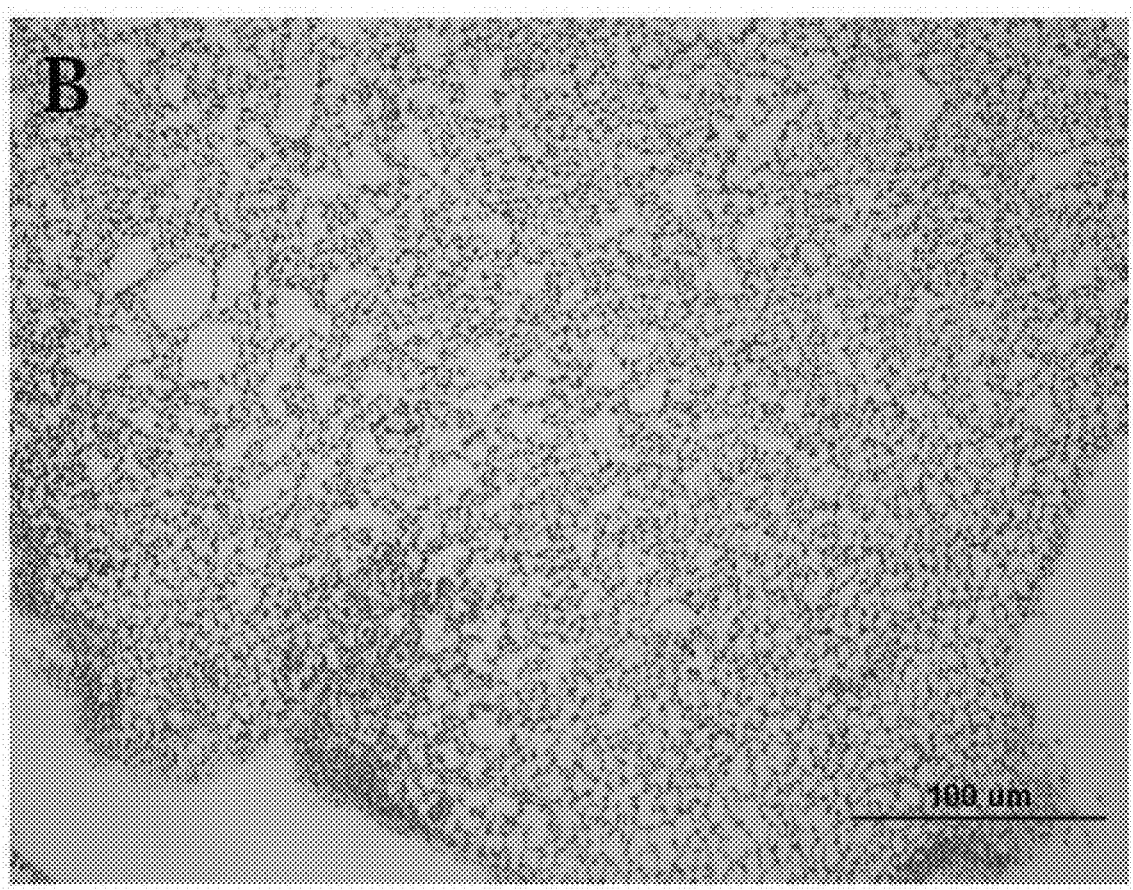
Figure 4C:
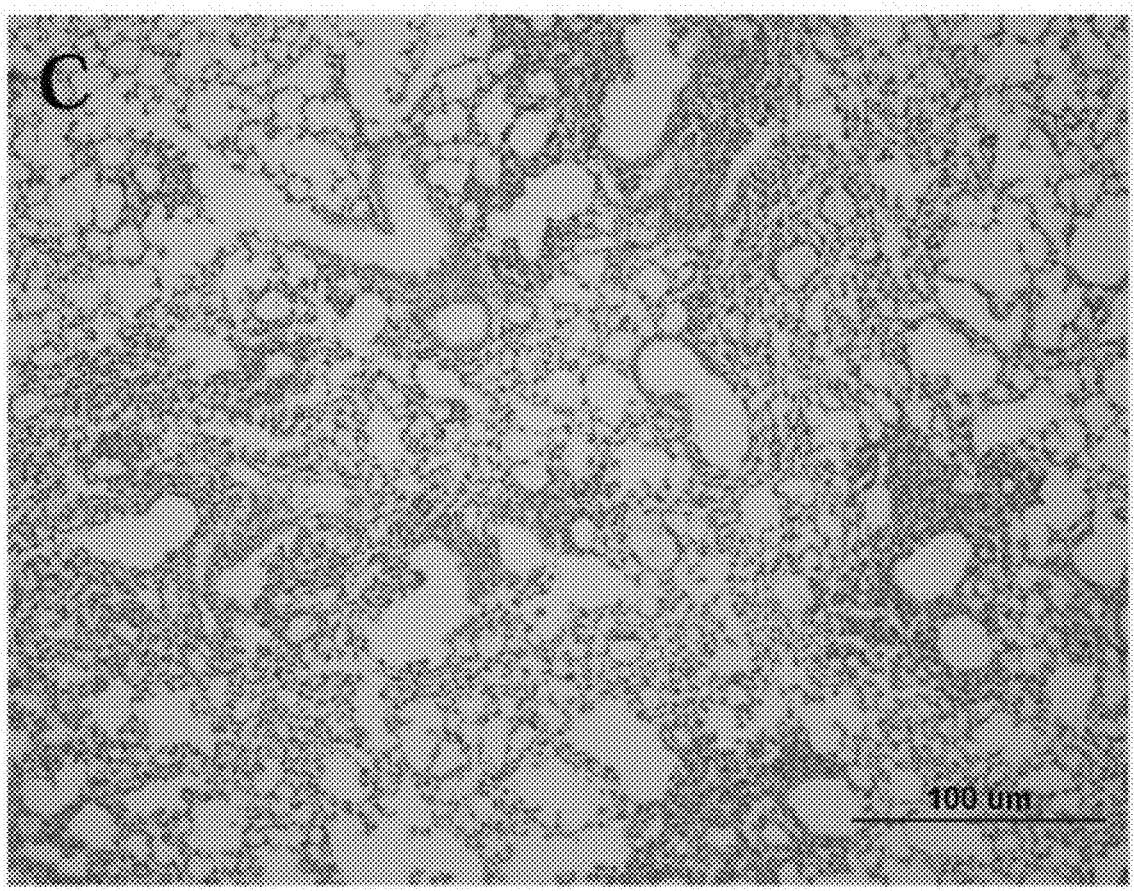
Figure 4D:
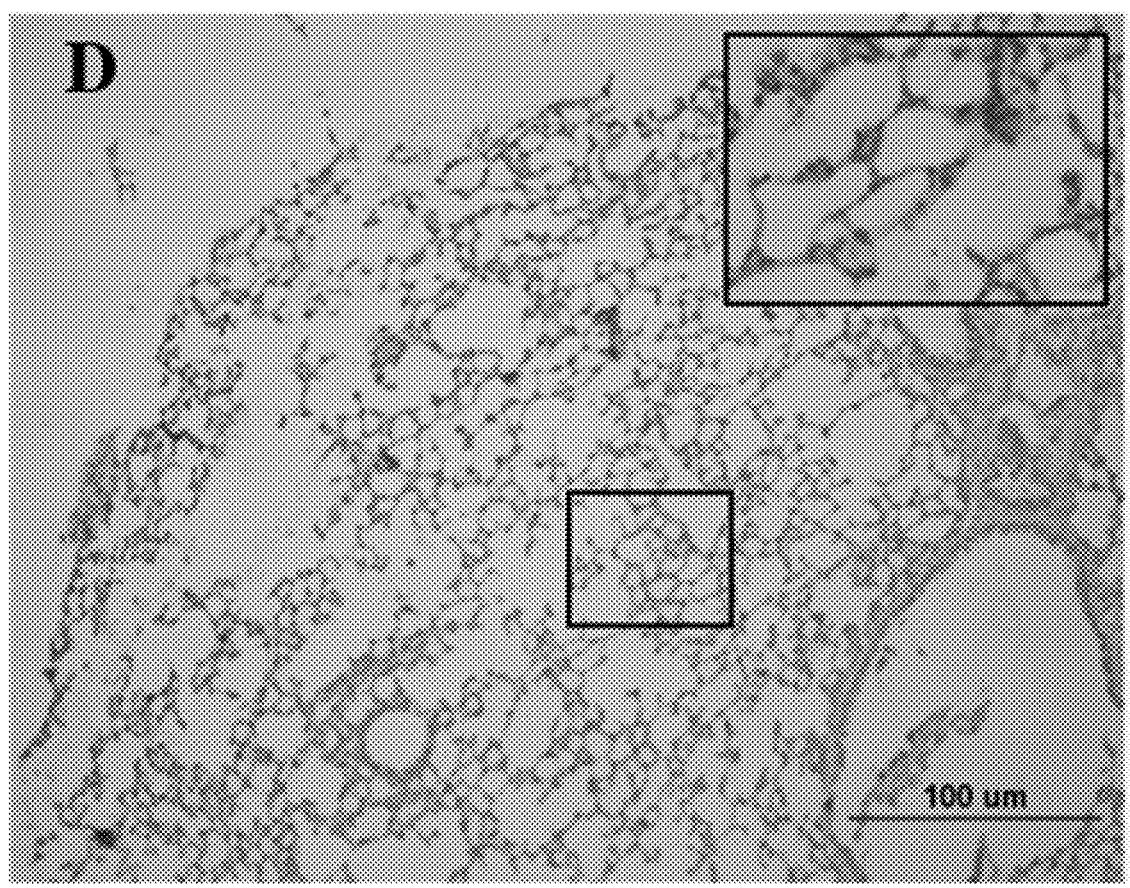
Figure 4E:
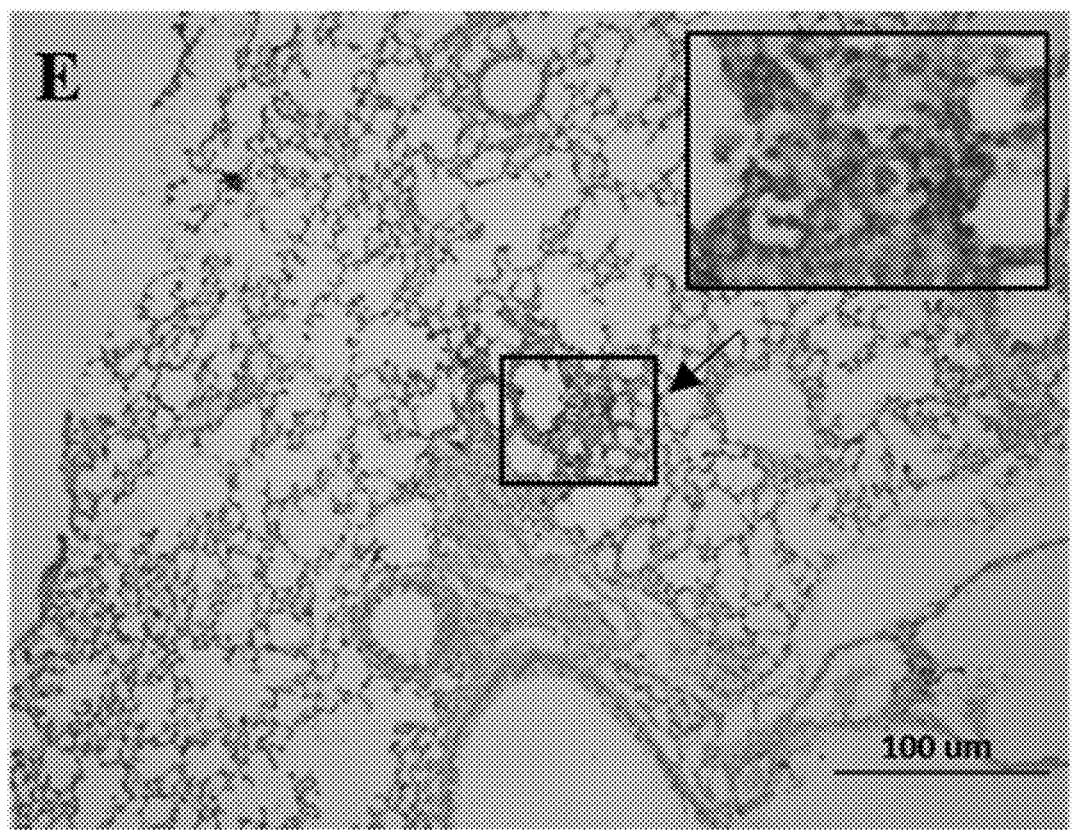
Figure 4F:
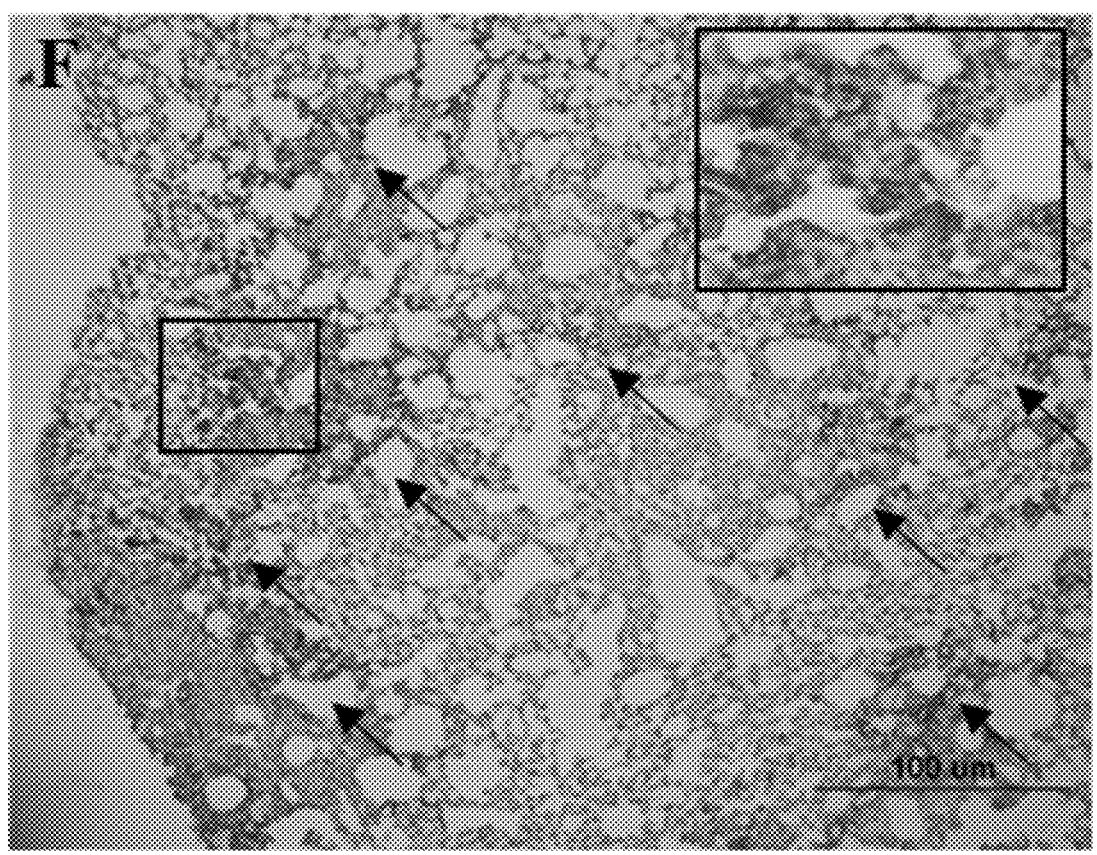
Figure 5A:
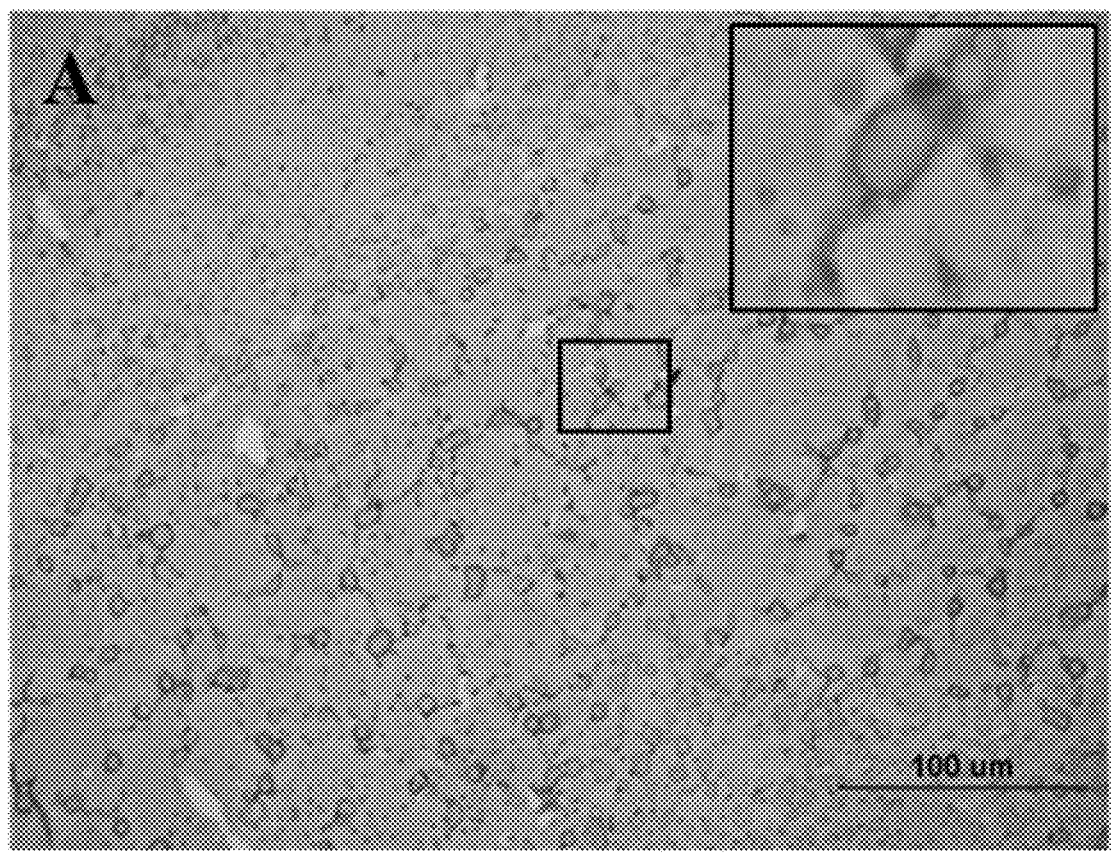
FIGS. 5A-5F show results of antigen staining of brain and kidney tissues from hACE2 transgenic mice infected with cold-adapted SARS-CoV-2: (A) brain tissue of PBS-mock mice; (B) brain tissue of mice intranasally infected with cold-adapted SARS-CoV-2 (CoV-2-CNUHV03-CA22° C.) ($2\times10^4$ pfu); (C) brain tissue of mice intranasally infected with wild-type SARS-CoV-2 (CoV-2-CNUHV03) ($2\times10^4$ pfu); (D) kidney tissue of PBS-mock mice; (E) kidney tissue of mice intranasally infected with cold-adapted SARS-CoV-2 (CoV-2-CNUHV03-CA22° C.) ($2\times10^4$ pfu); (F) kidney tissue of mice intranasally infected with wild-type SARS-CoV-2 (CoV-2-CNUHV03) ($2\times10^4$ pfu). Arrow refers to positive antigen staining.
Figure 5B:
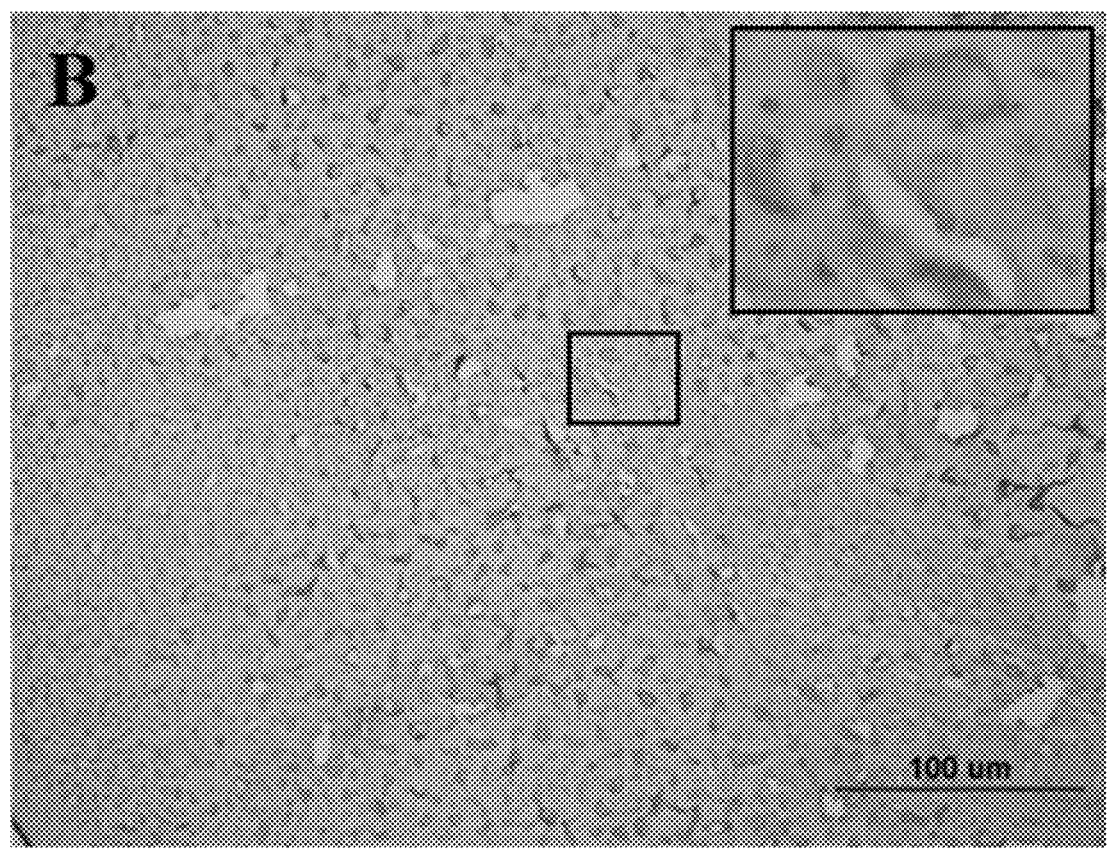
Figure 5C:
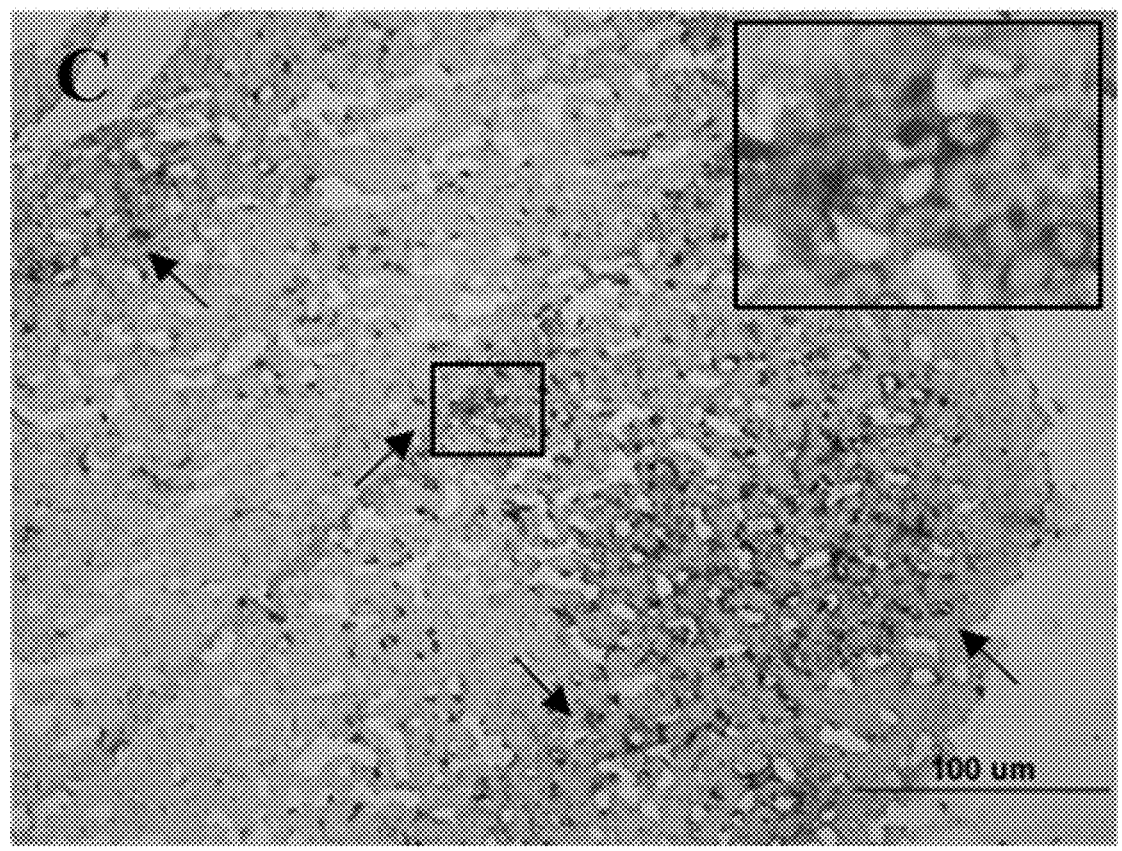
Figure 5D:
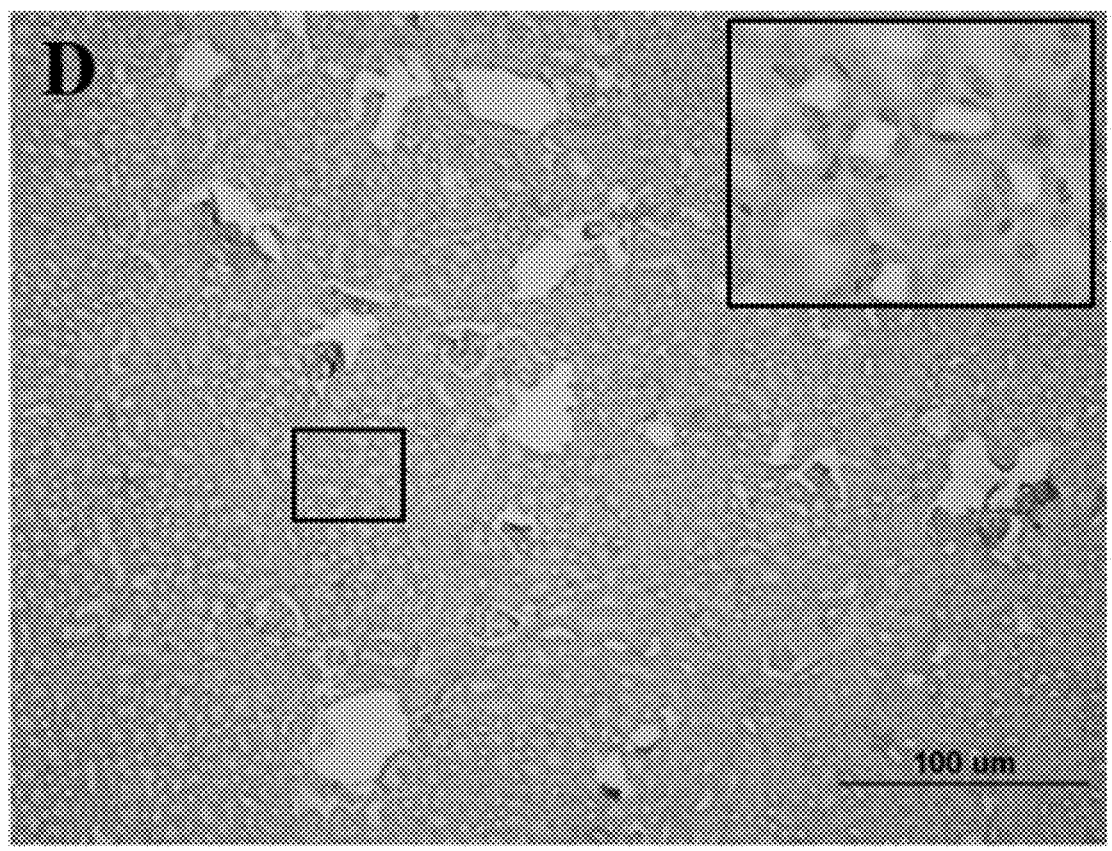
Figure 5E:
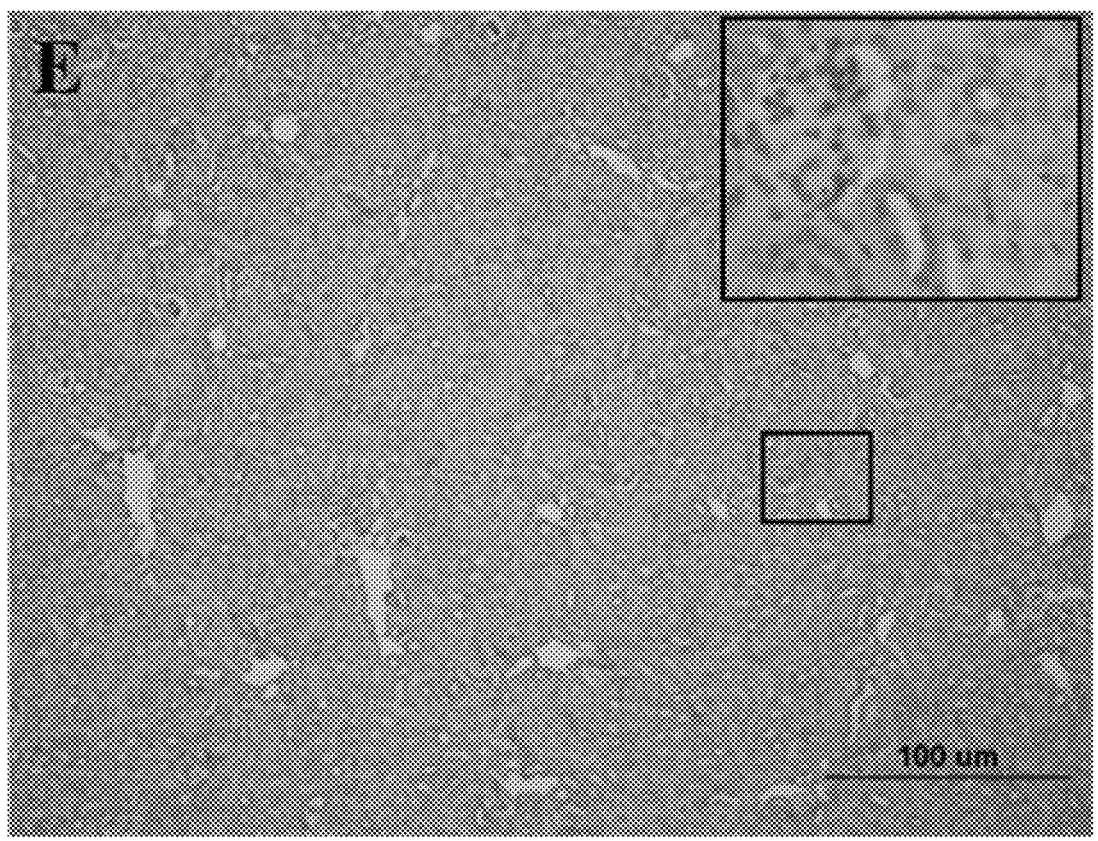
Figure 5F:
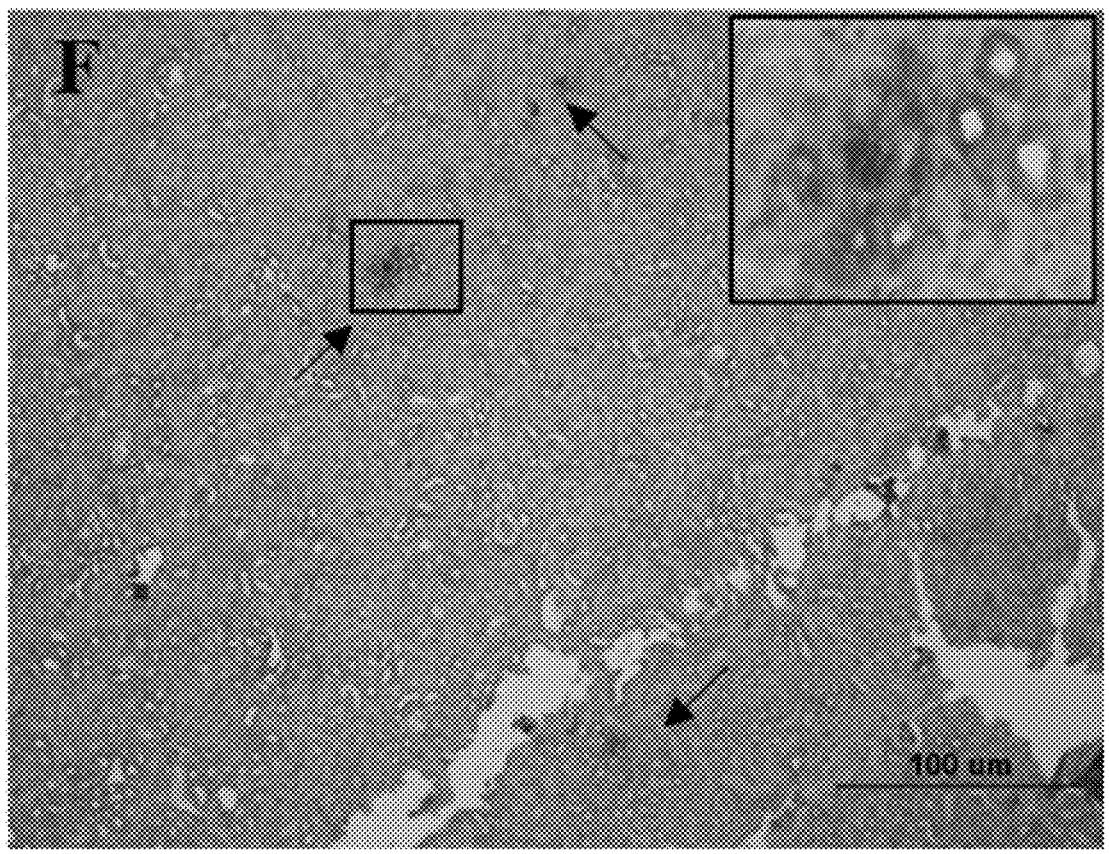
Figure 6A:
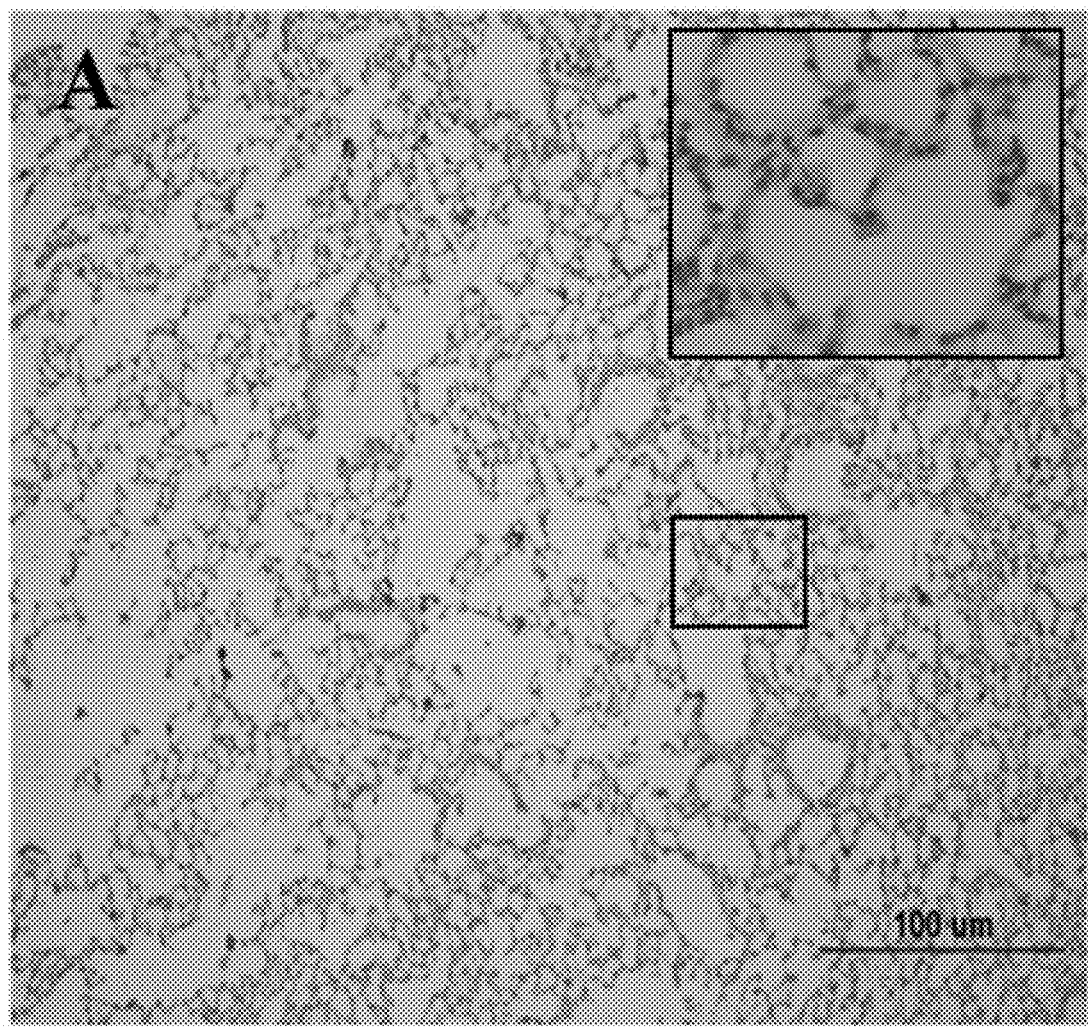
FIGS. 6A-6C show results of antigen staining in lung, brain and kidney tissues of hACE2 transgenic mice infected with cold-adapted SARS-CoV-2 on day 14 after infection: (A) lung tissue of mouse intranasally infected with cold-adapted SARS-CoV-2 (CoV-2-CNUHV03-CA22° C.) ($2\times10^4$ pfu), (B) brain tissue of mouse intranasally infected with cold-adapted SARS-CoV-2 (CoV-2-CNUHV03-CA22° C.) ($2\times10^4$ pfu), (C) kidney tissue of mouse intranasally infected with cold-adapted SARS-CoV-2 (CoV-2-CNUHV03-CA22° C.) ($2\times10^4$ pfu).
Figure 6B:
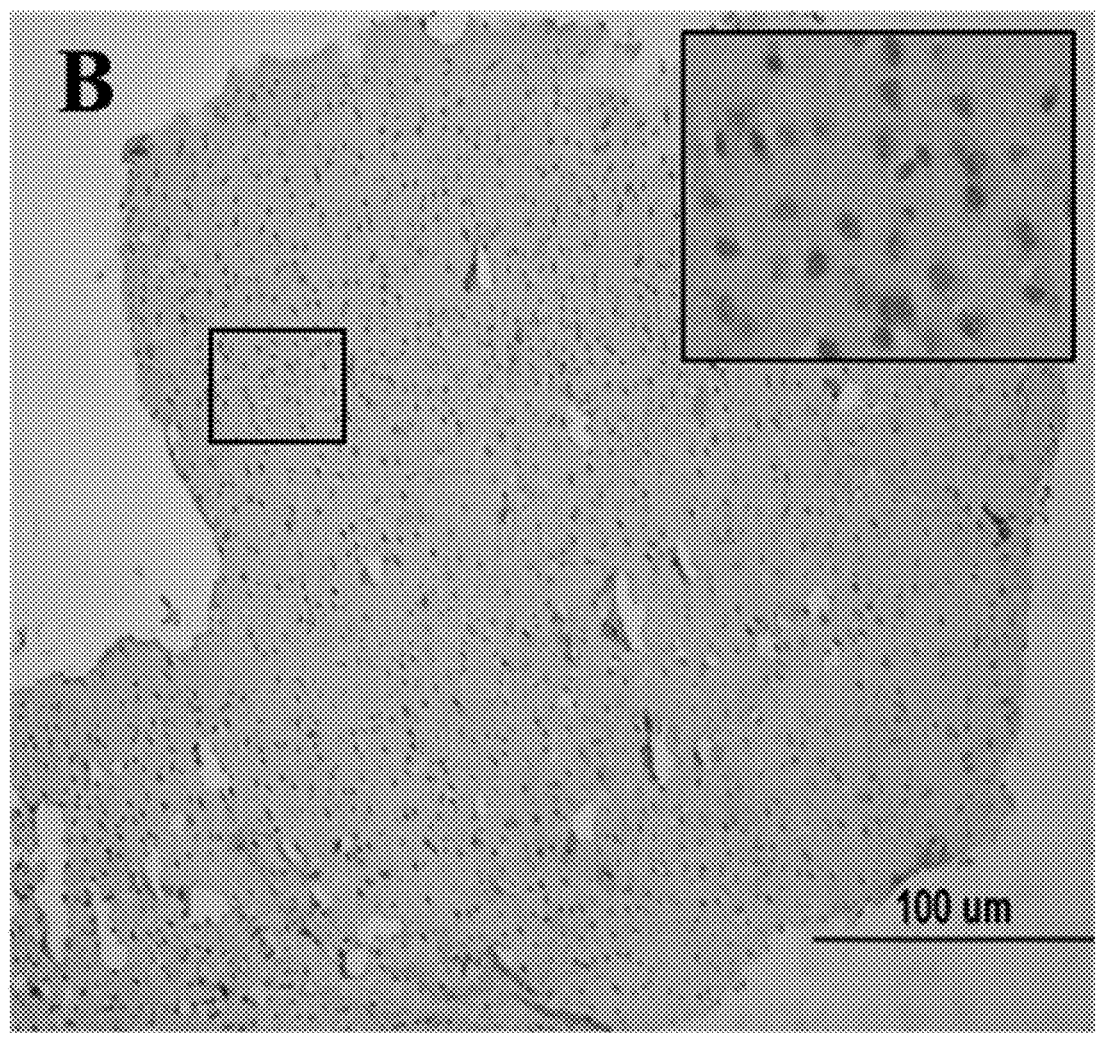
Figure 6C:
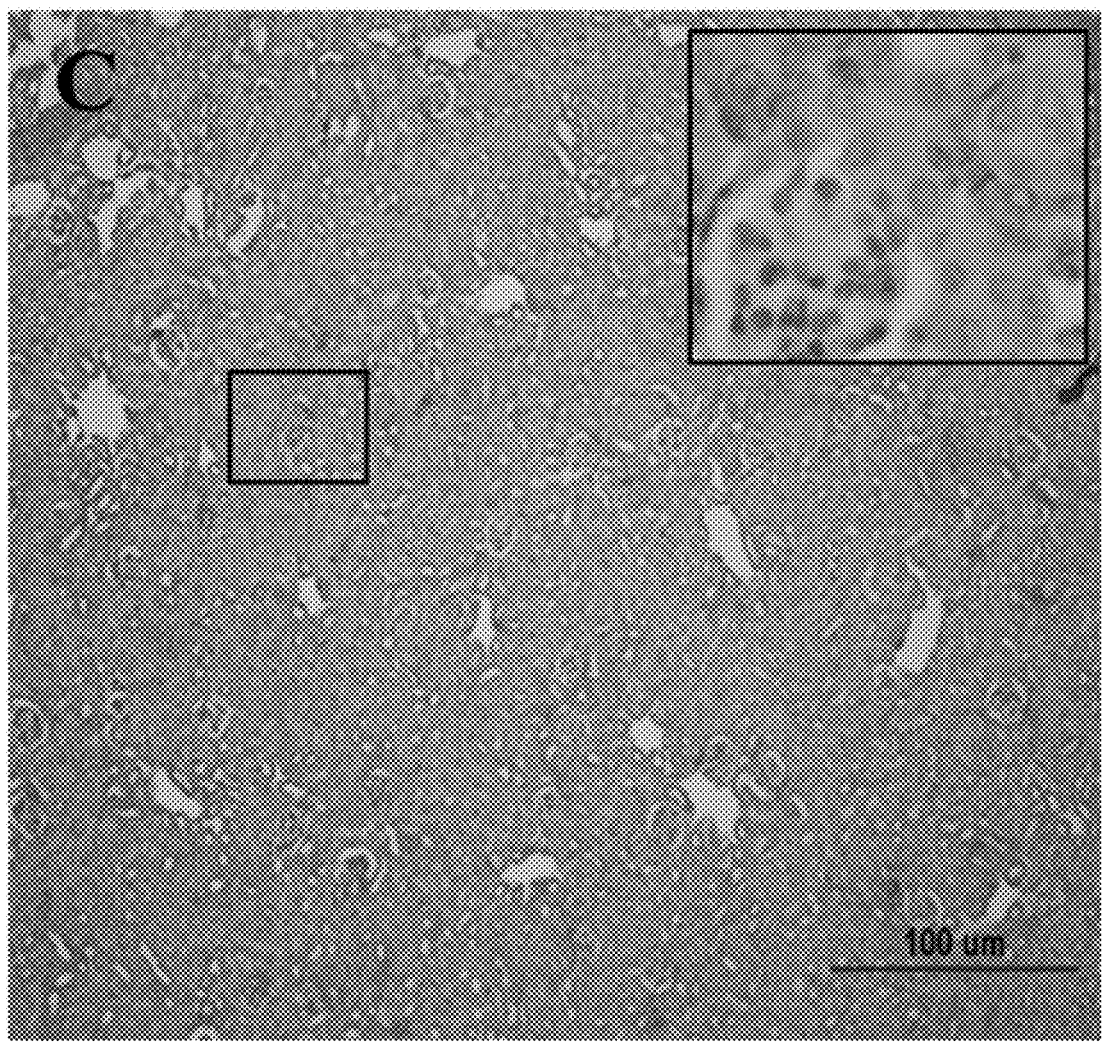

Sections of lung tissue of K18-hACE2 mice were stained with hematoxylin and eosin (H&E). Sections of brain, lung, and kidney tissues thereof were stained with SARS-CoV-2 NP antibody (FIGS. 4A-4F, FIGS. 5A-5F, & FIGS. 6A-6C). On the 6th day after the infection, the lung tissue of K18-hACE2 mice infected with CoV-2-CNUHV03-CA22° C. (FIG. 4B) exhibited lower pneumonia level than that of K18-hACE2 mice infected with CoV-2-CNUHV03 (FIG. 4C). On the 6th day after infection, antigen staining in the lungs of K18-hACE2 mice infected with CoV-2-CNUHV03-CA22° C. (FIG. 4E) exhibited a much sparser pattern than that in the lungs of K18-hACE2 mice infected with CoV-2-CNUHV03 (FIG. 4F). Antigen staining was not observed in the brain (FIG. 5B) and kidney (FIG. 5E) of K18-hACE2 mice infected with CoV-2-CNUHV03-CA22° C. on the 6th day after infection. A profuse antigen staining was observed in the brain (FIG. 5C) and kidney (FIG. 5F) of K18-hACE2 mice infected with CoV-2-CNUHV03 on the 6th day after infection. No antigen staining was observed in the lungs (FIG. 6A), brain (FIG. 6B), and kidney (FIG. 6C) of K18-hACE2 mice infected with CoV-2-CNUHV03-CA22° C. on 14 days after infection.

Figure 7:
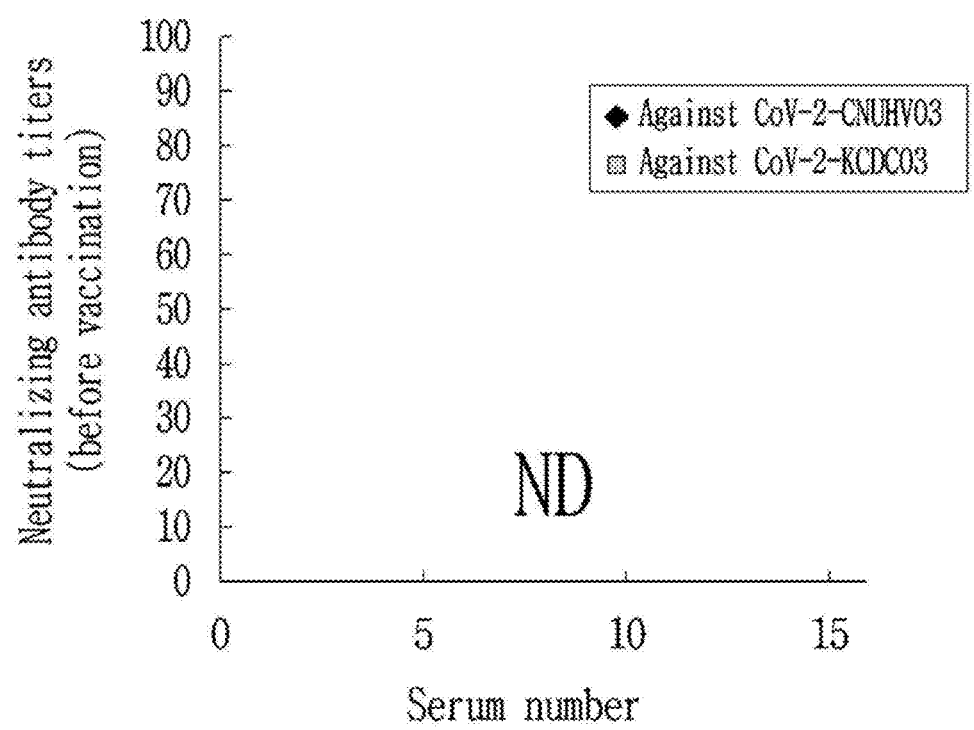
FIG. 7 shows neutralizing antibody titer of sera collected from hACE2 transgenic mice before immunization. Neutralizing antibody detection limit is 10.
Figure 8A:
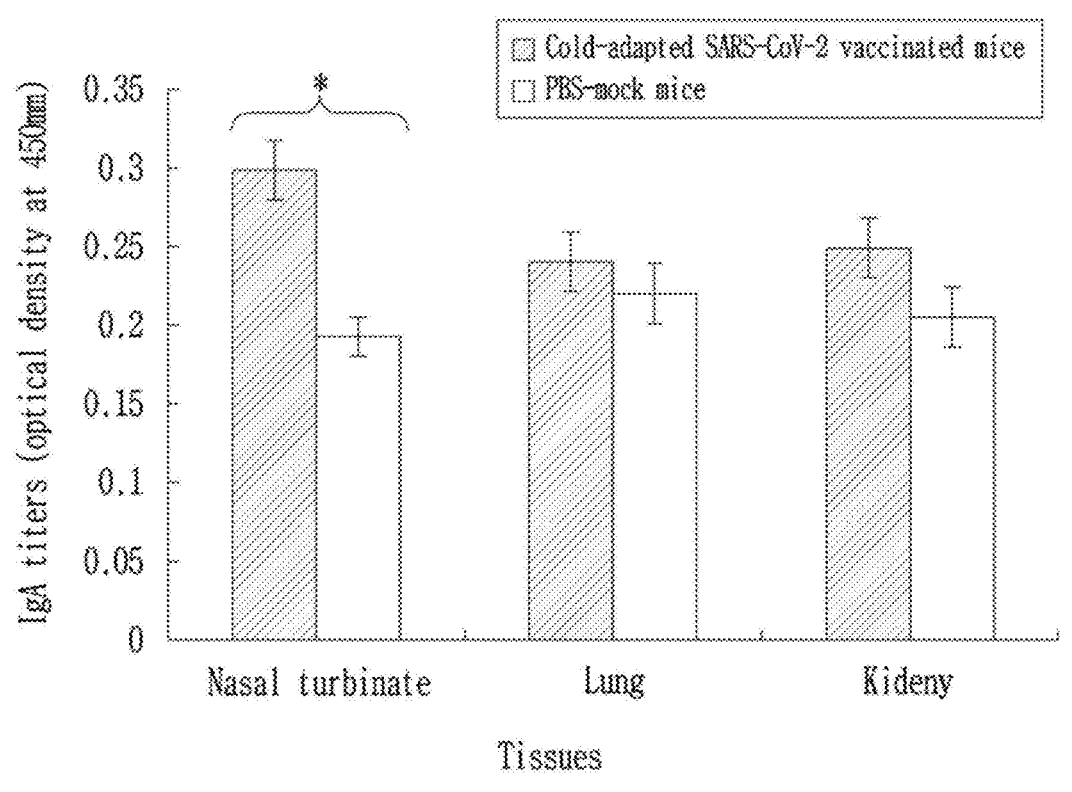
Figure 8B:
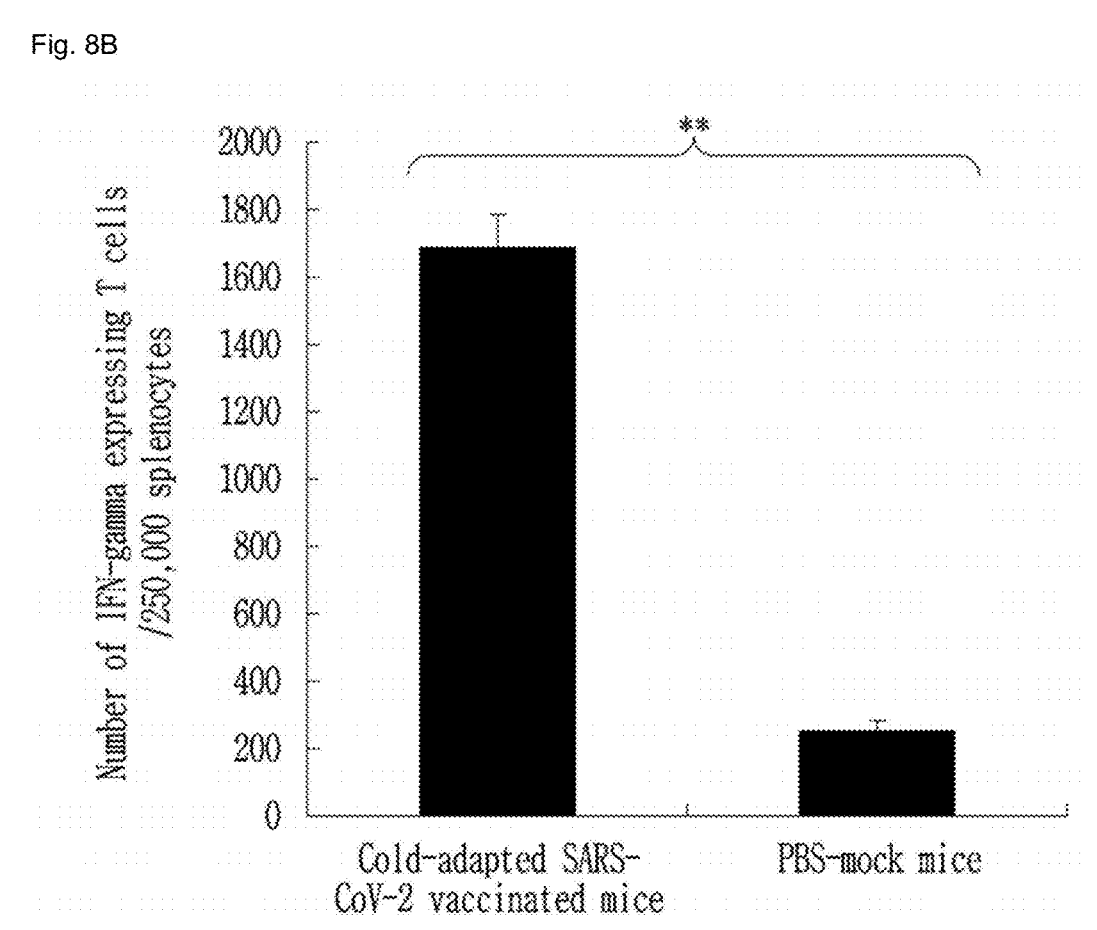
Figure 9A:
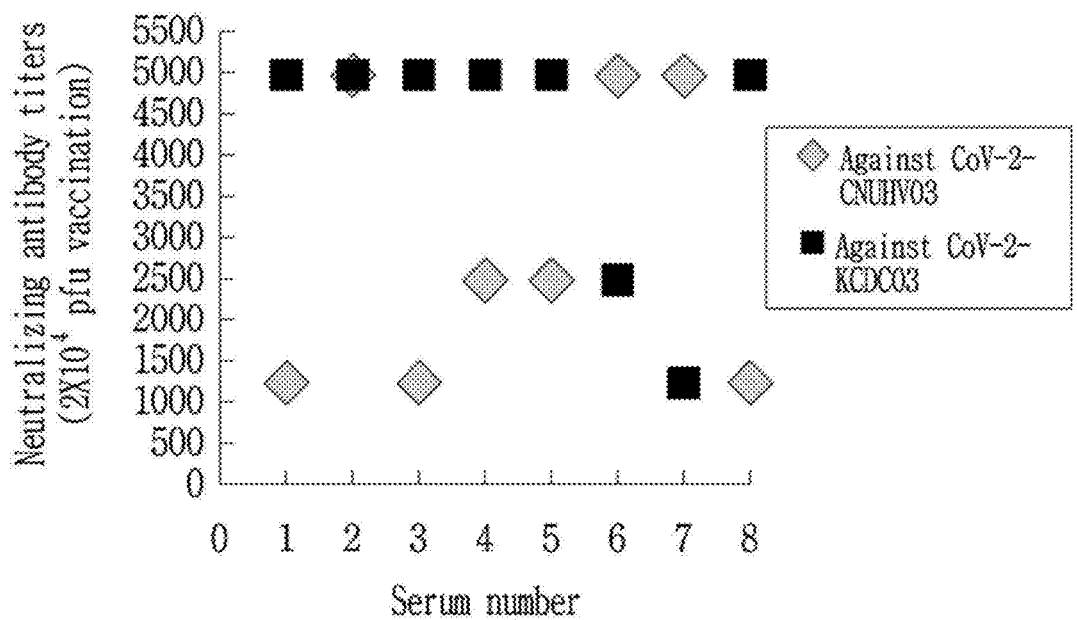
FIG. 9A shows neutralizing antibody titer of sera from of hACE2 transgenic mice immunized with $2\times10^4$ pfu CoV-2-CNUHV03-CA22° C. $*p<0.05$, $**p<0.001$.
Figure 9B:
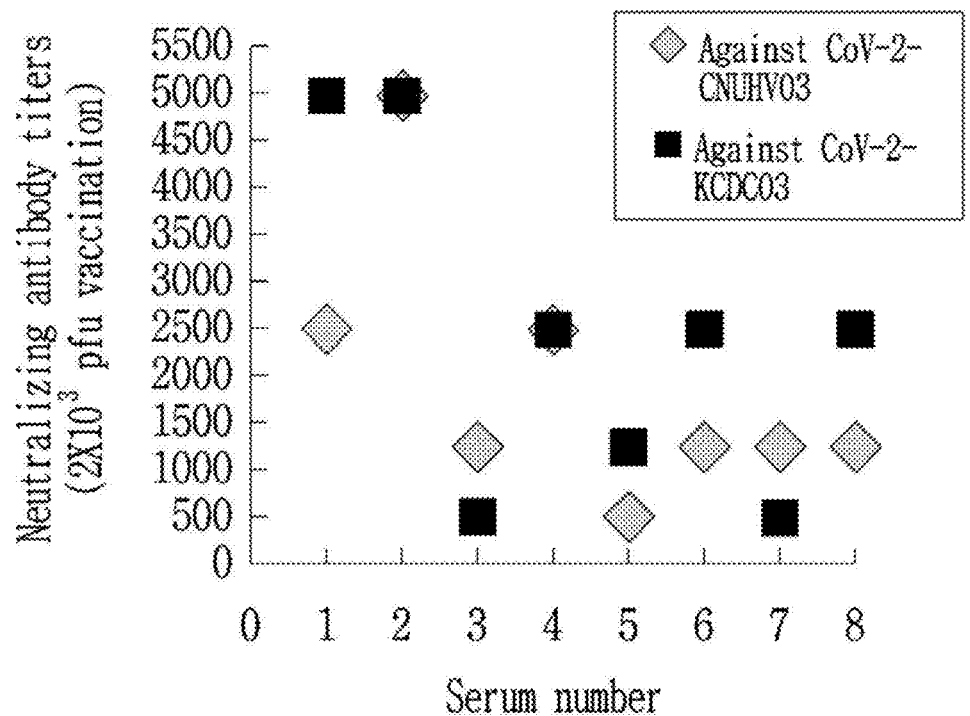
FIG. 9B shows neutralizing antibody titer of sera from of hACE2 transgenic mice immunized with $2\times10^3$ pfu CoV-2-CNUHV03-CA22° C. $*p<0.05$, $**p<0.001$.

K18-hACE2 mice was immunized by intranasally administering $2 \times 10^4$ or $2 \times 10^3$ pfu of CoV-2-CNUHV03-CA22° C. to the mice. Then, sera were collected therefrom on the 19th day after vaccination (p.v.). The titer of neutralizing antibody (NA) was measured using CoV-2-CNUHV03 and CoV-2-KCDC03 in Vero cells. A strong NA titers in the range of 640 to 4960 were induced in K18-hACE2 mice immunized with CoV-2-CNUHV03-CA22° C. of $2\times10^4$ (FIG. 9A) or $2\times10^3$ (FIG. 9B) pfu. NA was not detected in the sera of K18-hACE2 mice collected before vaccination (FIG. 7). Purified inactivated SARS-CoV-2 antigen (CoV-2-CNUHV03) and goat horseradish peroxidase (HRP)-labeled anti-mouse IgA antibody (FIG. 8A) and T cell expressing IFN-g (FIG. 8B) were used to measure the level of IgA antibody, which is responsible for mucosal immunity, in various tissues (nasal turbinate, lung, and kidney). Detection of IgA indicates that cellular immunity was induced in splenocytes of K18-hACE2 mice immunized with CoV-2-CNUHV03-CA22° C. ($2\times10^4$ pfu). IgA was detected in all the tissues that were assessed, with the highest amount detected in nasal turbinates (OD: 0.298) (FIG. 8A). The numbers of IFN-g-expressing T cells in immunized and PBS (mock)-immunized K18-hACE2 mice were 1682/250,000 and 249/250,000 splenocytes, respectively (FIG. 8B).

Figure 9D:
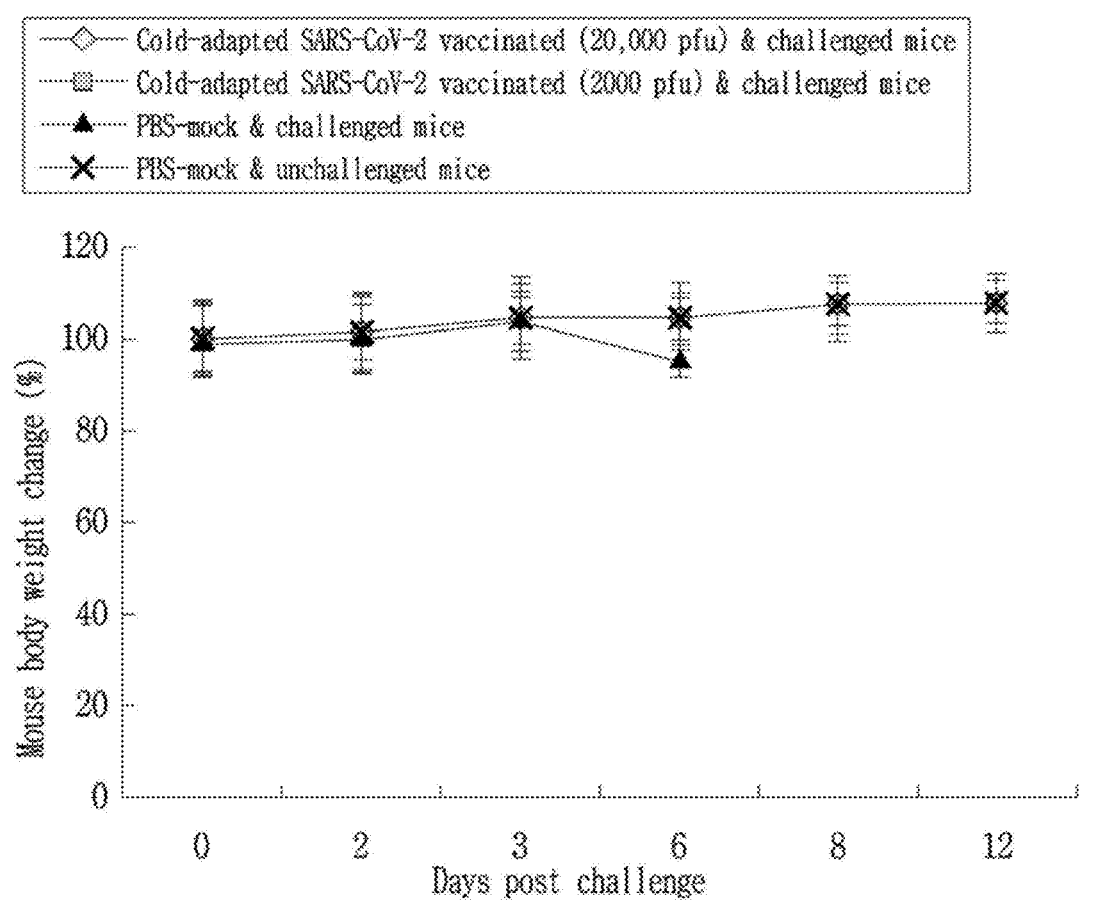
Figure 9E:
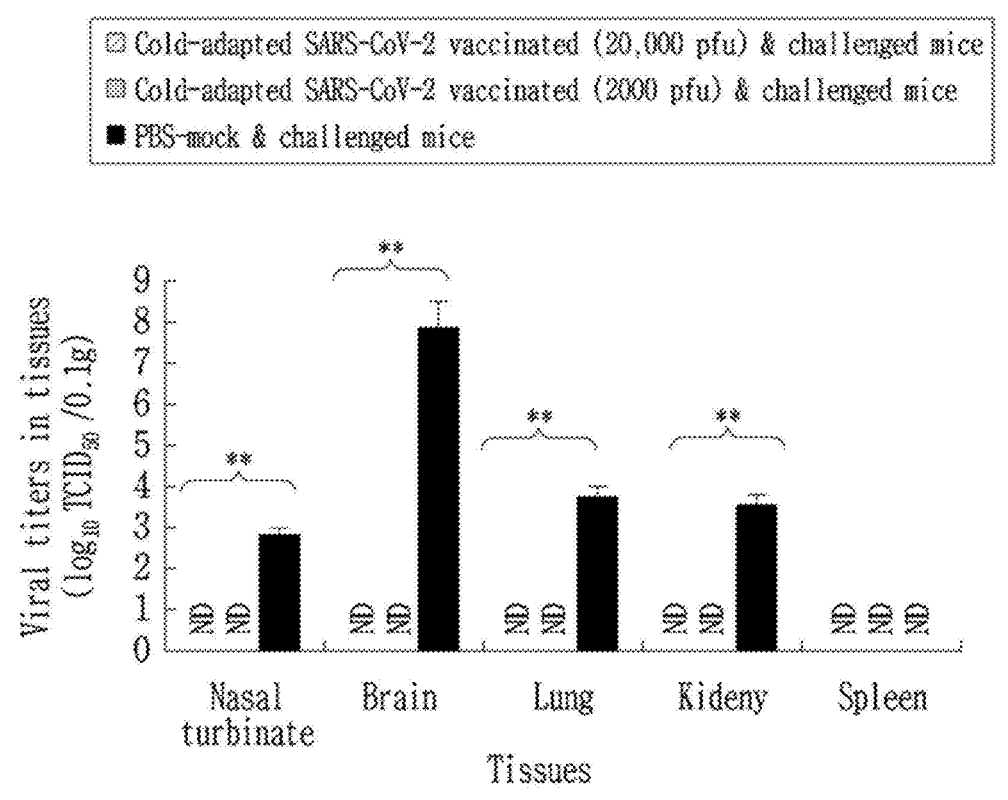
Figure 10B:
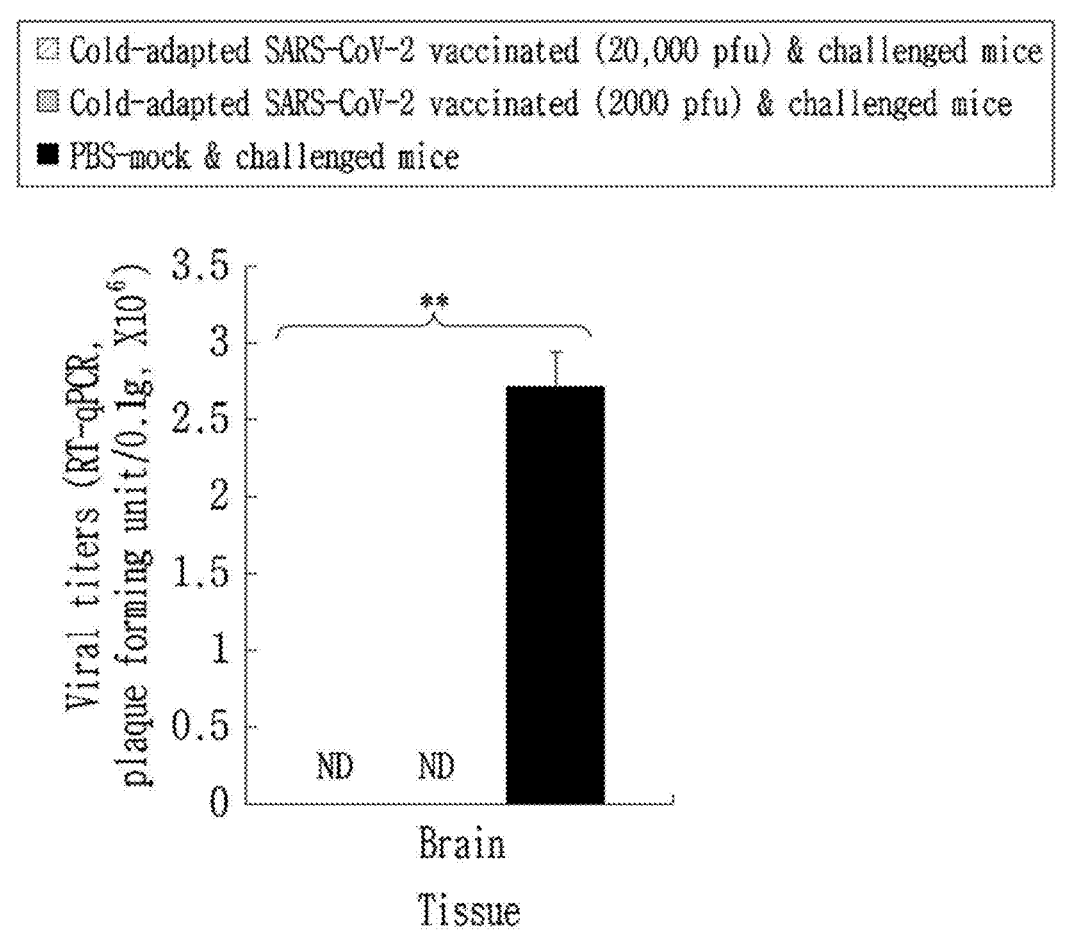
Figure 11A:
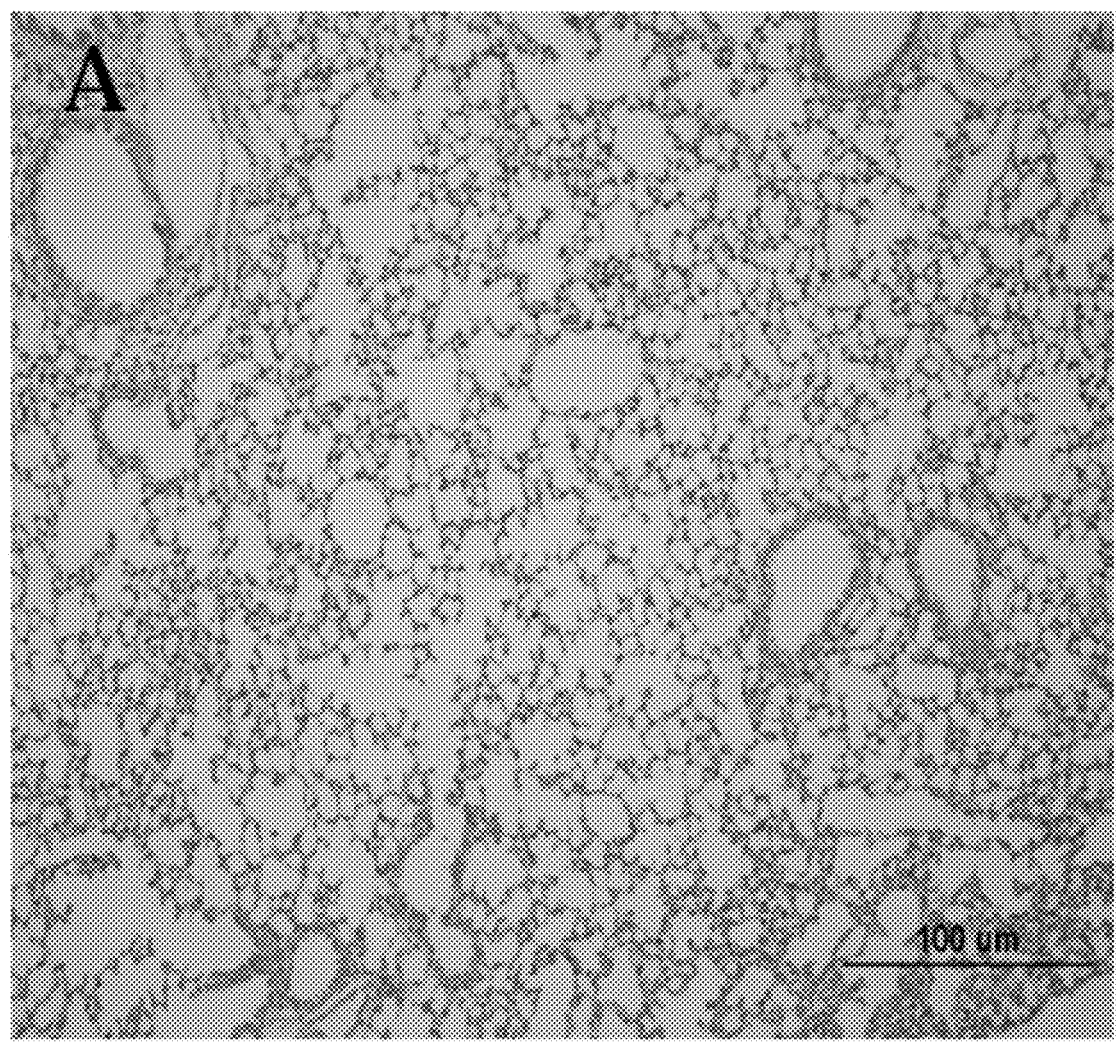
FIGS. 11A-11H show histopathology and antigen staining results of immunized and challenged hACE2 transgenic mice: (A) and (E) lung tissue of PBS-mock mice, (B) and (F) lung tissue of mice immunized with cold-adapted SARS-CoV-2 (CoV-2-CNUHV03-CA22° C.) ($2\times10^3$ pfu) and challenged with CoV-2-CNUHV03 ($2\times10^4$ pfu), (C) and (G) lung tissue of mice immunized with cold-adapted SARS-CoV-2 (CoV-2-CNUHV03-CA22° C.) ($2\times10^4$ pfu) and challenged with CoV-2-CNUHV03 ($2\times10^4$ pfu), and (D) and (H) lung tissue of PBS-mock mice challenged with CoV-2-CNUHV03 ($2\times10^4$ pfu). Arrow refers to positive antigen staining.
Figure 11B:
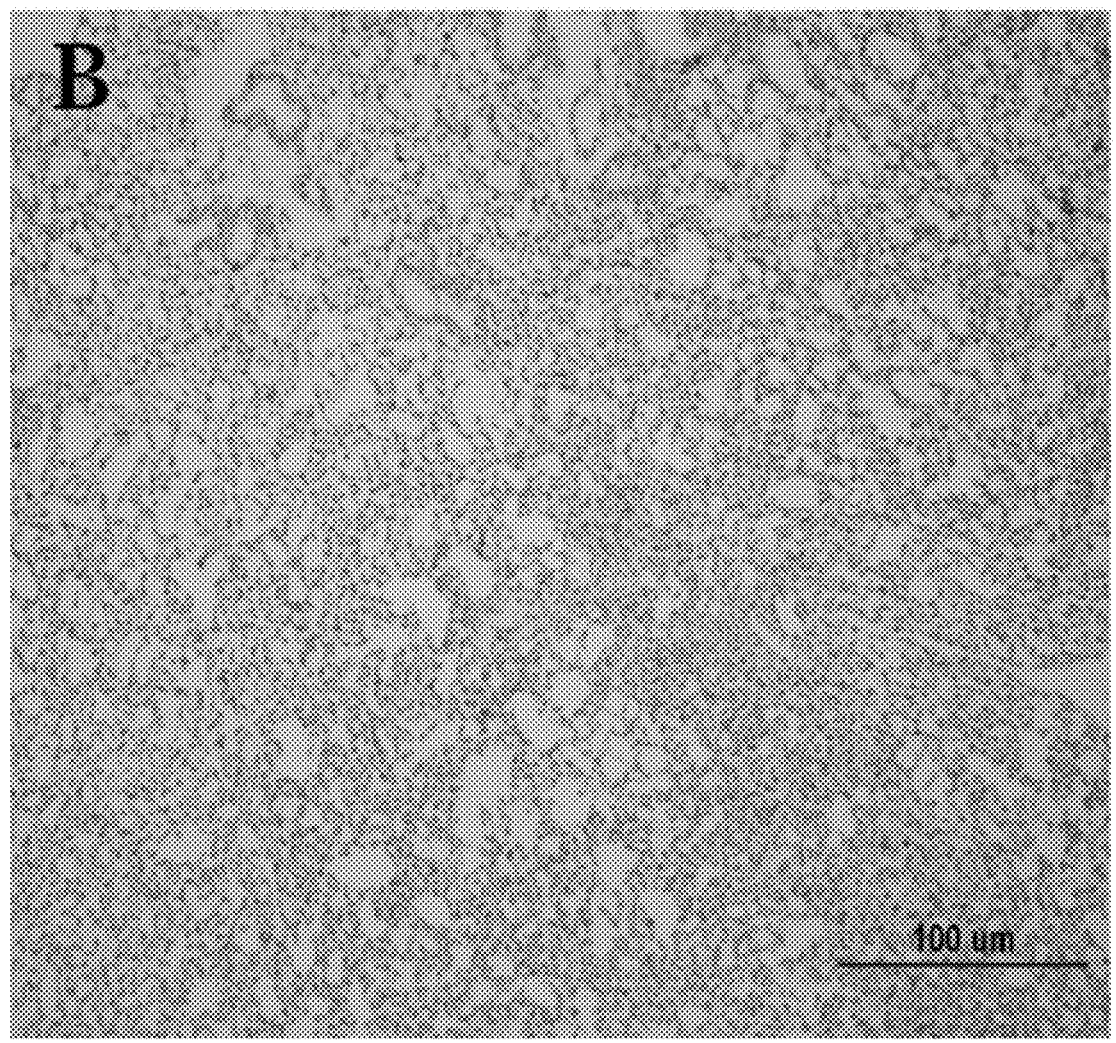
Figure 11C:
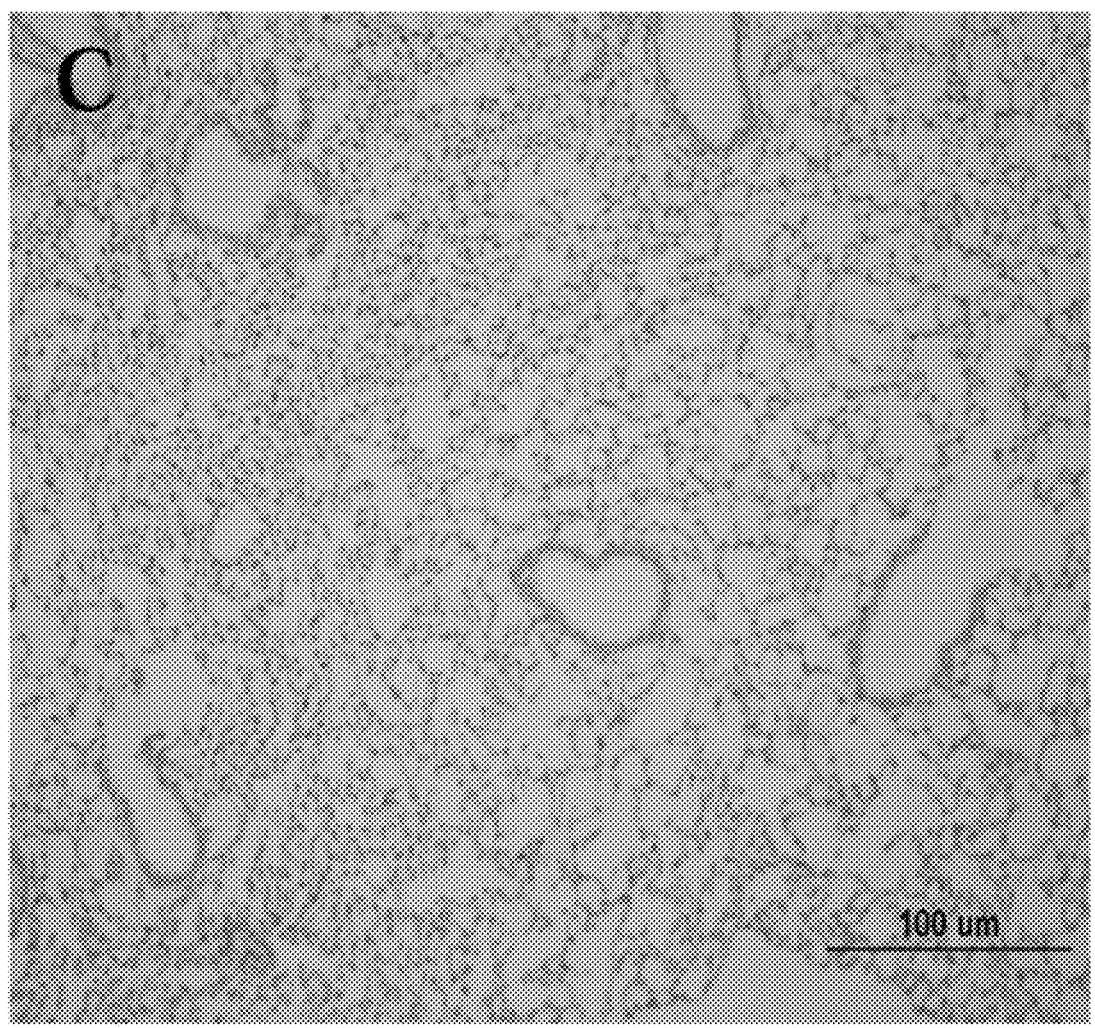
Figure 11D:
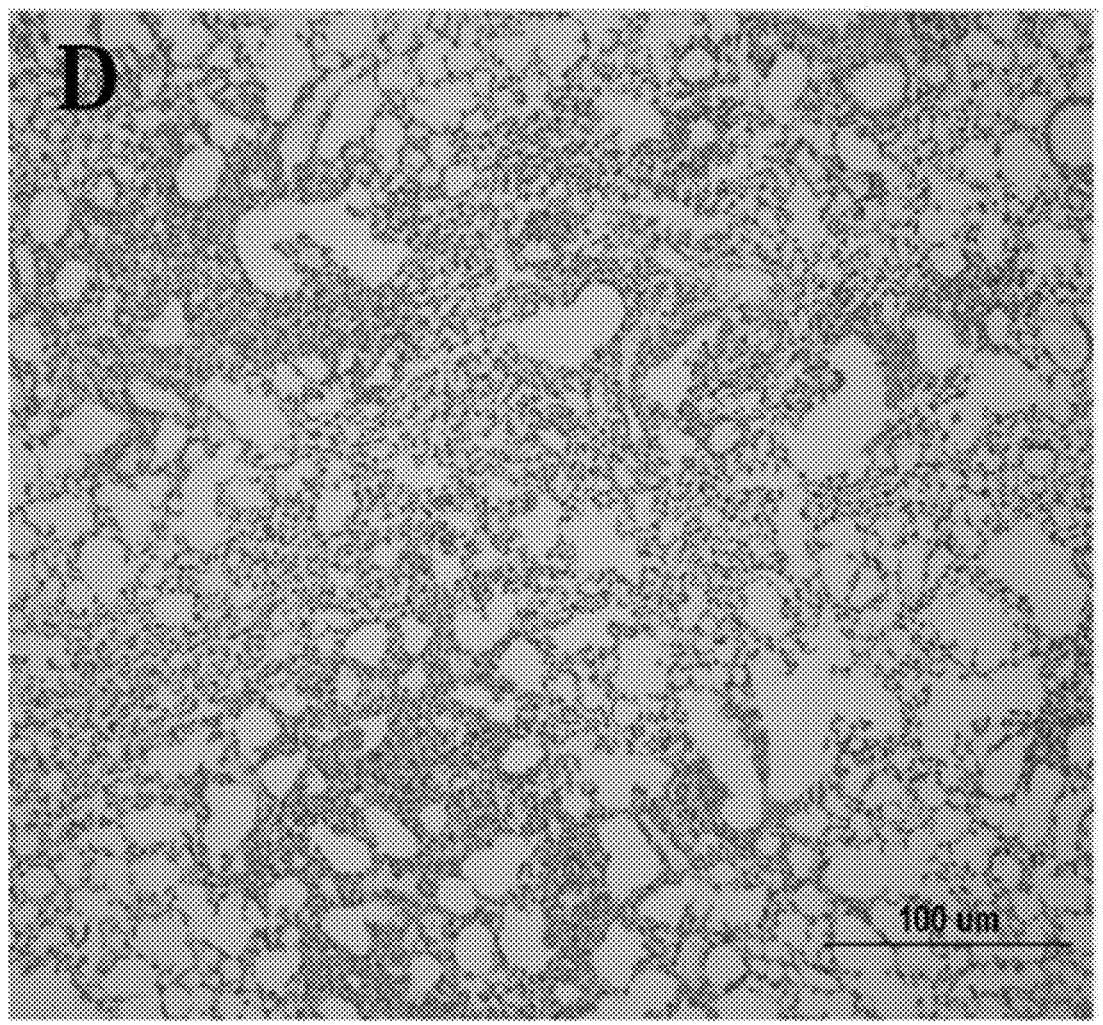
Figure 11E:
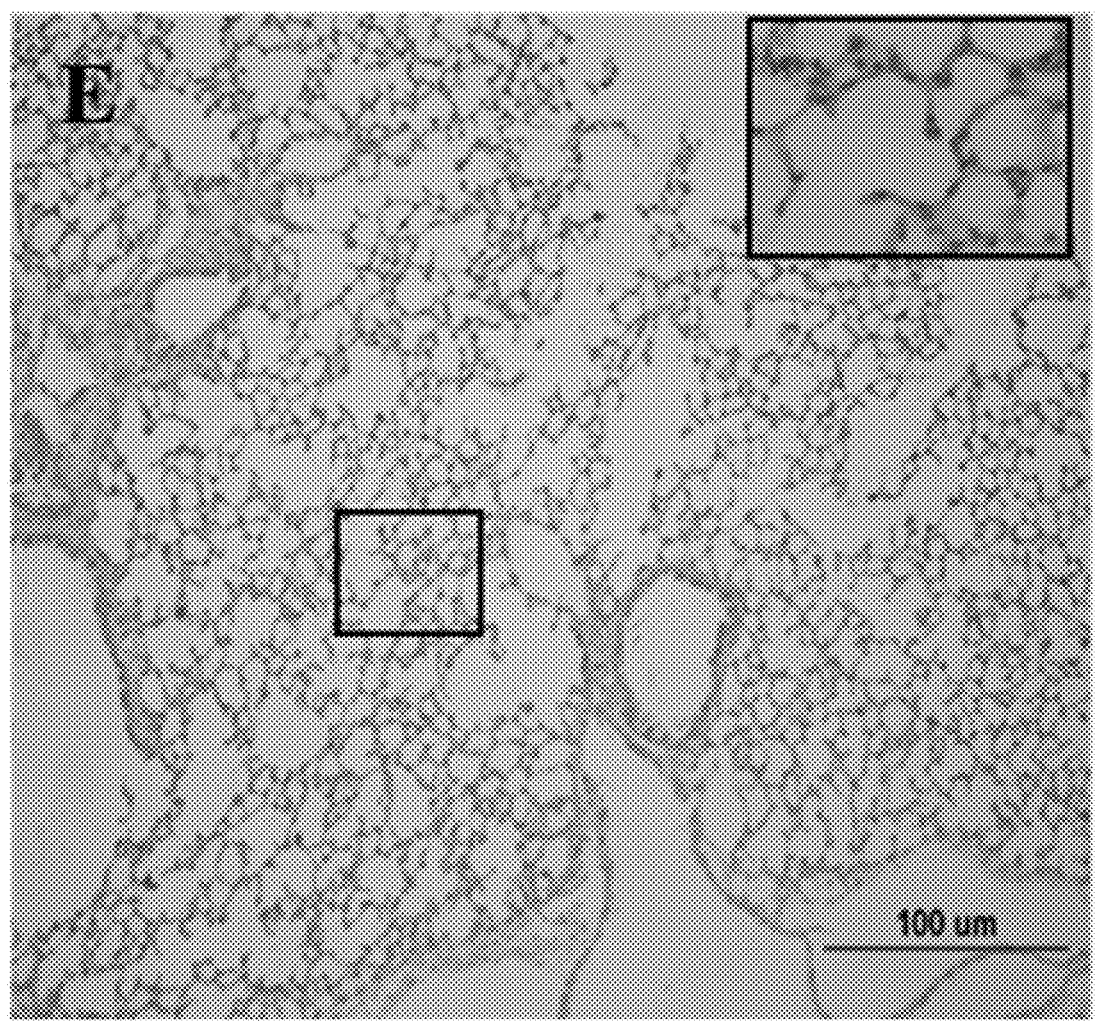
Figure 11F:
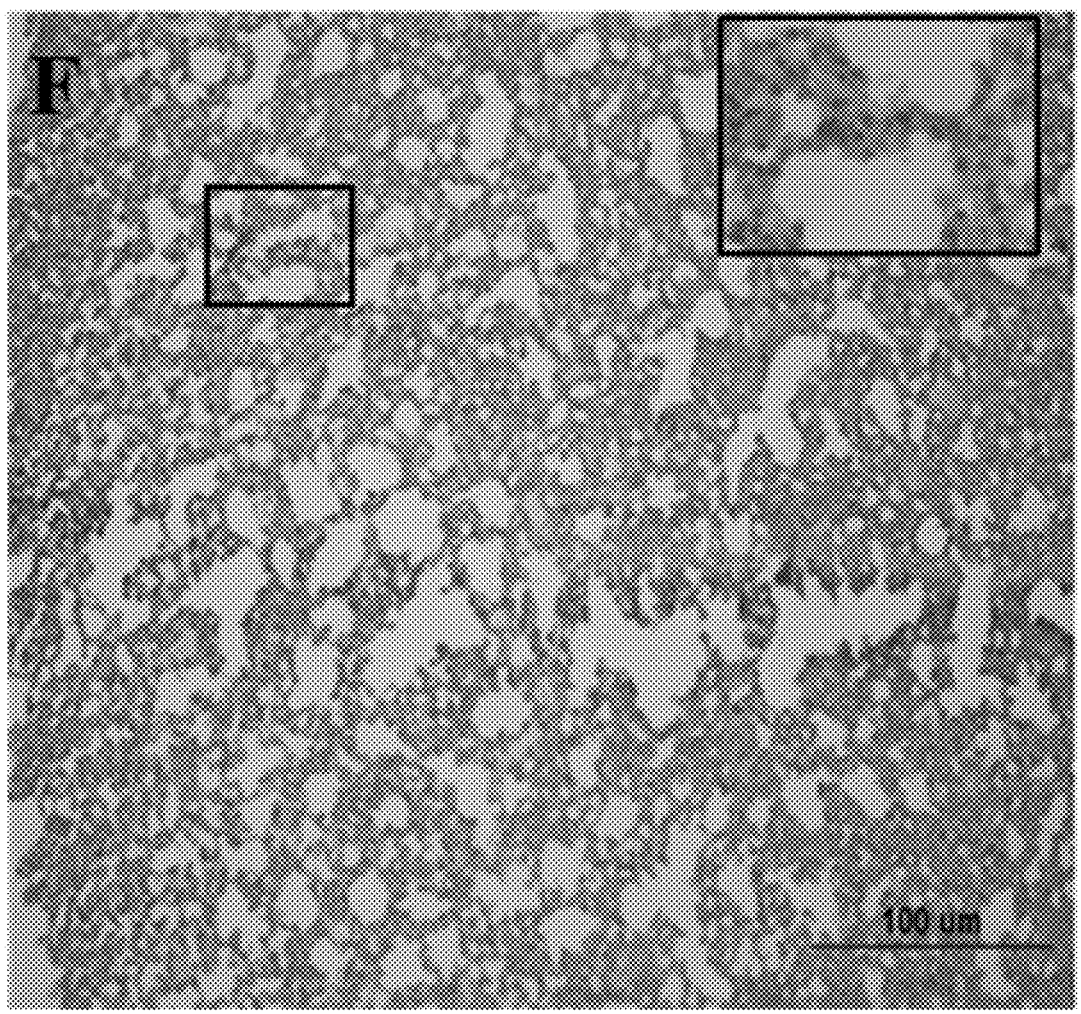
Figure 11G:
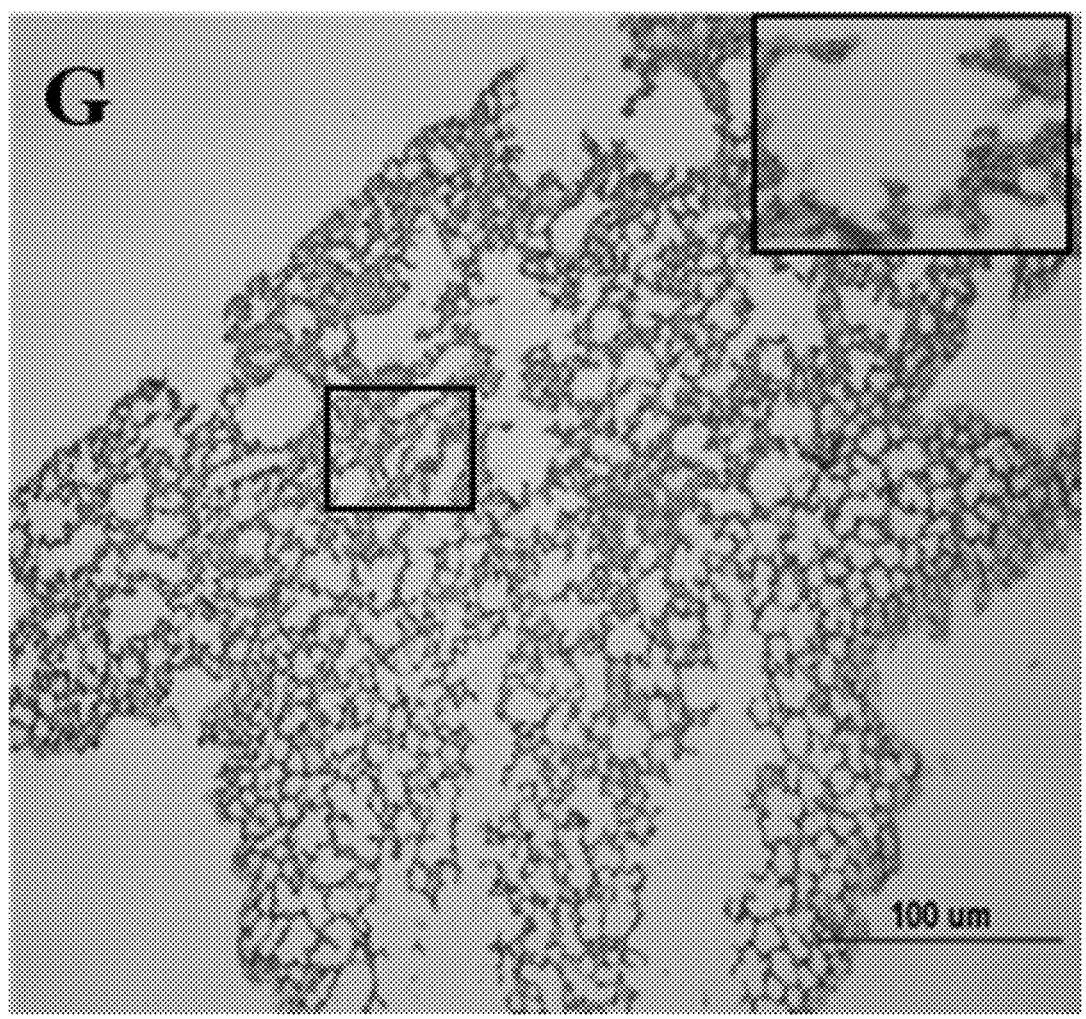
Figure 11H:
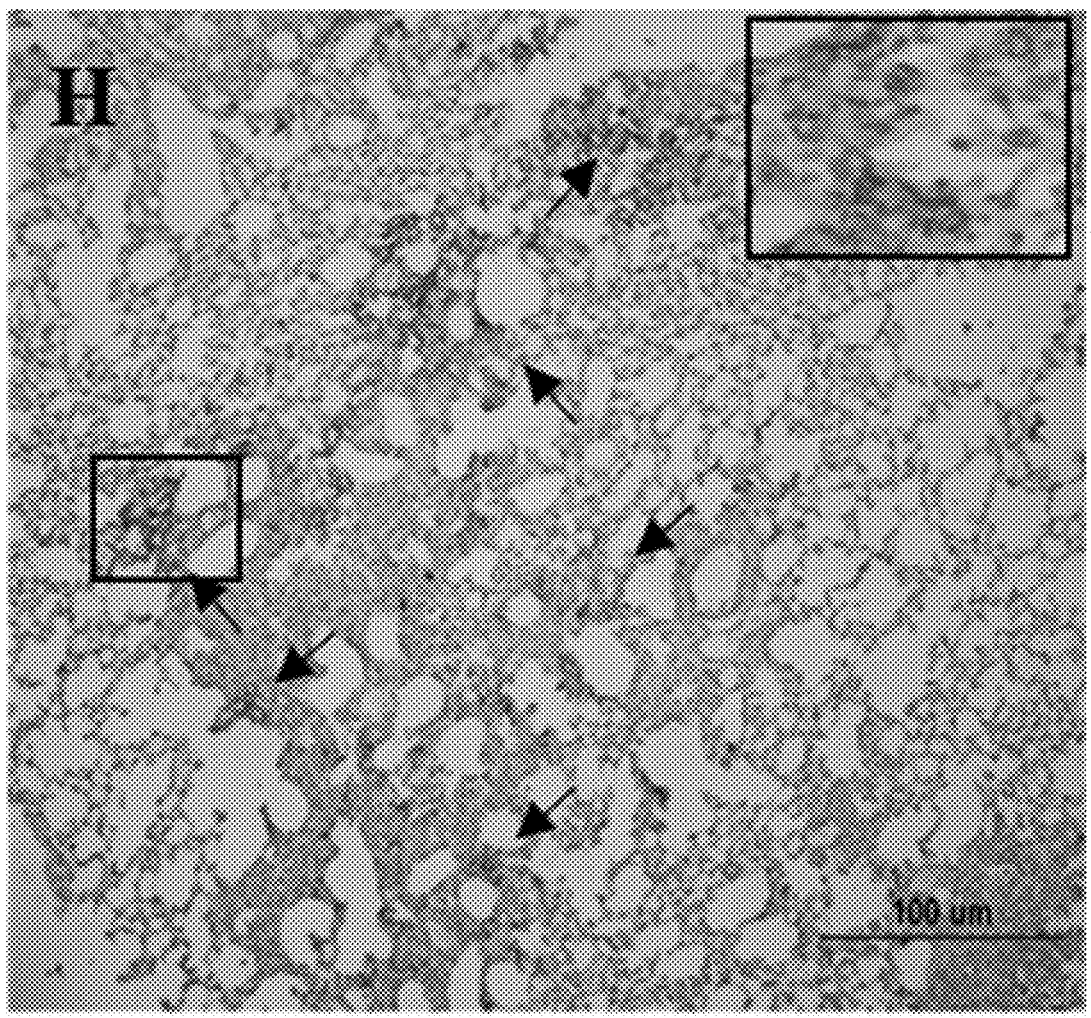
Figure 12A:
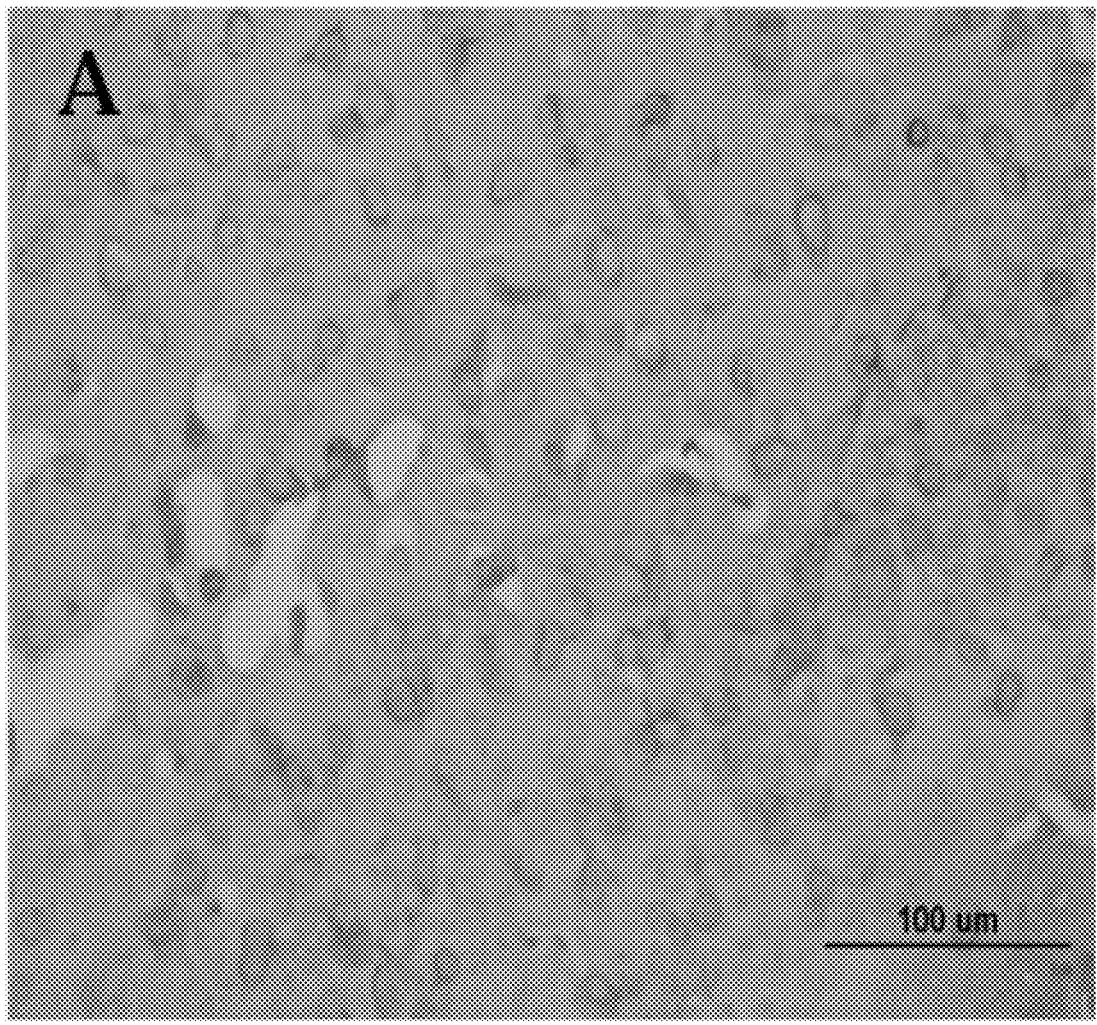
FIGS. 12A-12H show brain and kidney antigen staining results of immunized and challenged hACE2 transgenic mice: (A) brain tissue of PBS-mock mice; (B) brain tissue of mice vaccinated with CoV-2-CNUHV03-CA22° C. ($2\times10^3$ pfu) and challenged with CoV-2-KCDC03 ($2\times10^4$ pfu); (C) brain tissue of mice vaccinated with CoV-2-CNUHV03-CA22° C. ($2\times10^4$ pfu) and challenged with CoV-2-KCDC03
Figure 12B:
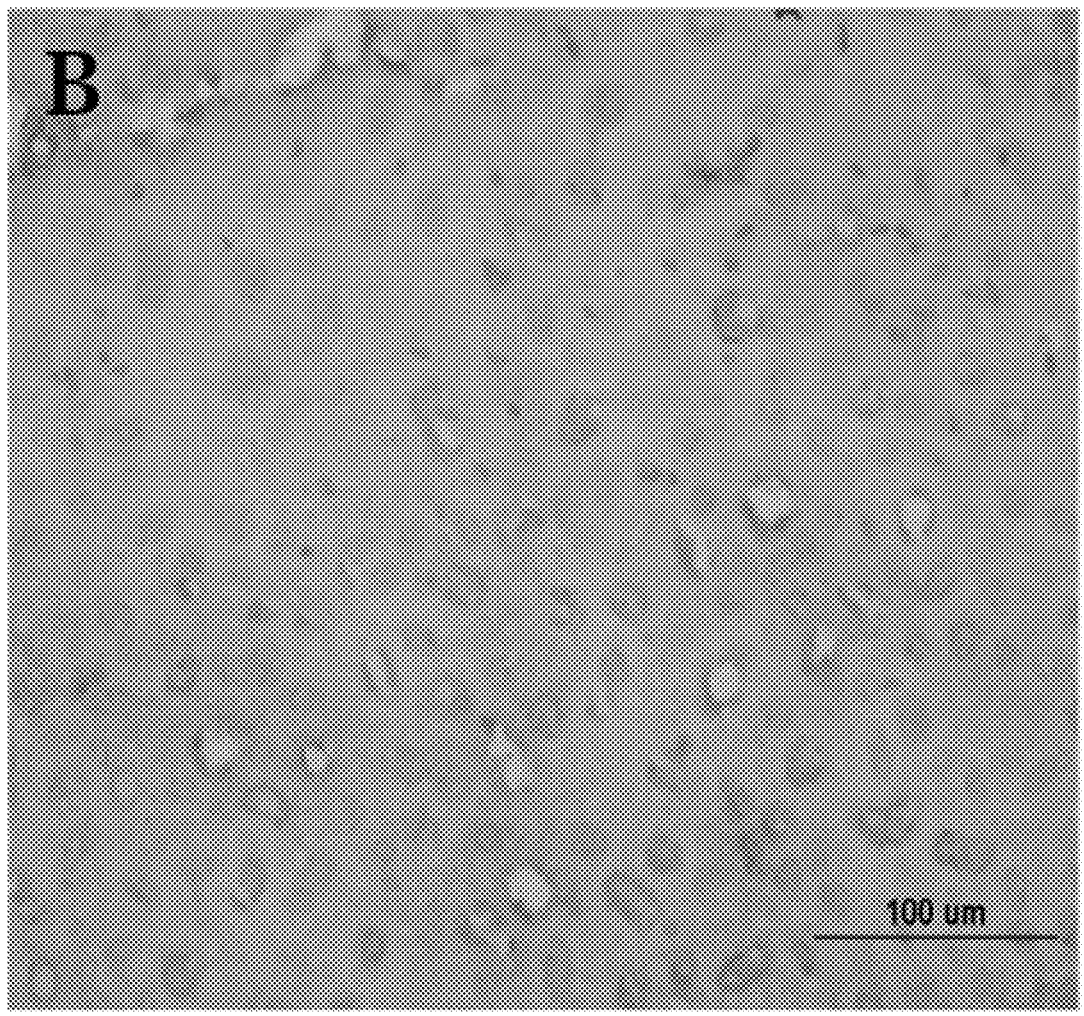
Figure 12C:
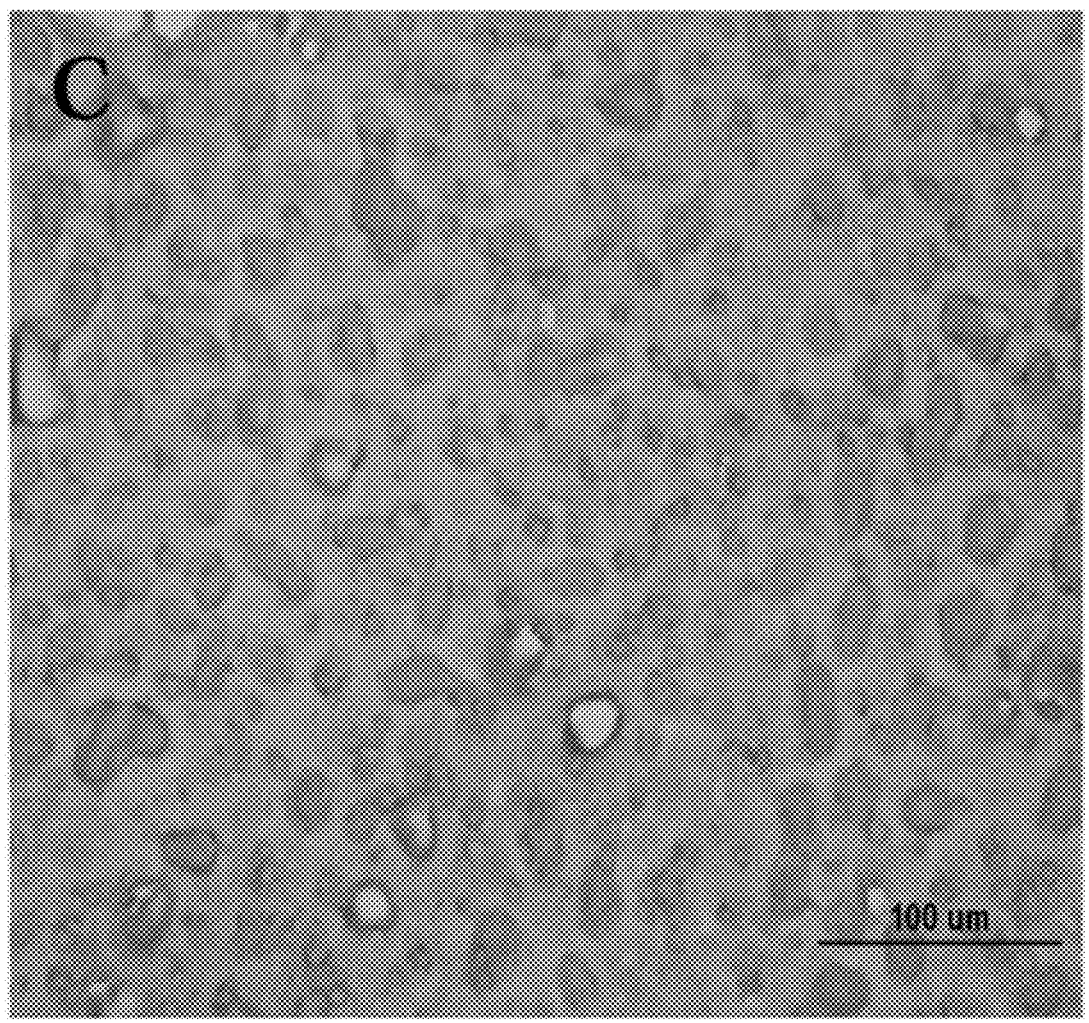
Figure 12D:
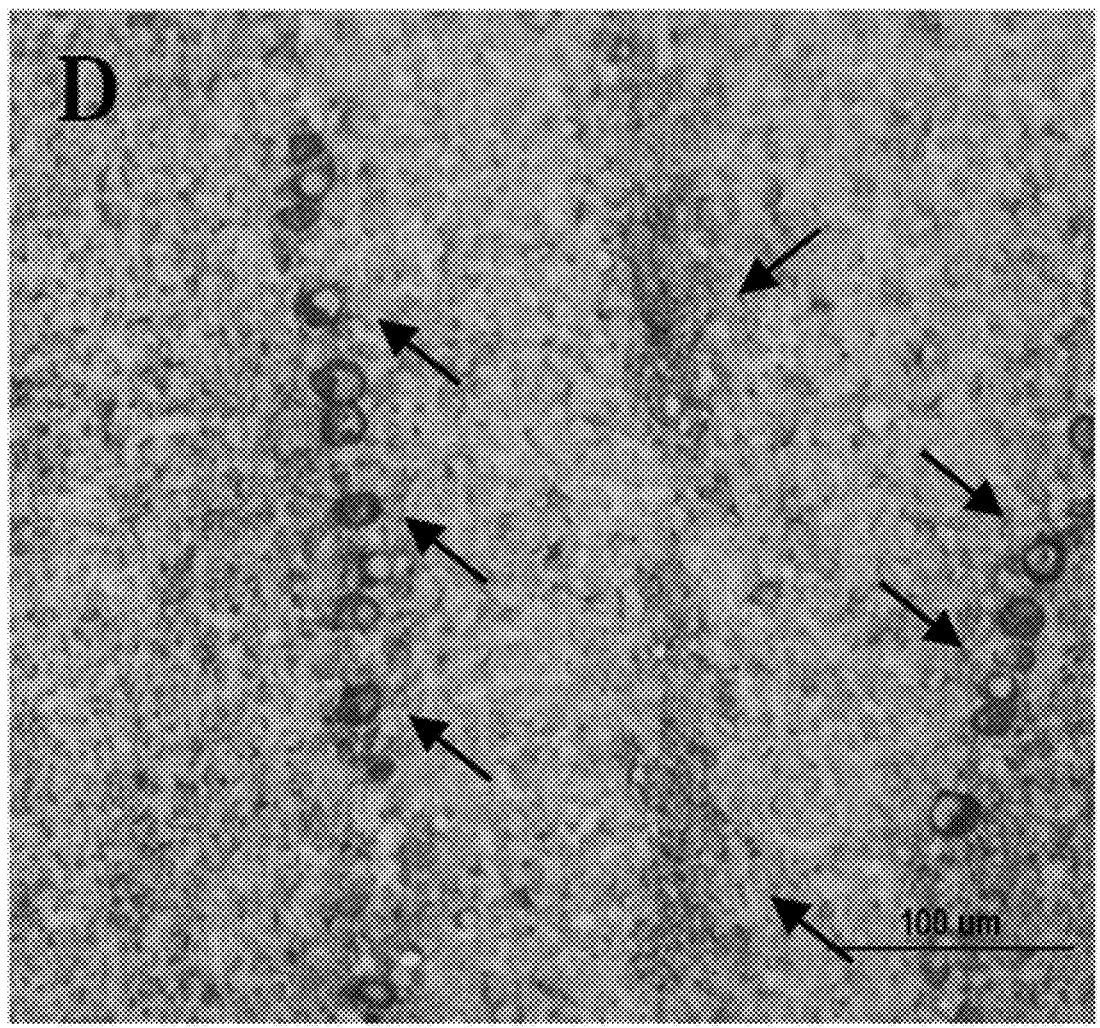
Figure 12E:
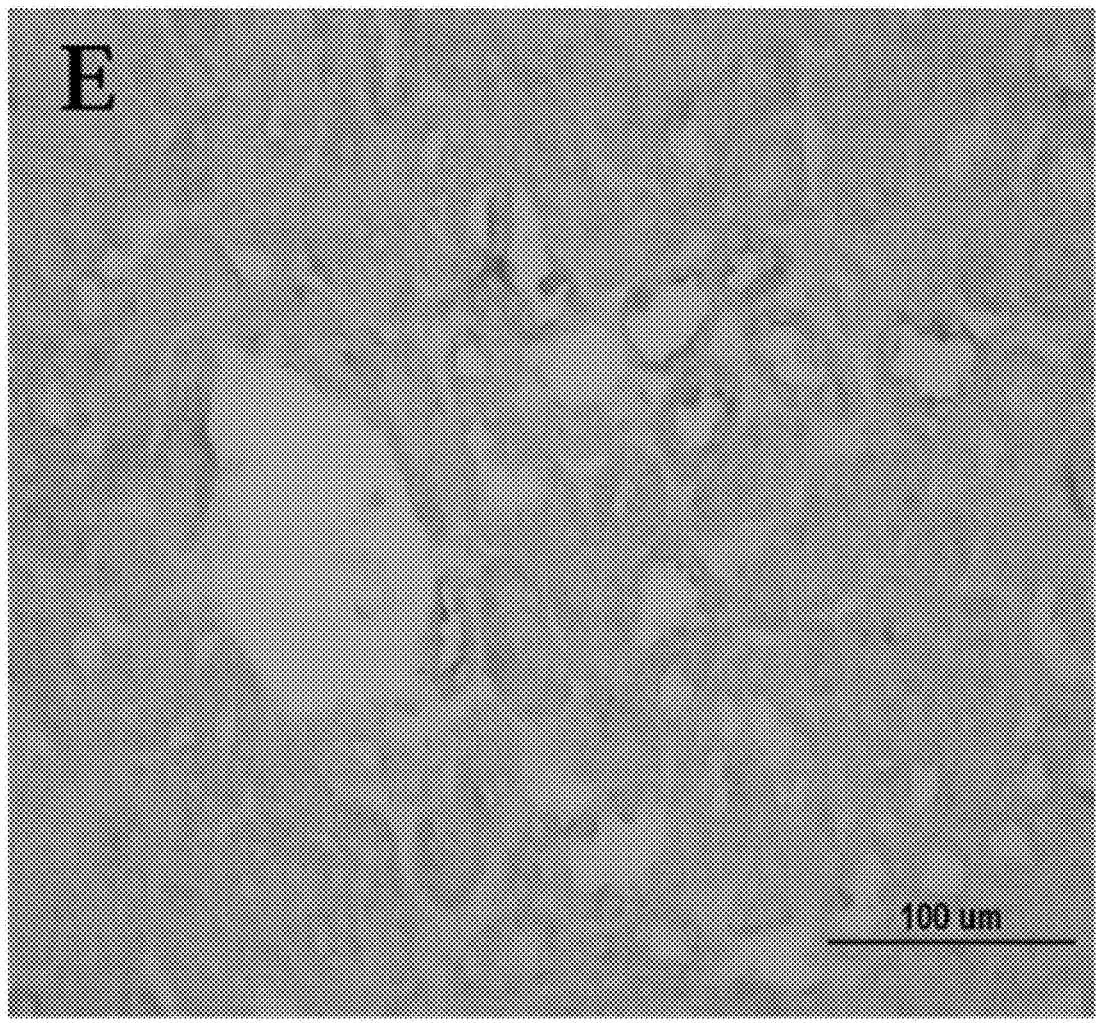
Figure 12F:
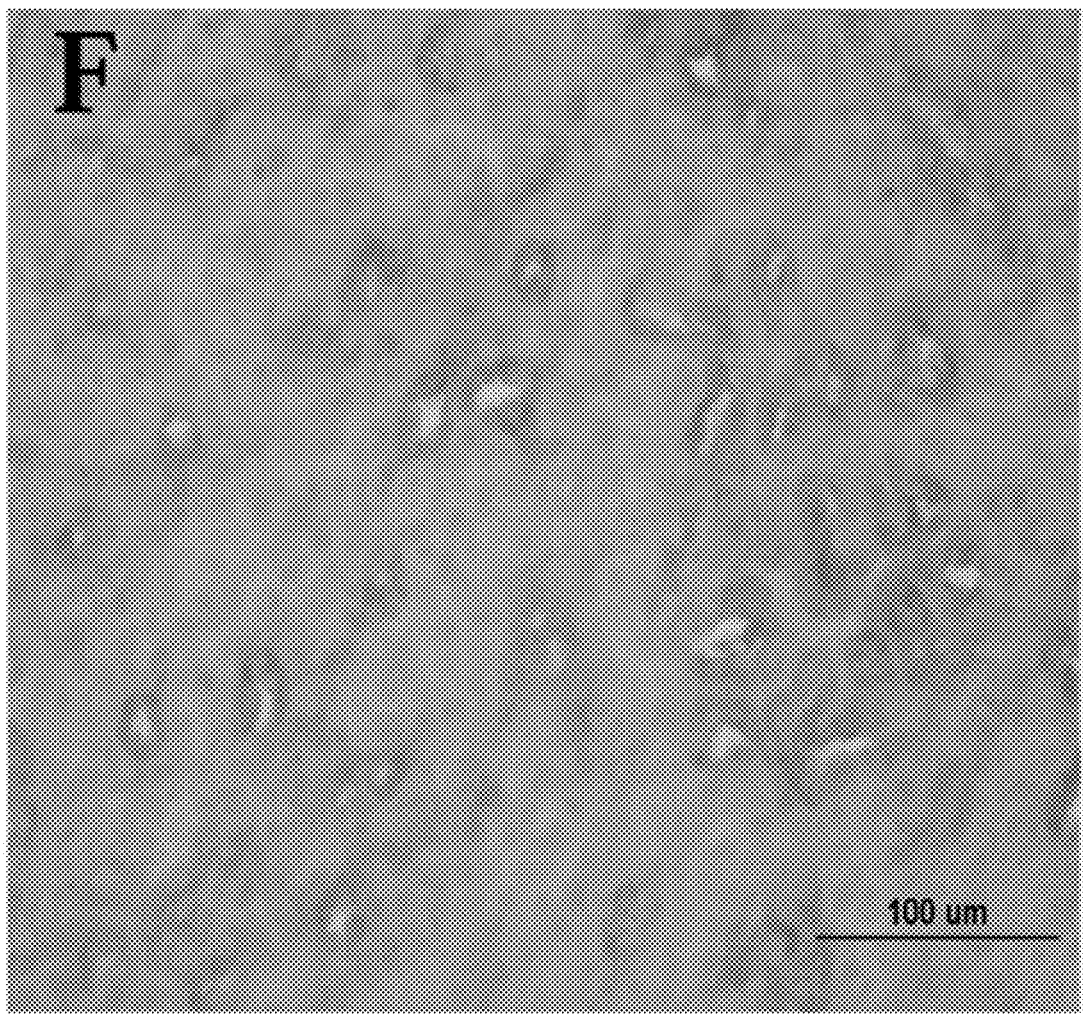
Figure 12G:
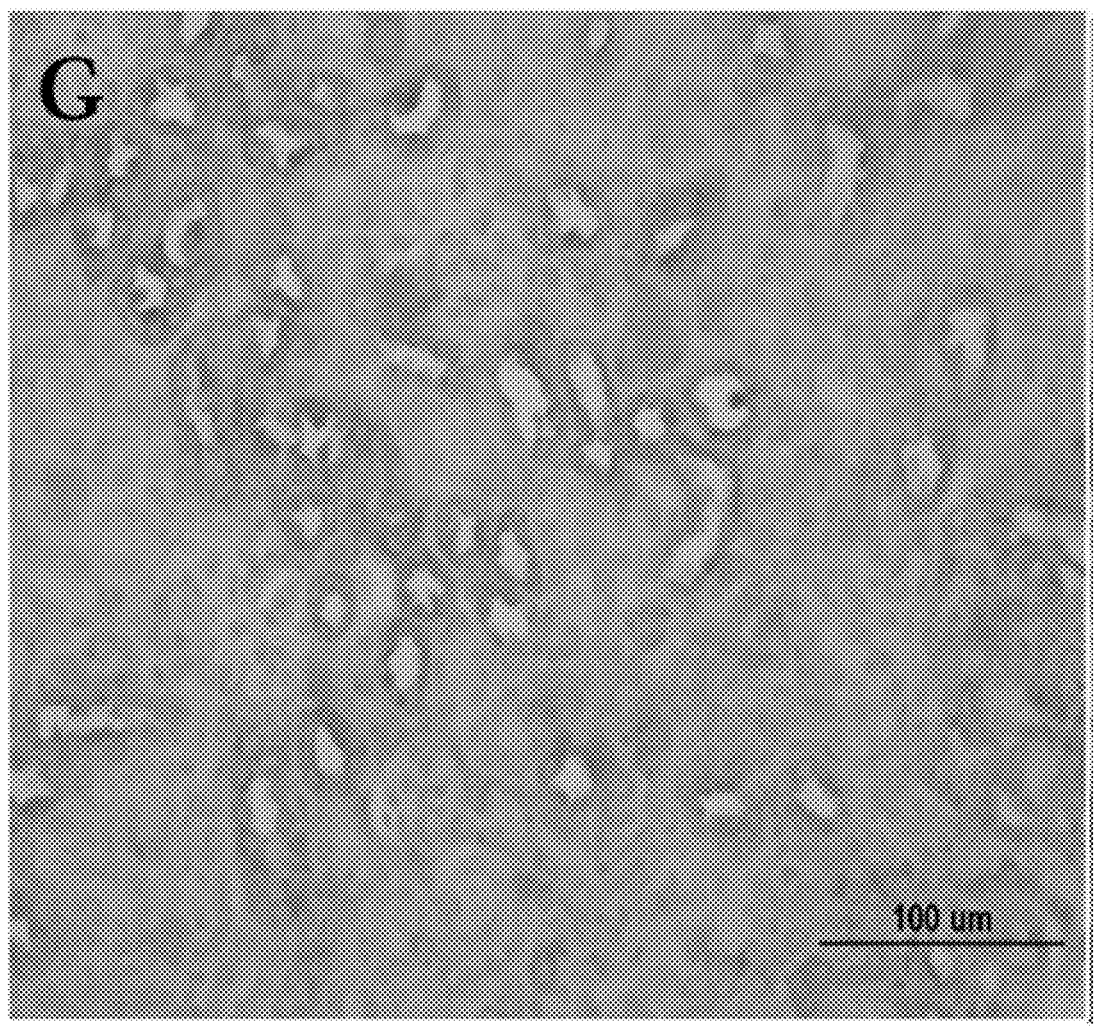
Figure 12H:
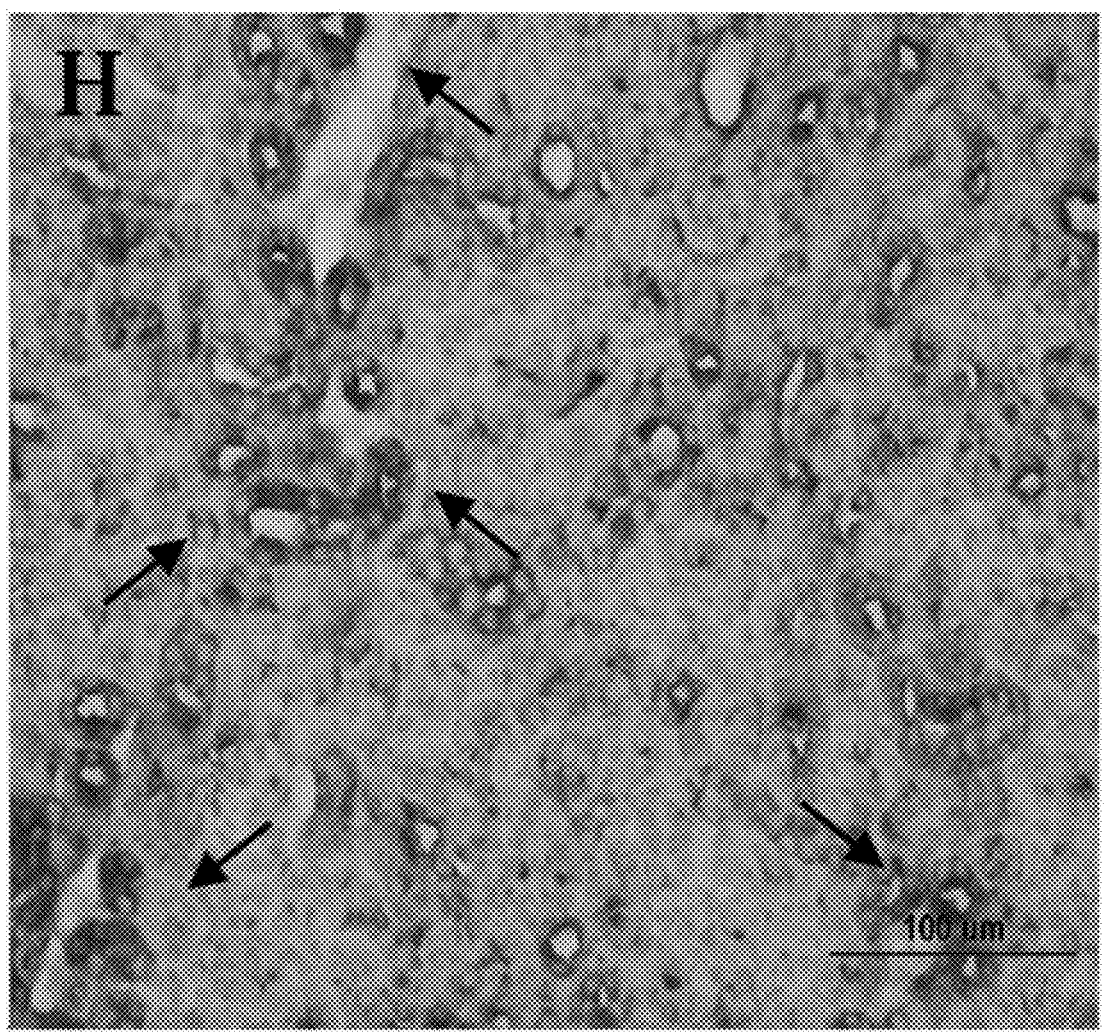

K18-hACE2 mice was intranasally immunized with $2\times10^4$ or $2\times10^3$ pfu of CoV-2-CNUHV03-CA22° C., and challenged intranasally with $2\times10^4$ pfu of CoV-2-KCDC03 on the 21st day after vaccination. The mortality rate (FIG. 9C), and body weight change (FIG. 9D) of the challenged K18-hACE2 mice were monitored for 12 days after infection; the virus titers in various tissues (nasal turbinate, lung, brain, kidney, and spleen) were measured by determining $\log_{10} TCID_{50}$ values on 6 days after the challenge (p.c.) (FIG. 9E) and by performing RT-qPCR (FIG. 10A & 10B). While all immunized and challenged K18-hACE2 mice survived (FIG. 9C) and exhibited no body weight loss (FIG. 9D). All PBS (mock)-immunized and challenged K18-hACE2 mice died within 8 days after the challenge (FIG. 9C) and exhibited lost body weight (4.6%) (FIG. 9D). No virus titers were detected in nasal turbinate, brain, lung, kidney, and spleen of immunized K18-hACE2 mice not only based on determining in terms of $\log_{10} TCID_{50}$ value (FIG. 9E) but also by RT-qPCR (FIG. 10A & 10B). A considerable virus titer was detected at nasal turbinate ($2.8 TCID_{50}/0.1$ g, $12.0\times10^3$ pfu/0.1 g), brain ($7.8 TCID_{50}/0.1$ g, $2.7\times10^6$ pfu/0.1 g), lung ($3.7 TCID_{50}/0.1$ g, $15.0\times10^3$ pfu/0.1 g), and kidney ($3.5 TCID_{50}/0.1$ g, $1.4\times10^3$ pfu/0.1 g) of PBS (mock)-immunized and challenged K18-hACE2 mice (FIG. 9E & FIG. 10A & 10B). As in the PBS (mock)-immunized and non-challenged K18-hACE2 mice (FIG. 11A), H&E staining of lung tissue samples from challenged K18-hACE2 mice immunised with $2\times10^3$ pfu (FIG. 11B) and $2\times10^4$ pfu (FIG. 11C) of CoV-2-CNUHV03-CA22° C. showed mild pneumonia and no pneumonia, respectively. The lung tissue of PBS (mock)-immunised and challenged K18-hACE2 mice exhibited severe interstitial pneumonia with infiltration of inflammatory cells (FIG. 11D). As in the PBS (mock)-immunized and non-challenged K18-hACE2 mice (FIG. 11E), positive staining in which SARS-CoV-2 NP antibody was detected was absent in the lung tissue of K18-hACE2 mice immunized with CoV-2-CNUHV03-CA22° C. at $2\times10^3$ pfu (FIG. 11F) or $2\times10^4$ pfu (FIG. 11G) and then challenged. Many positive staining areas were observed in lung tissue of PBS (mock)-immunized and challenged K18-hACE2 mice (FIG. 11H). The antigen staining was not observed in the brain (FIG. 12B) and kidney (FIG. 12F) of challenged K18-hACE2 mice (immunized with $2\times10^3$ pfu), as well as the brain (FIG. 12C) and kidney (FIG. 12G) of challenged K18-hACE2 mice (immunized with $2\times10^4$ pfu). This is as observed in the brain (FIG. 12A) and kidney (FIG. 12E) of PBS (mock)-immunized and non-challenged K18-hACE2 mice. Strong positive antigen staining was found in the brain (FIG. 12D) and kidney (FIG. 12H) of PBS (mock)-immunized and challenged K18-hACE2 mice.

The genes of CoV-2-CNUHV03-CA22° C. were fully sequenced (SEQ ID NOs: 13 to 24) and weres compared with those of wild-type SARS-CoV-2 (CoV-2-CNUHV03) (SEQ ID NOs: 1 to 12) (Table 3, Table 4, Table 5). Among 29,874 nucleotides, 59 nucleotides containing 37 nonsynonymous substitutions and 22 synonymous substitutions occurring at CoV-2-CNUHV03-CA22° C. were compared with CoV-2-CNUHV03 (Table 4). Among 9,755 amino acid residues, 31 amino acid residues were mutated in CoV-2-CNUHV03-CA22° C., compared to CoV-2-CNUHV03 (Table 5). To identify possible unique mutations in CoV-2-CNUHV03-CA22° C., amino acids changed in CoV-2-CNUHV03-CA22° C. (SEQ ID NOs: 37 to 48) were compared with the genes of SARS-CoV-2 (SEQ ID NOs: 25 to 36) present in GenBank (https://www.ncbi.nlm.nih.gov/nuccore) and GISAID (https://www.gisaid.org/). Thus, among the 9755 amino acids of CoV-2-CNUHV03-CA22° C., 11 amino acids were found (Table 3). In nsp2 (non-structural protein 2) with no known function, amino acid residues of 82 to 84 [glycine (G), histidine (H), and valine (V)] were deleted, and one mutation (M (methionine) 85V) was present. In nsp6 which functions as a potential transmembrane scaffold protein, two mutations [N (asparagine) 3609K (lysine), D (aspartic acid) 3671T (threonine)] were present. In nsp7 which functions as a processivity clamp for RNA polymerase, there was one mutation [D3926A (alanine)]. In helicase (nsp13) acting as RNA 5'-triphosphatase, there was one mutation [L (leucine) 5604F (phenylalanine)]. In the S protein that binds to the receptor, three mutations [T95I (isoleucine), N185K, S (Serine) 968A] were present. When the genome of the cold-adapted live attenuated SARS-CoV-2 vaccine strain (CoV-2-CNUHV03-CA22° C.) in the lung tissue of infected K18-ACE2 mice was sequenced on 6 days after infection, no reverted changes of genes were found (data not shown). The virus growth titer of the cold-adapted live attenuated SARS-CoV-2 vaccine strain in Vero cells in a tissue culture flask (75 cm²) at 22° C.° C. was about $2.7\times10^6$ pfu/ml, which is comparable to the viral growth titer of wild-type SARS-CoV-2 (CoV-2-CNUHV03) ($3.0\times10^6$ pfu/ml) at 37° C. (data not shown).

TABLE 3

Unique sequences of amino acids in cold-adapted live attenuated SARS-CoV-2 vaccine strain (SARS-Co-V-2/human/Korea/CNUHV03-CA22° C./2020)

| Protein name | | | Difference of amino acid sequences | The number of changed sequence |
|---|---|---|---|---|
| ORF1ab polyprotein | ORF1a polyprotein | nsp2 | Deletion: GHV(82~84), M85V | 4/461 |
| | | nsp6 | N3609K, D3671T | 2/290 |
| | | nsp7 | D3926A | 1/83 |
| | ORF1b | helicase | L5604F | 1/601 |
| S protein | | | T95I, N185K, S968A | 3/1274 |
| Total amino acids | | | | 11/9755 (including nonchanged ORFs) |

We compared the amino acid sequences of SARS-CoV-2/human/Korea/CNUHV03-CA22° C./2020 with those in GenBank (https://www.ncbi.nlm.nih.gov/nuccore) and GISAID (https://www.gisaid.org/). We found out the unique amino acids in our cold-adapted live attenuated SARS-CoV-2 vaccine strain (SARS-CoV-2/human/Korea/CNUHV03-CA22° C./2020).

Single letter abbreviation name of amino acid: Glycine(G), Alanine(A), Valine(V), Leucine(L), Isoleucine(I), Methionine(M), Phenylalanine(F), Serine(S), Threonine(T), Asparagine(N), Lysine(K), Histidine(H), Aspartic Acid(D)

TABLE 4

The changed nucleotide sequences in cold-adapted live attenuated SARS-CoV-2 vaccine strain (SARS-CoV-2/human/Korea/CNUHV03-CA22° C./2020)

| Gene name | | | Changed nucleotide sequences | The number of changed sequence |
|---|---|---|---|---|
| ORF1ab | ORF1a | nsp2 | Deletion: GGTCATGTT(244~252) (NS), A253G (NS), G698A (NS), T2271C (S) | 12 [11 (NS) + 1 (S)]/1923 |
| | | nsp3 | G3288A (S), A3550G (NS), C3855T (S), G4754A (NS), G5765A (NS), G6126A (S), G6240A (S), C6933T (S), C7115T (NS), C7311T (S), A7419G (S), C8031T (S), C8174T (NS), C8258T (NS) | 14 [6 (NS) + 8 (S)]/5835 |
| | | nsp4 | A8611G (NS), C8914T (NS), G8953A (NS) | 3 (NS)/1500 |
| | | nsp6 | T10818G (NS), T10827A (NS), T10851G (S) | 3 [2 (NS) + 1 (S)]/870 |
| | | nsp7 | A11777C (NS) | 1 (NS)/249 |
| | | nsp10 | C12882T (S), G13050A (S) | 2 (S)/417 |
| | ORF1b | RNA-dependent RNA polymerase | C13822T (NS), G14417A (NS), C15464T (NS) | 3 (NS)/2796 |
| | | helicase | C16810T (NS), C17508T (S), G17545A (NS) | 3 [2 (NS) + 1 (S)]/1803 |
| | | 3'-to-5' exonuclease | C18349T (S) | 1 (S)/1581 |
| | | endoRNAse | T19506G (S) | 1 (S)/1038 |
| | | 2'-0-ribose methyl transferase | G21113C (NS), C21168T (S), C21175T (NS) | 3 [2 (NS) + 1 (S)]/894 |
| | S | | G113A (NS), C257T (NS), C287A (NS), G451A (NS), C2511T (S), T2902G (NS), C3003T (S) | 7 [5 (NS) + 2 (S)]/3822 |
| | M | | C537T (S) | 1 (S)/669 |
| | ORF7a | | C141T (S), A201G (NS) | 2 [1 (NS) + 1 (S)]/366 |
| | ORF8 | | C63T (S) | 1 (S)/366 |
| | N | | N243T (S), T1082A (NS) | 2 [1 (NS) + 1 (S)]/1260 |
| | Total nucleotides | | | 59 [37 (NS) + 22 (S)]/29874 including non-coding nucleotides |

We compared the nucleotide sequences of cold-adapted live attenuated SARS-CoV-2 vaccine strain (SARS-CoV-2/human/Korea/CNUHV03-CA22° C./2020) with those in wild-type SARS-CoV-2: (SARS-CoV-2/human/Korea/CNUHV03/2020), which was used for developing cold-adapted live attenuated vaccine strain in Vero cells.
(S): (synonymous substitution),
(NS): (nonsynonymous substitution)

TABLE 5

Changed amino acid sequences in cold-adapted live attenuated SARS-CoV-2 vaccine strain (SARS-CoV-2/human/Korea/CNUHV03-CA22° C./2020)

| Protein name | | | Changed amino acid sequences | The number of changed sequence |
|---|---|---|---|---|
| ORF1ab polyprotein | ORF1a polyprotein | nsp2 | Deletion: GHV(82~84), M85V, G233E | 5/641 |
| | | nsp3 | N1184D, G1585D, S1922N, A2372V, P2725L, A2753V | 6/1945 |
| | | nsp4 | S2871G, P2972S, G2985R | 3/500 |
| | | nsp6 | F3606L, N3609K | 2/290 |
| | | nsp7 | D3926A | 1/83 |
| | ORF1b | RNA-dependent RNA polymerase | R4608W, S4806N, A5155V | 3/932 |
| | | helicase | L5604F, V5849I | 2/601 |
| | | 2'-0-ribose methyl transferase | C7038S, P7059S | 2/298 |
| | S protein | | C38Y, S86F, G96E, G151S, S968A | 5/1274 |

TABLE 5-continued

Changed amino acid sequences in cold-adapted live attenuated SARS-CoV-2 vaccine strain (SARS-CoV-2/human/Korea/CNUHV03-CA22° C./2020)

| Protein name | Changed amino acid sequences | The number of changed sequence |
| --- | --- | --- |
| ORF7a | Y67C | 1/122 |
| N protein | I361K | 1/420 |
|  |  | 31/9755 |
| Total amino acids |  | 31/9755 (including non-changed ORFs) |

We compared the amino acid sequences of cold-adapted live attenuated SARS-CoV-2 vaccine strain (SARS-CoV-2/human/Korea/CNUHV03-CA22° C./2020) with those in wild-type SARS-CoV-2 (SARS-CoV-2/human/Korea/CNUHC03/2020), which was used for developing cold-adapted live attenuated vaccine strain in Vero cells.
Single letter abbreviation name of amino acid: Glycine(G), Alanine(A), Valine(V), Cysteine(C), Proline(P), Leucine(L), Isoleucine(I), Methionine(M), Trypotphan(W), Phenylalanine(F), Serine(S), Tyrosine(Y), Asparagine(N), Lysine(K), Arginine(R), Histidine(H), Aspartic Acid(D), Glutamic Acid(E)

Strong neutralization (640 to 4960) was induced in 16 immunized K18-hACE2 mice inoculated with one dose ($2\times10^4$ or $2\times10^3$ pfu) of CoV-2-CNUHV03-CA22° C. SARS-CoV-2-specific IgA antibody was also induced in nasal turbinate, lung, and kidney. Further, T lymphocytes expressing IFN-γ, which are specific for SARS-CoV-2, were strongly induced in the spleen of vaccinated mice at 19 days after infection. In a study on a measles virus (MeV)-based vaccine expressing the spike protein of SARS-CoV-2 (MeV-vac2-SARS-S(H)) (C. Horner et al., A Highly Immunogenic Measles Virus-based Th1-biased COVID-19 Vaccine bioRxiv (2020)), it was observed that after secondary immunization, the neutralization body titer for measles virus was from 257 to 800 in all immunized mice. The titer for SARS-CoV-2 was 15 to 80 in 3 of 6 immunized mice.

All the K18-hACE2 mice intranasally immunized with a one dose ($2\times10^4$ or $2\times10^3$ pfu) of CoV-2-CNUHV03-CA22° C. completely protected from the infection of wild-type SARS-CoV-2 (CoV-2-KCDC03). There were no body weight loss and no virus detection in various tissues (nasal turbinate, brain, lung, kidney) in terms of the $\log_{10}$ TCID$_{50}$ values or as determined by RT-qPCR. The study on the adenovirus-based ChAdOX1 nCoV-19 vaccine, expressing the spike protein of SARS-CoV-2, showed significantly reduced virus titres in bronchoalveolar lavage fluid and respiratory tract tissues of vaccinated rhesus macaques that were challenged with SARS-CoV-2 (N. v. Doremalen et al., ChAdOx1 nCoV-19 vaccination prevents SARS-CoV-2 pneumonia in rhesus macaque. nature (2020)).

As a result, the cold-adapted live attenuated SARS-CoV-2 vaccine (CoV-2-CNUHV03-CA22° C.) is safe in K18-hACE2 mice, and even a one-dose vaccination thereof may completely protect the K18-hACE2 mice from the challenge with SARS-CoV-2.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. Cold-adapted live attenuated severe acute respiratory syndrome coronavirus (SARS-CoV-2) prepared by infecting cells with severe acute respiratory syndrome coronavirus (SARS-CoV-2) and then gradually adapting the severe acute respiratory syndrome coronavirus (SARS-CoV-2) to a temperature from 37° C. to 22° C., wherein the cold-adapted live attenuated severe acute respiratory syndrome coronavirus (SARS-CoV-2) contains polynucleotides represented by nucleotide sequence represented by SEQ ID NOs: 13 to 24, or amino acid sequences represented by SEQ ID NOs: 37 to 48.

2. The cold-adapted live attenuated severe acute respiratory syndrome coronavirus (SARS-CoV-2) of claim 1, wherein the cells are Vero cells, Calu-3, A549, HUH7.0 or HEK-293T cells.

3. A severe acute respiratory syndrome coronavirus (SARS-CoV-2) vaccine containing the cold-adapted live attenuated severe acute respiratory syndrome coronavirus (SARS-CoV-2) of claim 1 as an active ingredient.

4. The severe acute respiratory syndrome coronavirus (SARS-CoV-2) vaccine of claim 3, wherein the vaccine is administered intranasally.

5. A method inducing an immune response against a severe acute respiratory syndrome coronavirus (SARS-CoV-2) infectious disease, comprising administering the vaccine of claim 3 to a subject.

6. The method of claim 5, wherein the severe acute respiratory syndrome coronavirus (SARS-CoV-2) infectious disease is a coronavirus disease-19 (COVID-19).

7. The method of claim 5, wherein the vaccine is administered intranasally.

* * * * *